United States Patent
Mizuki et al.

(10) Patent No.: US 9,991,455 B2
(45) Date of Patent: Jun. 5, 2018

(54) AMINE COMPOUND AND ORGANIC ELECTROLUMINESCENT ELEMENT

(71) Applicant: IDEMITSU KOSAN CO., LTD., Chiyoda-ku (JP)

(72) Inventors: Yumiko Mizuki, Basel (CH); Hirokatsu Ito, Ichihira (JP); Tasuku Haketa, Chiba (JP); Tomoharu Hayama, Utsunomiya (JP); Masahiro Kawamura, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 119 days.

(21) Appl. No.: 15/023,264

(22) PCT Filed: Sep. 19, 2014

(86) PCT No.: PCT/JP2014/074960
§ 371 (c)(1),
(2) Date: Mar. 18, 2016

(87) PCT Pub. No.: WO2015/041352
PCT Pub. Date: Mar. 26, 2015

(65) Prior Publication Data
US 2016/0268520 A1    Sep. 15, 2016

(30) Foreign Application Priority Data
Sep. 20, 2013  (JP) .................. 2013-196193

(51) Int. Cl.
*C07F 7/08*    (2006.01)
*H01L 51/00*   (2006.01)
(Continued)

(52) U.S. Cl.
CPC ........ *H01L 51/0094* (2013.01); *C07F 7/0809* (2013.01); *C07F 7/0818* (2013.01);
(Continued)

(58) Field of Classification Search
CPC .......................... C07F 7/0809; C07F 7/0818
See application file for complete search history.

(56) References Cited

U.S. PATENT DOCUMENTS

2012/0043533 A1    2/2012  Mizuki et al.
2014/0131681 A1*   5/2014  Ito .................. H01L 51/006
                                                  257/40

FOREIGN PATENT DOCUMENTS

JP    2011 219461       11/2011
KR    10 2012 0083203   7/2012
(Continued)

OTHER PUBLICATIONS

Michael Schmittel, et al., "Thermal $C^2$-$C^6$ Cyclization of Enyne-Allenes. Experimental Evidence for a Stepwise Mechanism and for an Unusual Thermal Silyl Shift", Journal of Organic Chemistry, vol. 72, No. 6, 2007, pp. 2166-2173.
(Continued)

*Primary Examiner* — Vu A Nguyen
(74) *Attorney, Agent, or Firm* — Oblon, McClelland, Maier & Neustadt, L.L.P.

(57) ABSTRACT

An organic electroluminescence device having good emission efficiency is provided. The organic electroluminescence device includes an amine compound which includes a benzofluorene structure and an aryl group and/or a heteroaryl group, wherein the benzofluorene structure has a specific substituent at 9-position of the fluorene ring.

27 Claims, 1 Drawing Sheet

(51) Int. Cl.
*C09K 11/06* (2006.01)
*H01L 51/50* (2006.01)
(52) U.S. Cl.
CPC .......... *C09K 11/06* (2013.01); *H01L 51/006* (2013.01); *H01L 51/0059* (2013.01); *C09K 2211/1007* (2013.01); *C09K 2211/1011* (2013.01); *C09K 2211/1014* (2013.01); *H01L 51/0054* (2013.01); *H01L 51/5012* (2013.01)

(56) References Cited

FOREIGN PATENT DOCUMENTS

| | | |
|---|---|---|
| KR | 10 2012 0116884 | 10/2012 |
| WO | 2007 148660 A1 | 12/2007 |
| WO | 2010 016405 A1 | 2/2010 |
| WO | 2010 122799 A1 | 10/2010 |
| WO | 2014 069602 A1 | 5/2014 |

OTHER PUBLICATIONS

International Search Report dated Dec. 2, 2014, in PCT/JP2014/074960 Filed Sep. 19, 2014.

\* cited by examiner

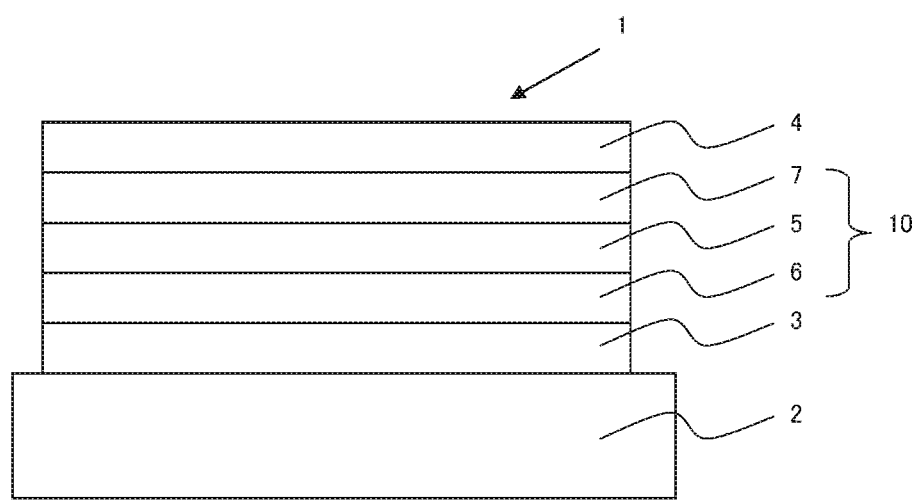

AMINE COMPOUND AND ORGANIC ELECTROLUMINESCENT ELEMENT

TECHNICAL FIELD

The present invention relates to amine compounds and organic electroluminescence devices employing the amine compounds.

BACKGROUND ART

An organic electroluminescence (EL) device is generally composed of an anode, a cathode, and one or more organic thin film layers sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light.

Many researches have been made on the applications of organic EL device to display, etc. because of its possibility of a wide selection of emission colors by using various emitting materials in a light emitting layer. Particularly, the research on the materials which emit three primary red, green, and blue colors has been made most actively, and the intensive research has been made to improve their properties.

One of the most important problems involved in organic EL devices is the improvement of the emission efficiency. To obtain an organic EL device with high emission efficiency, it has been known to form a light emitting layer by doping a host material with a several percent of a dopant material. The host material is required to have a high carrier mobility, a uniform film-forming property, etc. The dopant material is required to have a high fluorescent quantum yield, a uniform dispersibility, etc.

Patent Literatures 1, 2 and 3 describe benzofluorene compounds as the materials for a light emitting layer.

CITATION LIST

Patent Literature

Patent Literature 1: WO 07/148660
Patent Literature 2: KR 10-2012-0083203A
Patent Literature 3: KR 10-2012-0116884A

SUMMARY OF INVENTION

Technical Problem

The inventors have found that the benzofluorene disclosed in Patent Literature 1 is still insufficient in improving the emission efficiency and a further improvement is required. The substituent at 9-position of the benzofluorene disclosed in Patent Literatures 2 and 3 is mainly an alkyl substituent and an aryl substituent, and a silyl substituent is not explicitly described in these patent literatures.

The present invention has been made to solve the above problem and an object thereof is to provide an organic EL device with a good emission efficiency.

Solution to Problem

As a result of extensive research in view of achieving the above object, the inventors have found that the above problem is solved by an amine compound comprising a benzofluorene structure and an aryl group and/or a heteroaryl group, wherein the benzofluorene structure has a specific substituent at 9-position of the fluorene ring.

In an aspect of the invention, the following [1] to [3] are provided:

[1] an amine compound represented by formula (1):

$$B\text{-}(A)_n \quad (1)$$

in formula (1):

n represents an integer of 1 to 4, B represents a structure represented by formula (2), and A represents an amine moiety represented by formula (4);

when n is 2 or more, the amine moieties A may be the same or different;

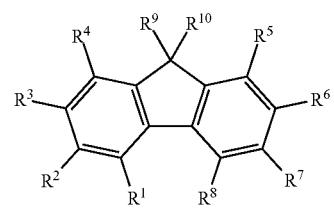

(2)

in formula (2):

at least one pair selected from $R^1$ and $R^2$, $R^2$ and $R^3$, $R^3$ and $R^4$, $R^5$ and $R^6$, $R^6$ and $R^7$, and $R^7$ and $R^8$ represents a bond to a divalent group represented by formula (3);

$R^9$ represents a hydrogen atom, a substituted or unsubstituted alkyl group having 1 to 20 carbon atoms, a substituted or unsubstituted cycloalkyl group having 3 to 20 carbon atoms, a substituted or unsubstituted aryl group having 6 to 30 ring carbon atoms, a substituted or unsubstituted heteroaryl group having 5 to 30 ring atoms, or a group represented by formula (I);

$R^{10}$ is represented by formula (II):

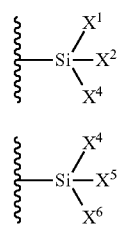

in formulae (I) and (II):

$X^1$ to $X^6$ each independently represent a hydrogen atom, a substituted or unsubstituted alkyl group having 1 to 20 carbon atoms, a substituted or unsubstituted cycloalkyl group having 3 to 20 carbon atoms, a substituted or unsubstituted alkenyl group having 2 to 20 carbon atoms, a substituted or unsubstituted alkoxy group having 1 to 20 carbon atoms, a substituted or unsubstituted aryl group having 6 to 30 ring carbon atoms, or a substituted or unsubstituted aralkyl group having 7 to 20 carbon atoms, and $X^1$ to $X^6$ may be bonded to each other to form a ring;

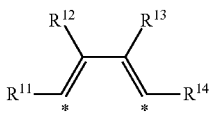

(3)

in formula (3) each * represents a bonding site to which the at least one pair representing the bond to the divalent group represented by formula (3) as defined in formula (2) is bonded;

in formulae (2) and (3), n variable or variables selected from $R^1$ to $R^8$ and $R^{11}$ to $R^{14}$ represents or represent a bond or bonds to A;

$R^1$ to $R^8$ and $R^{11}$ to $R^{14}$ other than those defined above each independently represent a hydrogen atom, a fluorine atom, a cyano atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a mono-, di- or tri-substituted silyl group wherein the substituent is selected from an alkyl group having 1 to 20 carbon atoms and an aryl group having 6 to 30 ring carbon atoms, a substituted or unsubstituted aryl group having 6 to 30 ring carbon atoms, or a substituted or unsubstituted heteroaryl group having 5 to 30 ring atoms;

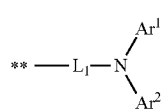

(4)

in formula (4), $Ar^1$ and $Ar^2$ each independently represent a substituted or unsubstituted aryl group having 6 to 30 ring carbon atoms or a substituted or unsubstituted heteroaryl group having 5 to 30 ring carbon atoms;

$L_1$ represents a single bond, an arylene group having 6 to 30 ring carbon atoms, a heteroarylene group having 5 to 30 ring atoms, or a divalent linking group wherein two to four selected from the arylene group and the heteroarylene group are linked together; and

** represents a bonding site to B;

[2] an organic electroluminescence device comprising an organic thin film layer between a cathode and an anode, wherein the organic thin film layer comprises one or more layers which comprise a light emitting layer and at least one layer of the organic thin film layer comprises at least one compound selected from the compound described in [1]; and

[3] an electronic equipment comprising the organic electroluminescence device described in [2].

Advantageous Effects of Invention

According to the present invention, an organic EL device with a high emission efficiency is provided.

BRIEF DESCRIPTION OF DRAWINGS

FIG. 1 is a schematic view showing an example of the structure of the organic electroluminescence device (also referred to as "organic EL device") according to an embodiment of the present invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ. "YY" is larger than "XX" and each of "XX" and "YY" represents an integer of 1 or more.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ. "YY" is larger than "XX" and each of "XX" and "YY" represents an integer of 1 or more.

The term of "unsubstituted group ZZ" referred to by "a substituted or unsubstituted group ZZ" used herein means the group ZZ wherein no hydrogen atom is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms which are members forming the ring itself of a compound in which a series of atoms is bonded to form the ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The optional substituent referred to by "substituted or unsubstituted" used herein is preferably selected from the group consisting of an alkyl group having 1 to 50, preferably 1 to 10, more preferably 1 to 5 carbon atoms; a cycloalkyl group having 3 to 50, preferably 3 to 6, more preferably 5 or 6 ring carbon atoms; an aryl group having 6 to 50, preferably 6 to 24, more preferably 6 to 12 ring carbon atoms; an aralkyl group having 1 to 50, preferably 1 to 10, more preferably 1 to 12 carbon atoms having an aryl group having 6 to 50, preferably 6 to 24, more preferably 6 to 12 ring carbon atoms; an amino group; a mono- or dialkylamino group having an alkyl group having 1 to 50, preferably 1 to 10, more preferably 1 to 5 carbon atoms; a mono- or diarylamino group having an aryl group having 6 to 50, preferably 6 to 24, more preferably 6 to 12 ring carbon atoms; an alkoxy group having 1 to 50, preferably 1 to 10, more preferably 1 to 6 carbon atoms; an aryloxy group having 6 to 50, preferably 6 to 24, more preferably 6 to 12 ring carbon atoms; an alkylthio group having 1 to 20, preferably 1 to 10, more preferably 1 to 6 carbon atoms; an arylthio group having 6 to 30, preferably 6 to 24, more preferably 6 to 12 ring carbon atoms; a mono-, di- or tri-substituted silyl group, wherein the substituent is selected from an alkyl group having 1 to 50, preferably 1 to 10, more preferably 1 to 5 carbon atoms and an aryl group having 6 to 50, preferably 6 to 24, more preferably 6 to 12 ring carbon atoms; a heteroaryl group having 5 to 50, preferably 5 to 24, more preferably 5 to 12 ring atoms, which comprises 1 to 5, preferably 1 to 3, more preferably 1 to 2 heteroatoms, such as a nitrogen atom, an oxygen atom, and a sulfur atom; a haloalkyl group having 1 to 50, preferably 1 to 10, more preferably 1 to 5 carbon atoms; a halogen atom, such as a fluorine atom, a chlorine atom, a bromine atom, and an iodine atom; a cyano group; and a nitro group.

Of the above, a substituent selected from the group consisting of an alkyl group having 1 to 5 carbon atoms, a cycloalkyl group having 5 or 6 carbon atoms, and an aryl group having 6 to 12 ring carbon atoms is more preferred. These optional substituents may further have a substituent mentioned above.

The amine compound of the invention is represented by formula (1):

$$B(-A)_n \quad (1).$$

In formula (1), n represents an integer of 1 to 4, B represents a structure represented by formula (2), and A represents an amine moiety represented by formula (4)

When n is 2 or more, the amine moieties A may be the same or different.

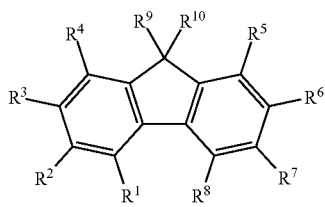

(2)

In formula (2), at least one pair selected from $R^1$ and $R^2$, $R^2$ and $R^3$, $R^3$ and $R^4$, $R^5$ and $R^6$, $R^6$ and $R^7$, and $R^7$ と $R^8$ represents a bond to a divalent group represented by formula (3).

$R^9$ represents a hydrogen atom, a substituted or unsubstituted alkyl group having 1 to 20 carbon atoms, a substituted or unsubstituted cycloalkyl group having 3 to 20 carbon atoms, a substituted or unsubstituted aryl group having 6 to 30 ring carbon atoms, a substituted or unsubstituted heteroaryl group having 5 to 30 ring atoms, or a group represented by formula (I).

$R^{10}$ is represented by formula (II):

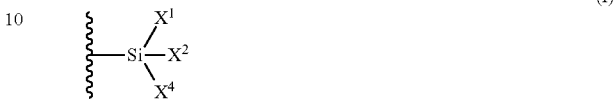

In formulae (I) and (II), $X^1$ to $X^6$ each independently represent a hydrogen atom, a substituted or unsubstituted alkyl group having 1 to 20 carbon atoms, a substituted or unsubstituted cycloalkyl group having 3 to 20 carbon atoms, a substituted or unsubstituted alkenyl group having 2 to 20 carbon atoms, a substituted or unsubstituted alkoxy group having 1 to 20 carbon atoms, a substituted or unsubstituted aryl group having 6 to 30 ring carbon atoms, or a substituted or unsubstituted aralkyl group having 7 to 20 carbon atoms. $X^1$ to $X^6$ may be bonded to each other to form a ring.

Examples of formulae (I) and (II) include a trimethylsilyl group, a triethylsilyl group, a t-butyldimethylsilyl group, a vinyldimethylsilyl group, a propyldimethylsilyl group, an isopropyldimethylsilyl group, a triphenylsilyl group, a phenyldimethylsilyl group, a t-butyldiphenylsilyl group, and a tritolylsilyl group.

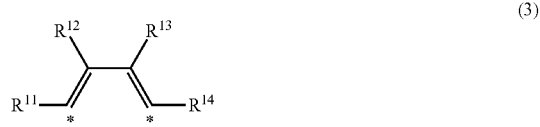

(3)

In formula (3), each * represents a bonding site to which the at least one pair representing the bond to the divalent group represented by formula (3) as defined in formula (2) is bonded.

In formulae (2) and (3), n variable or variables selected from $R^1$ to $R^8$ and $R^{11}$ to $R^{14}$ represents or represent a bond or bonds to A.

$R^1$ to $R^8$ and $R^{11}$ to $R^{14}$ other than those defined above each independently represent a hydrogen atom, a fluorine atom, a cyano atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted alkylsilyl group having 3 to 50 carbon atoms, a substituted or unsubstituted arylsilyl group having 6 to 50 ring carbon atoms, a substituted or unsubstituted aryl group having 6 to 30 ring carbon atoms, or a substituted or unsubstituted heteroaryl group having 5 to 30 ring atoms.
B in formula (1) is preferably represented by any of formulae (11) to (20):
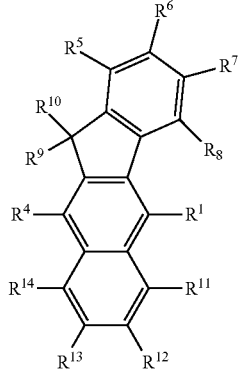
(11)
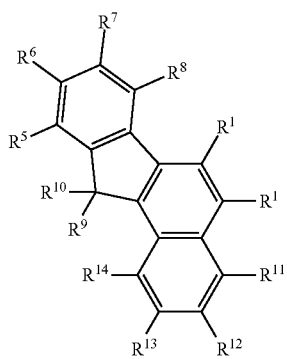
(12)
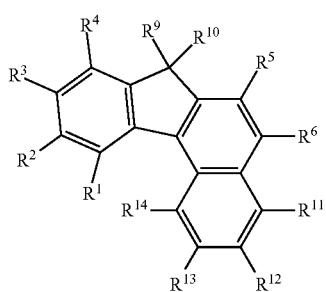
(13)
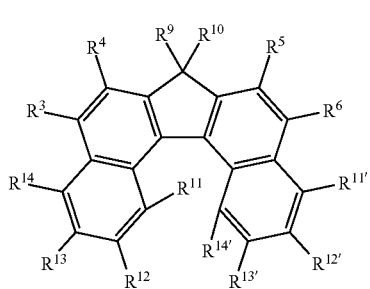
(14)
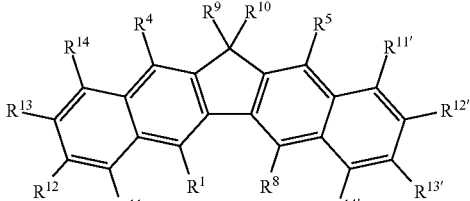
(15)
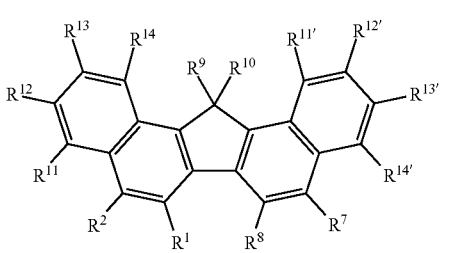
(16)
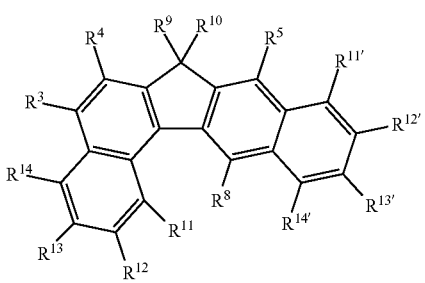
(17)
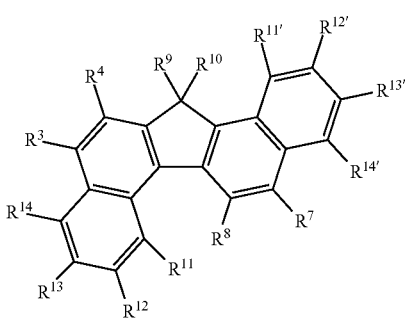
(18)
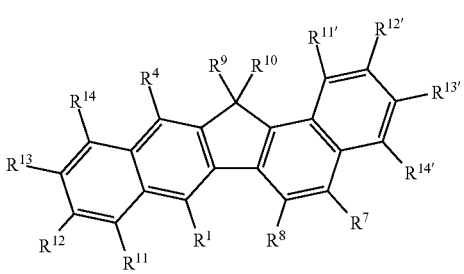
(19)

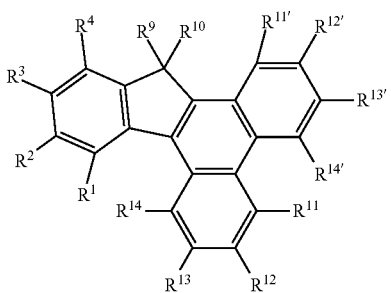
(20)
wherein $R^1$ to $R^{14}$ are as defined in formulae (2) and (3) and $R^{11'}$ to $R^{14'}$ are the same as $R^{11}$ to $R^{14}$.
B represented by any of formulae (11) to (20) is preferably represented by any of formulae (21) to (49):
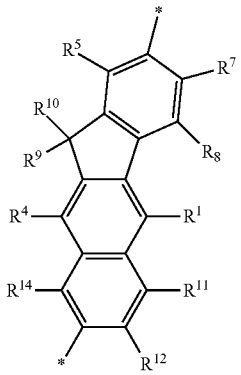
(21)
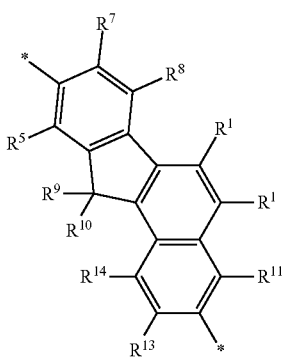
(22)
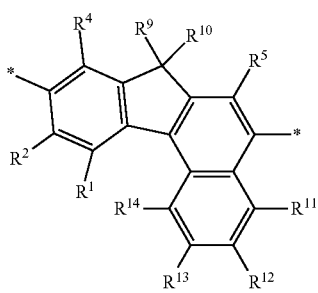
(23)
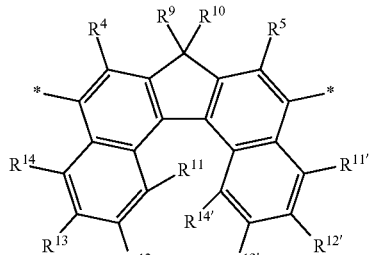
(24)
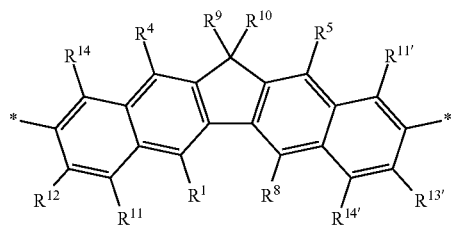
(25)
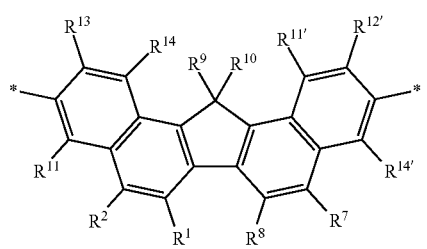
(26)
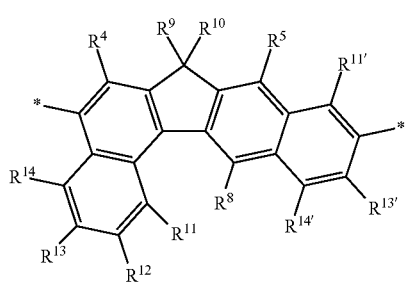
(27)
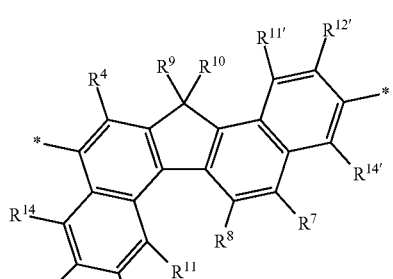
(28)
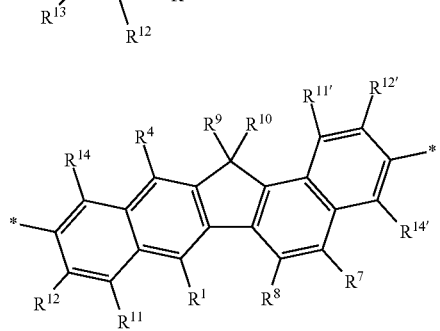
(29)

-continued
(30) 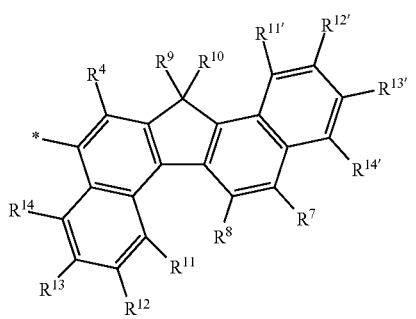
(31) 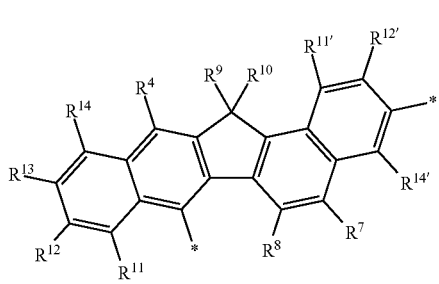
(32) 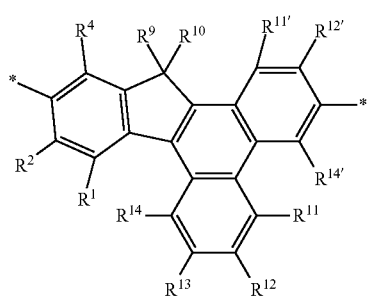
(33) 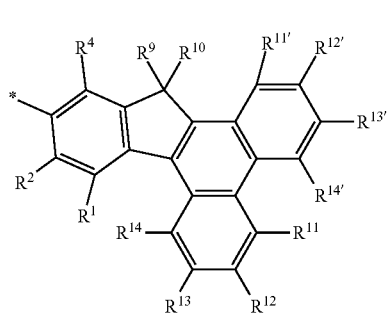
(34) 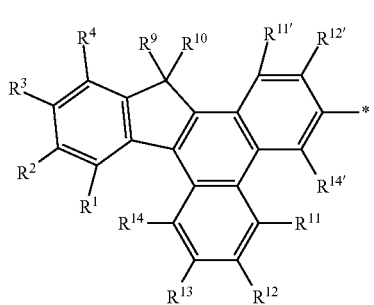
-continued
(35) 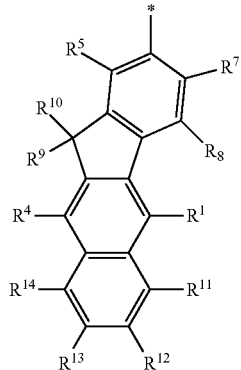
(36) 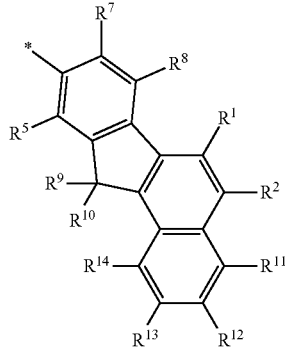
(37) 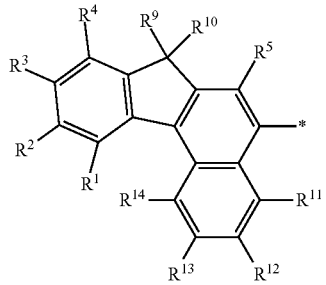
(38) 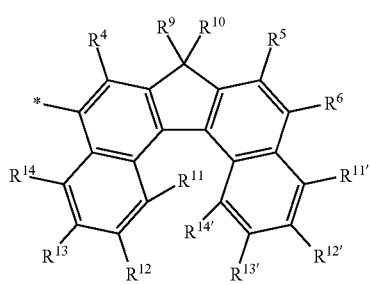
(39) 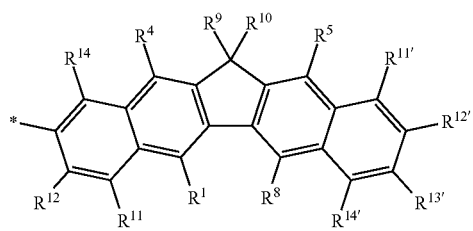

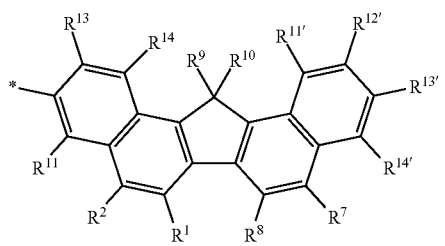
(40)
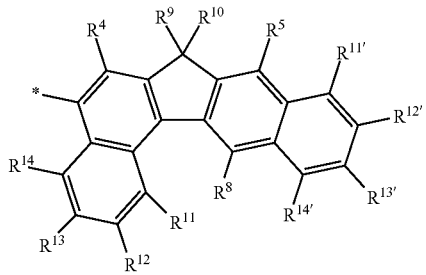
(41)
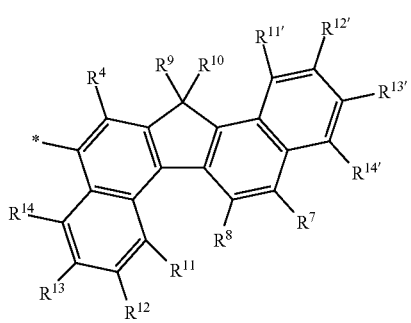
(42)
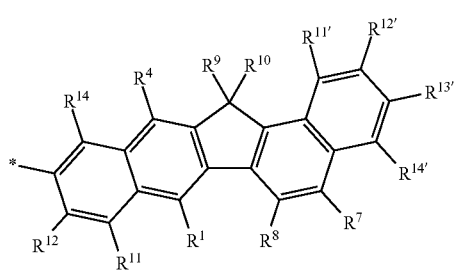
(43)
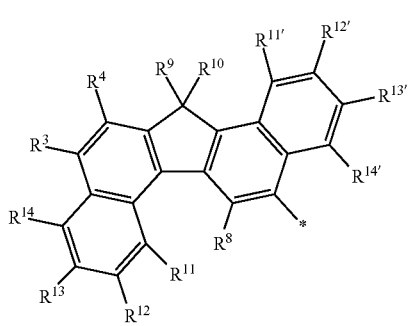
(44)
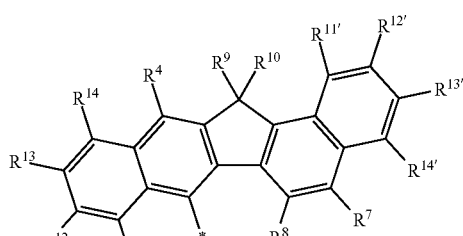
(45)
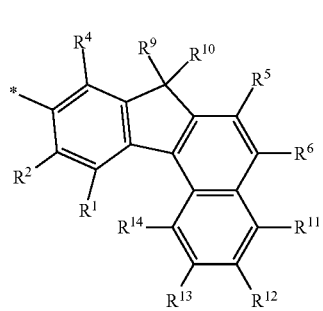
(46)
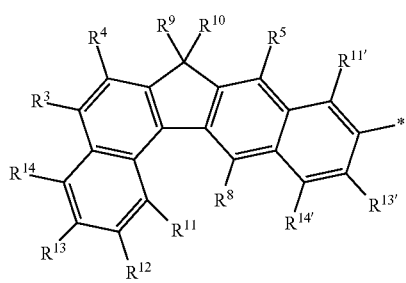
(47)
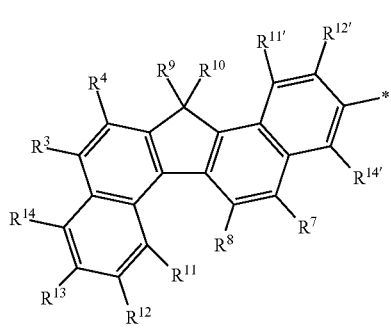
(48)
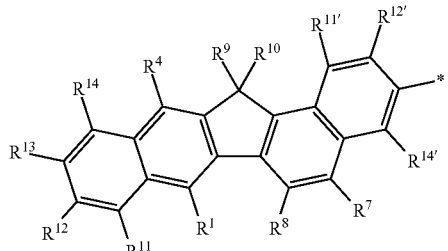
(49)
wherein $R^1$ to $R^{14}$ and $R^{11'}$ to $R^{14'}$ are as defined in formulae (11) to (20) and each * represent a bond to A.

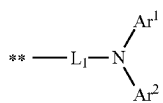
(4)

In formula (4):

Ar$^1$ and Ar$^2$ each independently represent a substituted or unsubstituted aryl group having 6 to 30 ring carbon atoms or a substituted or unsubstituted heteroaryl group having 5 to 30 ring carbon atoms;

L$_1$ represents a single bond, an arylene group having 6 to 30 ring carbon atoms, a heteroarylene group having 5 to 30 ring atoms, or a divalent linking group wherein two to four selected from the arylene group and the heteroarylene group are linked together; and

** represents a bonding site to B.

In a preferred amine compound represented by formula (1) of the invention, A is represented by formula (4) and B is represented by any of formulae (21) to (49). In a particularly preferred amine compound, n is 2.

In formula (1), n is preferably 1 or 2 and more preferably 2. When n is 1 or 2, the amine compound has a singlet energy (energy gap between the first excited singlet state and the ground state) within a range appropriate as the material of organic EL device.

In formulae (2), preferably, two pairs selected from R$^1$ and R$^2$, R$^2$ and R$^3$, R$^3$ and R$^4$, R$^5$ and R$^6$, R$^6$ and R$^7$, and R$^7$ and R$^8$ represent the bonds to the divalent group represented by formula (3).

In formula (4), L$_1$ is preferably a single bond.

In formula (1), R$^9$ in B is preferably represented by formula (I) and R$^{10}$ is preferably represented by formula (II). Alternatively, R$^9$ in B is preferably a substituted or unsubstituted alkyl group having 1 to 20 carbon atoms or a substituted or unsubstituted aryl group having 6 to 30 ring carbon atoms and R$^{10}$ is preferably represented by formula (II).

In formulae (I) and (II), preferably, X$^1$ to X$^6$ each independently represent a substituted or unsubstituted alkyl group having 1 to 20 carbon atoms, a substituted or unsubstituted cycloalkyl group having 3 to 20 carbon atoms, or a substituted or unsubstituted aryl group having 6 to 30 ring carbon atoms.

Examples of the aryl group having 6 to 30, preferably 6 to 24, and more preferably 6 to 18 ring carbon atoms include a phenyl group, a naphthylphenyl group, a biphenylyl group, a terphenylyl group, a naphthyl group, acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indacenyl group, an as-indacenyl group, a fluoranthenyl group, a benzo[k]fluoranthenyl group, a triphenylenyl group, a benzo[b]triphenylenyl group, and a perylenyl group. Preferred are a phenyl group, a biphenylyl group, a terphenylyl group, and a naphthyl group, with a phenyl group, a biphenylyl group, and a terphenylyl group being more preferred and a phenyl group being particularly preferred.

Examples of the substituted aryl group include a phenylnaphthyl group, a naphthylphenyl group, a tolyl group, a xylyl group, a trimethylsilylphenyl group, a 9,9-dimethylfluorenyl group, a 9,9-diphenylfluorenyl group, a 9,9'-spirobifluorenyl group, and a cyanophenyl group, with a tolyl group, a xylyl group, a trimethylsilylphenyl group, a 9,9-dimethylfluorenyl group, a 9,9-diphenylfluorenyl group, a 9,9'-spirobifluorenyl group, a cyanophenyl group, and a trimethylsilylphenyl group being more preferred.

The heteroaryl group having 5 to 30, preferably 6 to 24, and more preferably 6 to 18 ring atoms includes at least one and preferably 1 to 5 heteroatoms, for example, a nitrogen atom, a sulfur atom and an oxygen atom. Examples thereof include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, and a xanthenyl group. Preferred are a furyl group, a thienyl group, a pyridyl group, a pyridazinyl group, a pyrimidinyl group, a pyrazinyl group, a triazinyl group, a benzofuranyl group, a benzothiophenylphenyl group, a dibenzofuranyl group, and a dibenzothiophenyl group, with a benzofuranyl group, a benzothiophenylphenyl group, a dibenzofuranyl group, and a dibenzothiophenyl group being more preferred.

Examples of the alkenyl group having 2 to 20, preferably 3 to 18, and more preferably 4 to 10 carbon atoms include a vinyl group, a 2-propenyl group, an isopropenyl group, an allyl group, a butenyl group, a hexenyl group, and a decenyl group, with a vinyl group, a 2-propenyl group, an isopropenyl group, an allyl group being preferred and a vinyl group and a 2-propenyl group being more preferred.

Examples of the alkyl group having 1 to 20, preferably 1 to 18, more preferably 1 to 8 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, an octadecyl group, a tetracosanyl group, and a tetracontanyl group. Preferred are a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, and an octadecyl group. More preferred are a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), and an octyl group (inclusive of isomeric groups)

Examples of the cycloalkyl group having 3 to 20, preferably 3 to 10, more preferably 3 to 8, and still more preferably 5 or 6 carbon atoms include a cyclopropyl group, a cyclobutyl group, a cyclopentyl group, a cyclohexyl group, a cycloheptyl group, a cyclooctyl group, an adamantyl group, with a cyclopentyl group and a cyclohexyl group being preferred.

Examples of the alkoxy group having 1 to 20, preferably 1 to 18, and more preferably 1 to 8 carbon atoms include those having the alkyl group having 1 to 20 carbon atoms mentioned above and preferably a methoxy group and an ethoxy group.

Examples of the aryloxy group having 6 to 30, preferably 6 to 25, and more preferably 6 to 18 ring carbon atoms include those having the aryl group having 6 to 30 ring carbon atoms mentioned above and preferably a phenoxy group.

Examples of the alkylthio group having 1 to 20, preferably 1 to 18, and more preferably 1 to 8 carbon atoms include those having the alkyl group having 1 to 20 carbon atoms mentioned above.

Examples of the arylthio group having 6 to 30, preferably 6 to 25, and more preferably 6 to 18 ring carbon atoms include those having the aryl group having 6 to 30 ring carbon atoms mentioned above.

Examples of the mono-, di- or tri-substituted silyl group include those having a substituent selected from the alkyl group having 1 to 20, preferably 1 to 18, and more preferably 1 to 8 and the aryl group having 6 to 30, preferably 6 to 25, and more preferably 6 to 18 ring carbon atoms, each mentioned above, such as a trimethylsilyl group, a triethylsilyl group, a t-butyldimethylsilyl group, a vinyldimethylsilyl group, a propyldimethylsilyl group, an isopropyldimethylsilyl group, a triphenylsilyl group, a phenyldimethylsilyl group, a t-butyldiphenylsilyl group, and a tritolylsilyl group.

Examples of the aralkyl group having 7 to 20 carbon atoms include those having an alkyl portion selected from the alkyl group mentioned above and an aryl portion selected from the aryl group mentioned above.

Examples of the arylene group having 6 to 30 ring carbon atoms for $L_1$ include divalent groups which are derived from the aryl group having 6 to 30 ring carbon atoms mentioned above.

Examples of the heteroarylene group having 5 to 30 ring atoms for $L_1$ include divalent groups which are derived from the heteroaryl group having 5 to 30 ring atoms mentioned above.

Examples of the divalent linking group for $L_1$ include those wherein two or four selected from the arylene group having 6 to 30 ring carbon atoms and the heteroarylene group having 5 to 30 ring atoms each mentioned above are linked together.

In the following formula (13-1), $L_{1A}$ and $L_{1B}$ each independently represent $L_1$, $Ar^{1A}$ and $Ar^{1B}$ each independently represent $Ar^1$, and $Ar^{2A}$ and $Ar^{2B}$ each independently represent $Ar^2$.

Preferred examples of $R^9$ and $R^{10}$ are the same as those of $R^9$ and $R^{10}$ mentioned above, preferred examples of $L_{1A}$ and $L_{1B}$ are the same as those of $L_1$ mentioned above, preferred examples of $Ar^{1A}$ and $Ar^{1B}$ are the same as those of $Ar^1$ mentioned above, and preferred examples of $Ar^{2A}$ and $Ar^{2B}$ are the same as those of $Ar^2$ mentioned above.

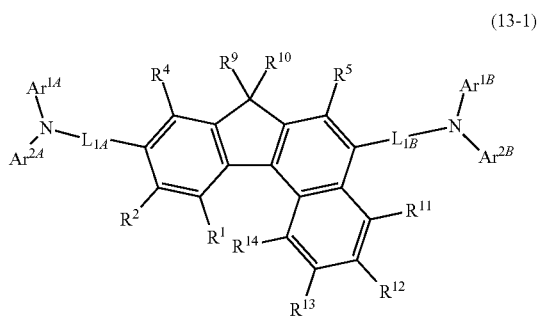

(13-1)

In the following formula (13-2), preferred examples of $R^9$ and $R^{10}$ are the same as those of $R^9$ and $R^{10}$ mentioned above, preferred examples of $L_1$, are the same as those of $L_1$ mentioned above, preferred examples of $Ar^1$ are the same as those of $Ar^1$ mentioned above, and preferred examples of $Ar^2$ are the same as those of $Ar^2$ mentioned above.

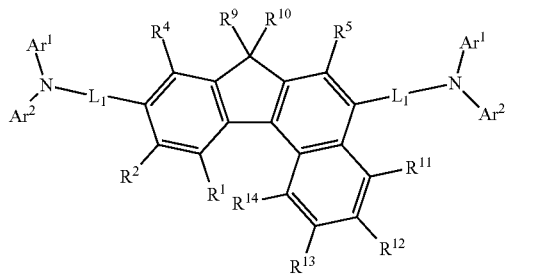

(13-2)

Examples of the amine compound represented by formula (1) are shown below, although not limited thereto.

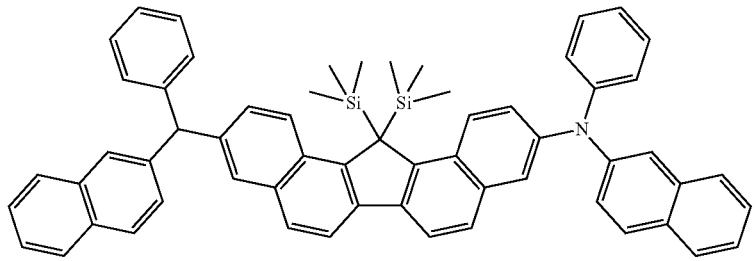

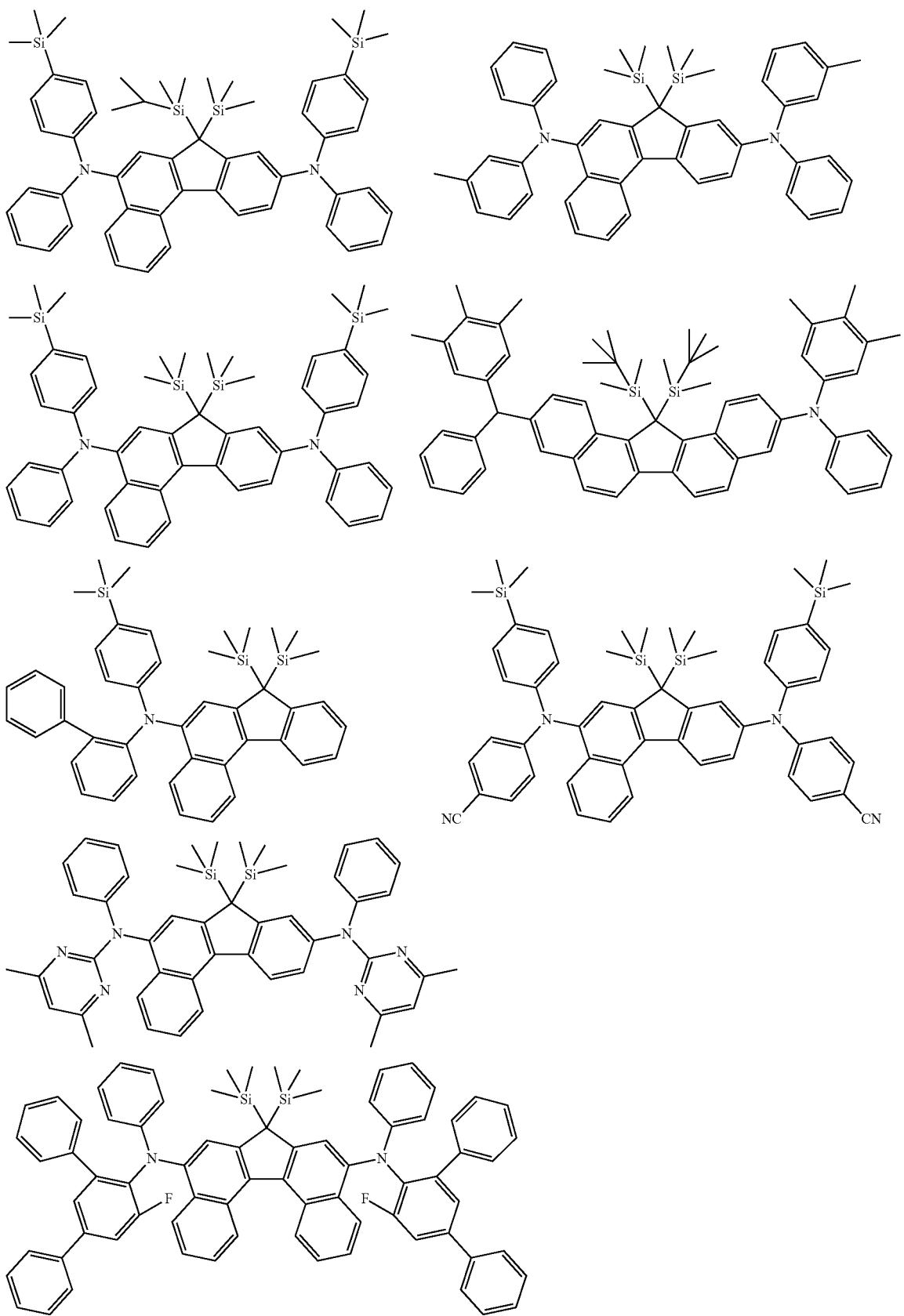

-continued
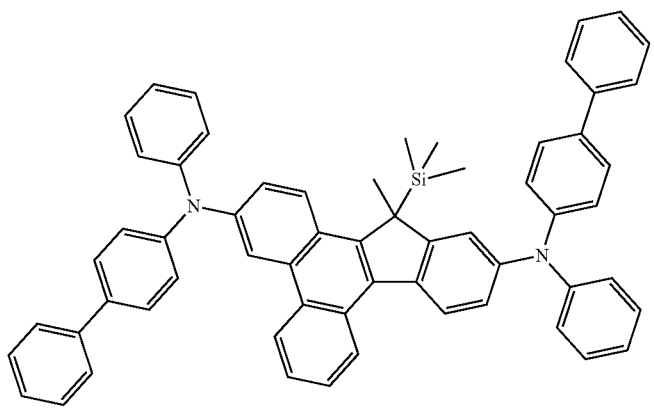
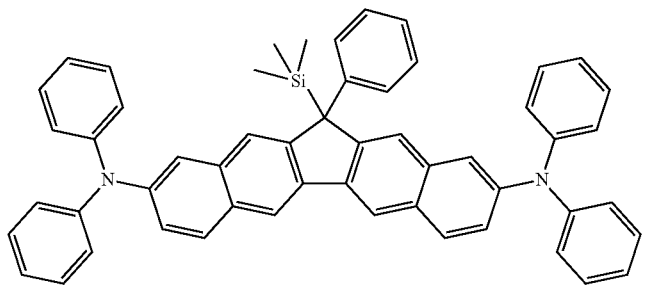
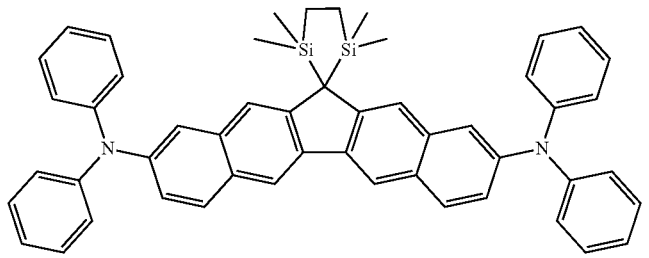
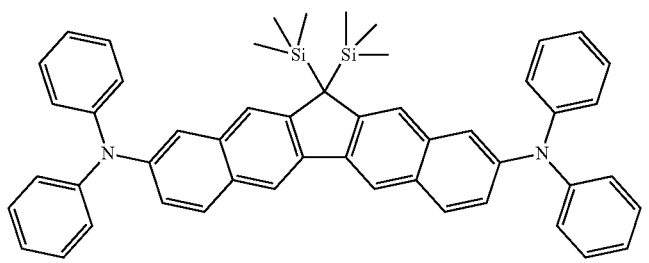
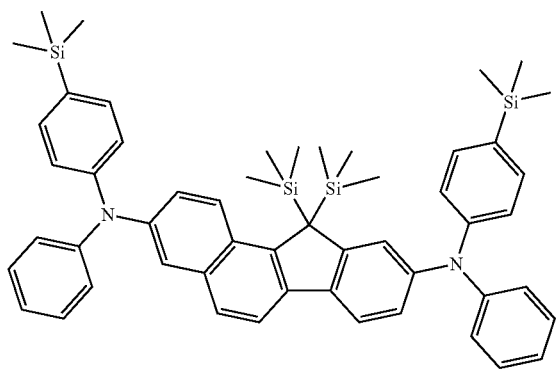

-continued
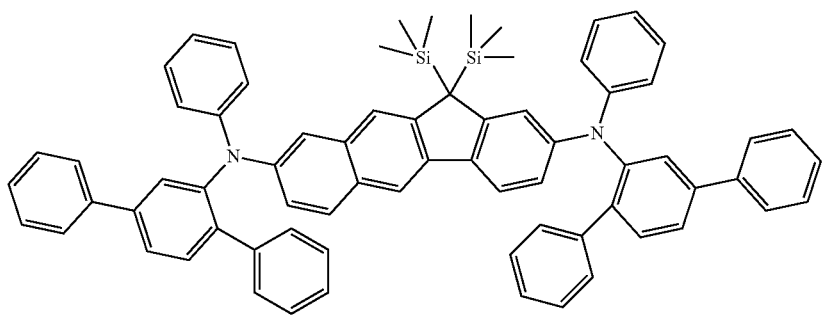
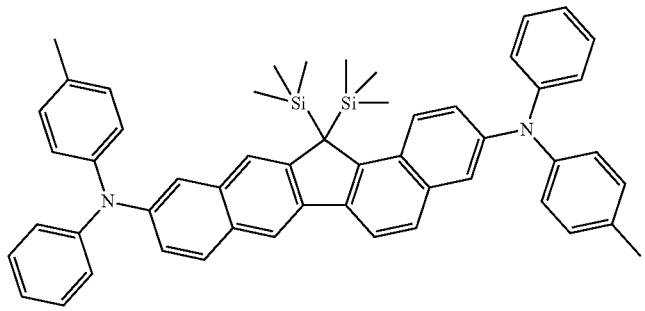
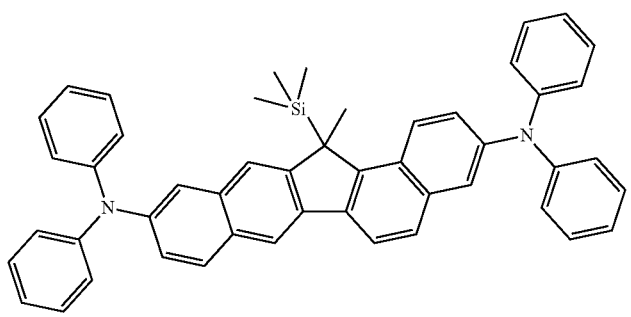
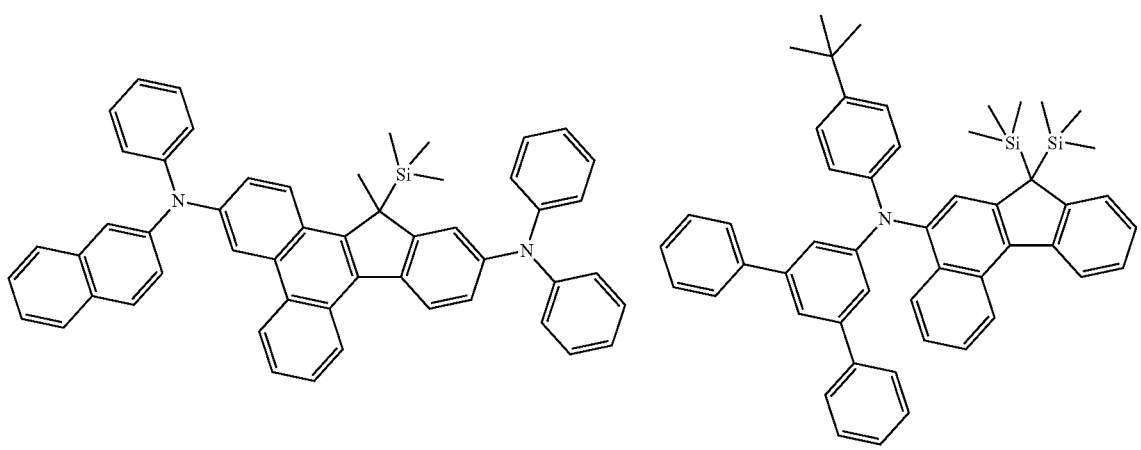
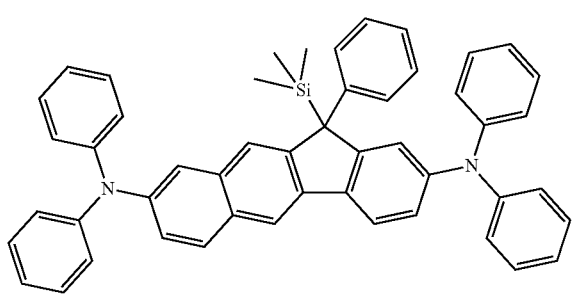

-continued
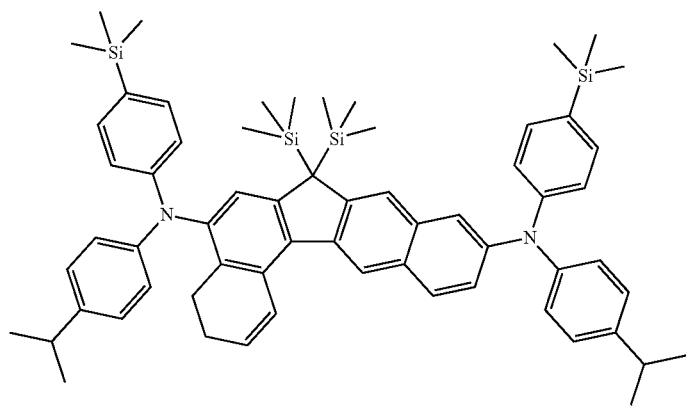
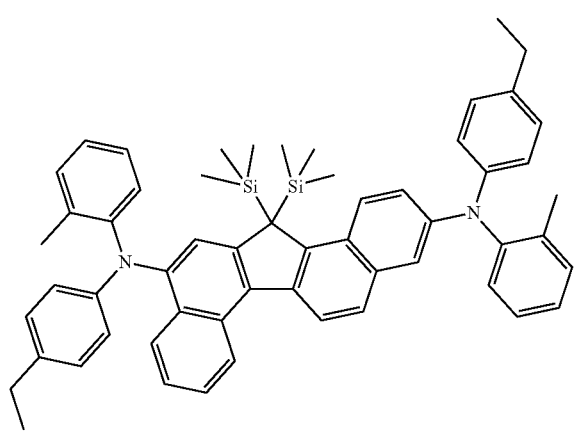
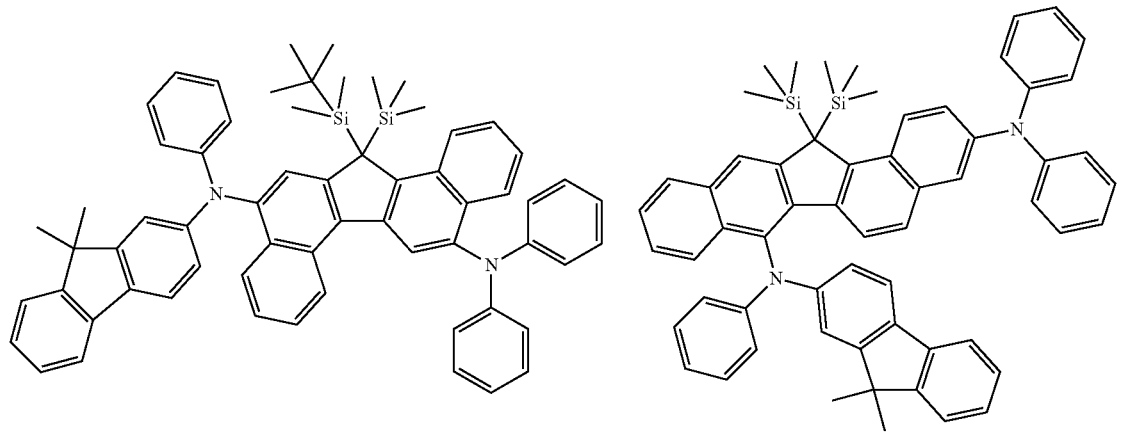
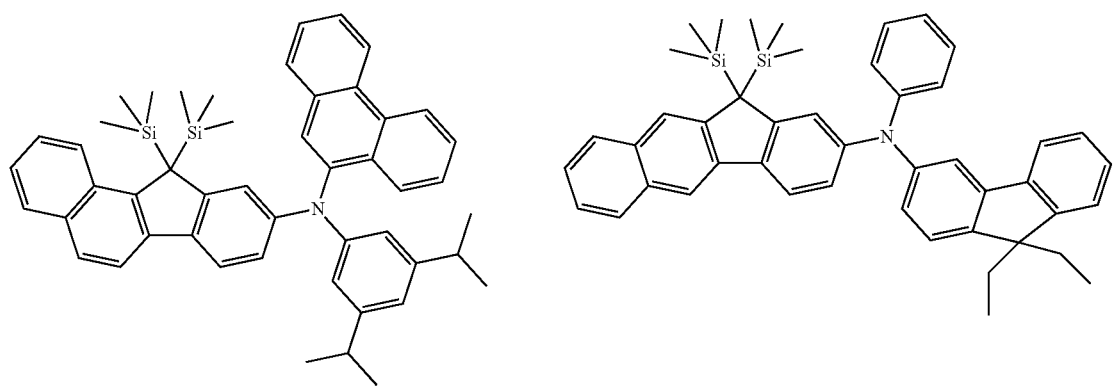

-continued
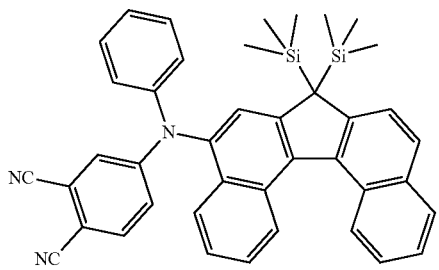
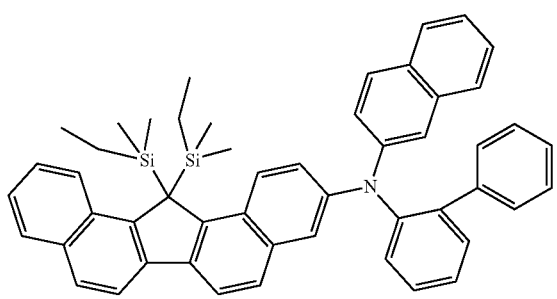
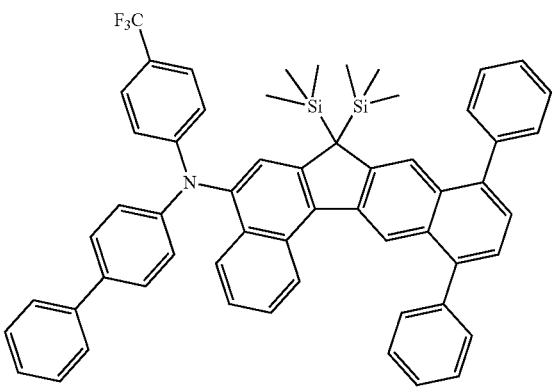
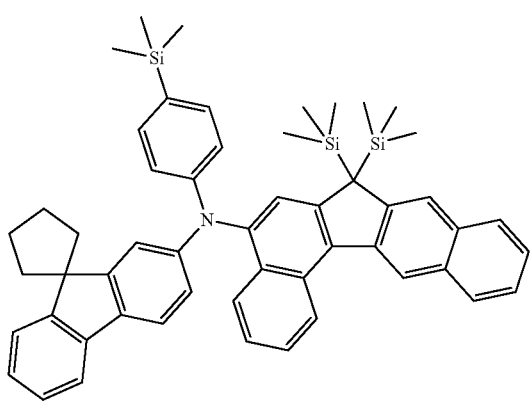
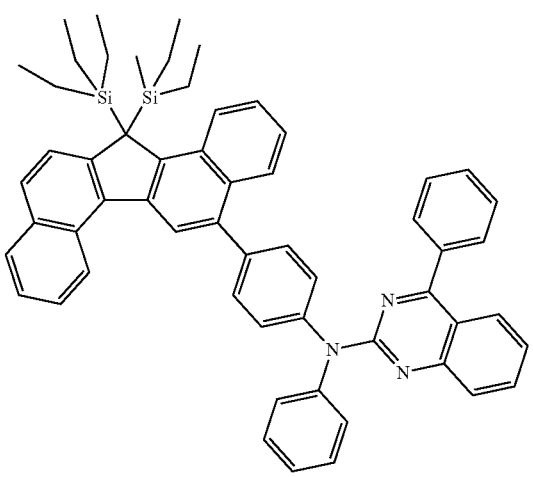
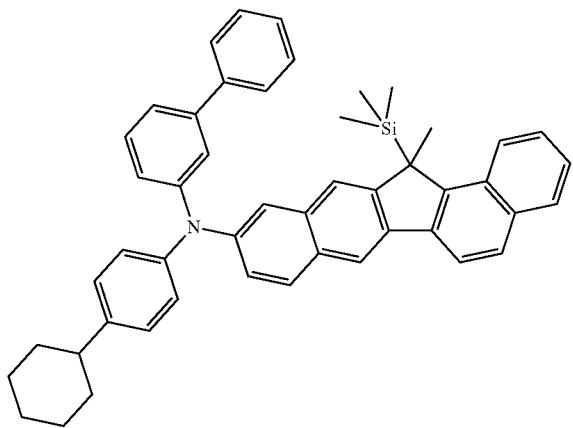
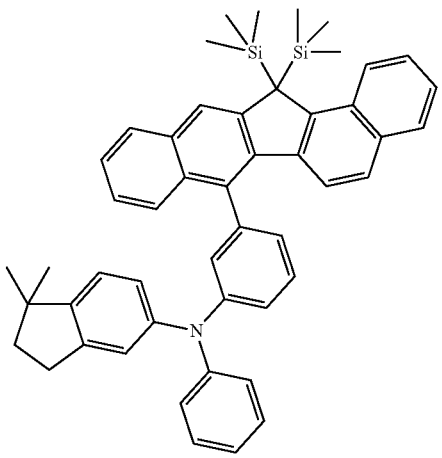

-continued
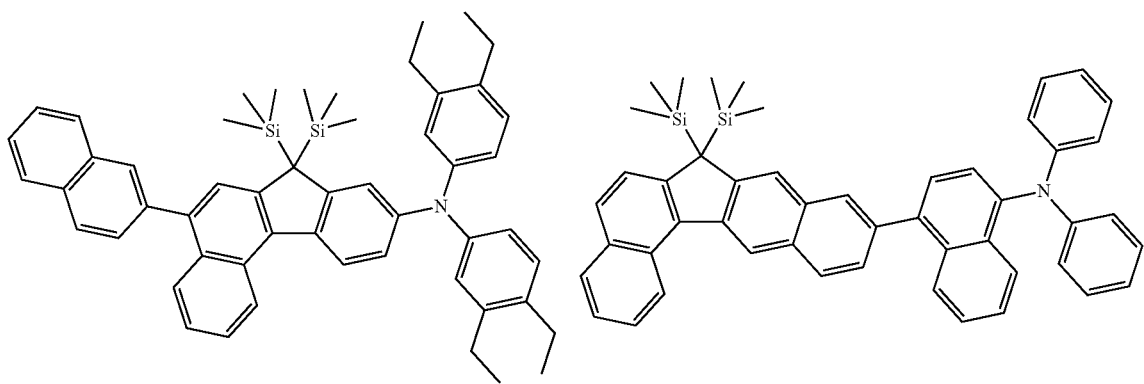
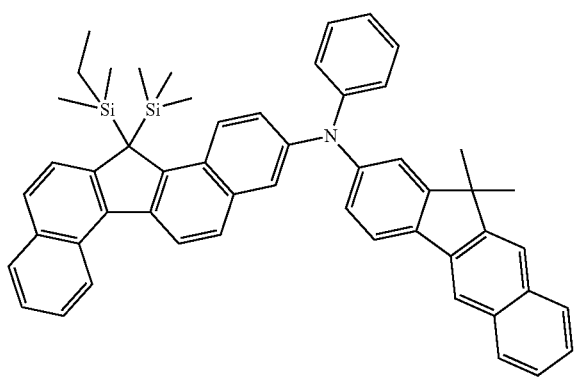
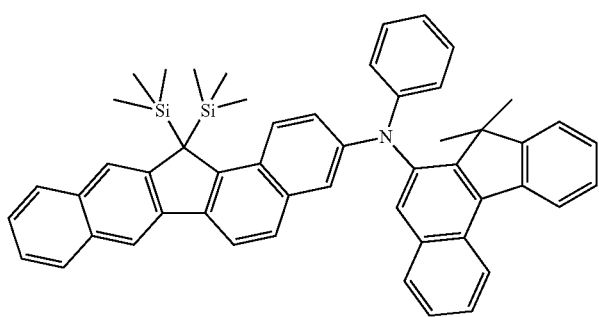
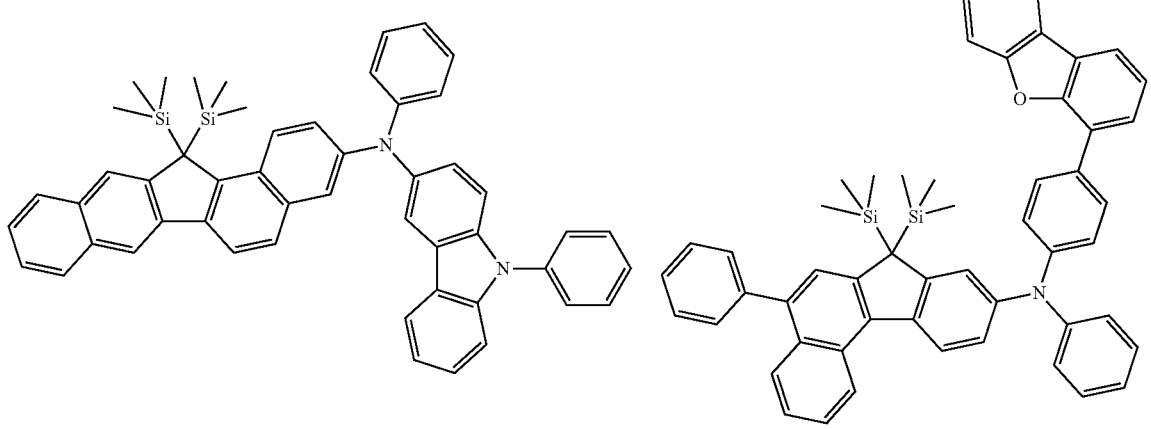

-continued
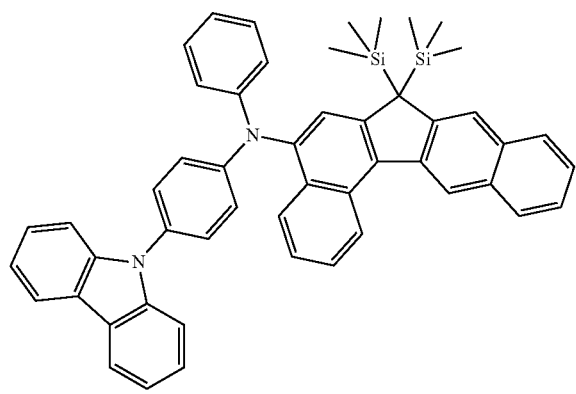
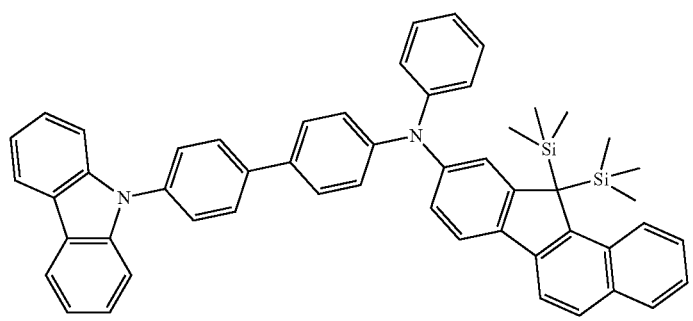
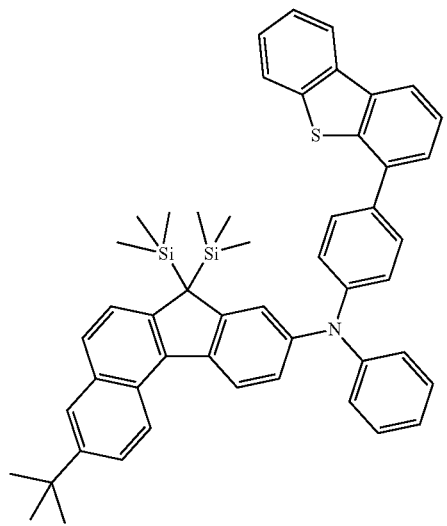
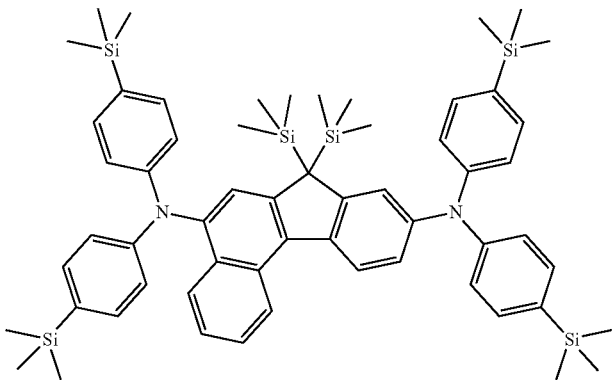
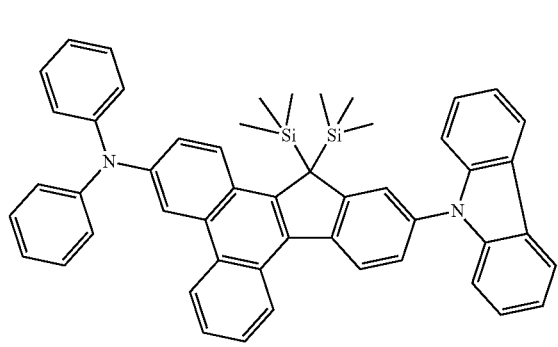
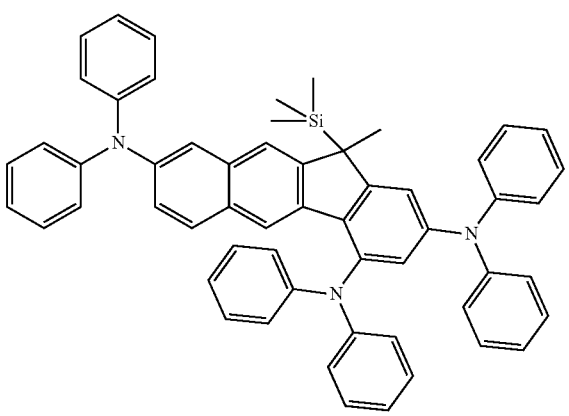

-continued
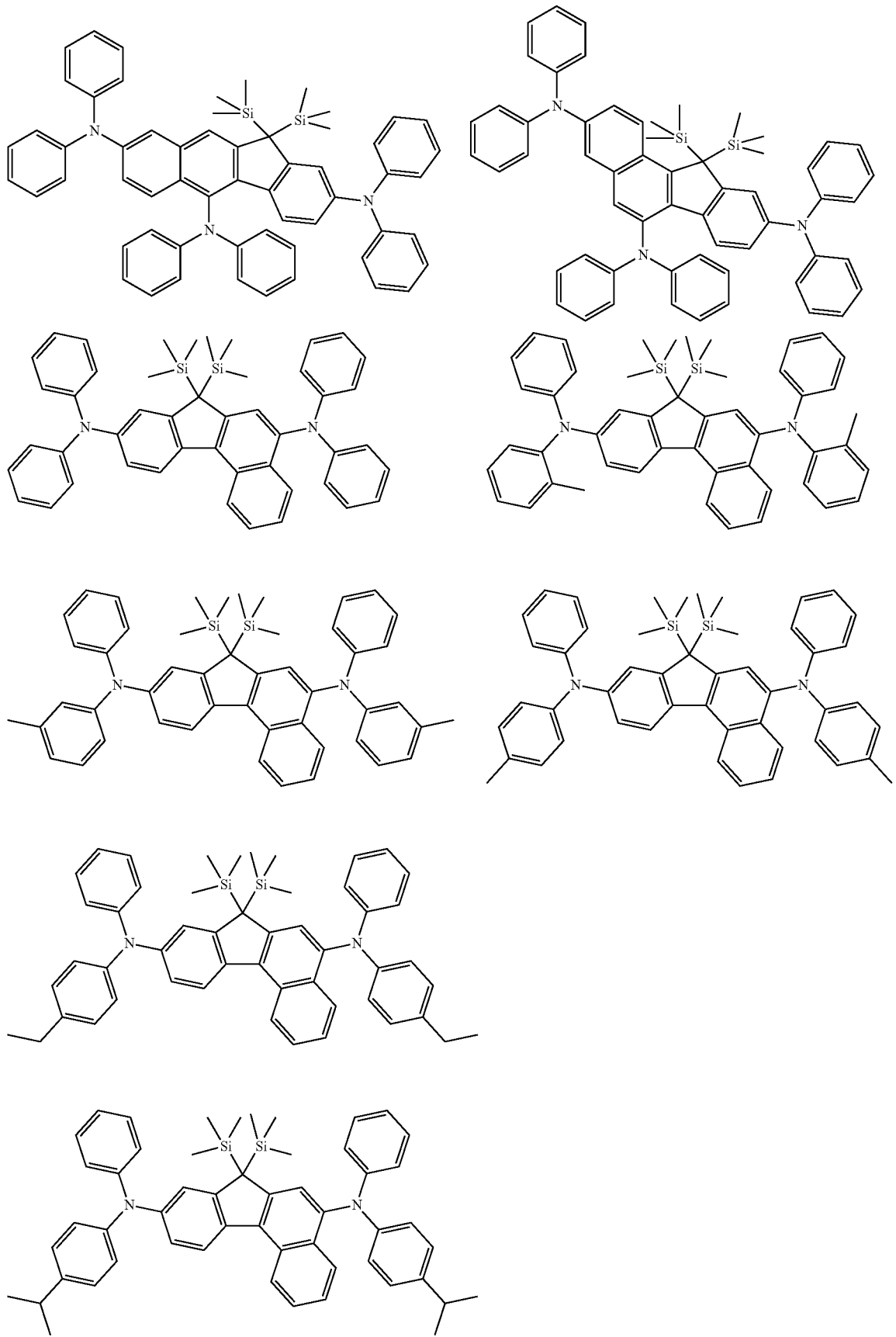

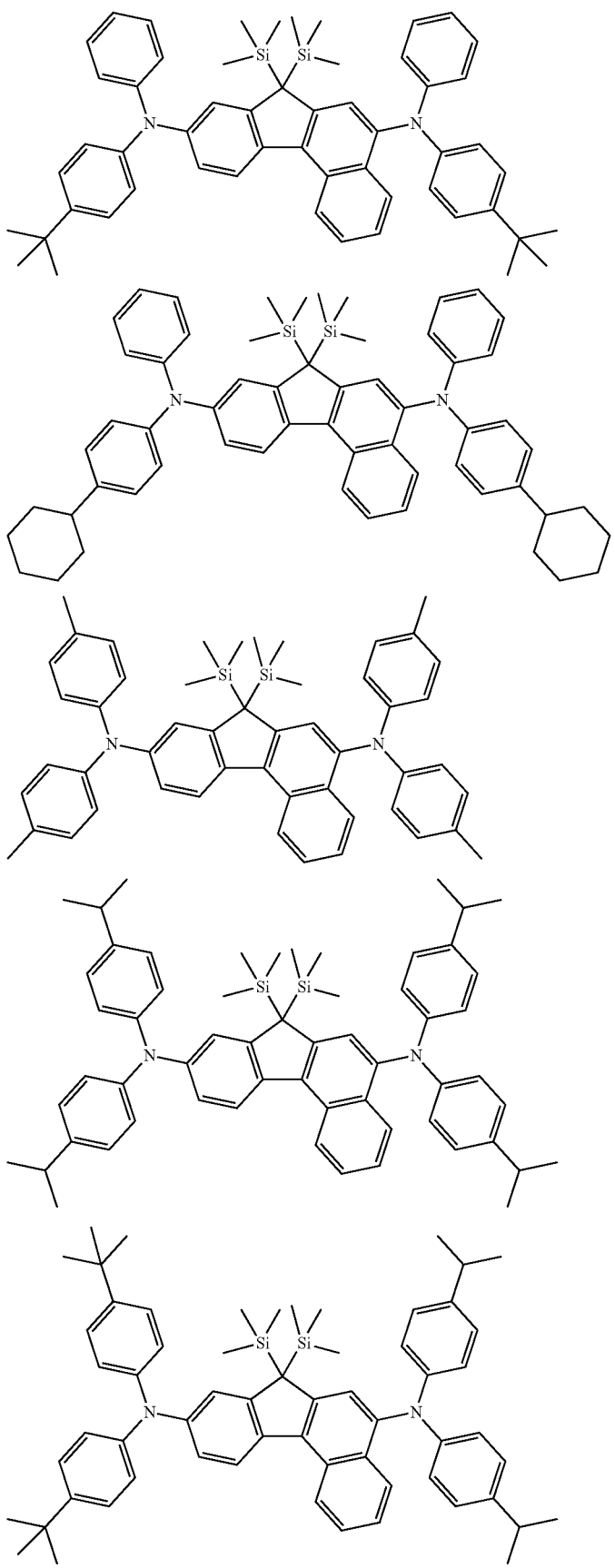

-continued
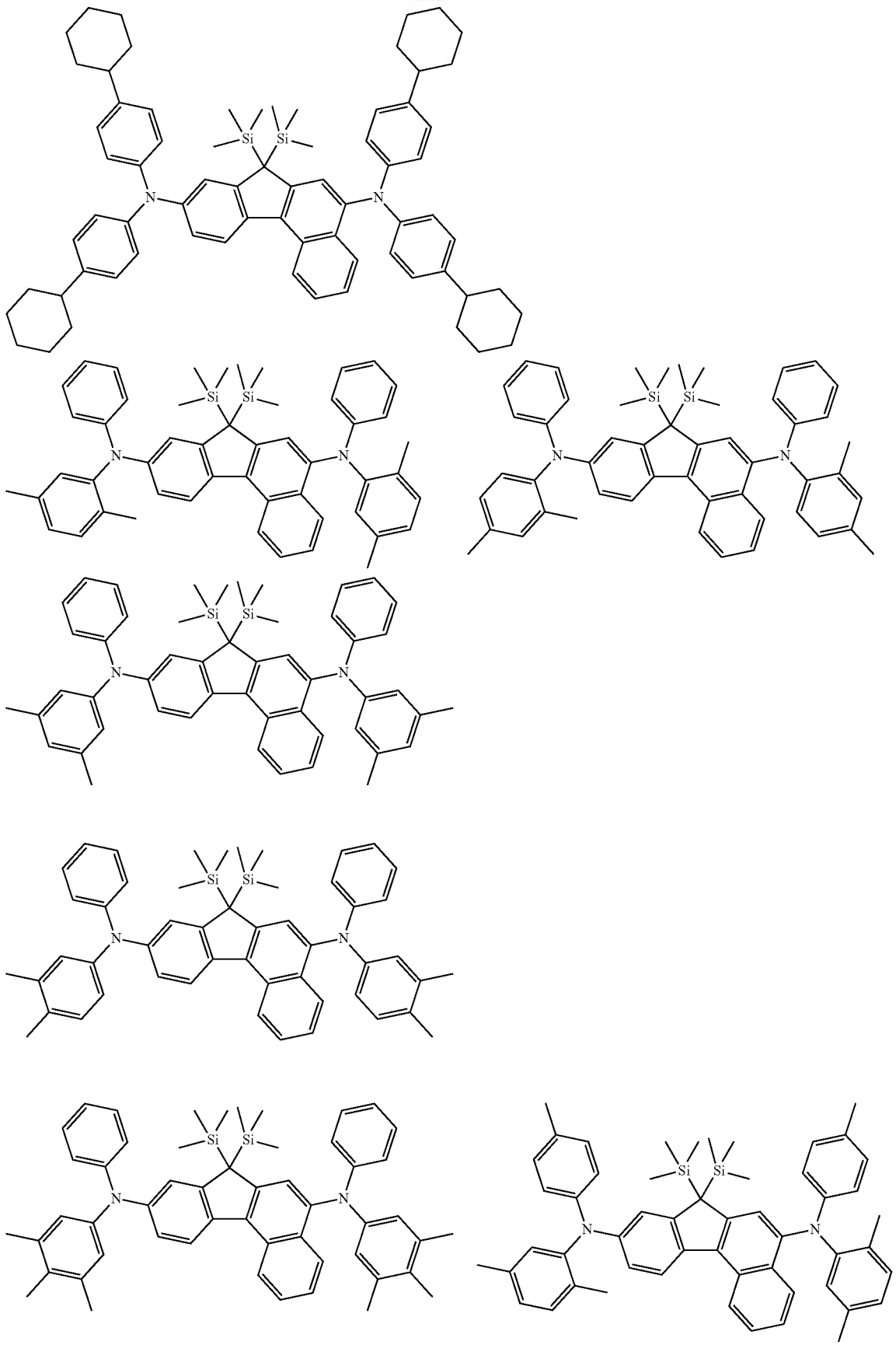

-continued
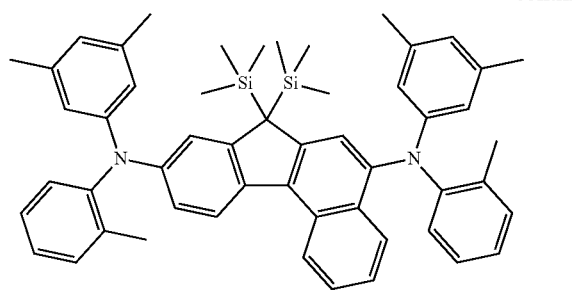
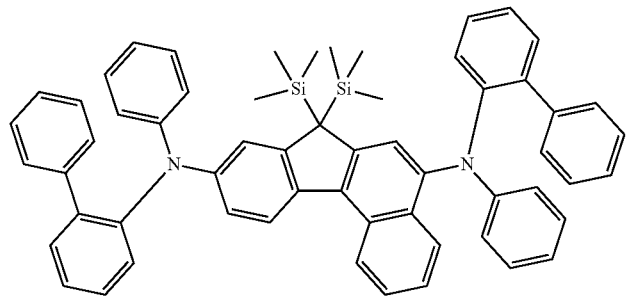
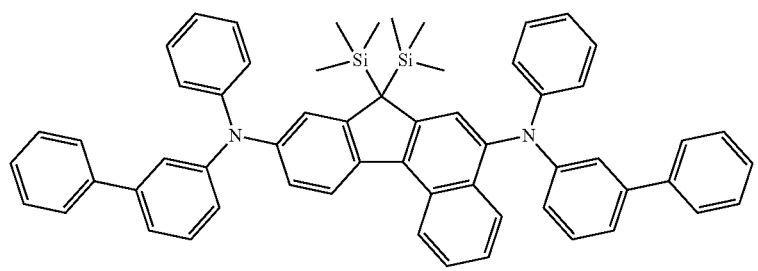
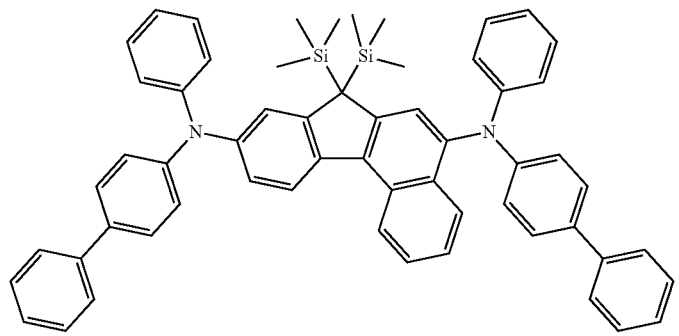
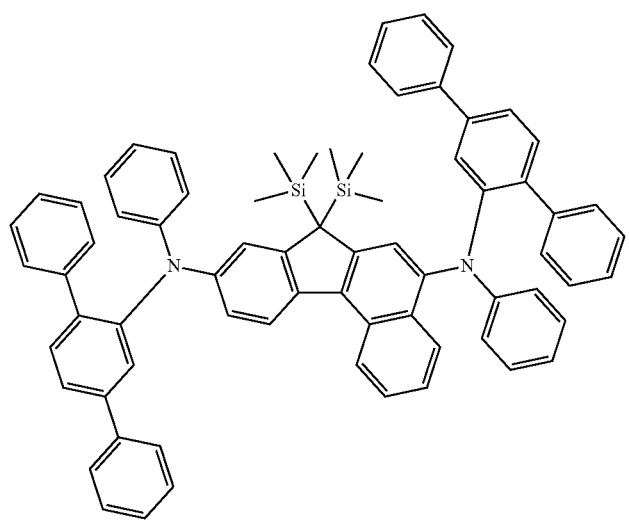

-continued
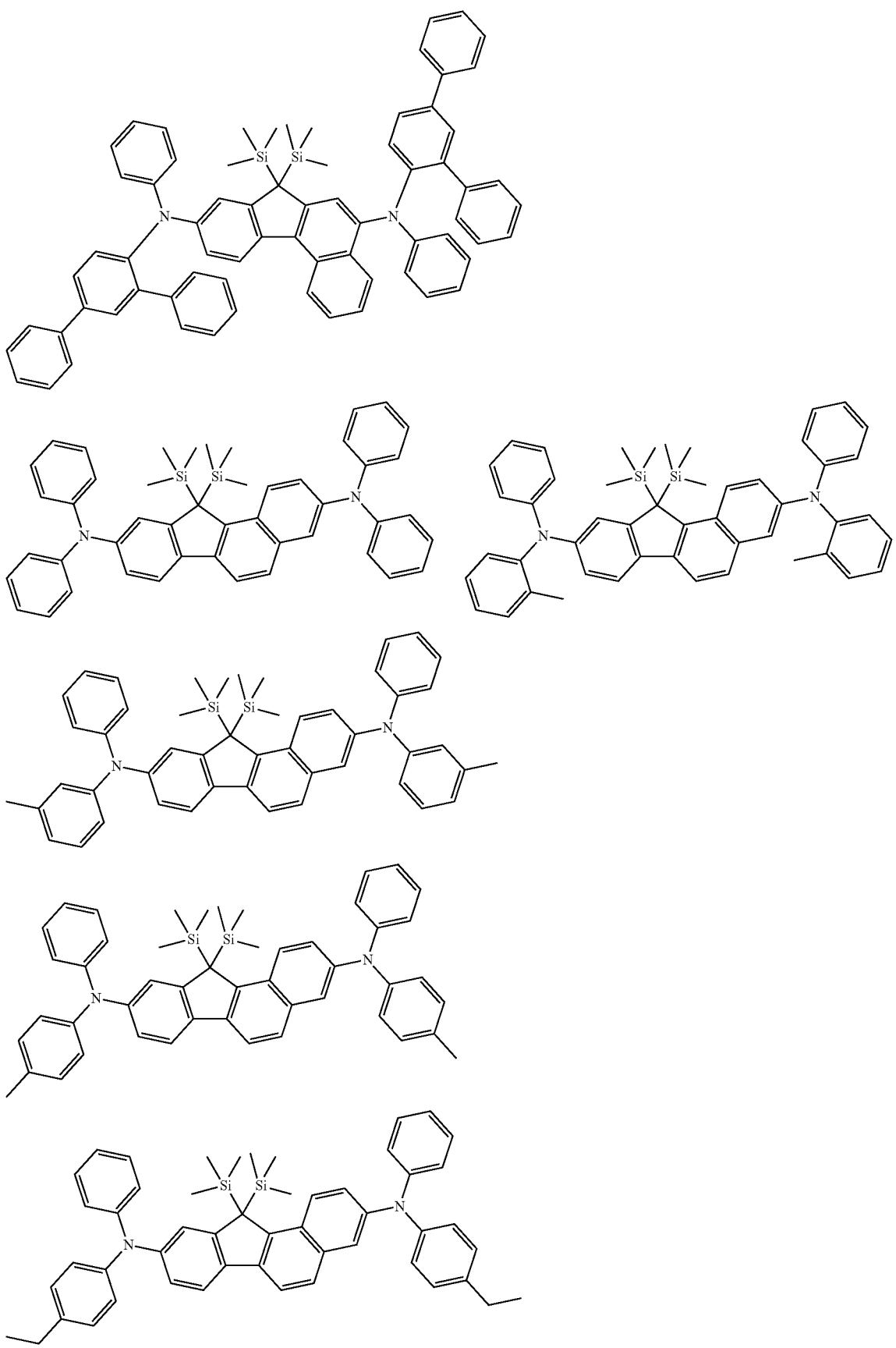

-continued
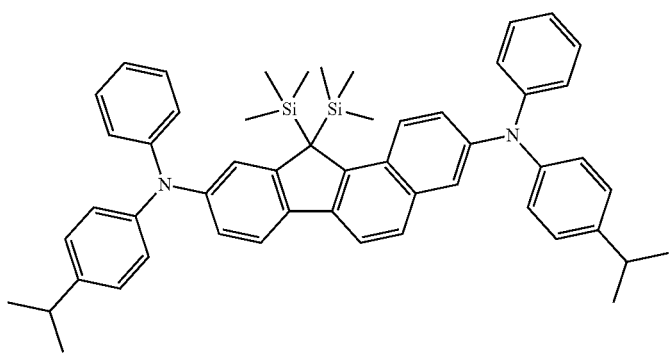
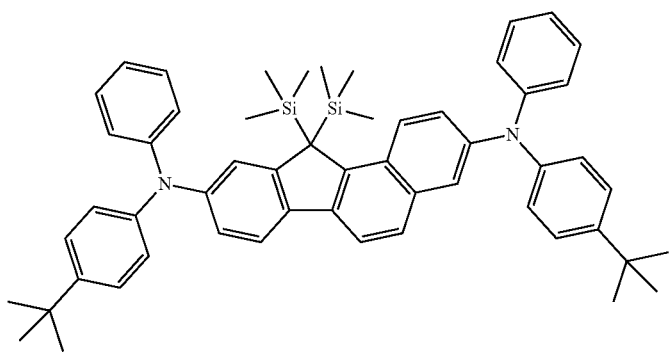
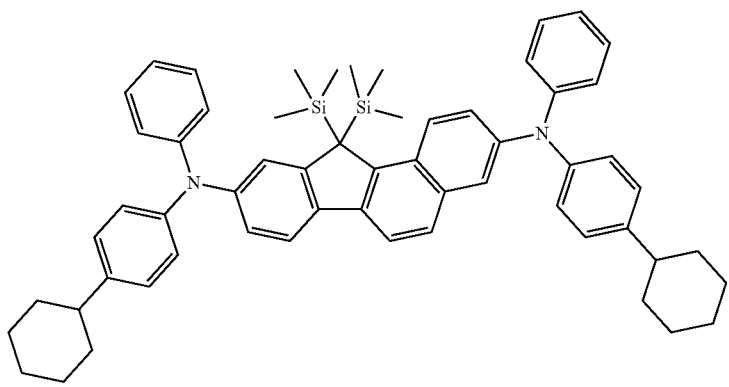
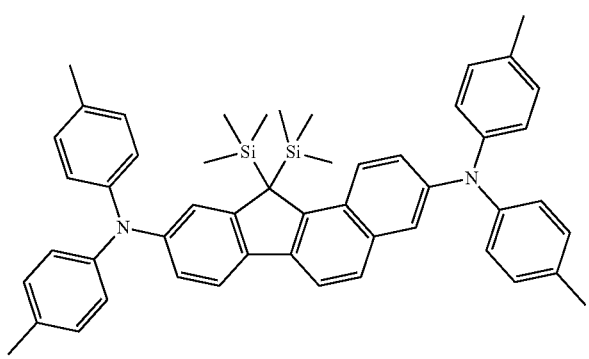

-continued
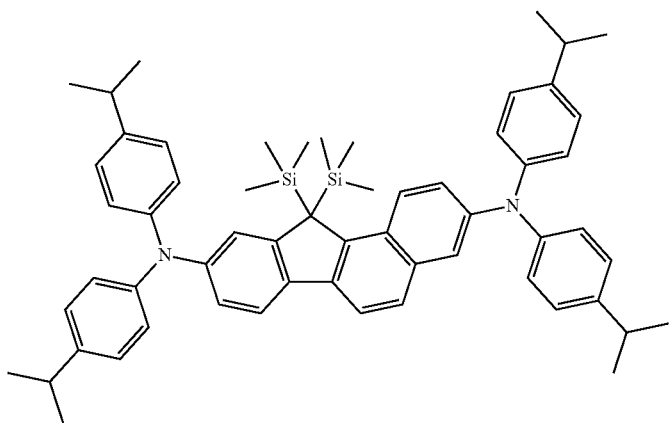
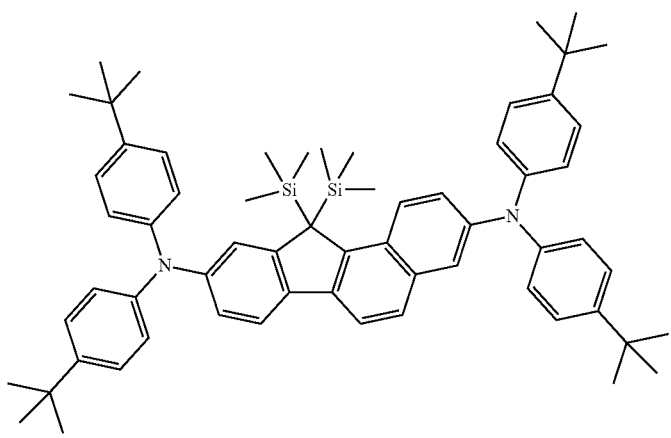
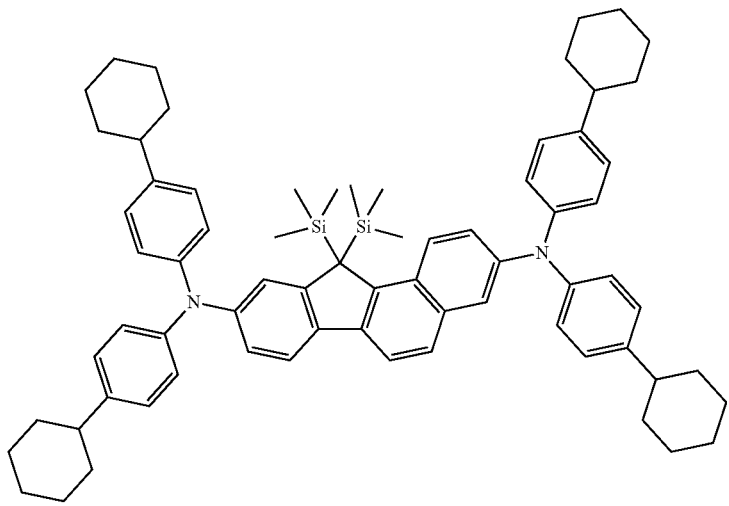
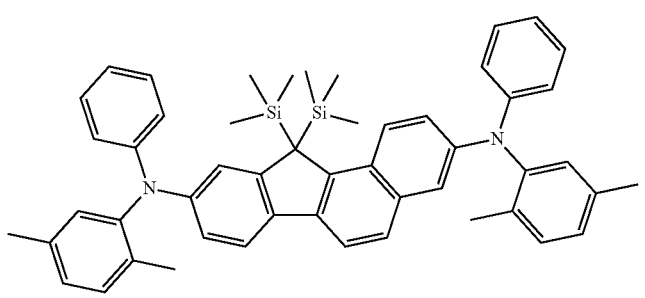

-continued
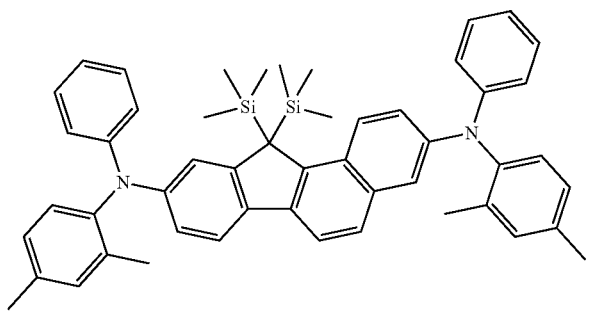
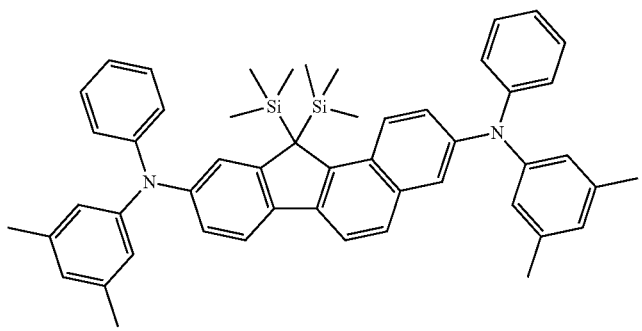
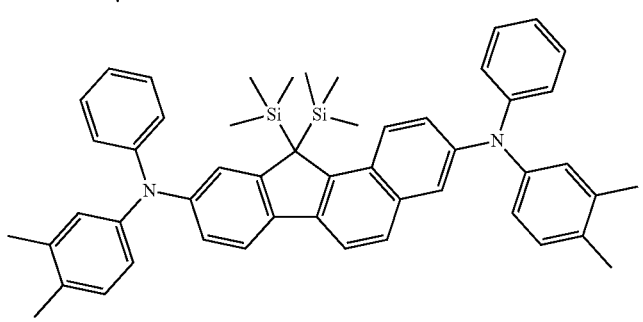
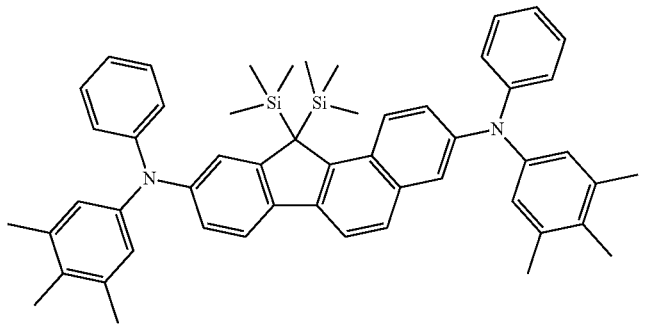
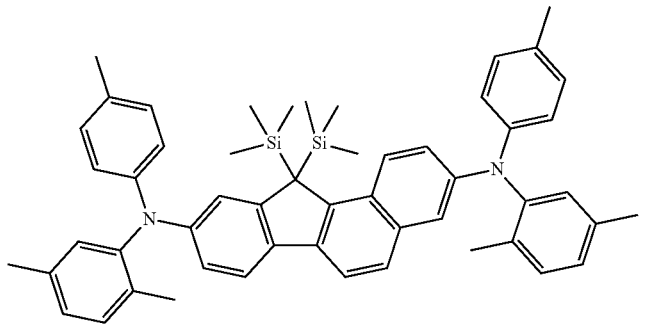

-continued
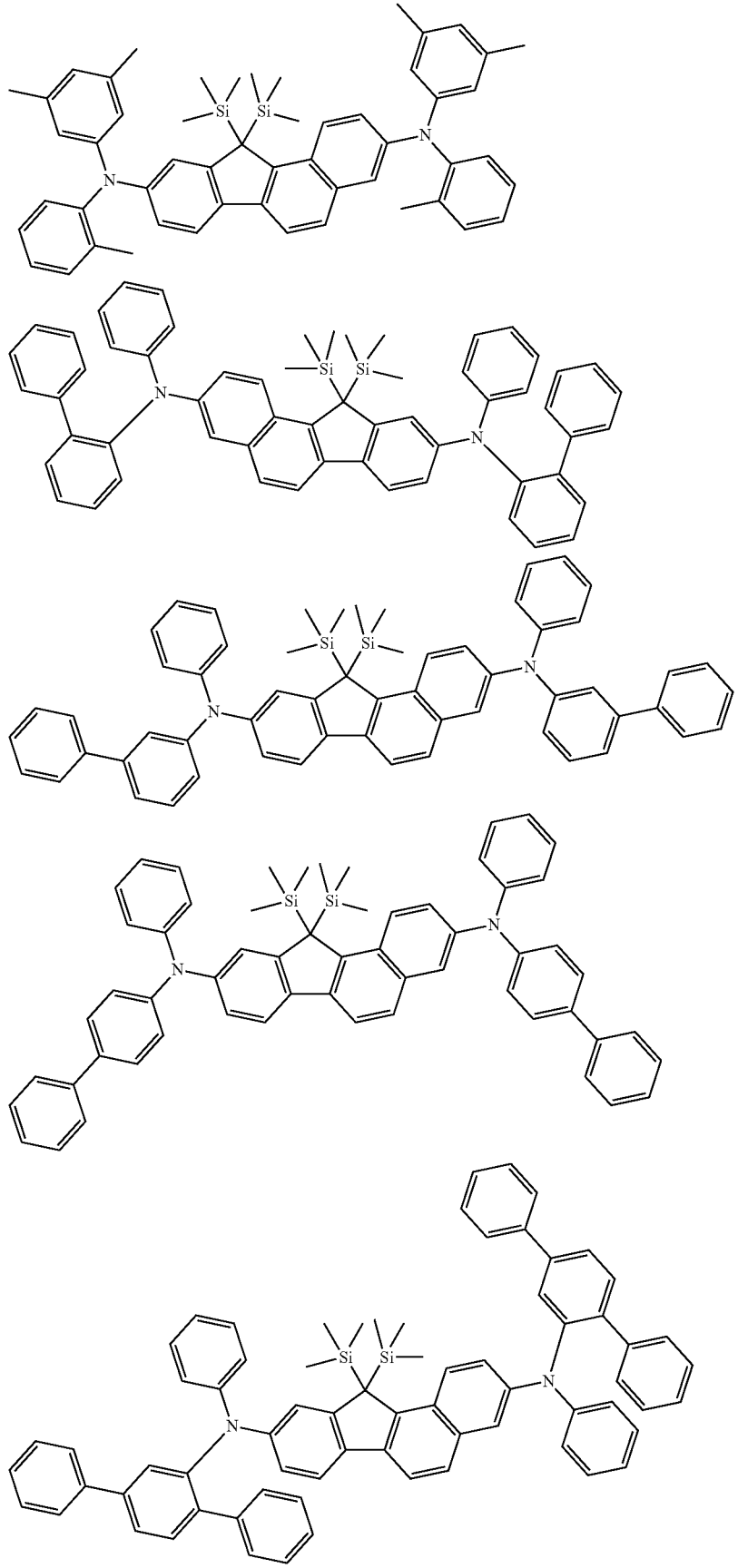

-continued
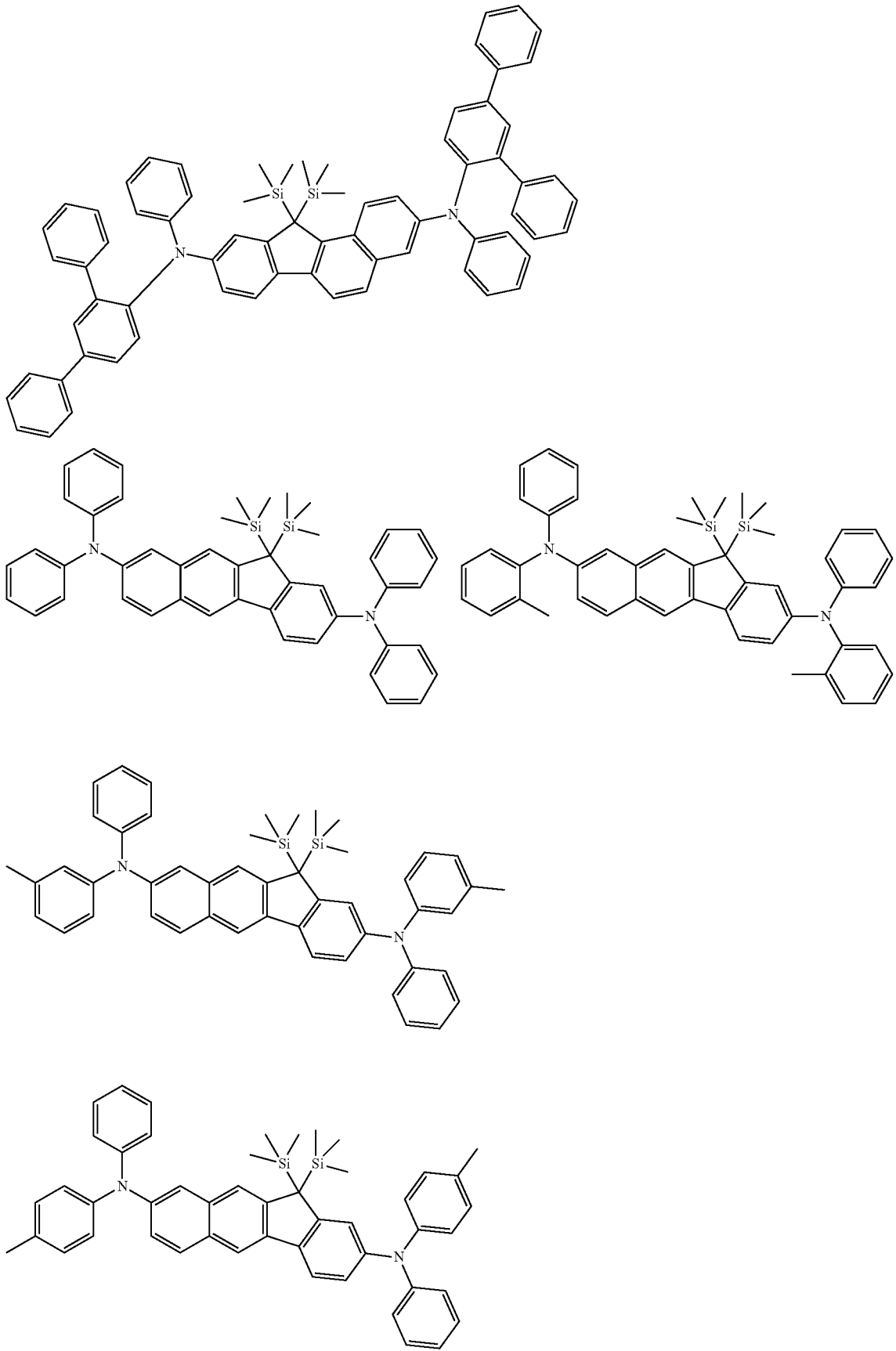

-continued
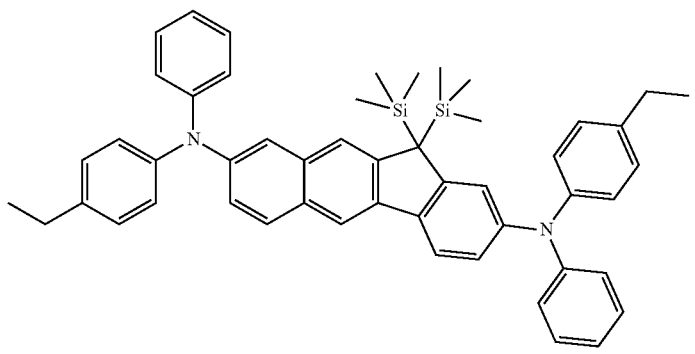
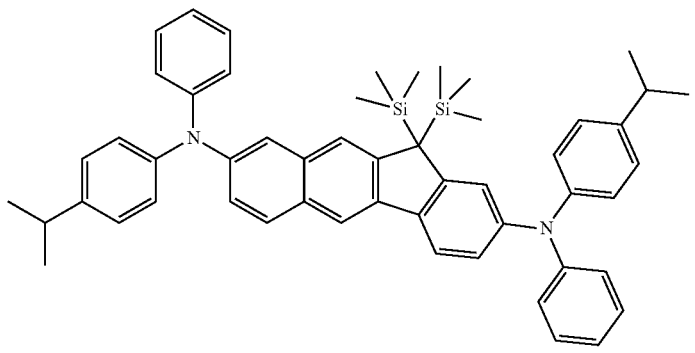
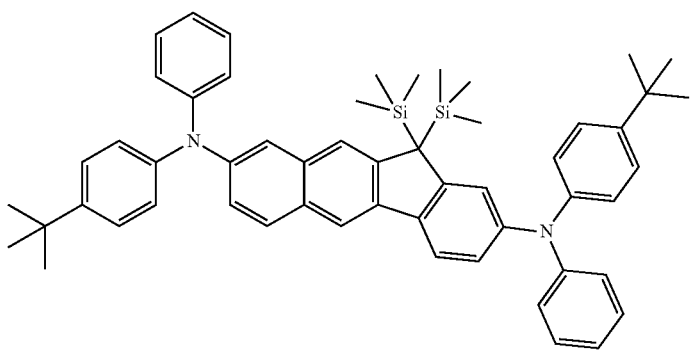
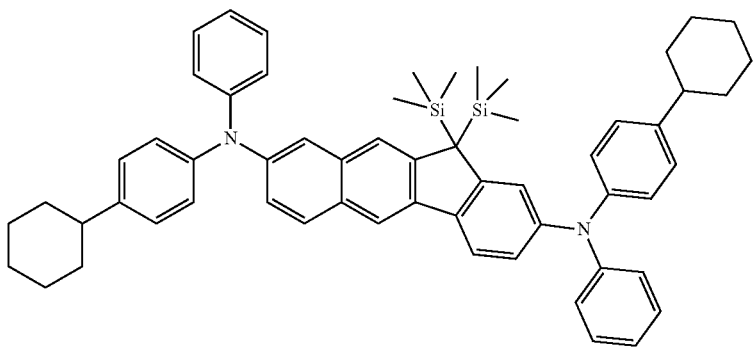

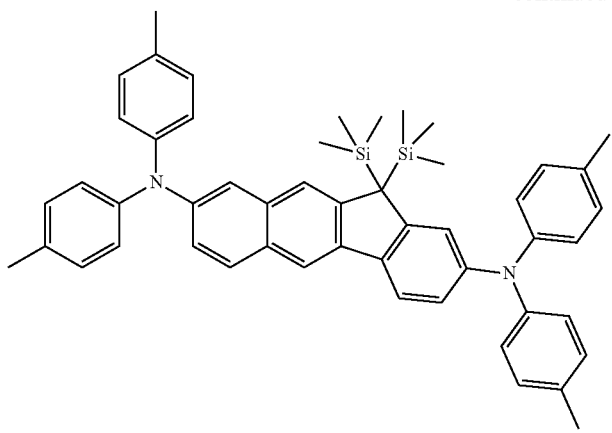
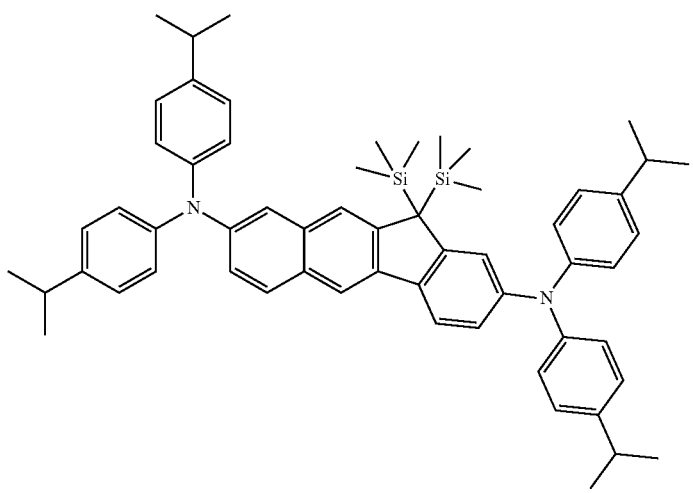
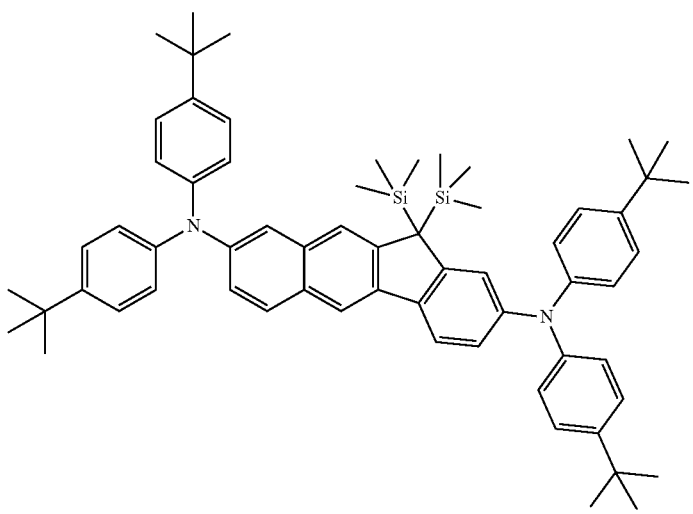

-continued
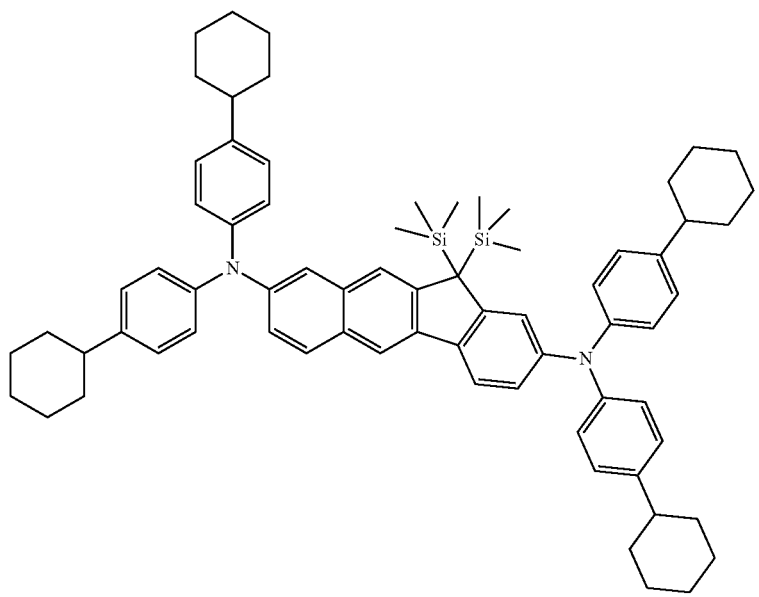
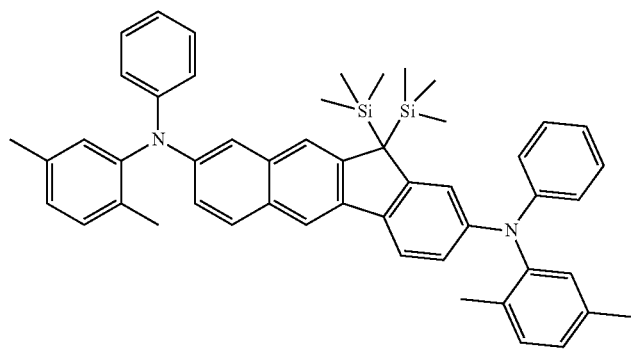
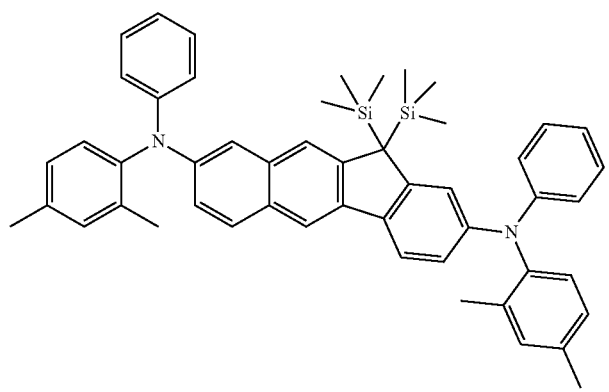
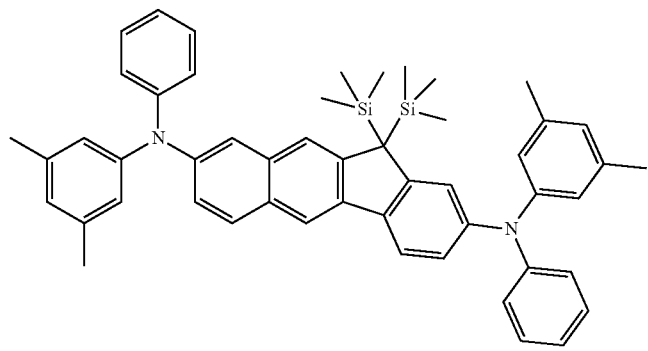

-continued
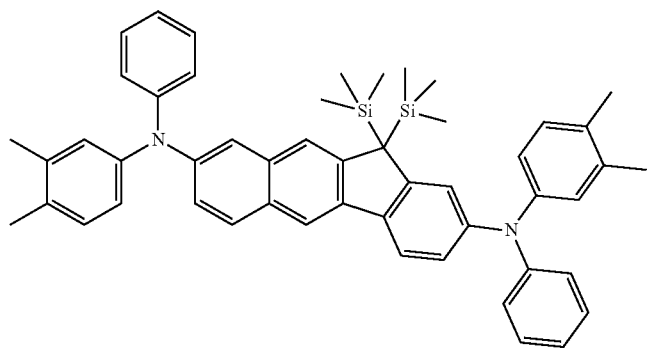
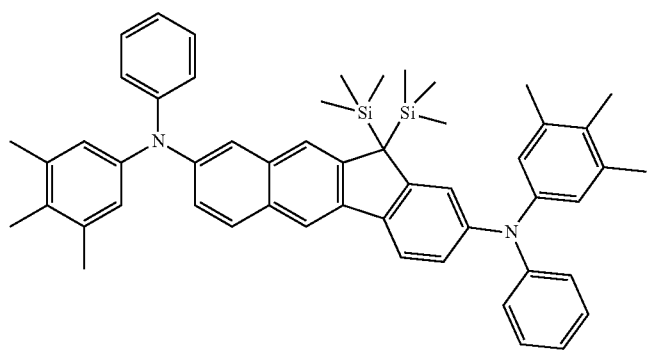
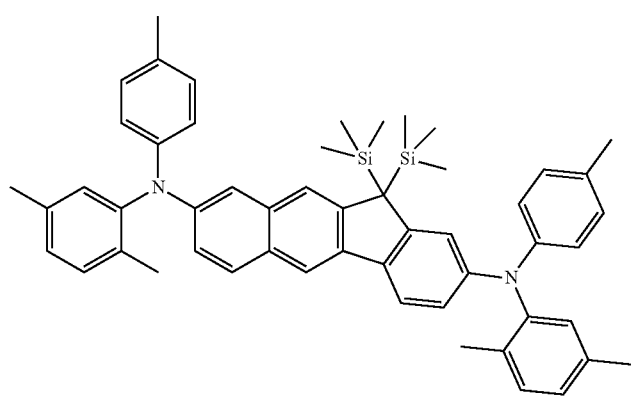
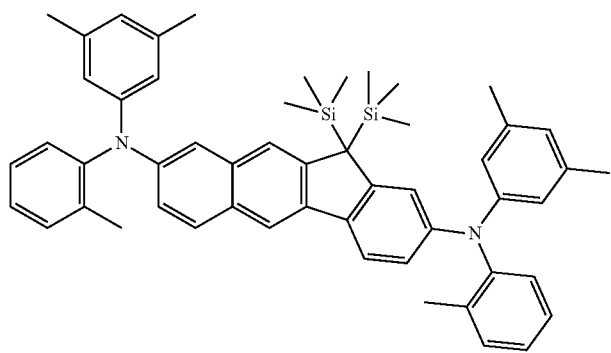

-continued
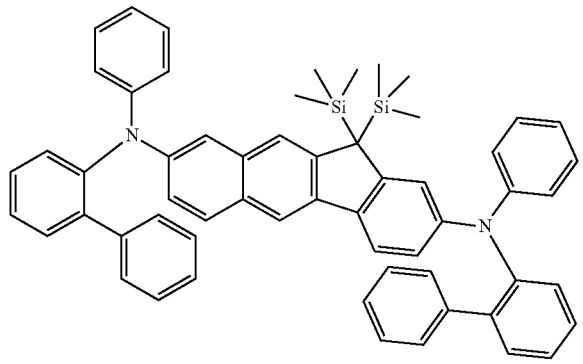
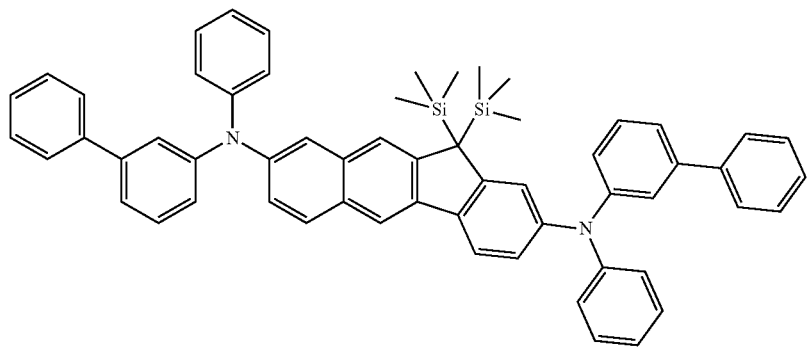
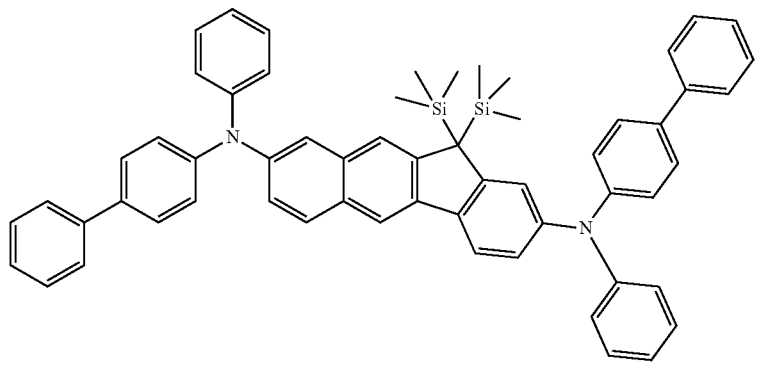
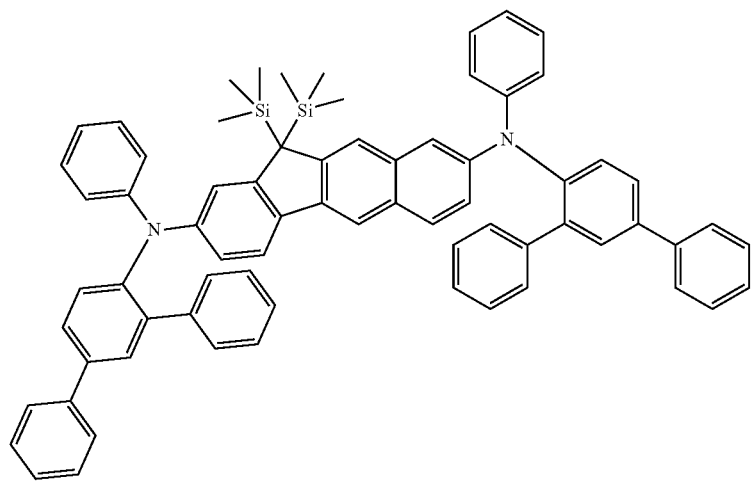

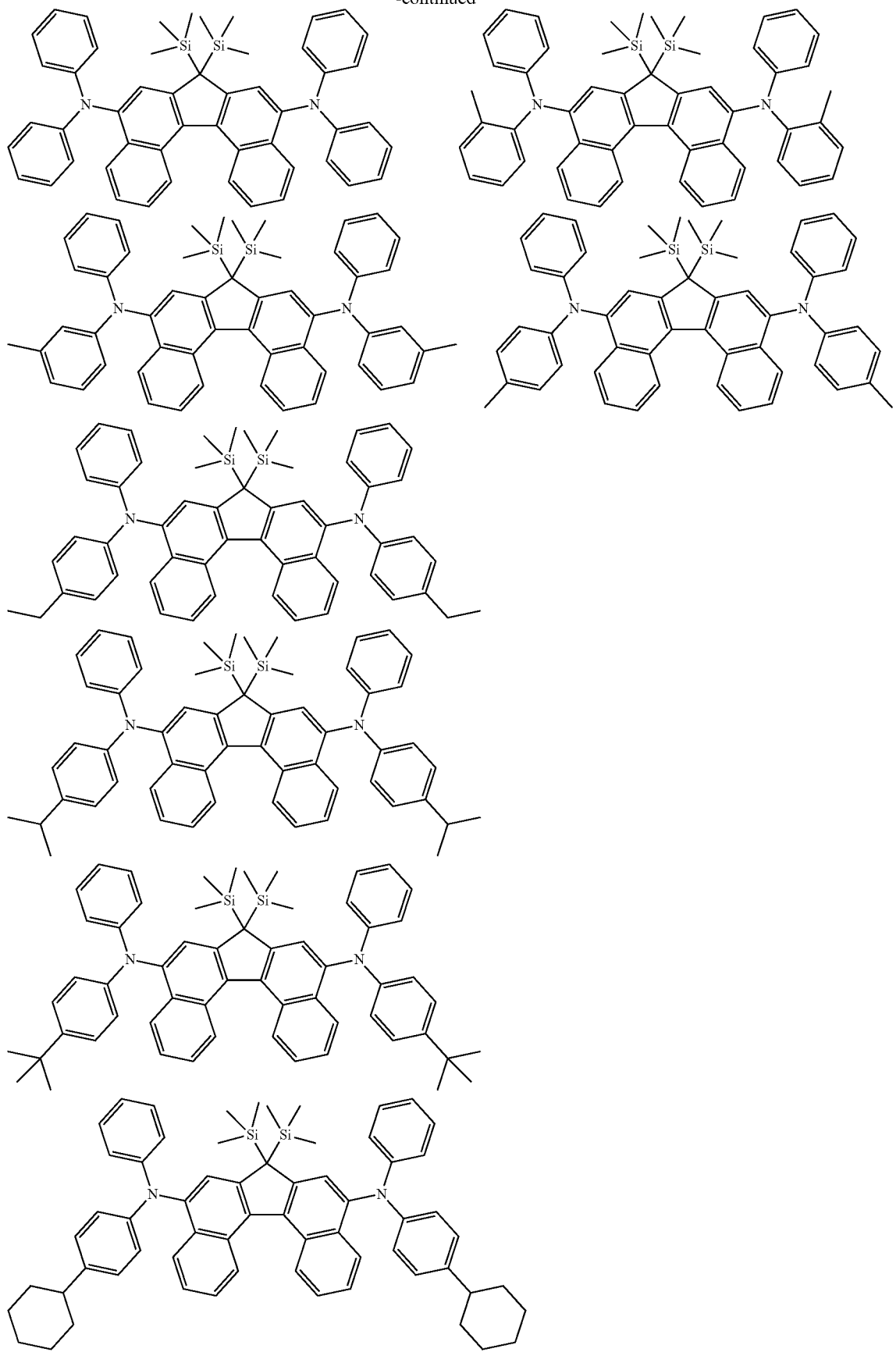

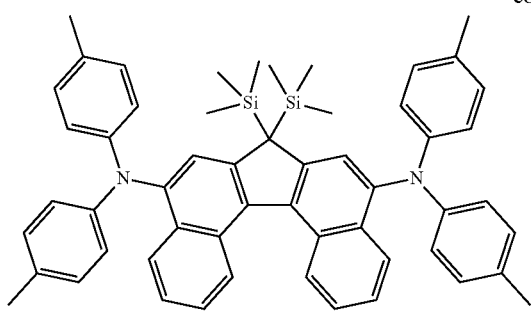
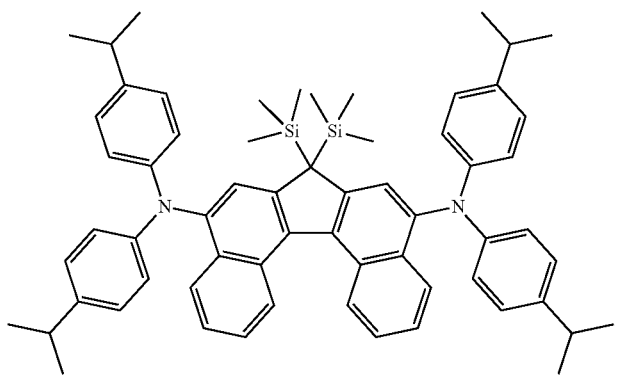
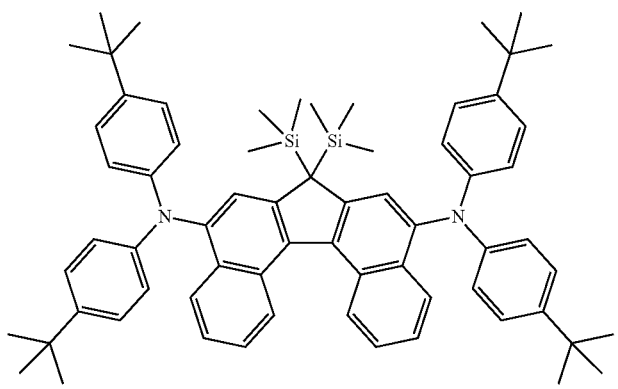
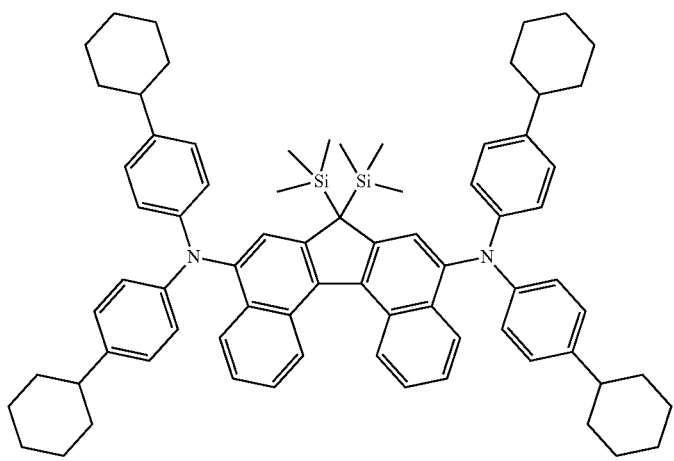

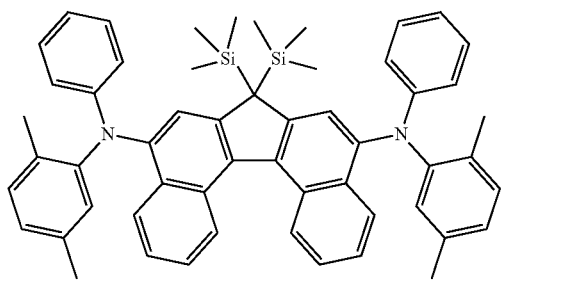
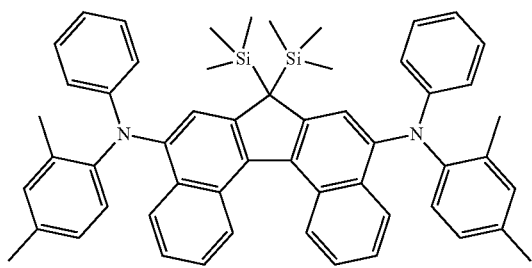
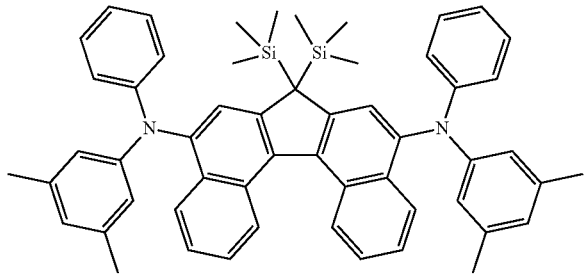
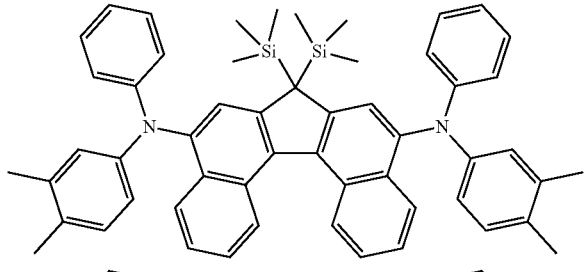
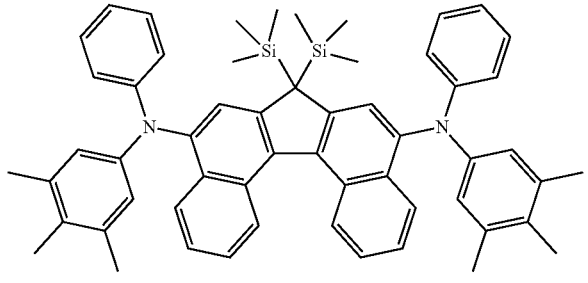
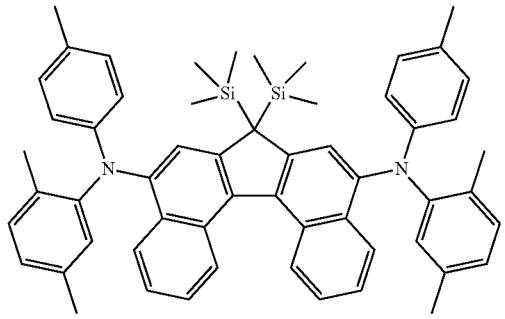
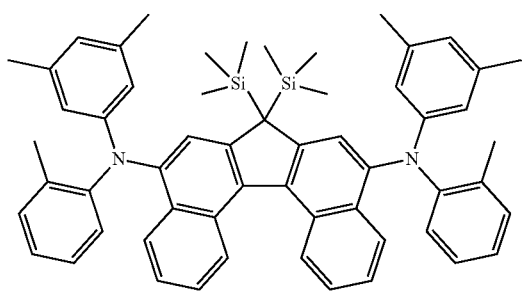
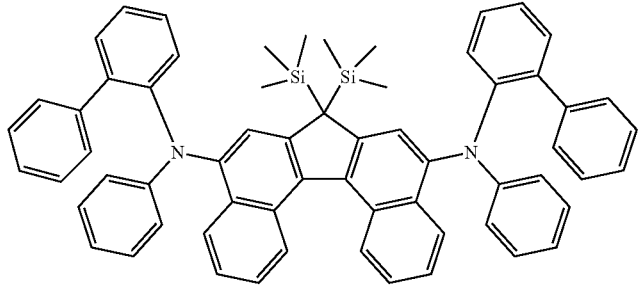

-continued
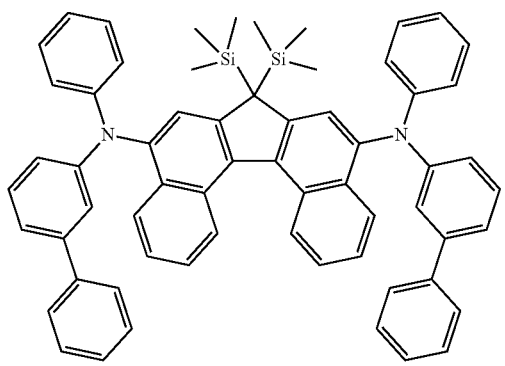
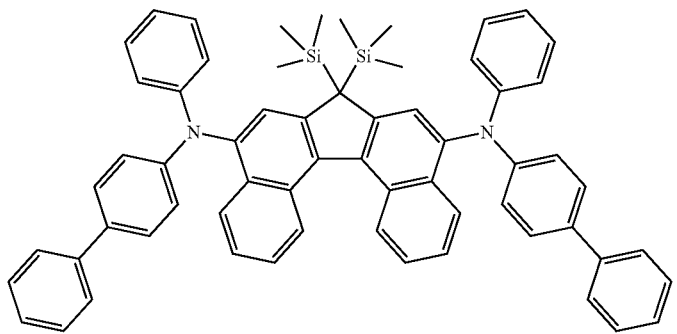
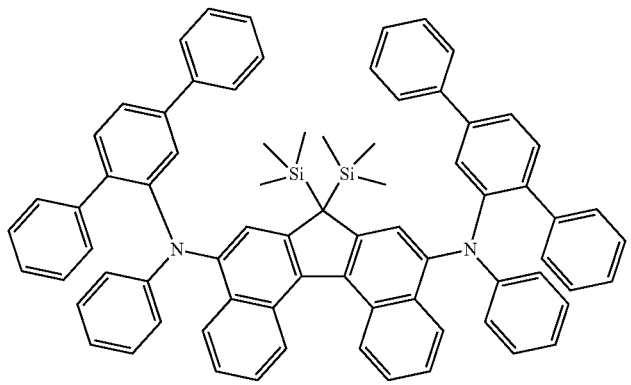
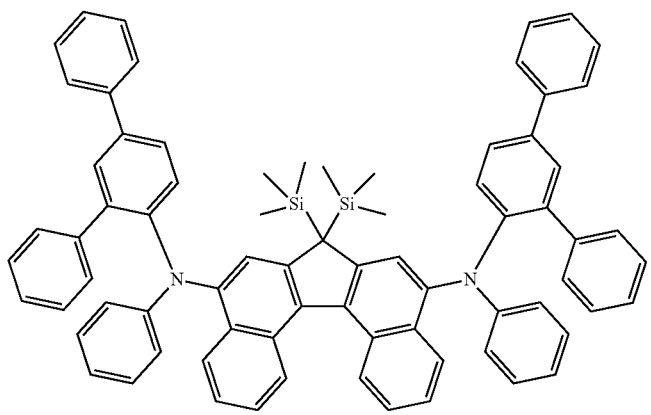

-continued
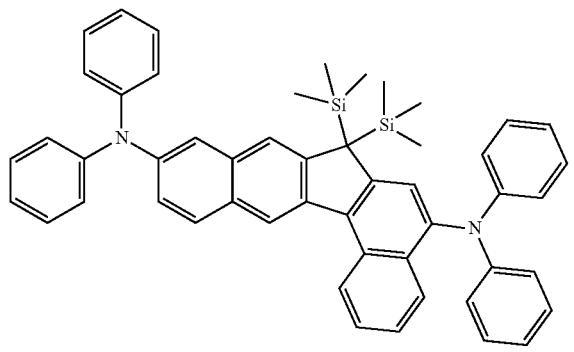
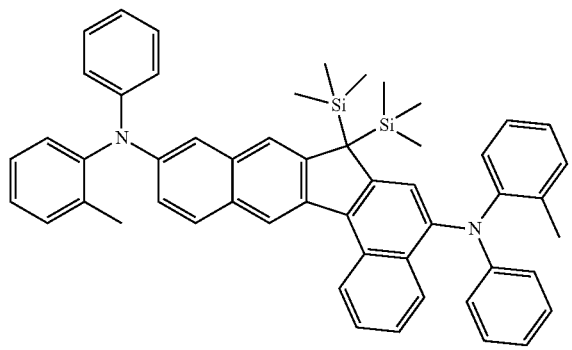
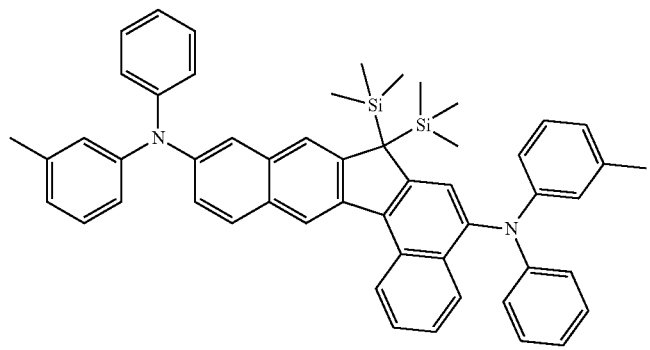
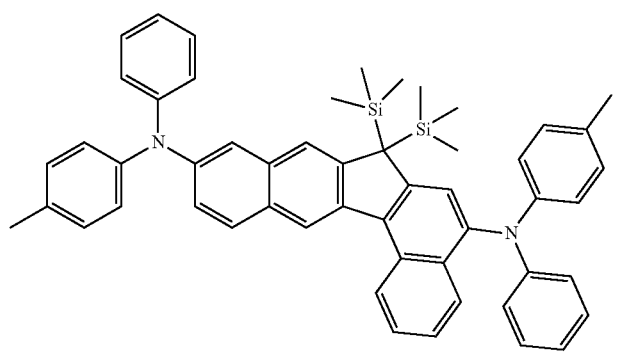

-continued
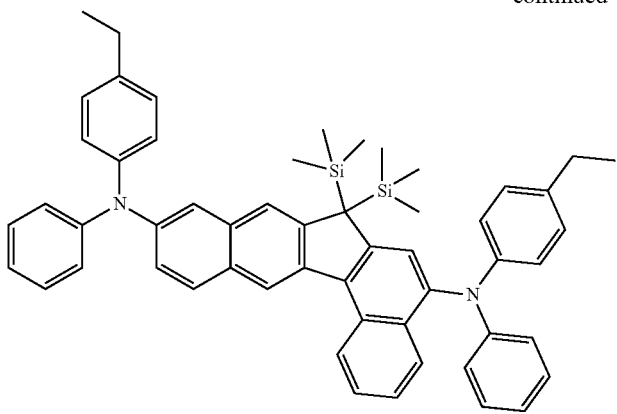
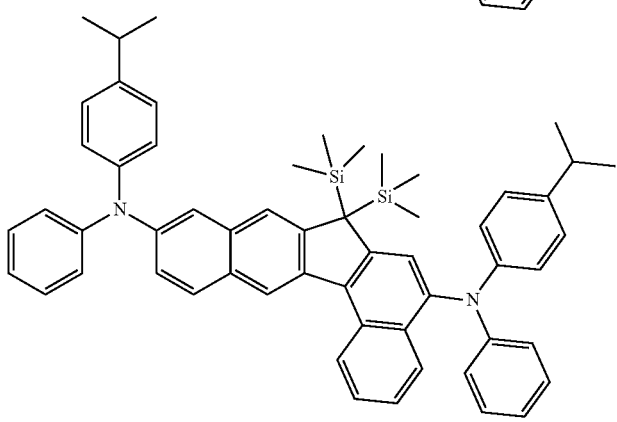
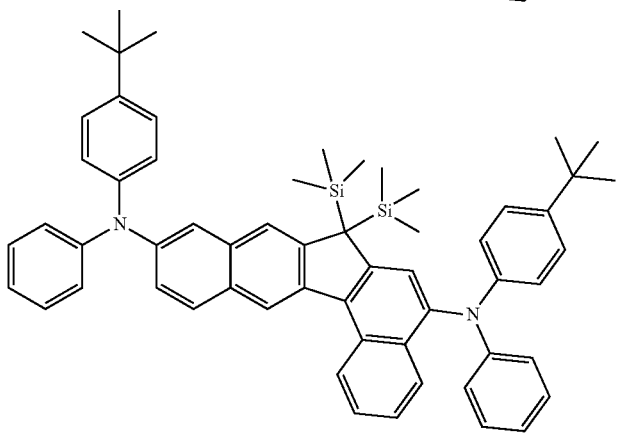
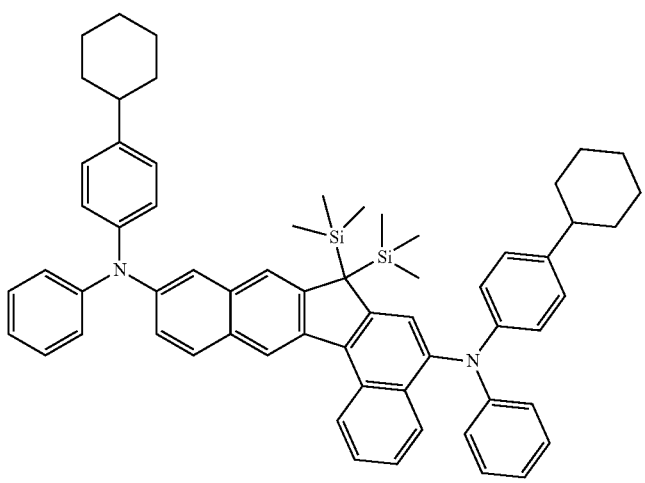

-continued
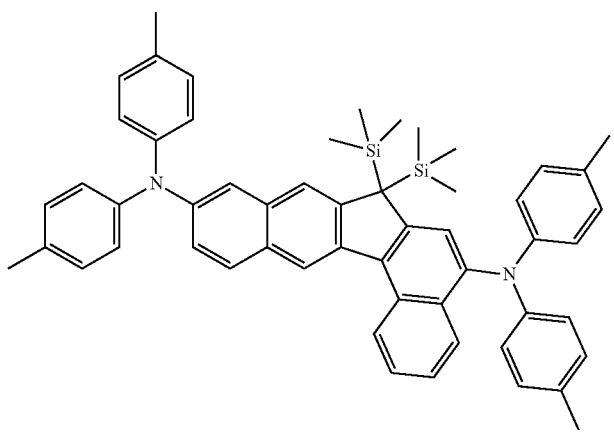
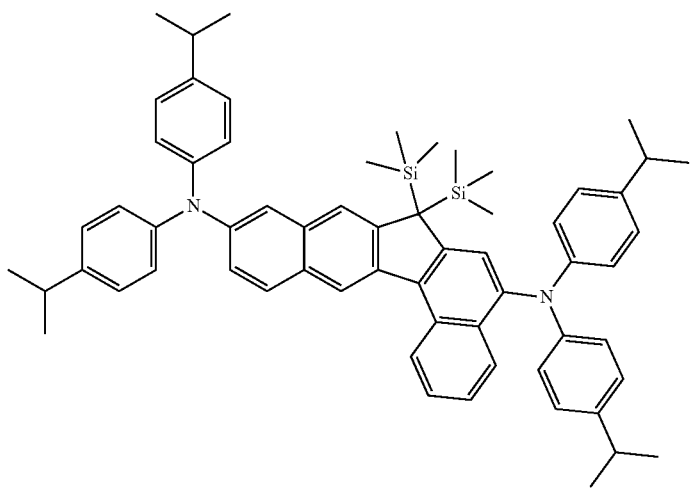
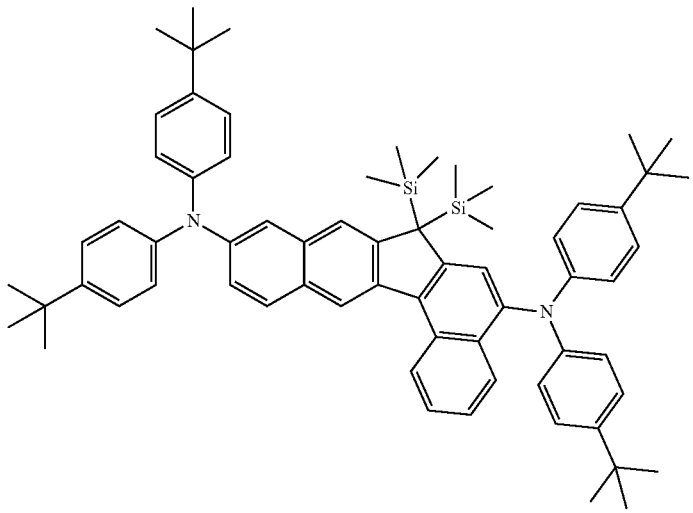

-continued
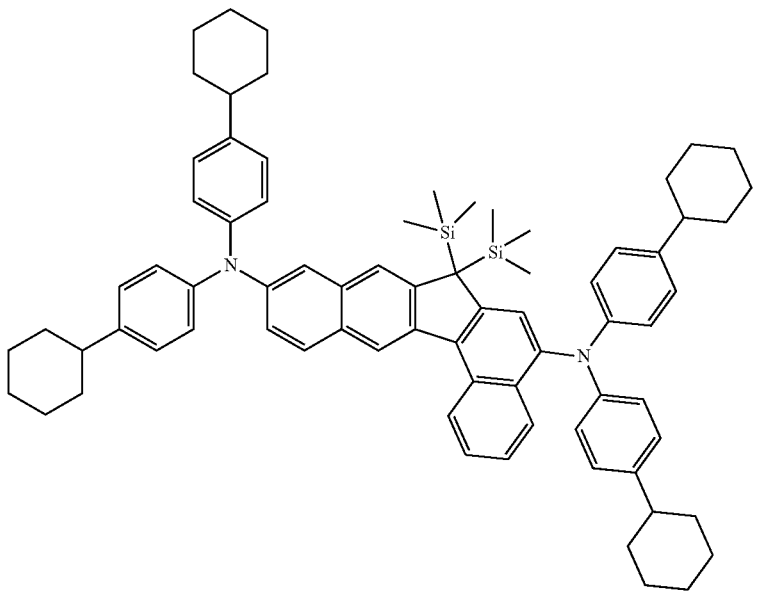
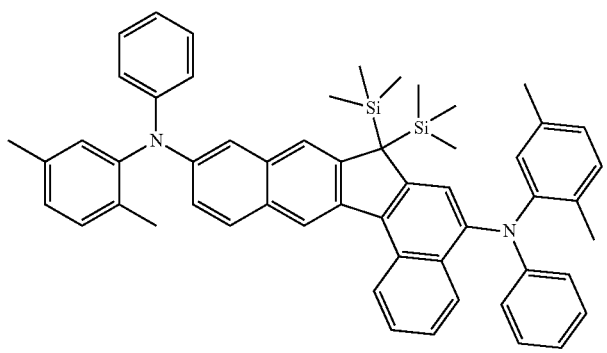
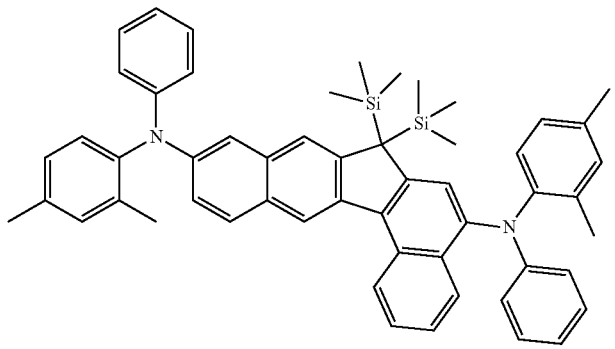
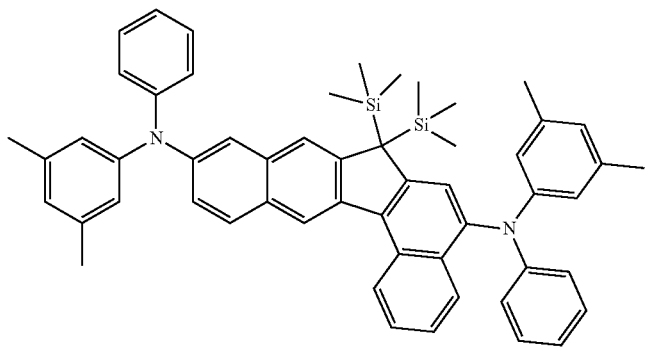

-continued
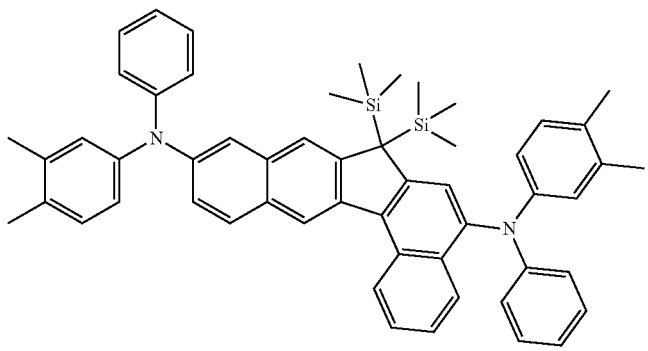
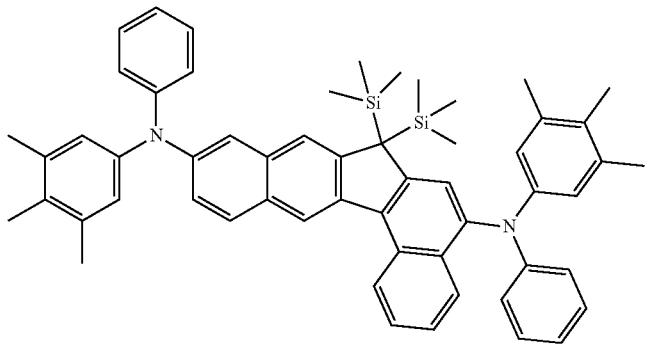
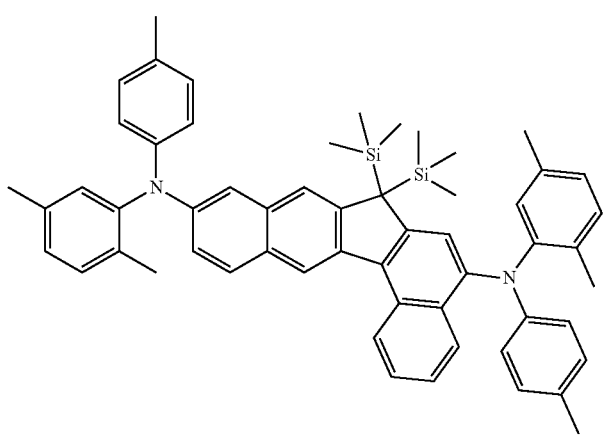
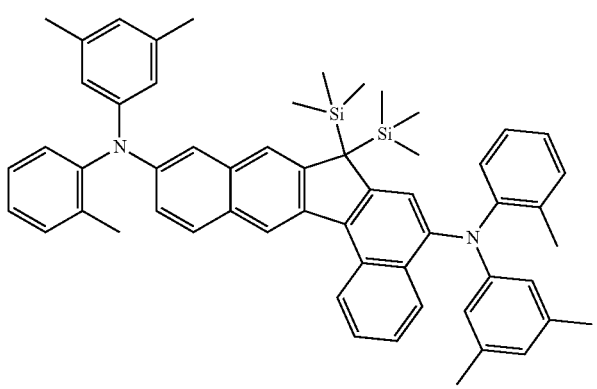

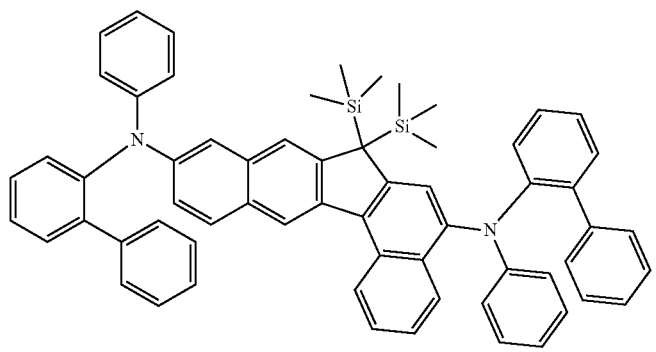
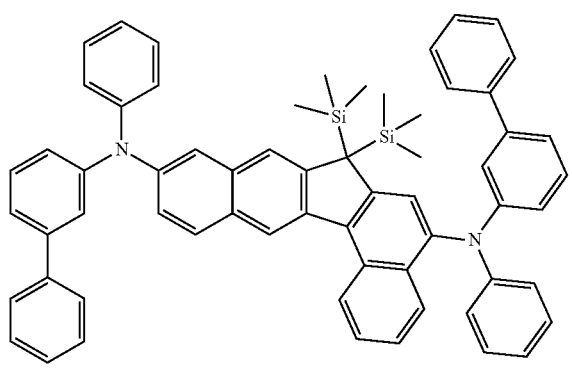
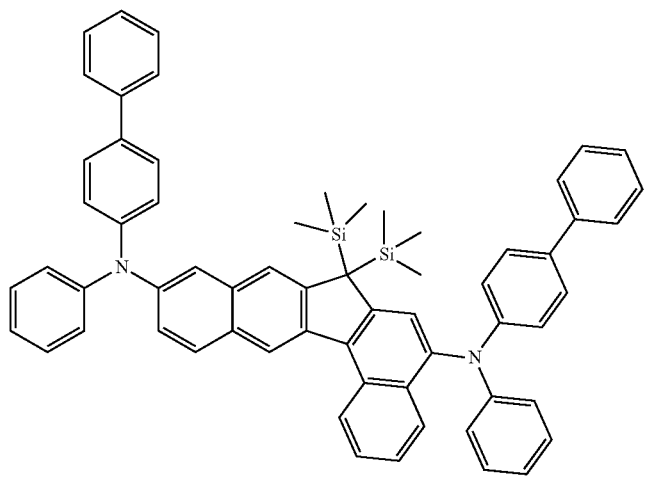
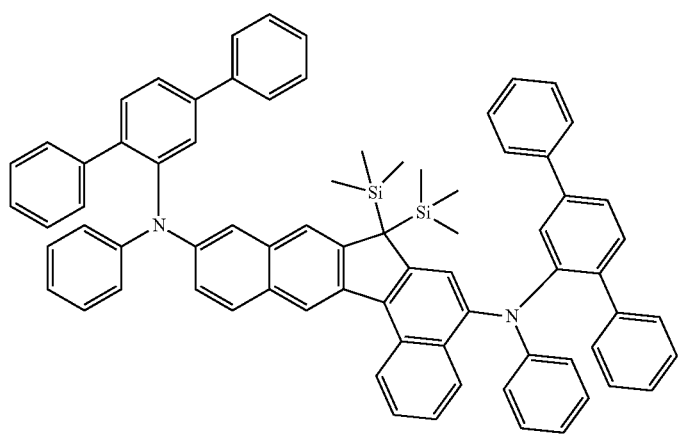

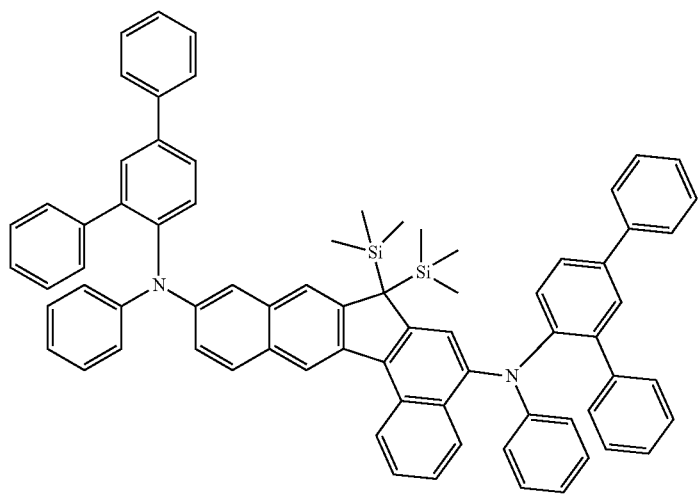
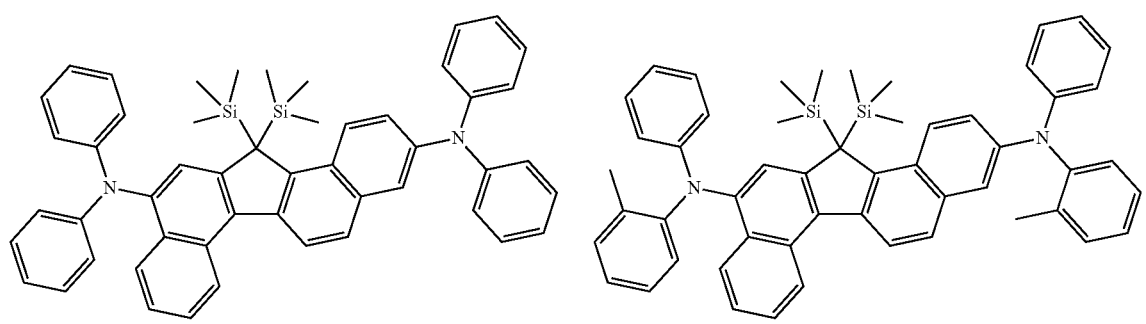
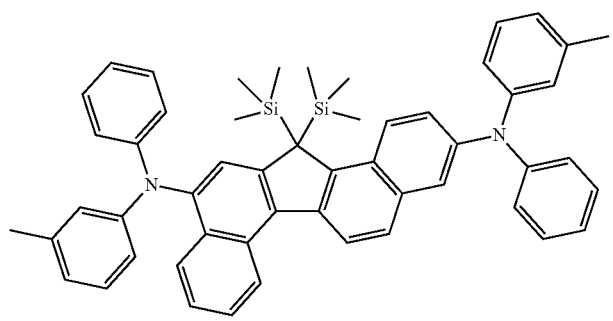
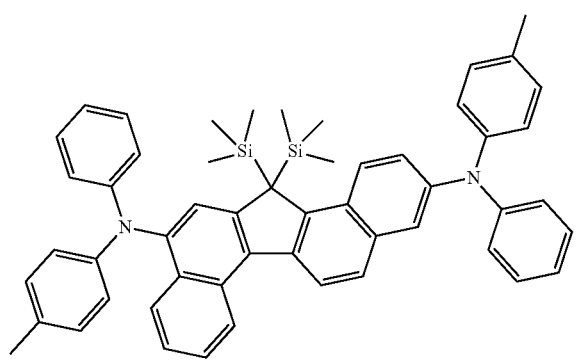

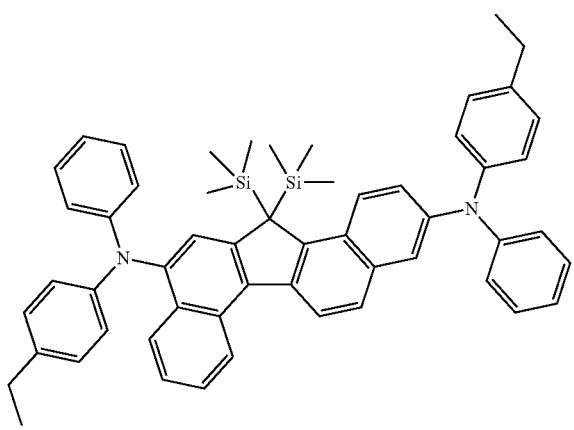
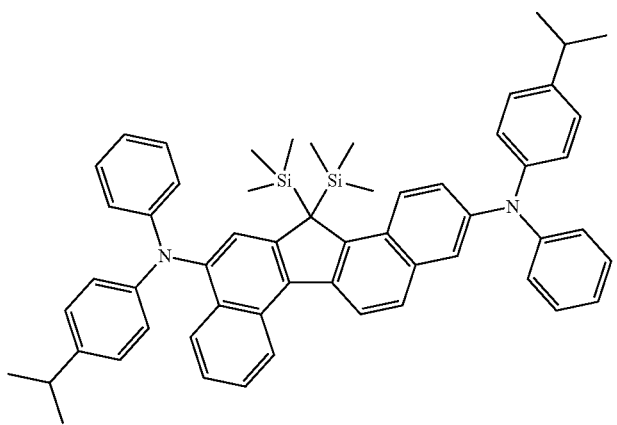
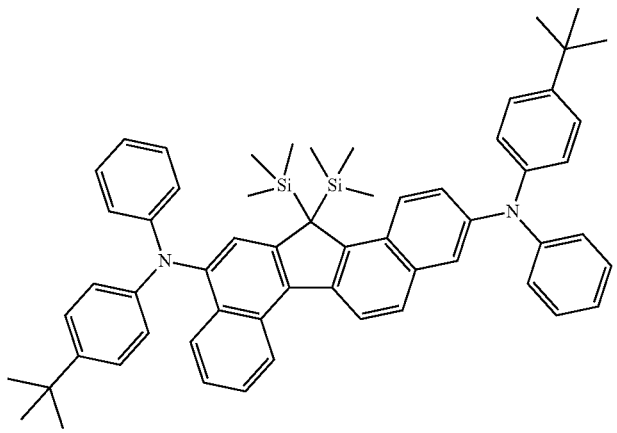

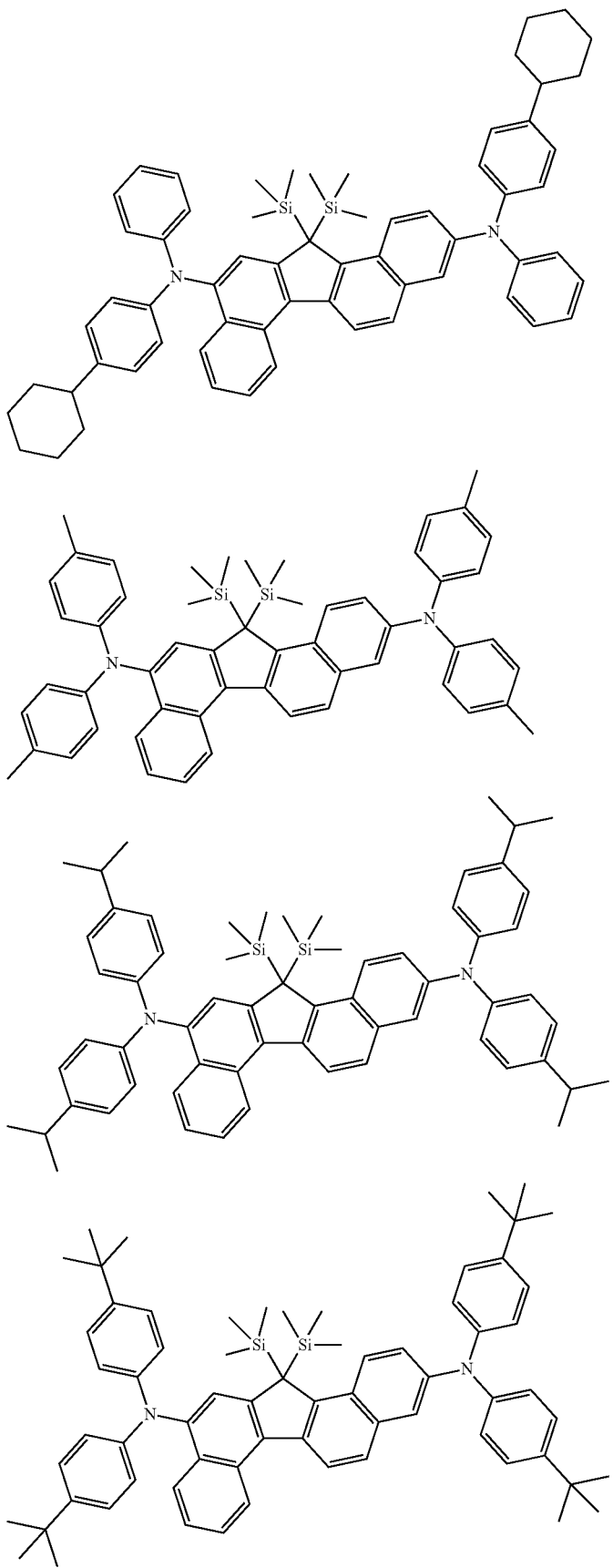

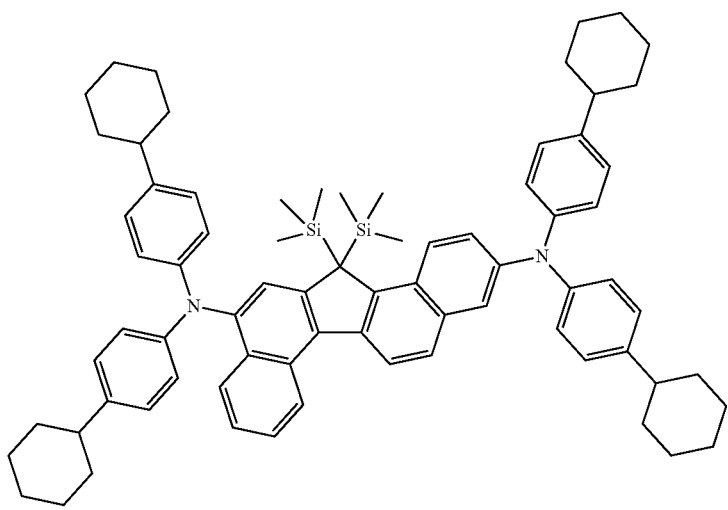
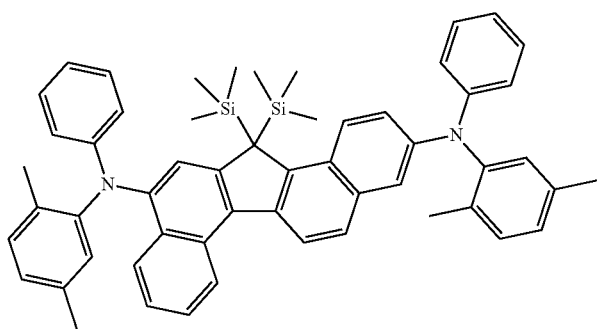
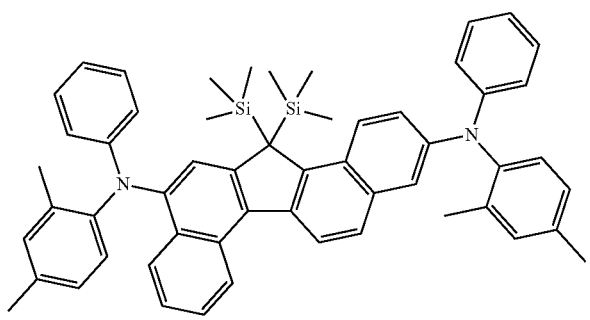
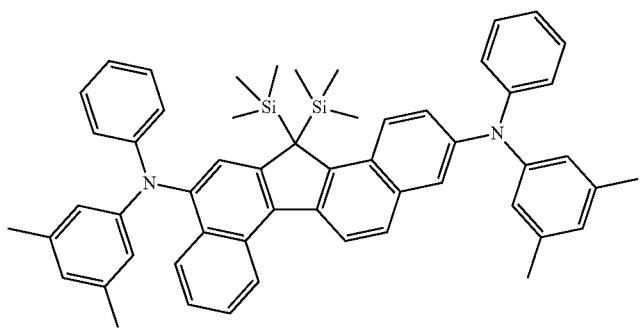

-continued
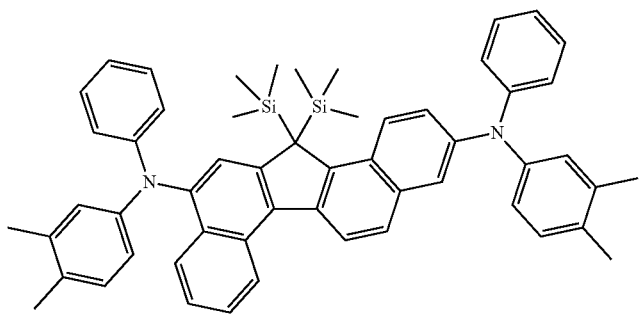
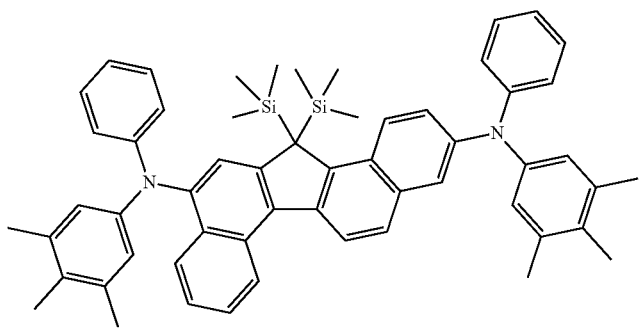
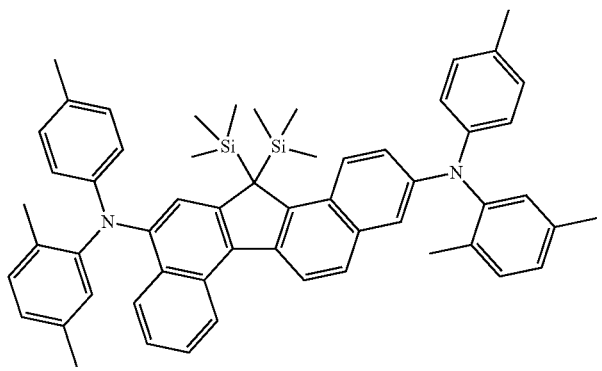
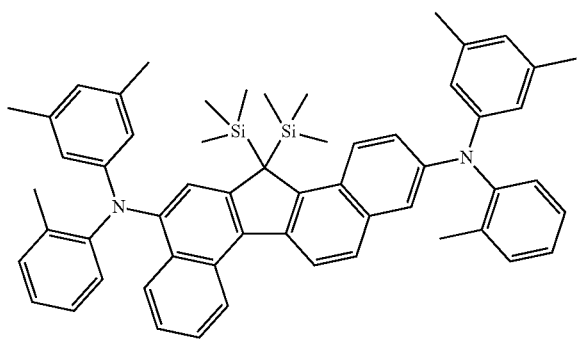
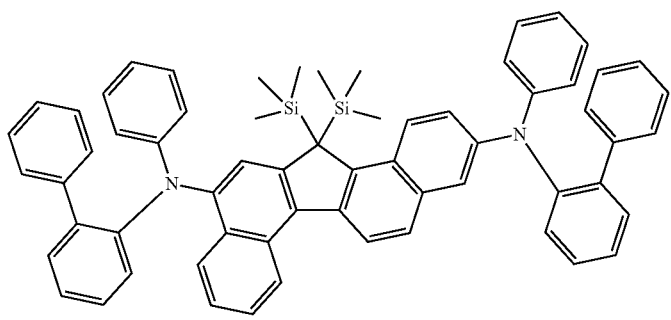

-continued
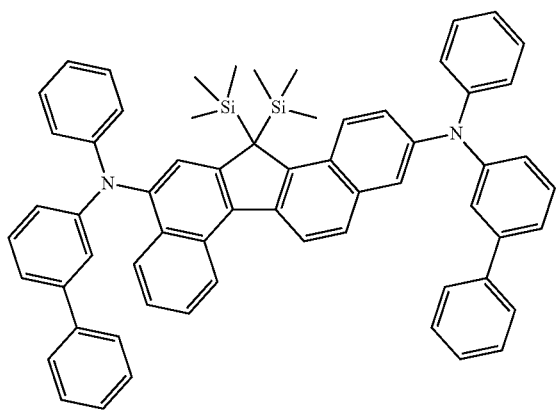
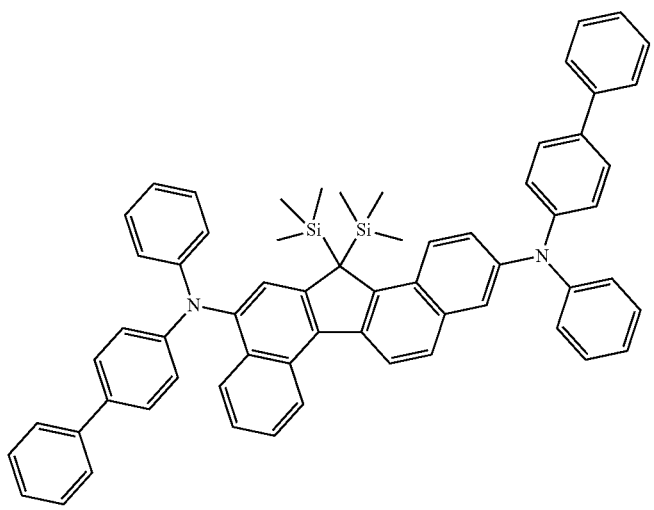
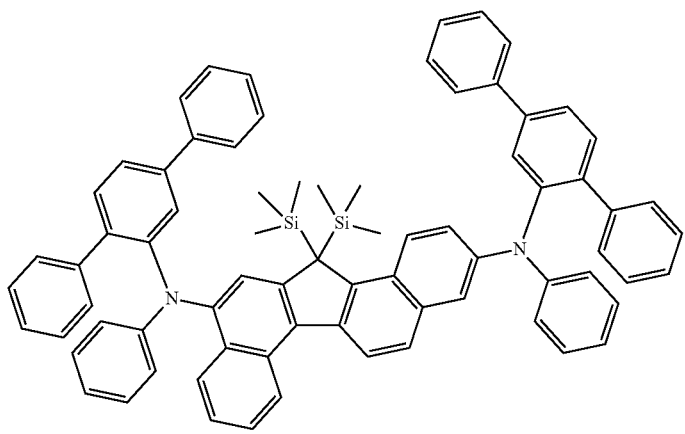

-continued
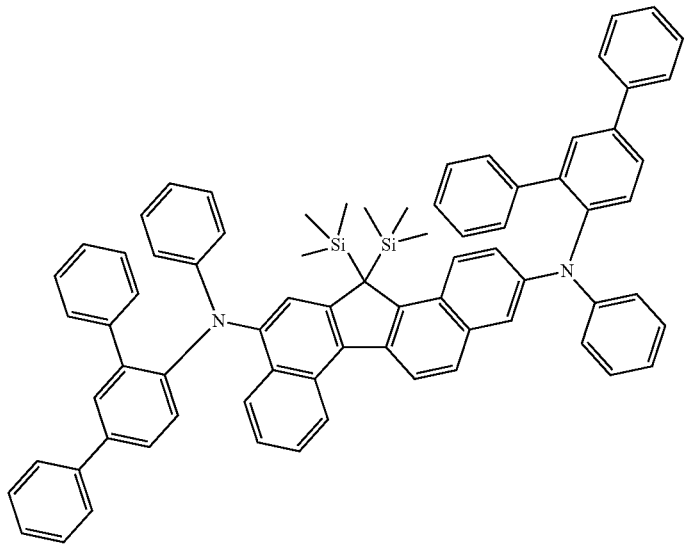
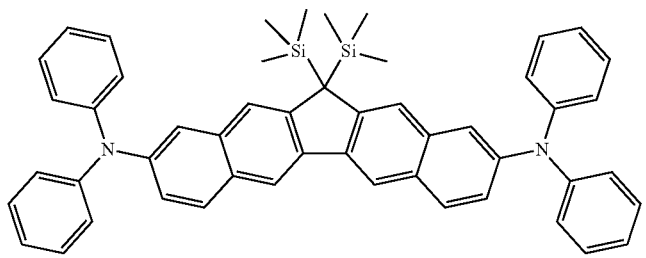
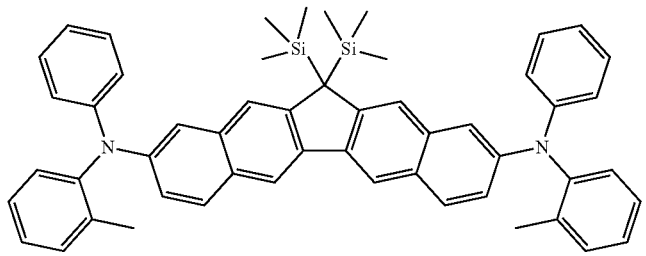
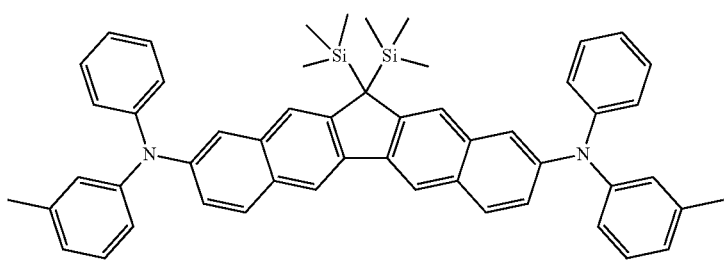
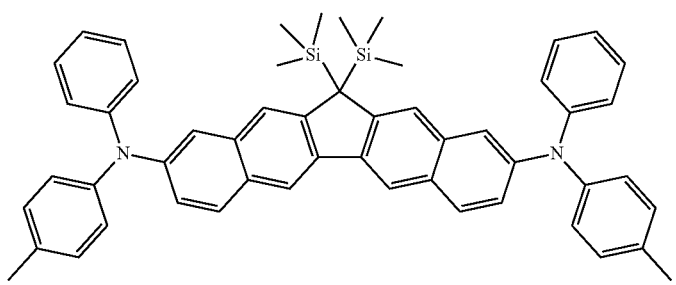

-continued
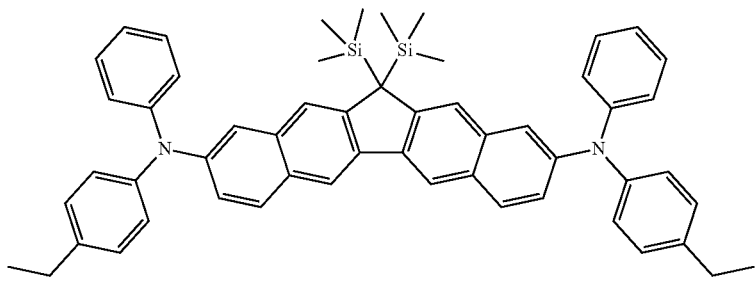
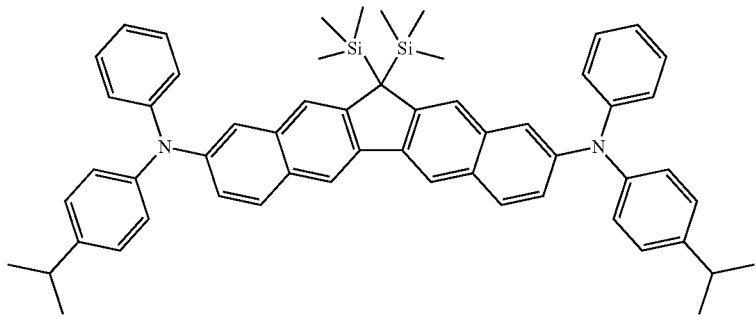
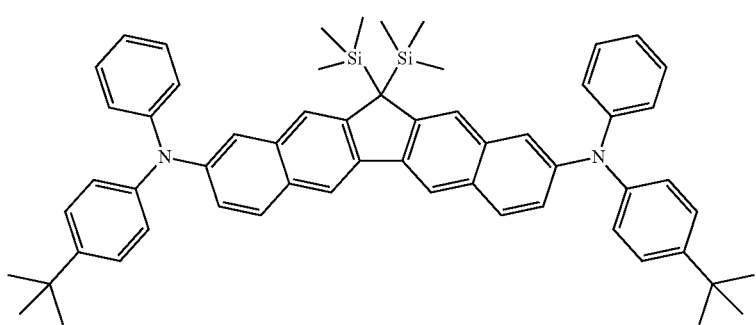
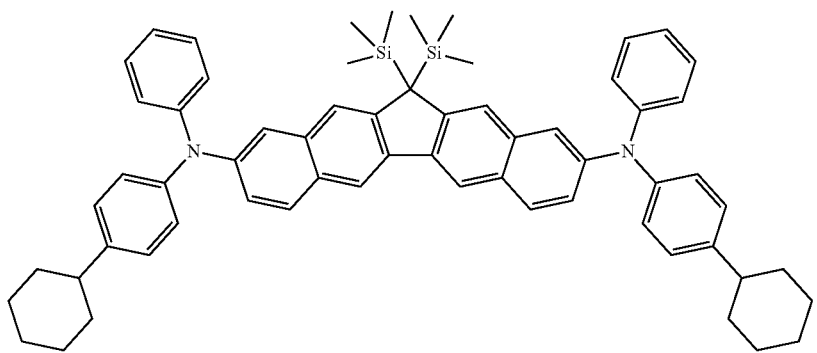
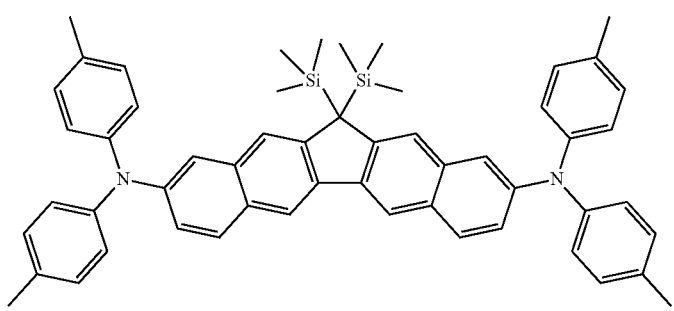

-continued
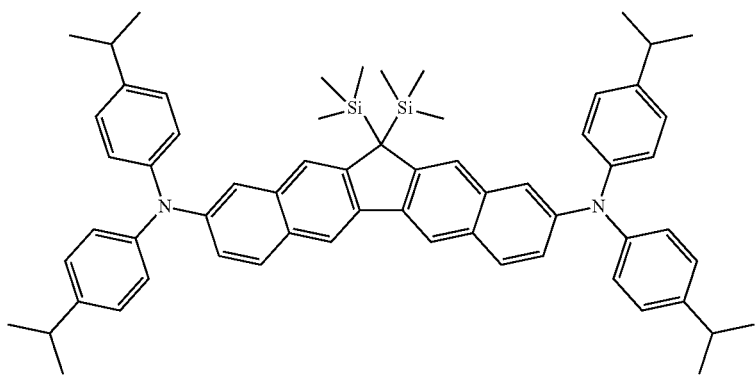
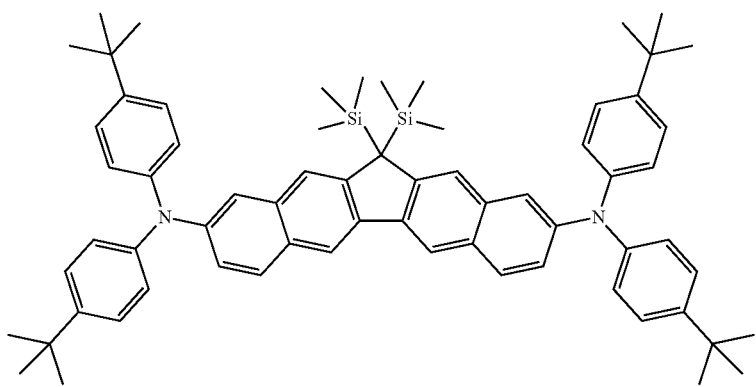
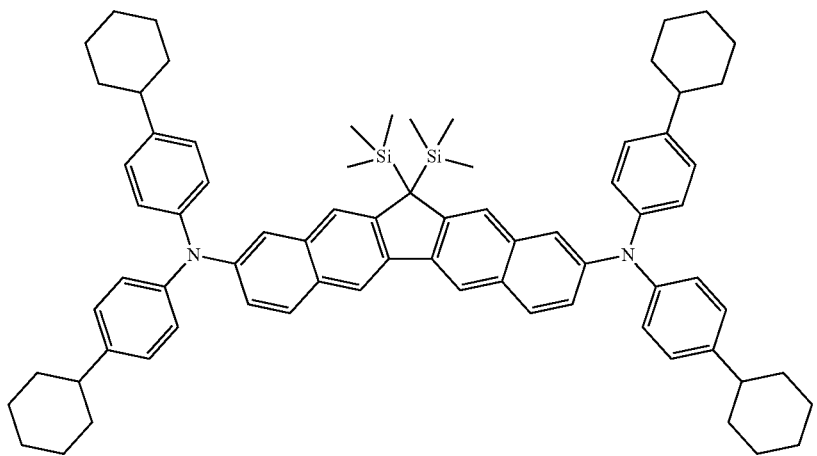
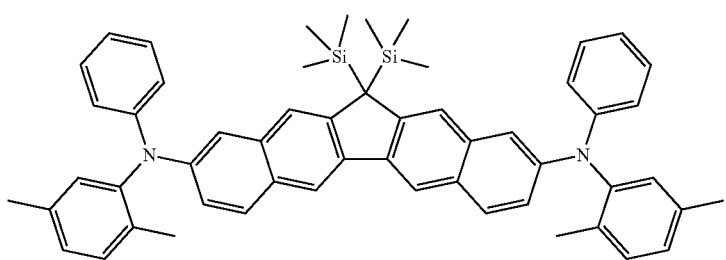

-continued
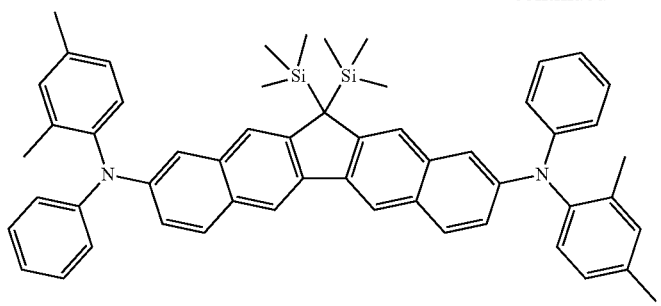
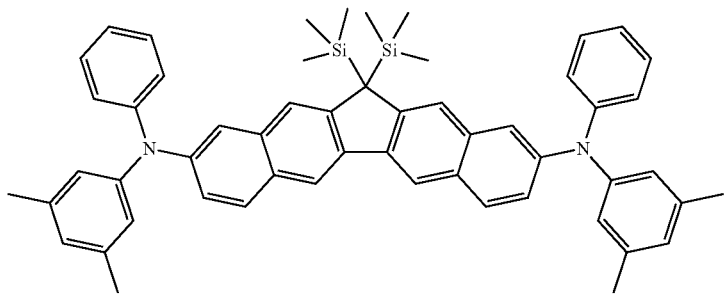
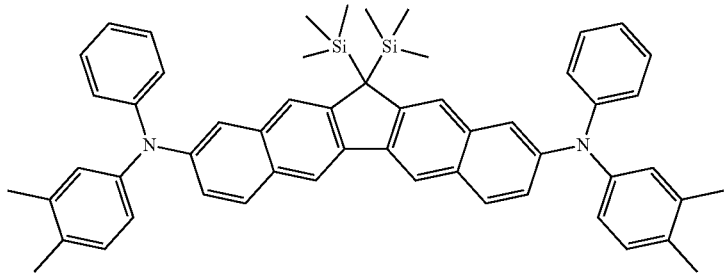
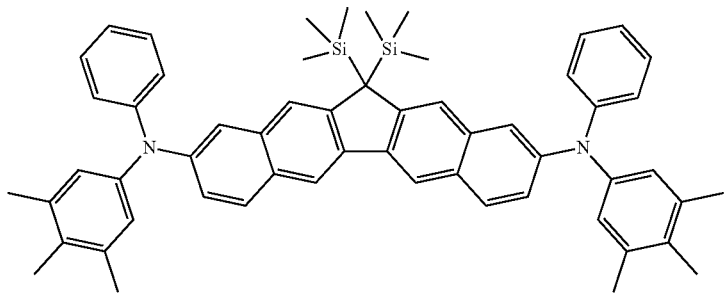
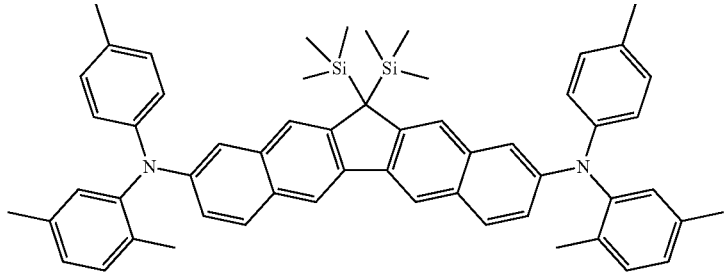
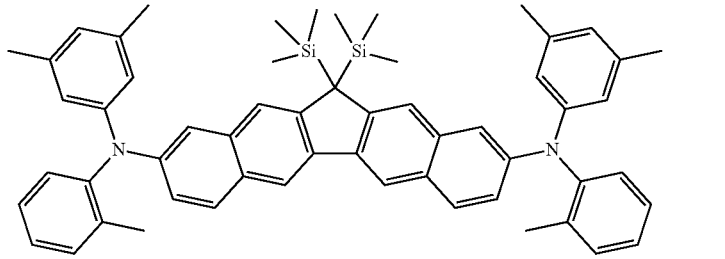

-continued
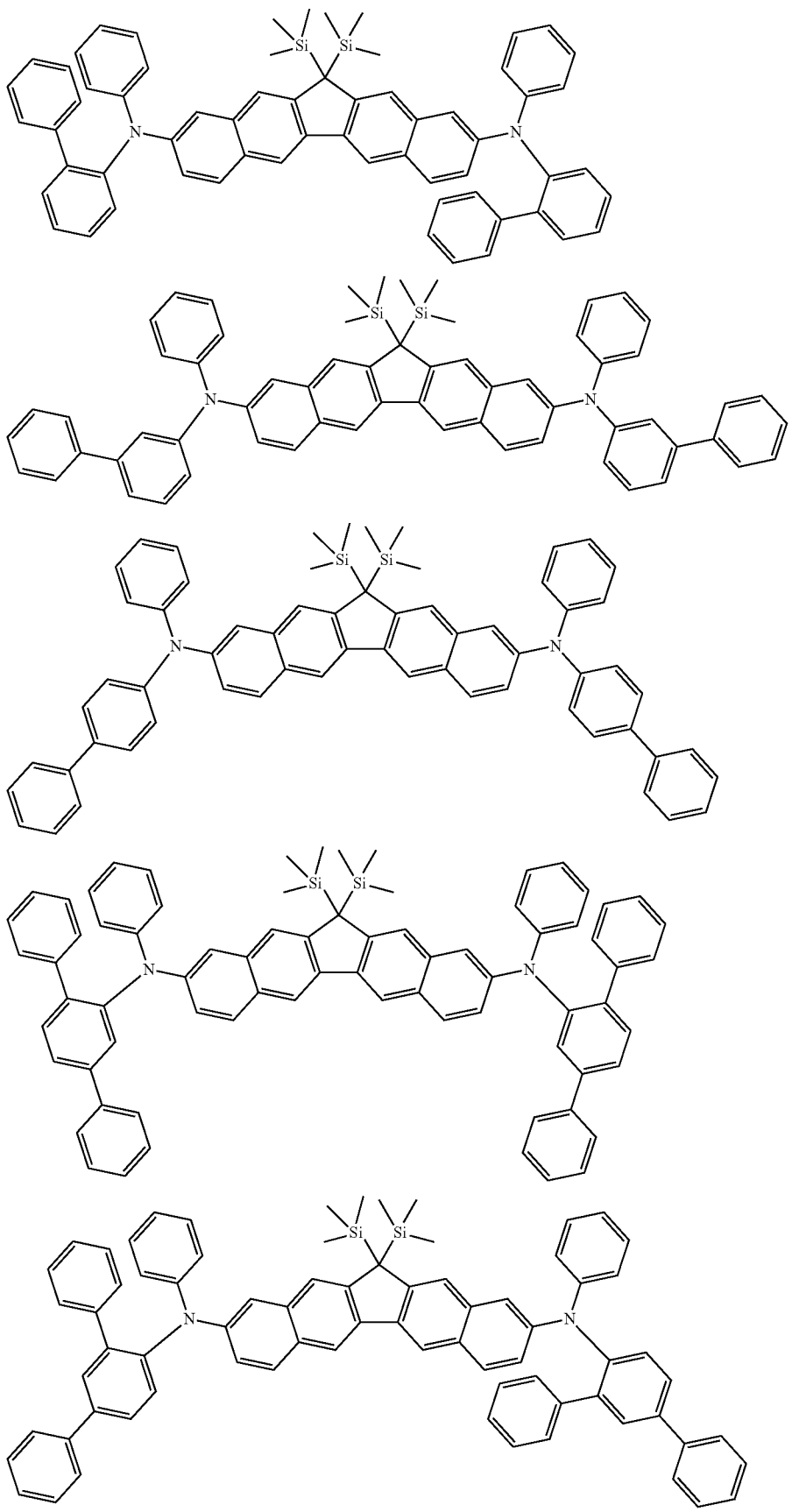

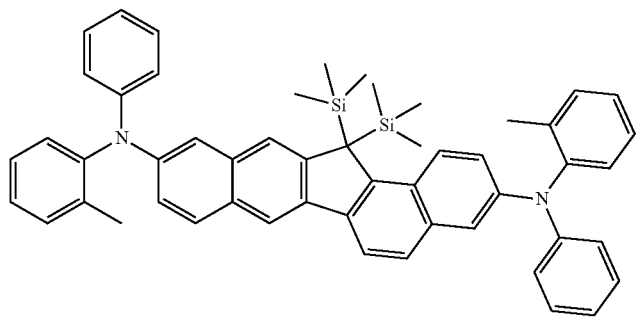
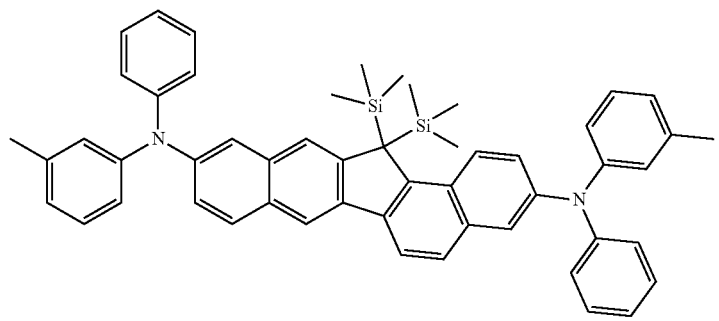
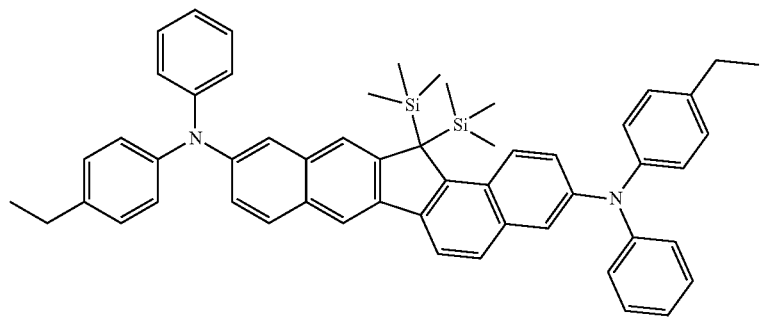
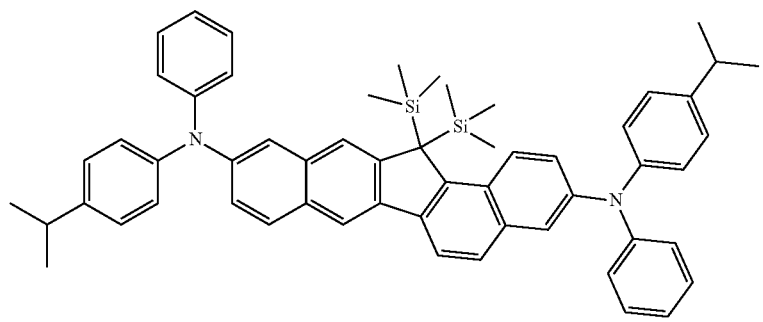
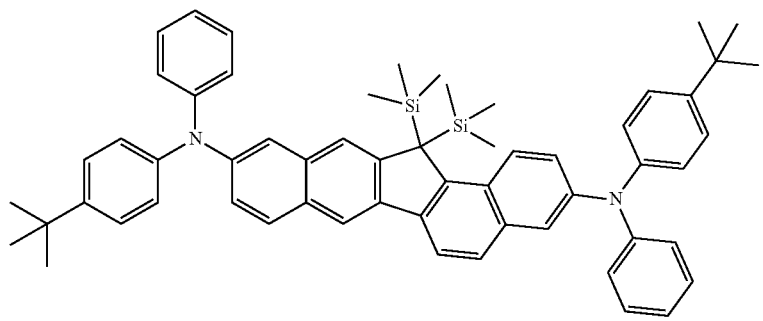

-continued
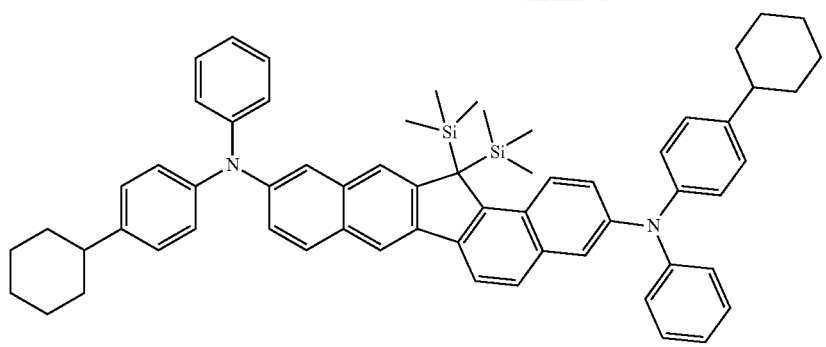
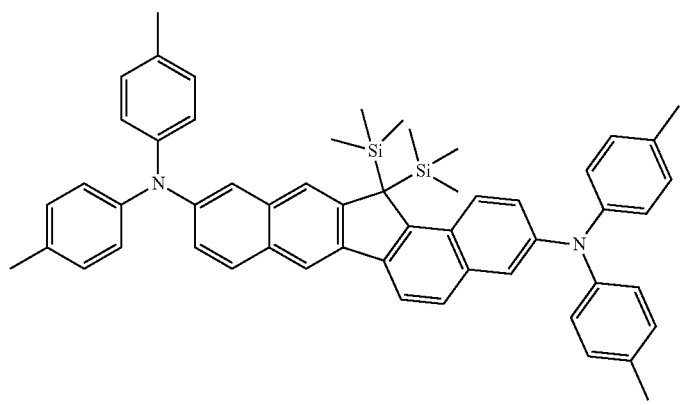
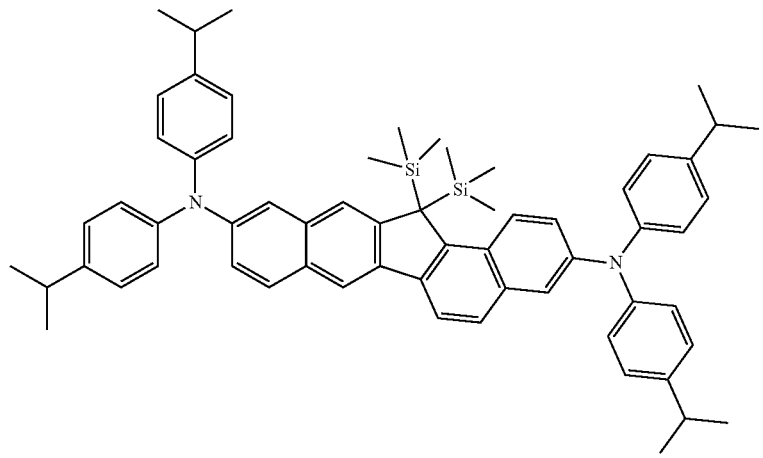
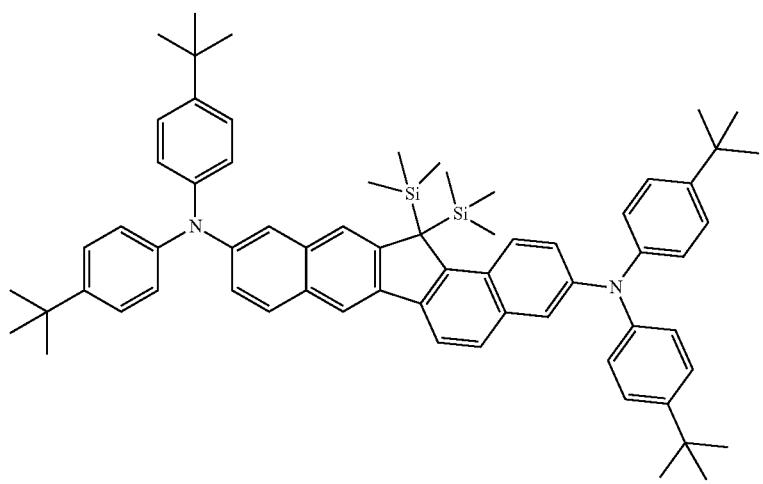

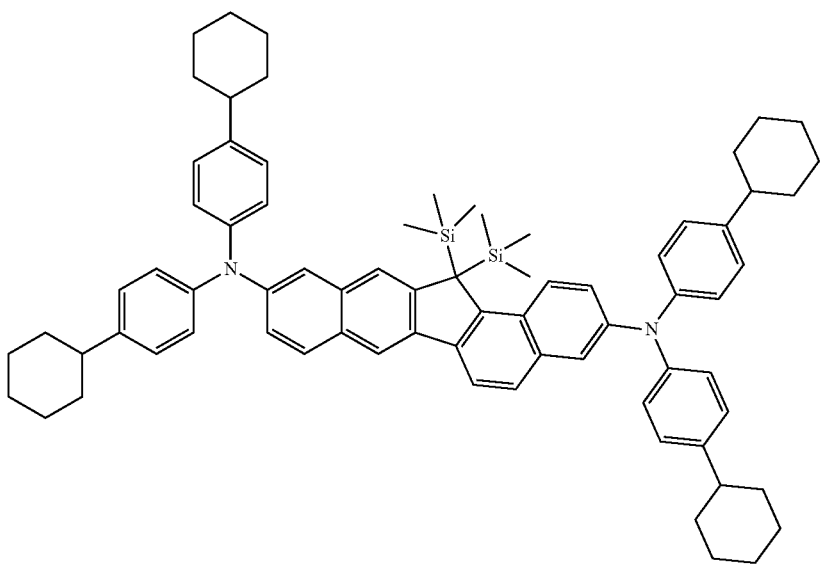
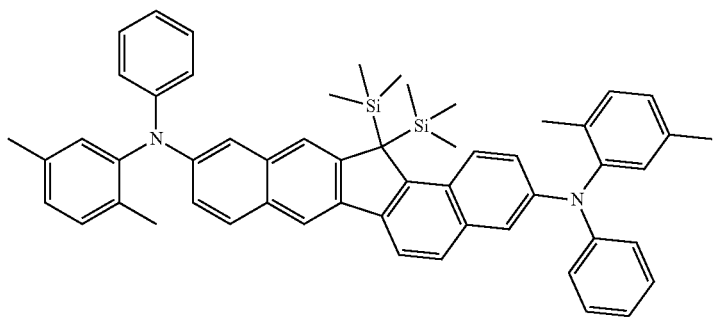
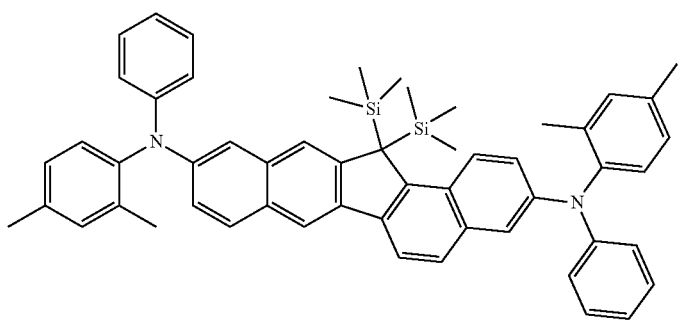
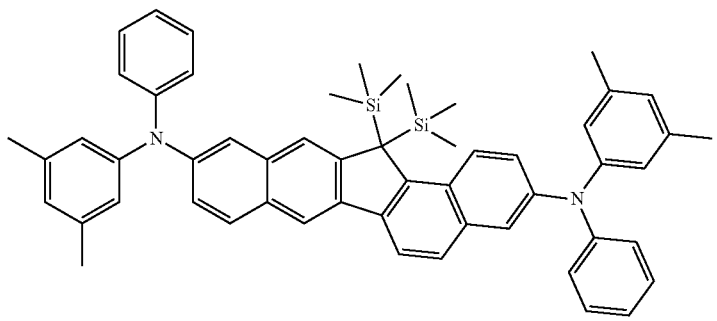

-continued
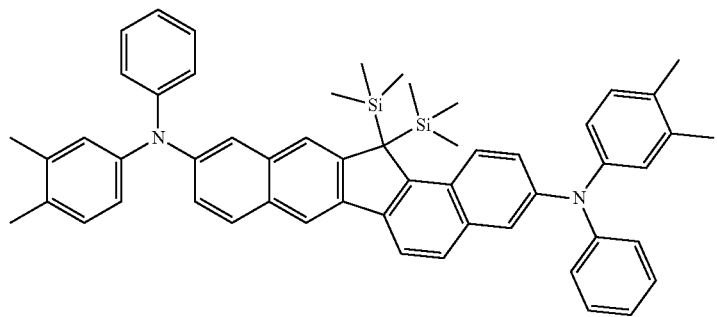
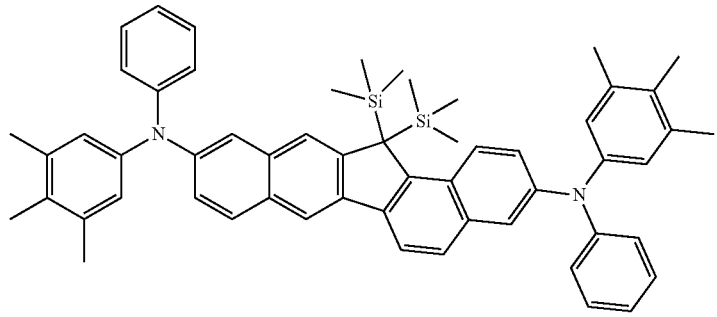
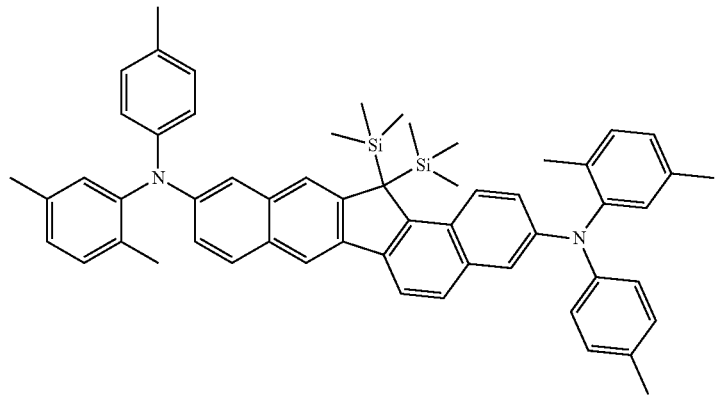
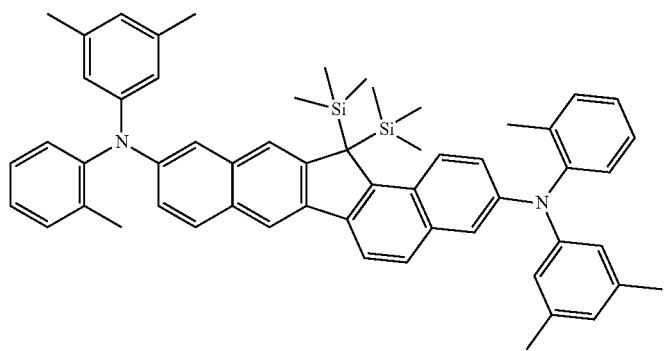
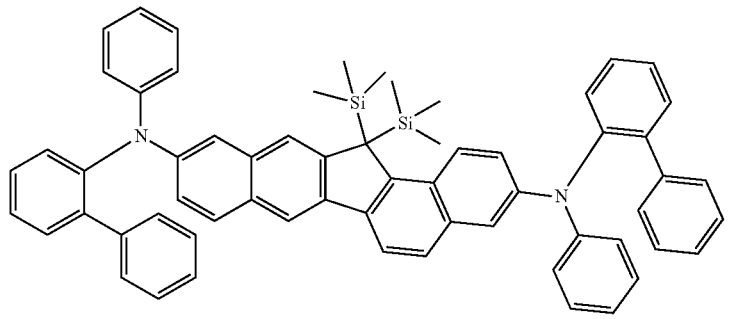

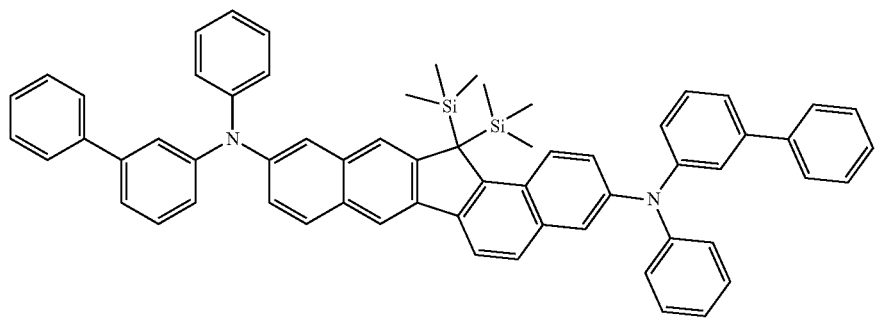
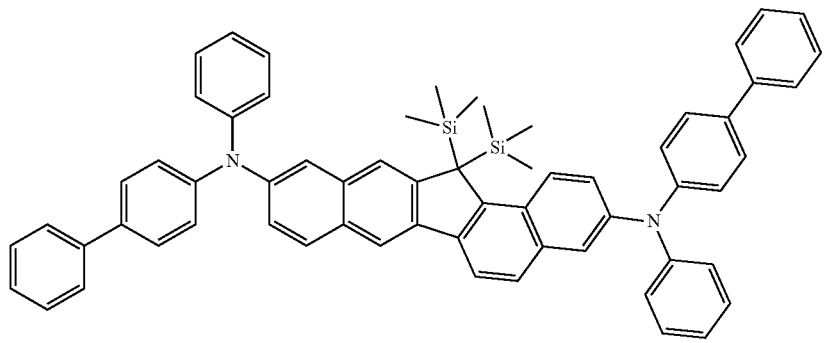
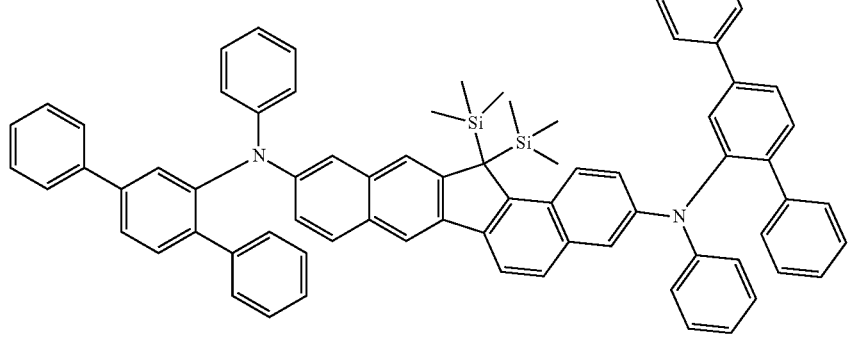
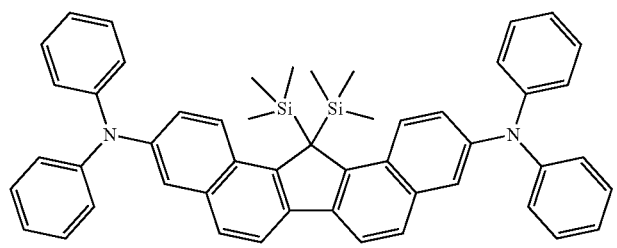
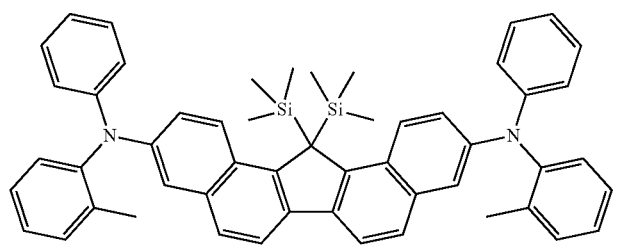

-continued
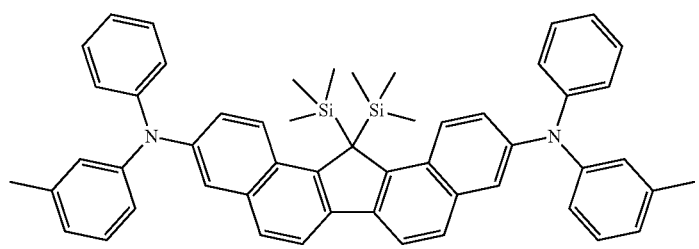
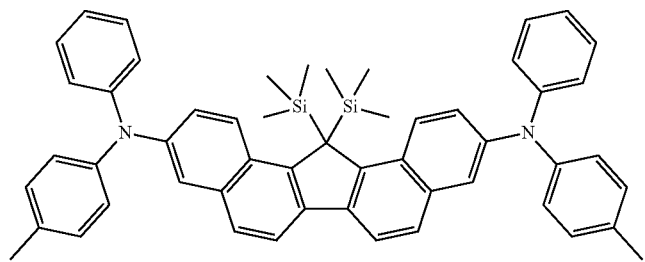
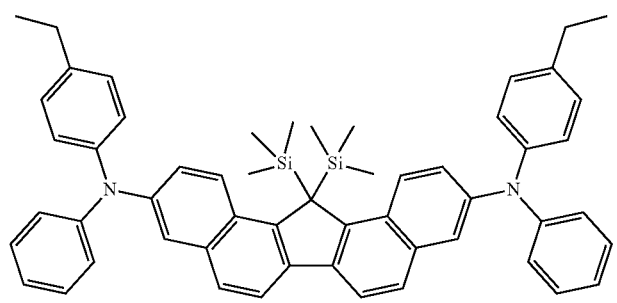
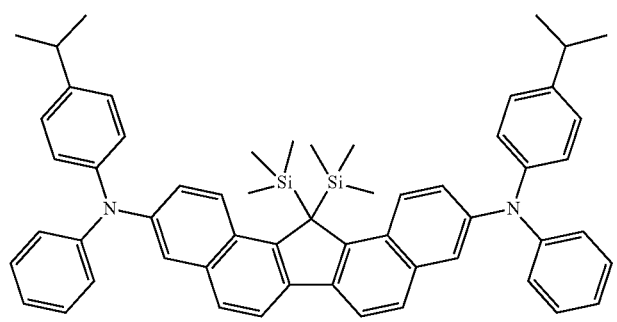
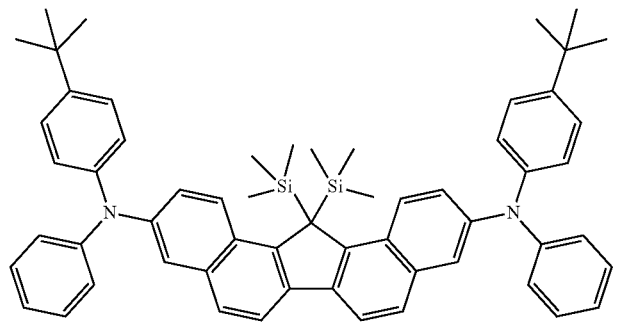

-continued
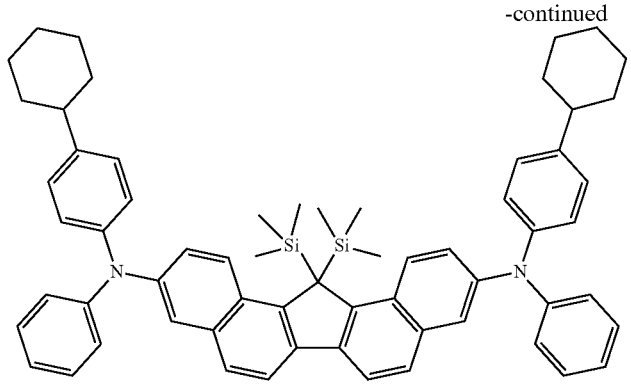
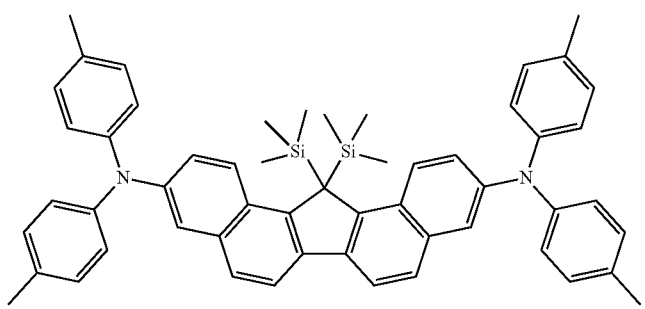
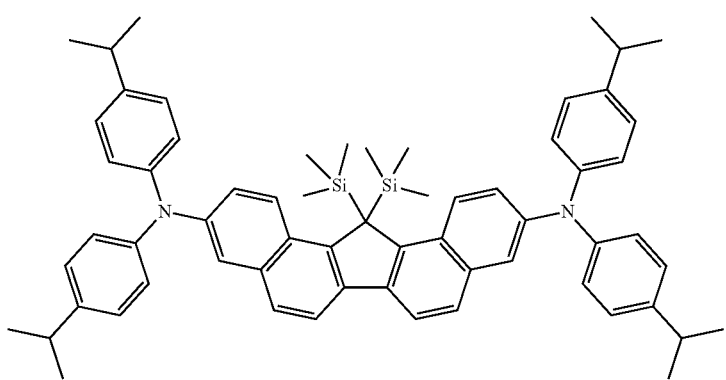
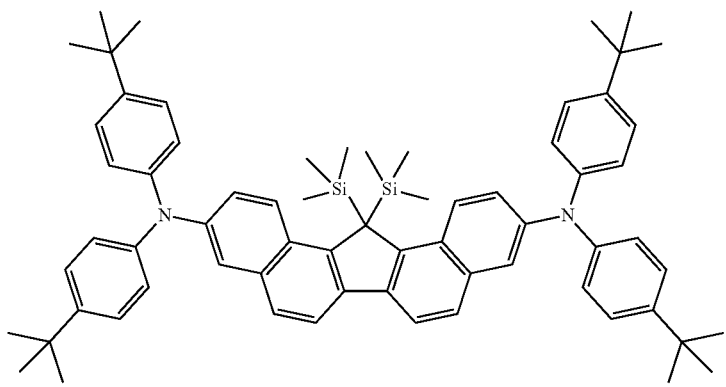

-continued
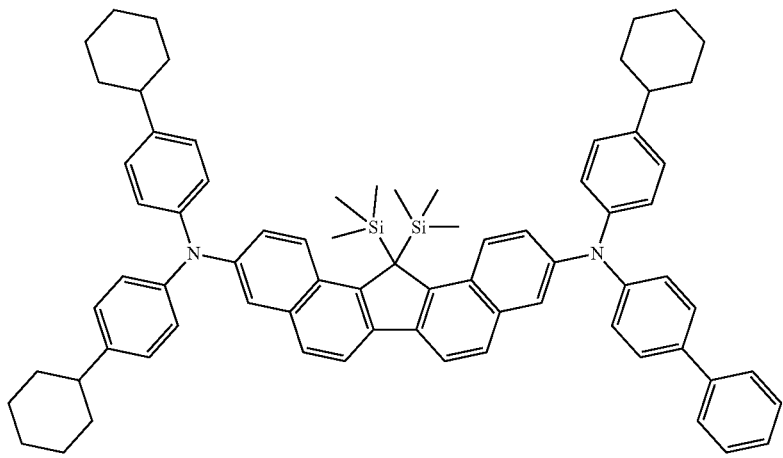
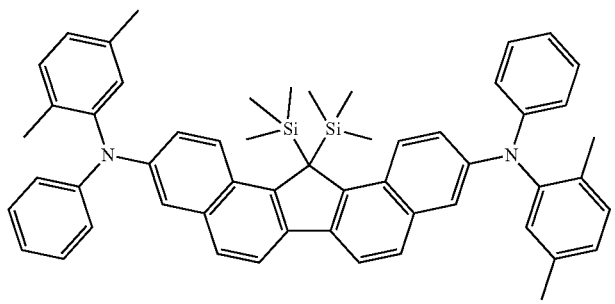
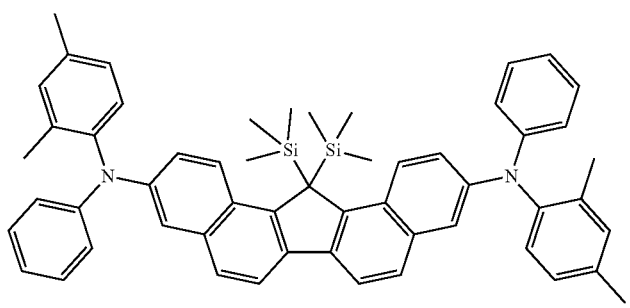
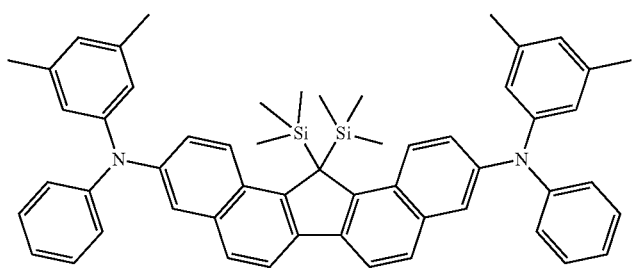
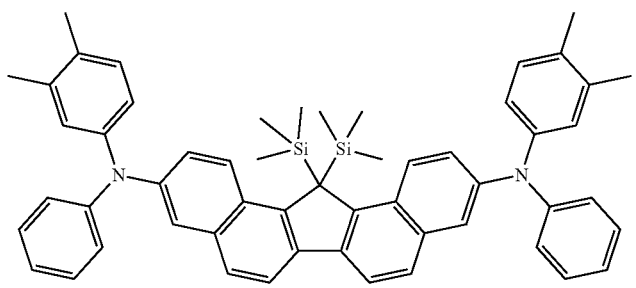

-continued
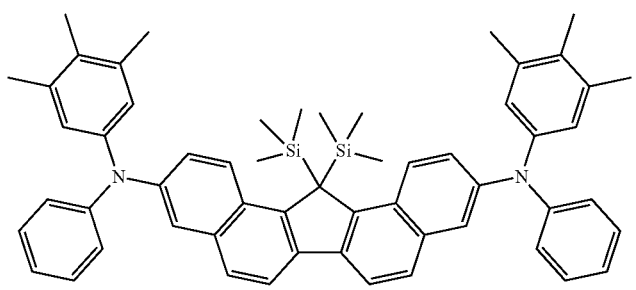
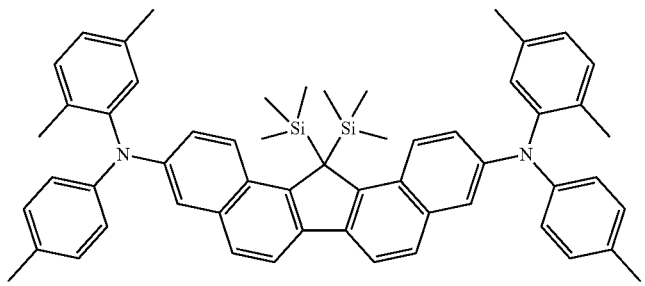
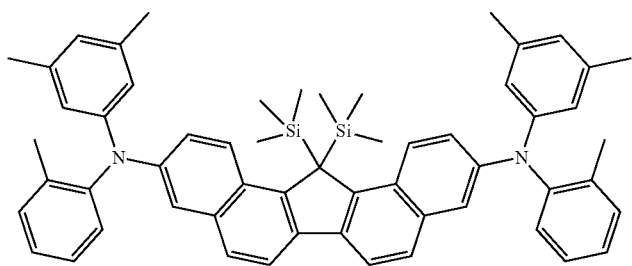
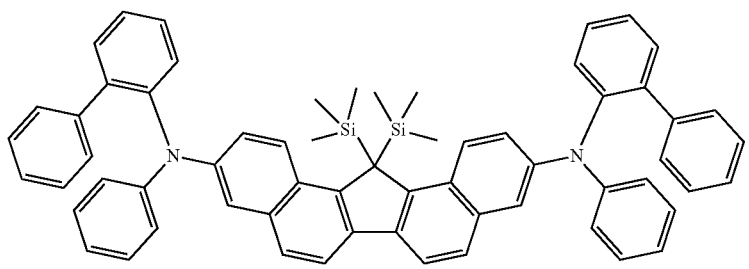
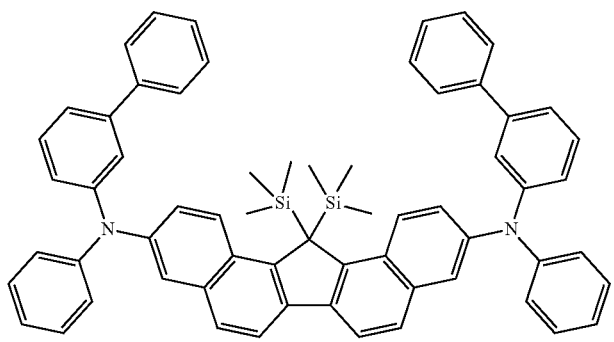

-continued
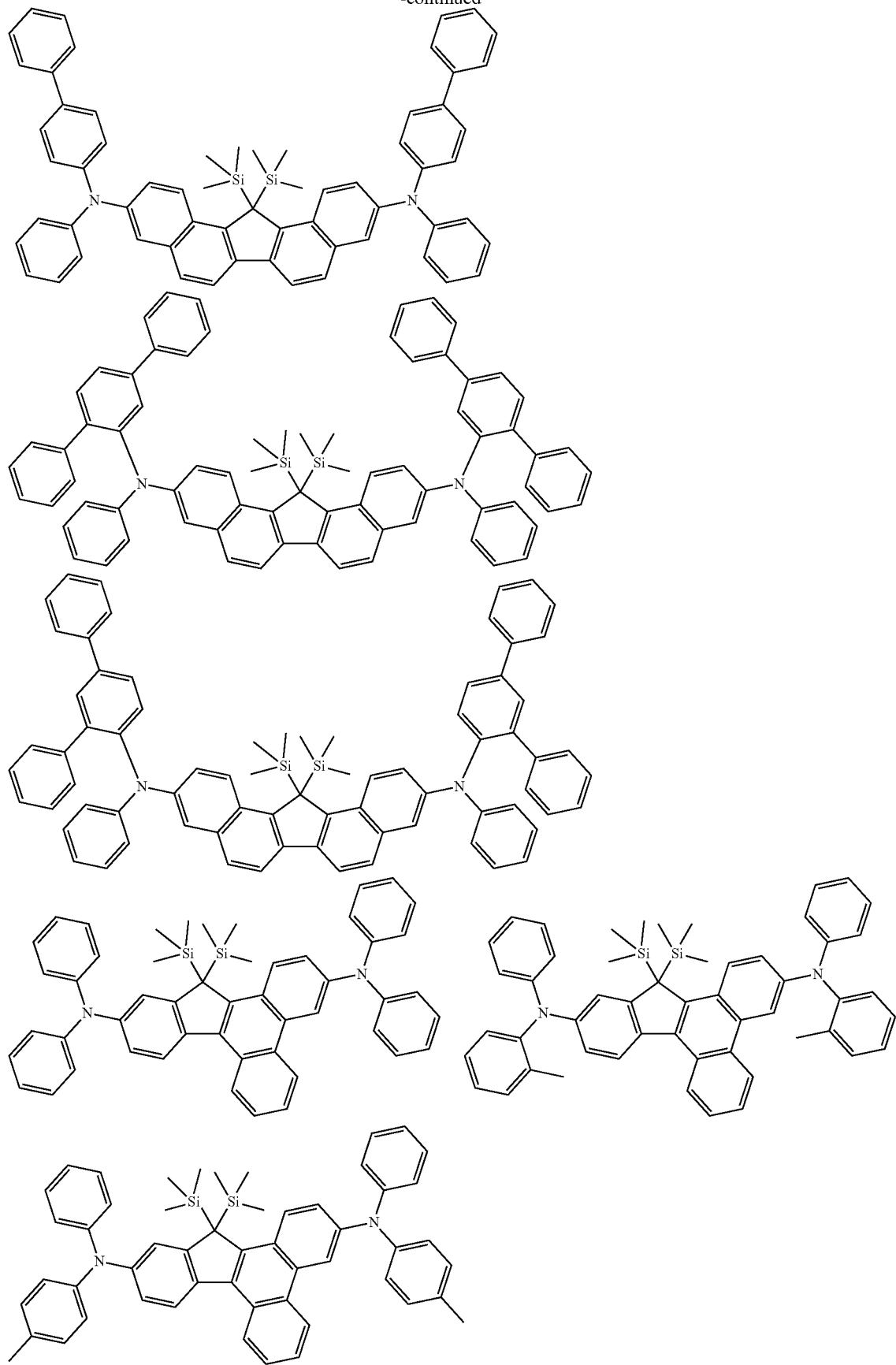

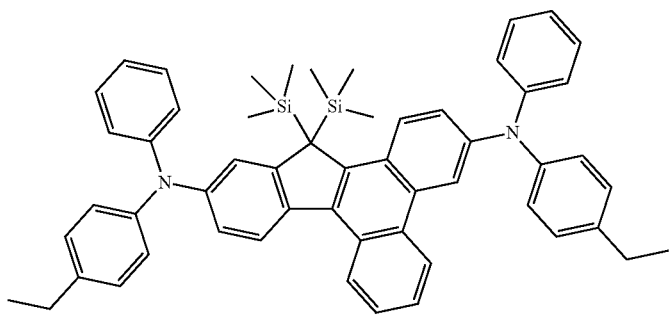
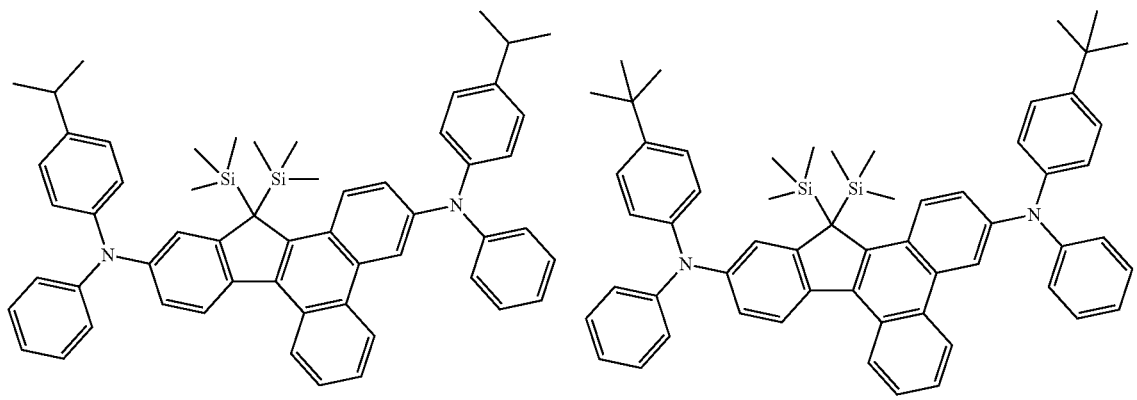
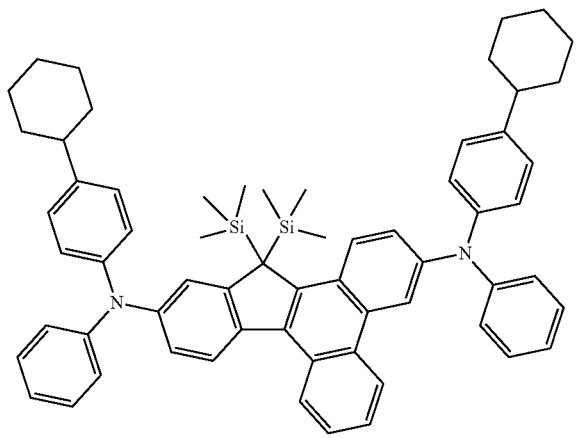
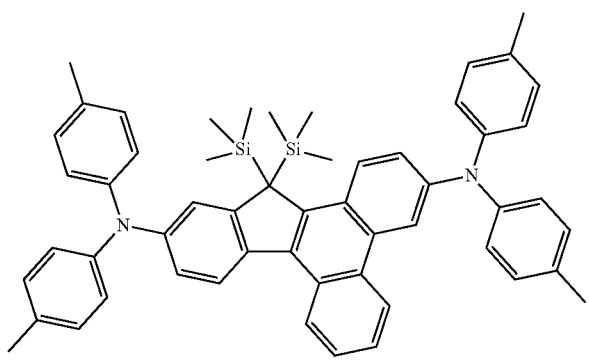

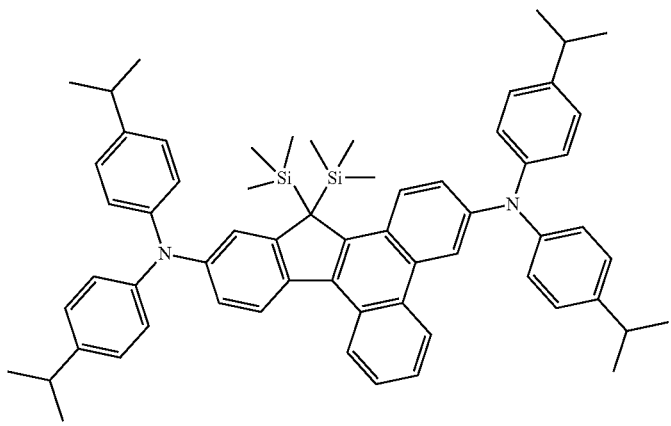
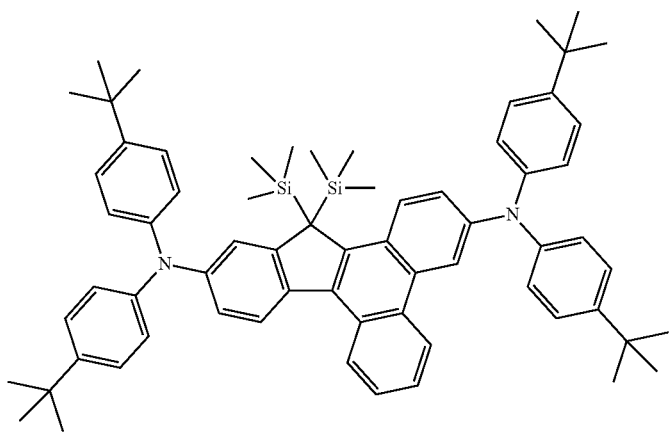
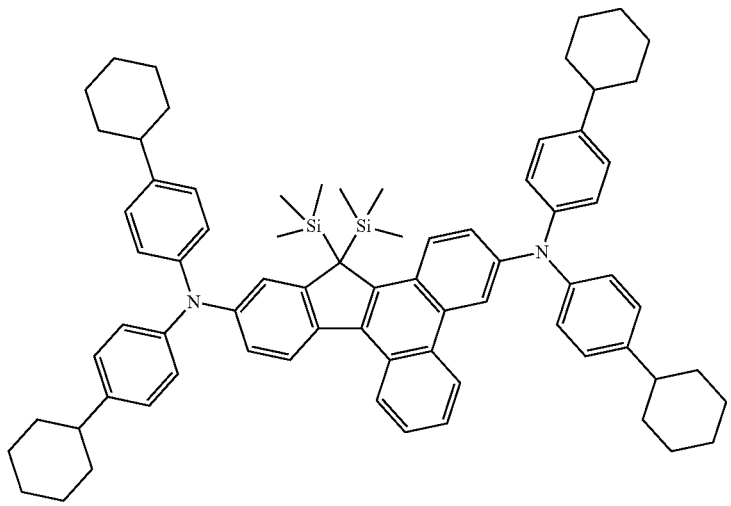
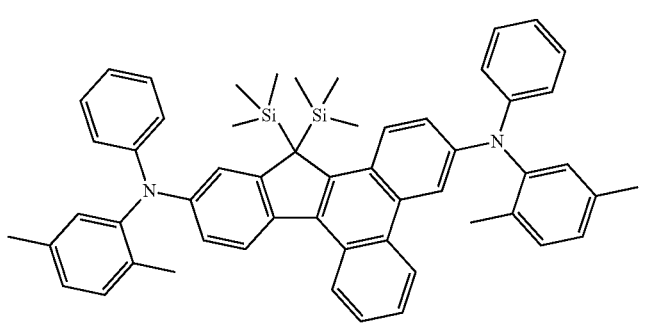

-continued
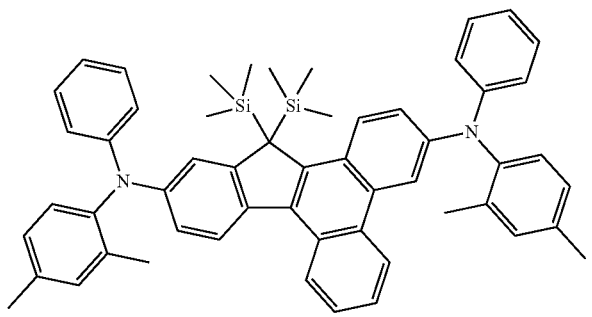
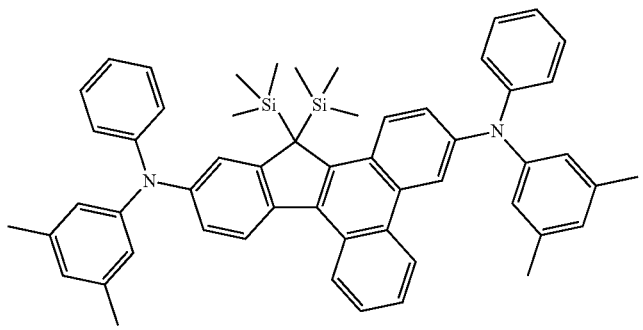
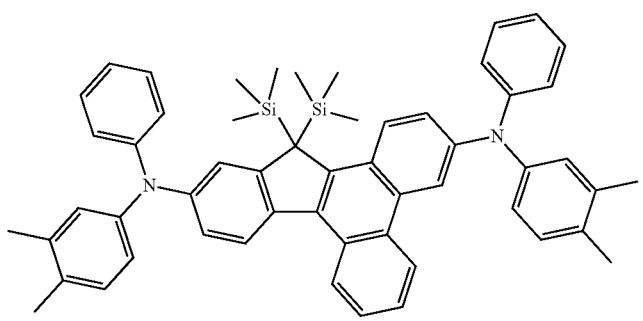
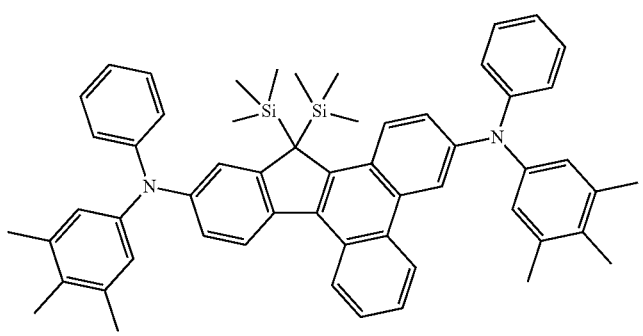
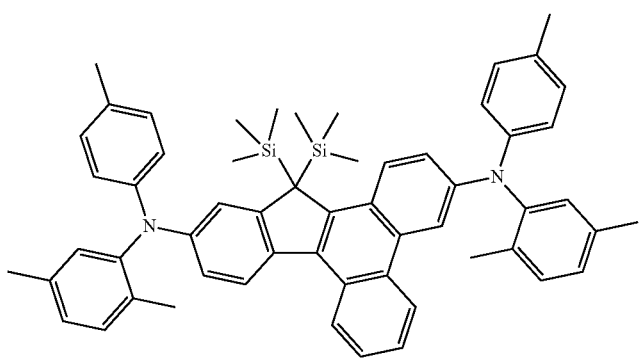

-continued
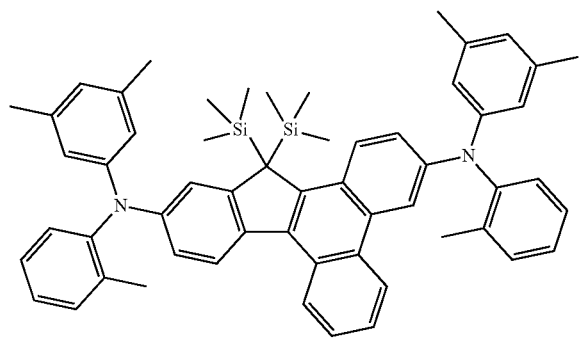
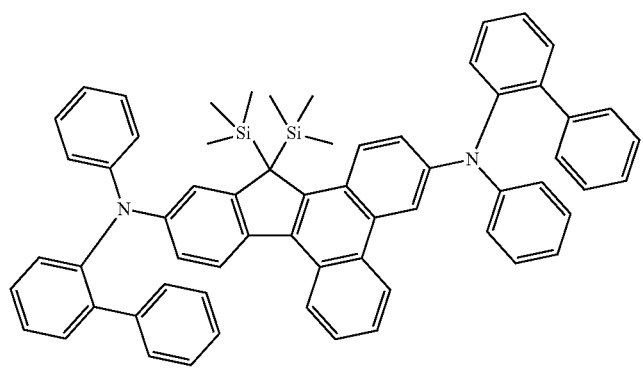
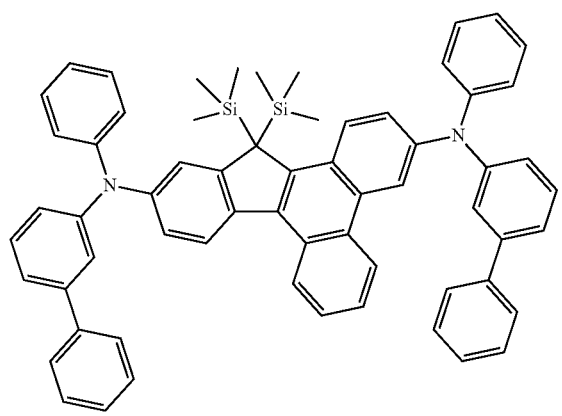
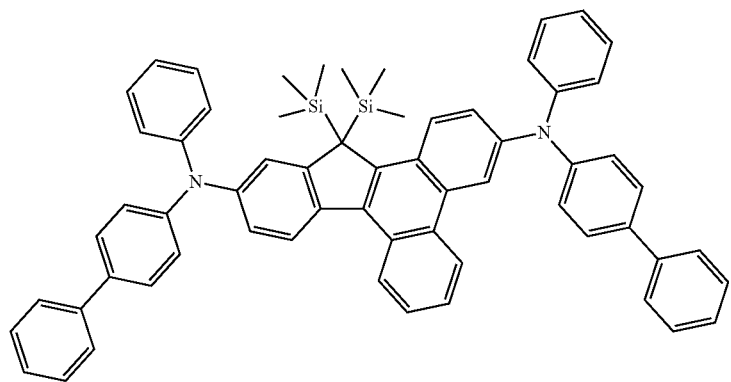

-continued

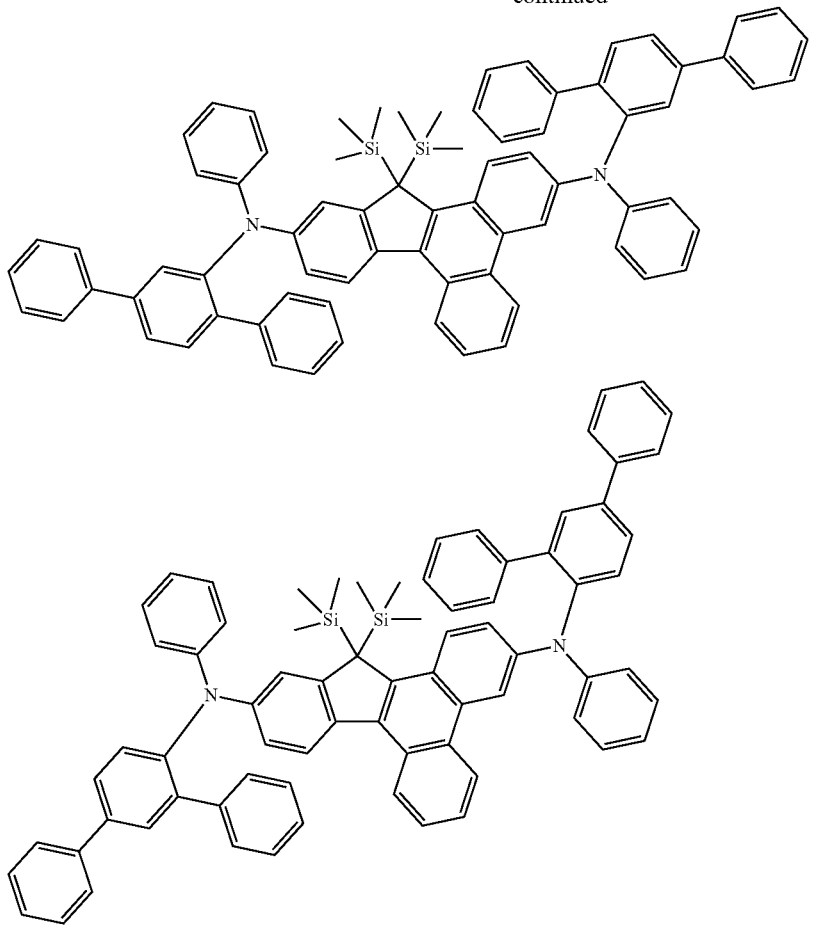

The amine compound mentioned above is useful as a material for organic EL devices, particularly as a dopant material for use in a fluorescent emitting layer. The production method of the amine compound is not particularly limited and one of ordinary skill in the art can easily produce it by utilizing or modifying known synthetic reactions while taking the examples described herein into consideration.

Material for Organic Electroluminescence Devices

The material for organic electroluminescence devices of the invention comprises the amine compound mentioned above. The content of the amine compound in the material for organic electroluminescence devices is not particularly limited and preferably 1 to 100% by mass.

Organic EL Device

The embodiment of the organic EL device of the invention will be described below.

In an embodiment of the invention, the organic EL device comprises an organic thin film layer between a cathode and an anode. The organic thin film layer comprises a light emitting layer and at least one layer of the organic thin film layer comprises the amine compound mentioned above.

Examples of the organic thin film layer which comprises the amine compound include a hole transporting layer, a light emitting layer, a space layer, and a blocking layer, although not limited thereto. The amine compound is preferably used in a light emitting layer, preferably in a fluorescent emitting layer as a dopant material. By using the amine compound, it is expected that the efficiency of an organic EL device is highly improved.

In an embodiment of the invention, the organic EL device may be any of a single color emitting device of fluorescent or phosphorescent type, a white-emitting device of fluorescent/phosphorescent hybrid type, an emitting device of a simple type having a single emission unit, and an emitting device of a tandem type having two or more emission units. The "emission unit" referred to herein is the smallest unit for emitting light by the recombination of injected holes and injected electrons, which comprises one or more organic layers wherein at least one layer is a light emitting layer.

A representative device structures of the simple-type organic EL device is:

(1) anode/emission unit/cathode.

The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below:

(a) hole transporting layer/light emitting layer (/electron transporting layer);
(b) hole transporting layer/first fluorescent emitting layer/second fluorescent emitting layer (/electron transporting layer);
(c) hole transporting layer/phosphorescent emitting layer/space layer/fluorescent emitting layer (/electron transporting layer);

(d) hole transporting layer/first phosphorescent emitting layer/second phosphorescent emitting layer/space layer/fluorescent emitting layer (/electron transporting layer);
(e) hole transporting layer/first phosphorescent emitting layer/space layer/second phosphorescent emitting layer/space layer/fluorescent emitting layer (/electron transporting layer); and
(f) hole transporting layer/phosphorescent emitting layer/space layer/first fluorescent emitting layer/second fluorescent emitting layer (/electron transporting layer).

The emission color of the phosphorescent light emitting layer may be different from that of the fluorescent light emitting layer. For example, the layered structure of the laminated light emitting layer (d) mentioned above may be hole transporting layer/first phosphorescent emitting layer (red emission)/second phosphorescent emitting layer (green emission)/space layer/fluorescent emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to facilitate the charge recombination in the light emitting layer, thereby improving the emission efficiency.

A representative device structure of the tandem-type organic EL device is:
(2) anode/first emission unit/intermediate layer/second emission unit/cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic electroluminescence device in an embodiment of the invention is shown in FIG. 1, wherein the organic EL device 1 comprises a an anode 3, a cathode 4, and an emission unit 10 disposed between the anode 3 and the cathode 4. The emission unit 10 comprises a light emitting layer 5 which comprises at least one fluorescent emitting layer containing a fluorescent host material and a fluorescent dopant material. A hole transporting layer 6 may be disposed between the light emitting layer 5 and the anode 3, and an electron transporting layer 7 may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to facilitate the exciton generation in the light emitting layer 5.

In the present invention, a host is referred to as a fluorescent host when combinedly used with a fluorescent dopant and referred to as a phosphorescent host when combinedly used with a phosphorescent dopant. Therefore, the fluorescent host and the phosphorescent host are not distinguished from each other merely by the difference in their molecular structures. Namely, the term "fluorescent host" means a material for constituting a fluorescent emitting layer containing a fluorescent dopant and does not mean a material that cannot be used in a phosphorescent emitting layer. The same applies to the phosphorescent host.

Substrate

In an embodiment of the invention, the organic EL device is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of the material for anode include indium tin oxide alloy (ITO), tin oxide (NESA), indium zinc oxide, gold, silver, platinum, and cupper. The anode is formed by making the electrode material into a thin film by a method, such as a vapor deposition method and a sputtering method. When getting the light emitted from the light emitting layer through the anode, the transmittance of anode to visible light is preferably 10% or more. The sheet resistance of anode is preferably several hundreds Ω/or less. The film thickness of anode depends upon the kind of material and generally 10 nm to 1 μm, preferably 10 to 200 nm. When the light transmittance of the thin film, the sheet resistance, and the film thickness are within the above ranges, the increase in the driving voltage and the decrease in the luminance are preferably prevented.

Cathode

The cathode injects electrons to an electron injecting layer, an electron transporting layer or a light emitting layer, and formed preferably by a material having a small work function. Examples of the material for cathode include, but not limited to, indium, aluminum, magnesium, a magnesium-indium alloy, a magnesium-aluminum alloy, an aluminum-lithium alloy, an aluminum-scandium-lithium alloy, and a magnesium-silver alloy. Like the anode, the cathode is formed by making the material into a thin film by a method, such as a vapor deposition method and a sputtering method. The emitted light may be taken through the cathode, if necessary.

Light Emitting Layer

The light emitting layer is an organic layer having a light emitting function and comprises a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, the light emitting layer may be a double host (host/co-host) layer, for example, a layer in which an electron transporting host and a hole transporting host are combinedly used.

The light emitting layer may be a double dopant layer in which two or more kinds of dopant materials having a high quantum yield are combinedly used and each dopant emits light with its own color. For example, a common light emitting layer formed by co-depositing a host, a red-emitting dopant and a green-emitting dopant emits yellow light.

The quantum efficiency of the light emitting layer can be improved by a laminate of two or more light emitting layers, because electrons and holes are accumulated in the interface between the light emitting layers, and therefore, the recombination region is localized in the interface between the light emitting layers.

The easiness of hole injection to the light emitting layer and the easiness of electron injection to the light emitting layer may be different from each other. Also, the hole transporting ability and the electron transporting ability each being expressed by mobility of holes and electrons in the light emitting layer may be different from each other.

The light emitting layer is formed, for example, by a known method, such as a vapor deposition method, a spin coating method, and LB method. The light emitting layer can be formed also by making a solution of a binder, such as resin, and the material for the light emitting layer in a solvent into a thin film by a method, such as a spin coating method.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The thickness of the light emitting layer is preferably 5 to 50 nm, more preferably 7 to 50 nm, and still more preferably 10 to 50 nm. If 5 nm or more, the light emitting layer can be formed easily. If 50 nm or less, the increase in the driving voltage can be prevented.

Dopant

The fluorescent dopant (fluorescent emitting material) used in the light emitting layer is a compound which emits light by releasing the energy of excited singlet state and is not particularly limited as long as capable of emitting light by releasing the energy of excited singlet state. The amine compound represented by formula (1) of the invention is preferably used as the fluorescent dopant. Other examples of the fluorescent dopant include a fluoranthene derivative, a styrylarylene derivative, a pyrene derivative, an arylacetylene derivative, a fluorene derivative, a boron complex, a perylene derivative, an oxadiazole derivative, an anthracene derivative, a styrylamine derivative, and an arylamine derivative, with an anthracene derivative, a fluoranthene derivative, a styrylamine derivative, an arylamine derivative, a styrylarylene derivative, a pyrene derivative, and a boron complex being preferred, and an anthracene derivative, a fluoranthene derivative, a styrylamine derivative, an arylamine derivative, and a boron complex being more preferred.

The content of the fluorescent dopant in the light emitting layer is not particularly limited and selected according to the use of the device, and preferably 0.1 to 70% by mass, more preferably 1 to 30% by mass, and still more preferably 1 to 20% by mass, and still further preferably 1 to 10% by mass. If being 0.1% by mass or more, the amount of light emission is sufficient. If being 70% by mass or less, the concentration quenching can be avoided.

Host Material

An anthracene derivative or a polycyclic aromatic compound, preferably an anthracene derivative is preferably used as the host for the light emitting layer.

For example, the following anthracene derivative represented by formula (5) is used as the host for a blue emitting layer:

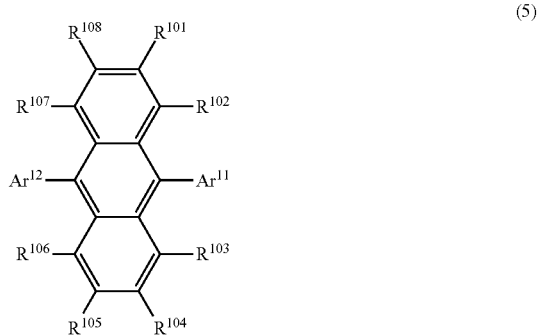

(5)

wherein $Ar^{11}$ and $Ar^{12}$ each independently represent a substituted or unsubstituted monocyclic group having 5 to 50 ring atoms or a substituted or unsubstituted fused ring group having 8 to 50 ring atoms; and $R^{101}$ to $R^{108}$ each independently represent a group selected from a hydrogen atom; a substituted or unsubstituted monocyclic group having 5 to 50, preferably 5 to 30, more preferably 5 to 20, and still more preferably 5 to 12 ring atoms; a substituted or unsubstituted fused ring group having 8 to 50, preferably 8 to 30, more preferably 8 to 20, and still more preferably 8 to 14 ring atoms; a group comprising a combination of the monocyclic group and the fused ring group; a substituted or unsubstituted alkyl group having 1 to 50, preferably 1 to 20, more preferably 1 to 10, and still more preferably 1 to 6 carbon atoms; a substituted or unsubstituted cycloalkyl group having 3 to 50, preferably 3 to 20, more preferably 3 to 10, and still more preferably 5 to 8 ring carbon atoms; a substituted or unsubstituted alkoxy group having 1 to 50, preferably 1 to 20, more preferably 1 to 10, and still more preferably 1 to 6 carbon atoms; a substituted or unsubstituted aralkyl group having 7 to 50, preferably 7 to 20, more preferably 7 to 14 carbon atoms; a substituted or unsubstituted aryloxy group having 6 to 50, preferably 6 to 20, more preferably 6 to 12 ring carbon atoms; a substituted or unsubstituted silyl group; a halogen atom; and a cyano group.

In a preferred anthracene derivative, $R^{101}$ to $R^{108}$ are all hydrogen atoms. In another preferred anthracene derivative, one of $R^{101}$ and $R^{108}$, one of $R^{104}$ and $R^{105}$, both of $R^{101}$ and $R^{105}$, or both of $R^{108}$ and $R^{104}$ are selected from a monocyclic group having 5 to 50 ring atoms, preferably a phenyl group, a biphenylyl group, and a terphenylyl group; a substituted or unsubstituted alkyl group having 1 to 50 carbon atoms, preferably a methyl group, an ethyl group, a n-propyl group, an isopropyl group, a n-butyl group, an isobutyl group, a s-butyl group, and a t-butyl group; and a substituted silyl group, preferably a trimethylsilyl group. An anthracene derivative wherein $R^{101}$ to $R^{108}$ are all hydrogen atoms is more preferred.

The monocyclic group of formula (5) is a group composed of only a non-fused ring structure.

Examples of the monocyclic group having 5 to 50 ring atoms include an aromatic group, such as a phenyl group, a biphenylyl group, a terphenylyl group, and a quaterphenylyl group; and a heterocyclic group, such as a pyridyl group, a pyrazyl group, a pyrimidyl group, a triazinyl group, a furyl group, and a thienyl group, with a phenyl group, a biphenylyl group, and a terphenylyl group being preferred.

The fused ring group of formula (5) is a group wherein two or more ring structures are fused to each other.

Examples of the fused ring group having 8 to 50 ring atoms include a fused aromatic ring group, such as a naphthyl group, a phenanthryl group, an anthryl group, a chrysenyl group, a benzanthryl group, a benzophenanthryl group, a triphenylenyl group, a benzochrysenyl group, an indenyl group, a fluorenyl group, a 9, 9-dimethylfluorenyl group, a benzofluorenyl group, a dibenzofluorenyl group, a fluoranthenyl group, and a benzofluoranthenyl group; and a fused heterocyclic group, such as a benzofuranyl group, a benzothiophenyl group, an indolyl group, a dibenzofuranyl group, a dibenzothiophenyl group, a carbazolyl group, a quinolyl group, and a phenanthrolinyl group; with a naphthyl group, a phenanthryl group, an anthryl group, a 9, 9-dimethylfluorenyl group, a fluoranthenyl group, a benzanthryl group, a dibenzothiophenyl group, a dibenzofuranyl group, and a carbazolyl group being preferred.

The substituent of $Ar^{11}$ and $Ar^{12}$ is preferably selected from the monocyclic groups and the fused ring groups mentioned above.

In formula (5), examples of the alkyl group, the cycloalkyl group, the alkoxy group, the aralkyl group, the aryloxy group, the substituted silyl group, and the halogen atom are the same as those mentioned above with respect to $R^1$ to $R^{14}$ of formulae (2) and (3) and those mentioned above with respect to the optional substituents.

Preferred examples of formula (5) will be described below.

The anthracene derivative represented by formula (5) is preferably any of the following anthracene derivatives (A), (B) and (C), which are selected according to the constitution and the required properties of the organic EL device to which the anthracene derivative is applied.

Anthracene Derivative (A)

The anthracene derivative (A) is represented by formula (5) wherein $Ar^{11}$ and $Ar^{12}$ may be the same or different and each independently represent a substituted or unsubstituted fused ring group having 8 to 50 ring atoms.

An anthracene derivative wherein $Ar^{11}$ and $Ar^{12}$ of formula (5) are different substituted or unsubstituted fused ring groups (inclusive of the difference in the positions connecting to the anthracene ring) is particularly preferable. Examples of the fused ring are as described above, with a naphthyl group, a phenanthryl group, a benzanthryl group, a 9, 9-dimethylfluorenyl group, and a dibenzofuranyl group being preferred.

Anthracene Derivative (B)

The anthracene derivative (B) is represented by formula (5) wherein one of $Ar^{11}$ and $Ar^{12}$ is a substituted or unsubstituted monocyclic group having 5 to 50 ring atoms and the other is a substituted or unsubstituted fused ring group having 8 to 50 ring atoms.

In a preferred anthracene derivative (B), $Ar^{12}$ is a naphthyl group, a phenanthryl group, a benzanthryl group, a 9, 9-dimethylfluorenyl group, or a dibenzofuranyl group; and $Ar^{11}$ is an unsubstituted phenyl group or a substituted phenyl group having a substituent selected from the monocyclic group and the fused ring group.

Preferred examples of the monocyclic group and the fused ring group are as described above.

In another preferred anthracene derivative (B), $Ar^{12}$ is the fused ring group and $Ar^{11}$ is an unsubstituted phenyl group. The fused ring group is particularly preferably a phenanthryl group, a 9, 9-dimethylfluorenyl group, a dibenzofuranyl group, or a benzanthryl group.

Anthracene Derivative (C)

The anthracene derivative (C) is represented by formula (5) wherein $Ar^{11}$ and $Ar^{12}$ each independently represent a substituted or unsubstituted monocyclic group having 5 to 50 ring atoms.

In a preferred anthracene derivative (C), both of $Ar^{11}$ and $Ar^{12}$ are substituted or unsubstituted phenyl groups.

In a more preferred anthracene derivative (C), $Ar^{11}$ is an unsubstituted phenyl group and $Ar^{12}$ is a phenyl group having a substituent selected from the monocyclic group and the fused ring group; or $Ar^{11}$ and $Ar^{12}$ each independently represent a phenyl group having a substituent selected from the monocyclic group and the fused ring group.

Examples of the monocyclic substituent and the fused ring substituent are as described above. The monocyclic substituent is preferably a phenyl group and a biphenyl group, and the fused ring substituent is preferably a naphthyl group, a phenanthryl group, a 9, 9-dimethylfluorenyl group, a dibenzofuranyl group, and a benzanthryl group.

Examples of the anthracene derivative represented by formula (5) are described below.

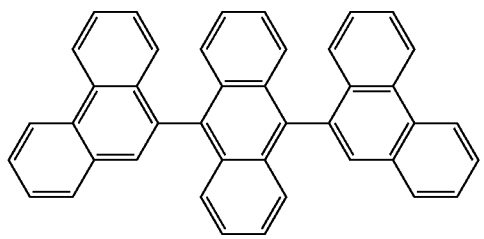

EM1

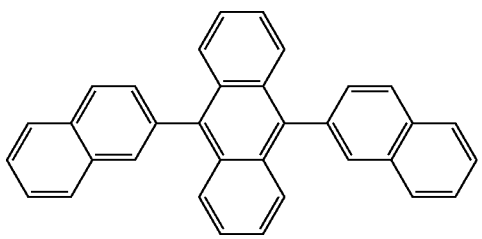

EM2

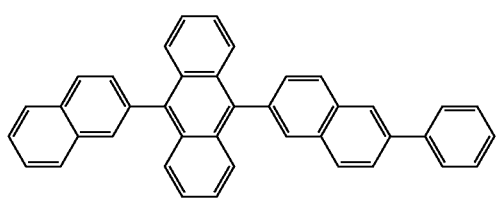

EM3

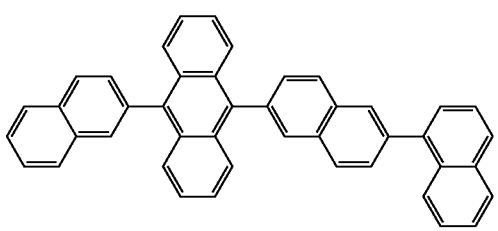

EM4

-continued
EM5
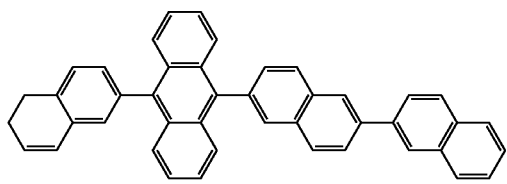
EM6
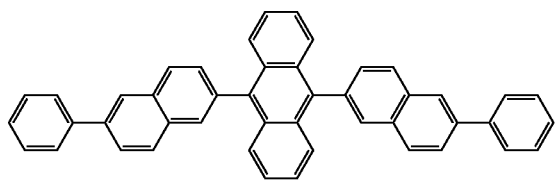
EM7
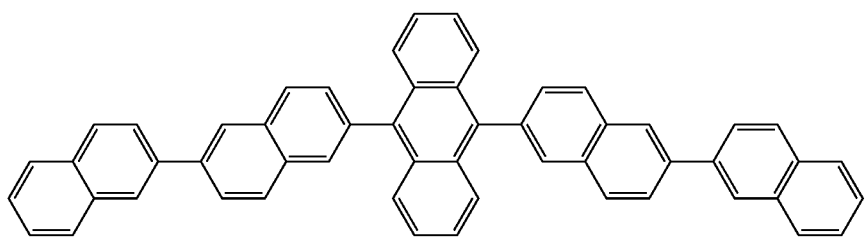
EM8
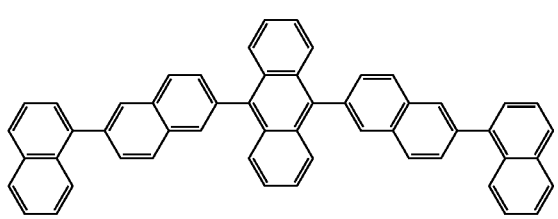
EM9
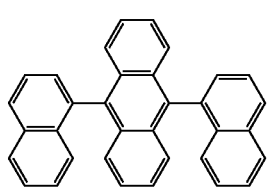
EM10
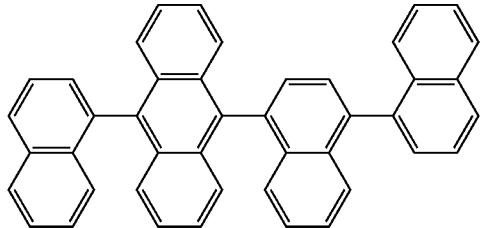
EM11
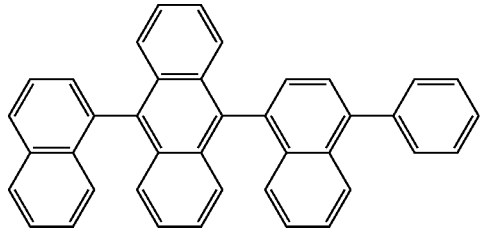
EM12
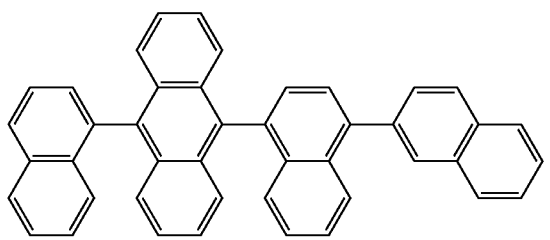
EM13
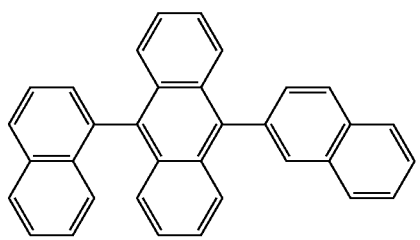
EM14
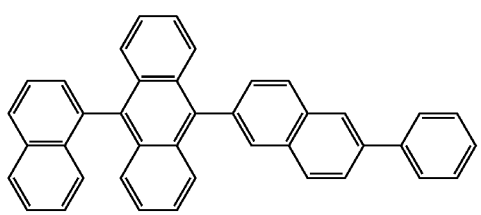
EM15
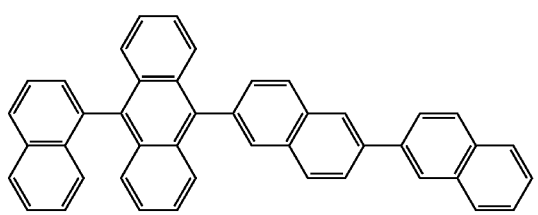

-continued

EM16, EM17, EM18, EM19, EM20, EM21, EM22, EM23, EM24, EM25, EM26, EM27

-continued
EM28
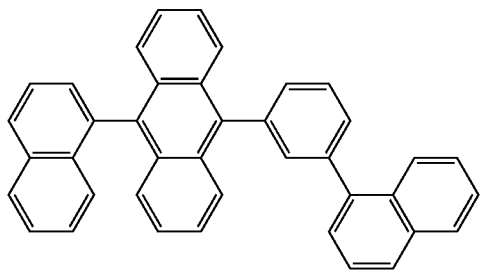
EM29
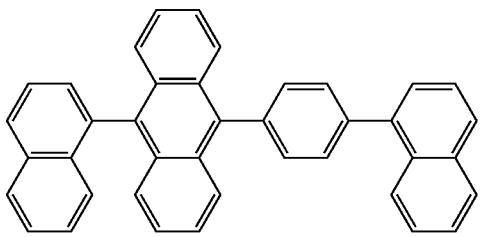
EM30
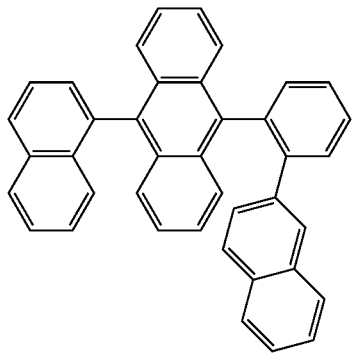
EM31
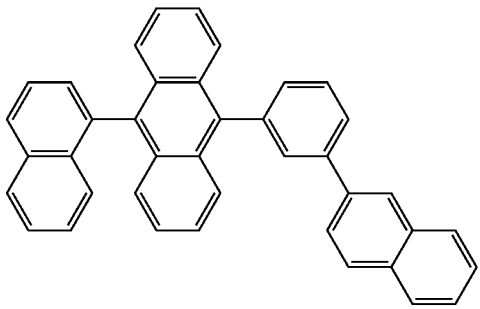
EM32
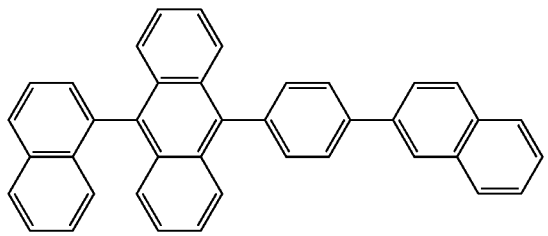
EM33
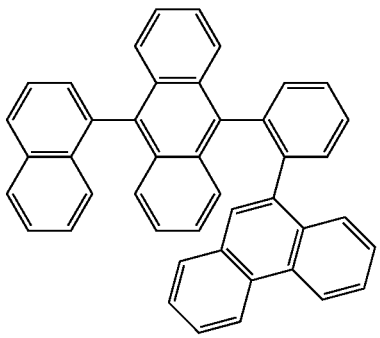
EM34
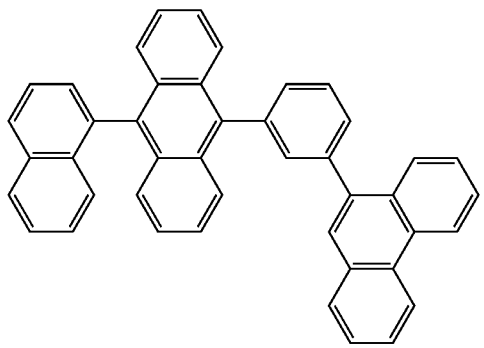
EM35
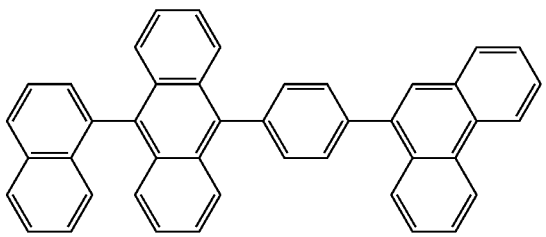
EM36
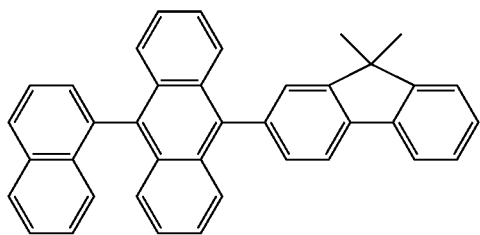
EM37
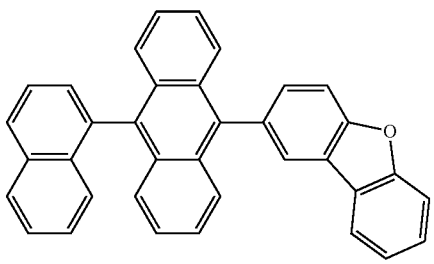

-continued
EM38
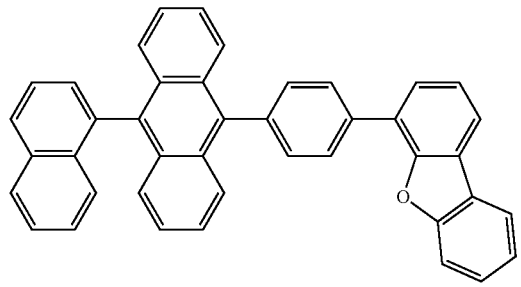
EM39
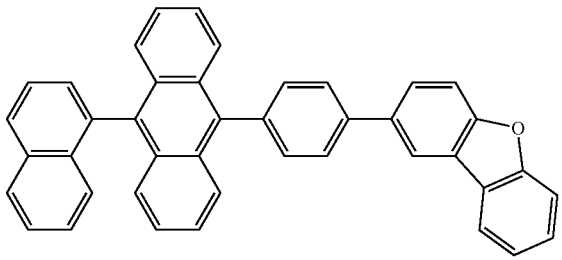
EM40
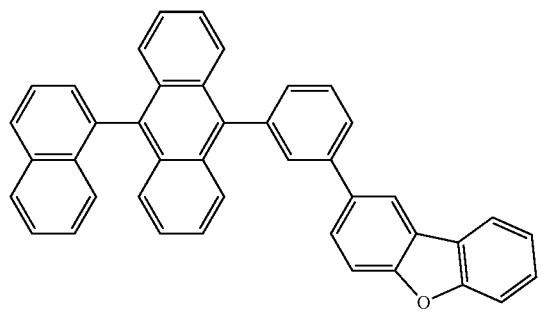
EM41
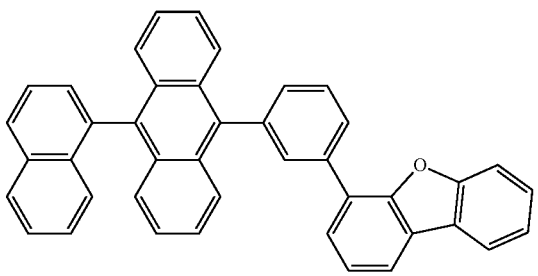
EM42
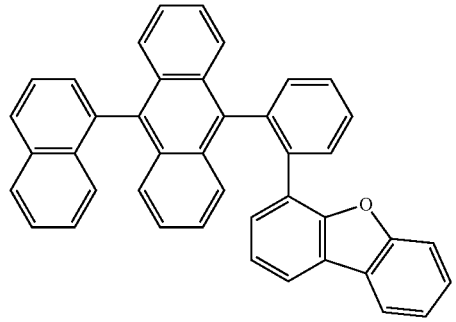
EM43
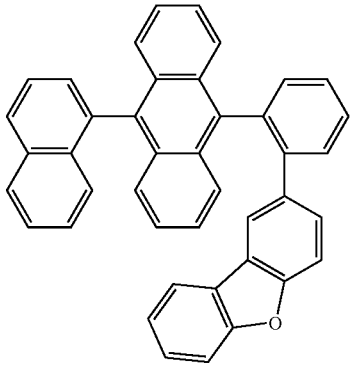
EM44
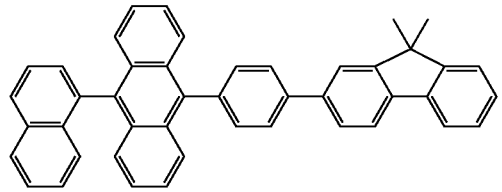
EM45
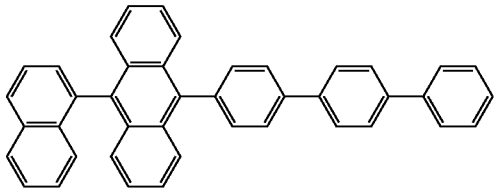
EM46
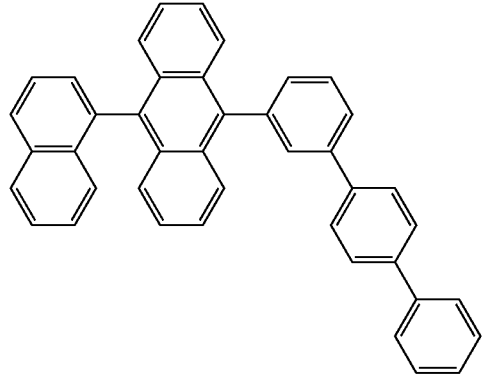
EM47
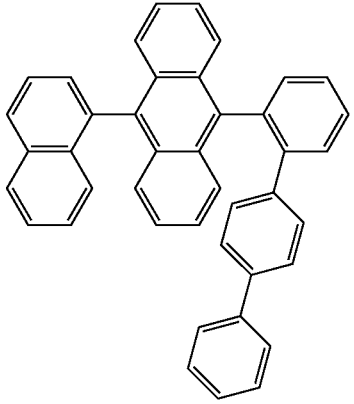

-continued
EM48
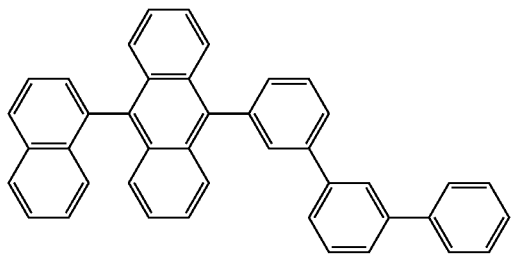
EM49
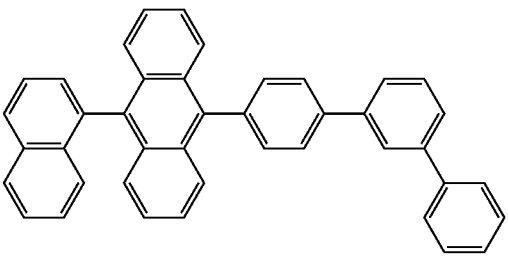
EM50
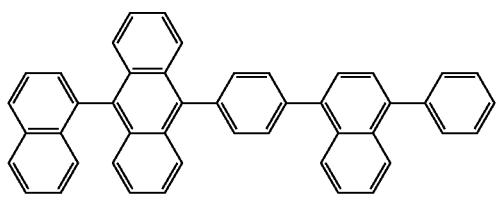
EM51
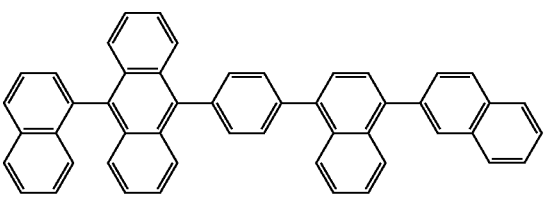
EM52
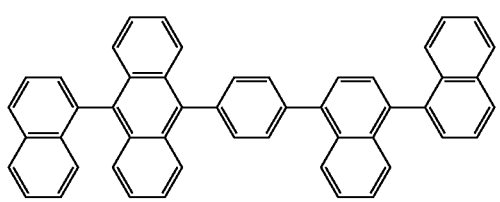
EM53
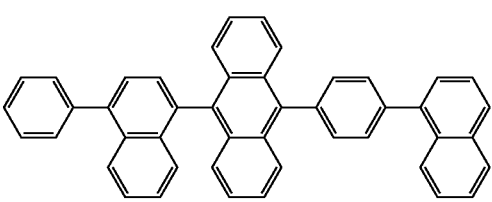
EM54
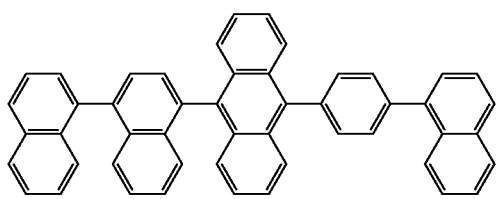
EM55
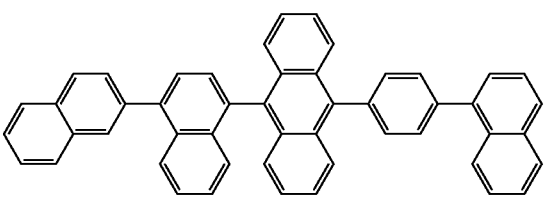
EM56
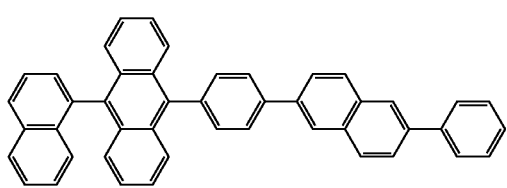
EM57
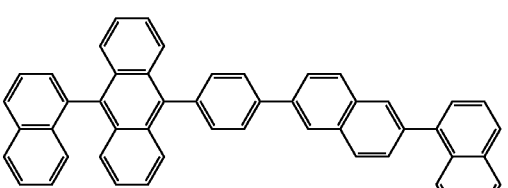
EM58
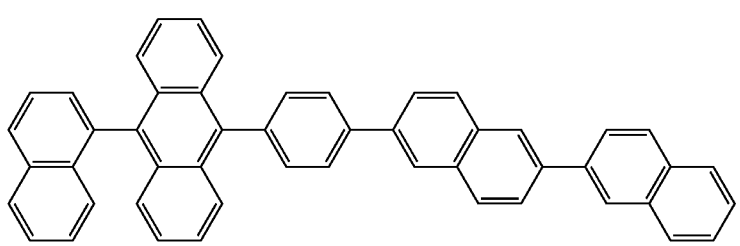

-continued
EM59
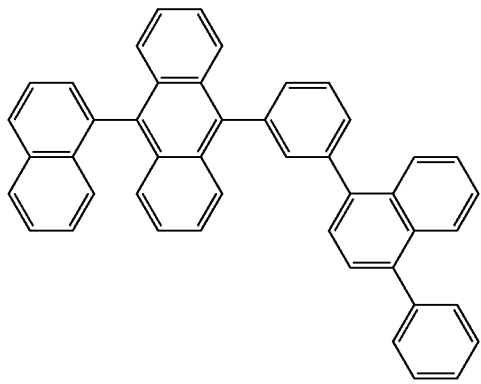
EM60
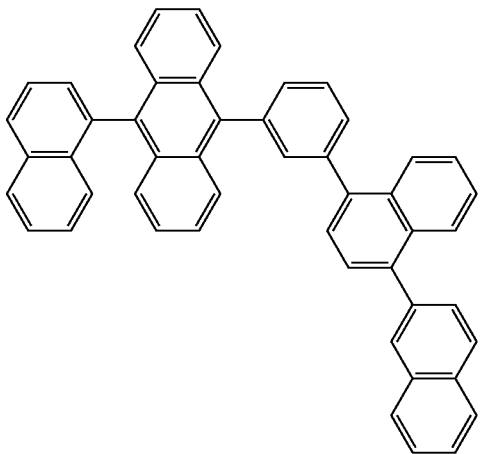
EM61
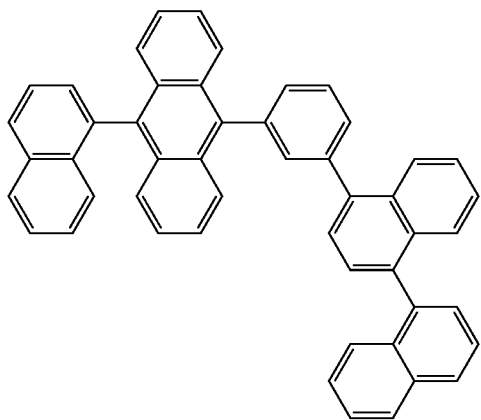
EM62
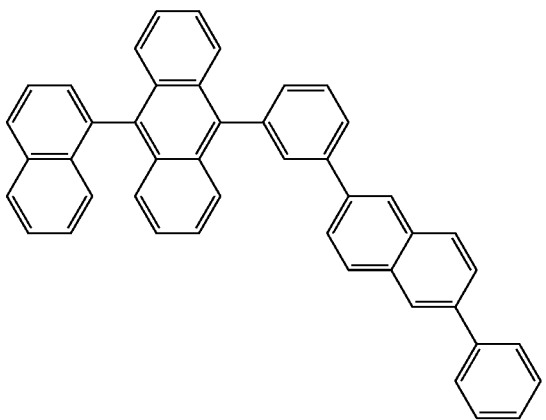
EM63
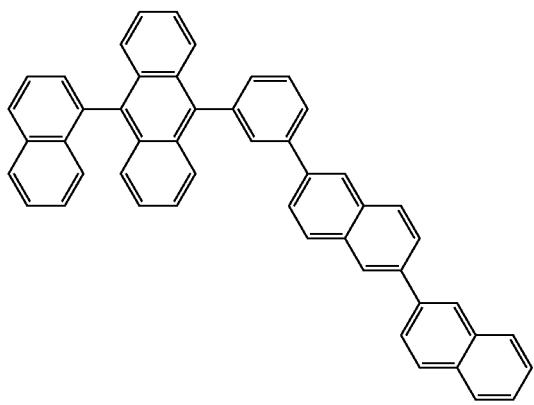
EM64
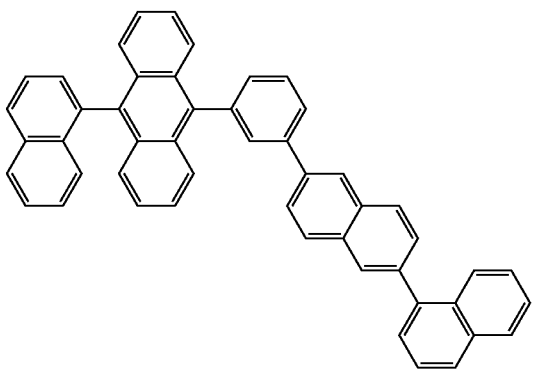
EM65
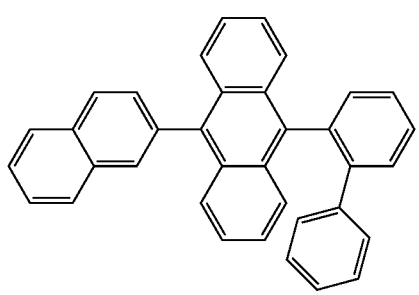
EM66
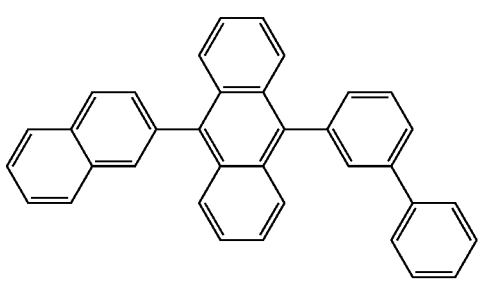

-continued
EM67
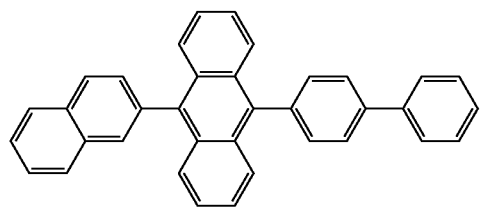
EM68
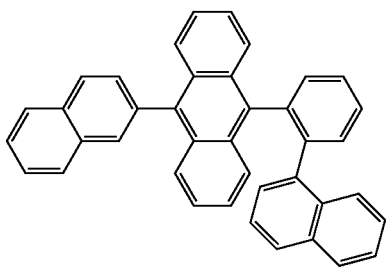
EM69
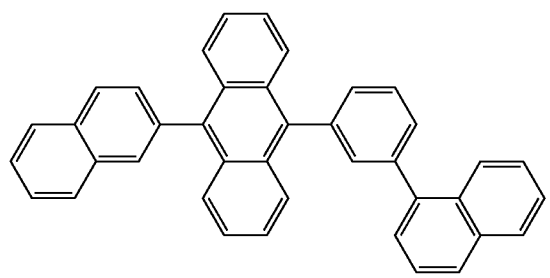
EM70
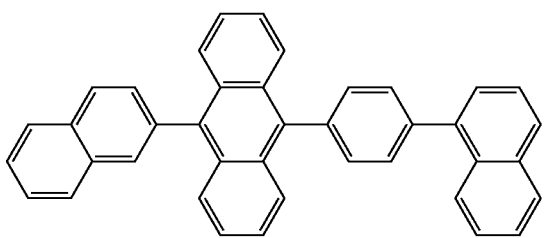
EM71
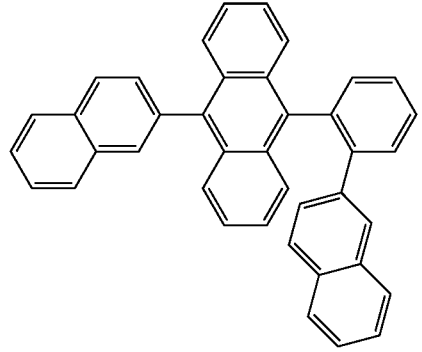
EM72
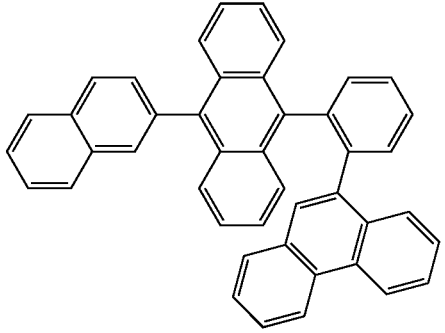
EM73
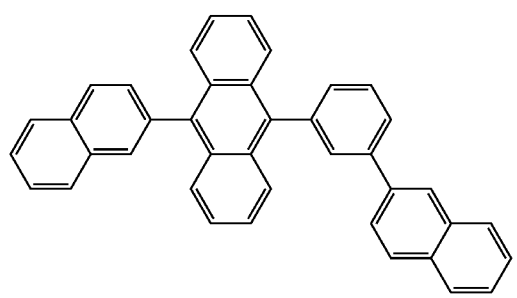
EM74
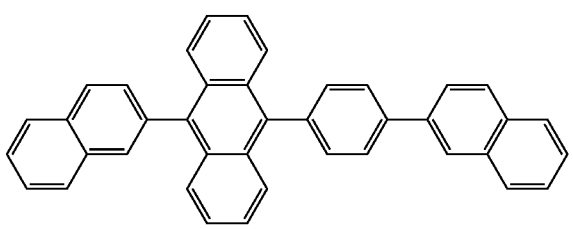
EM75
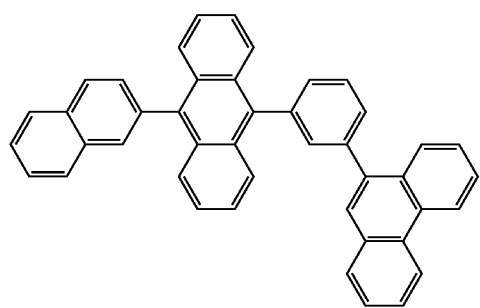
EM76
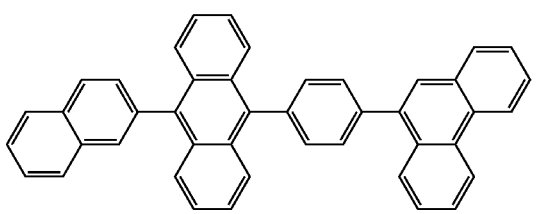

-continued
EM77
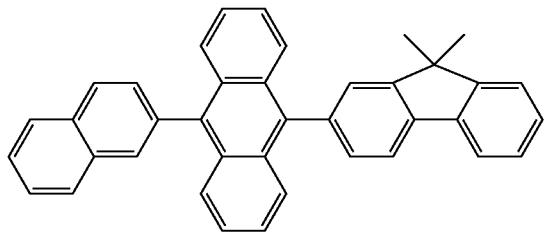
EM78
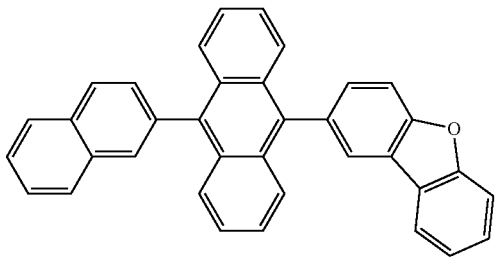
EM79
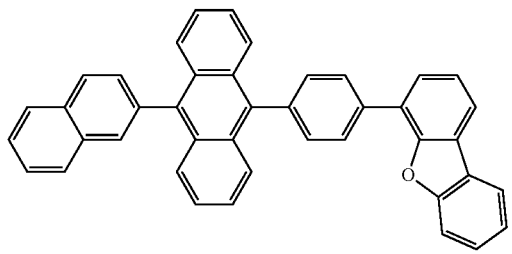
EM80
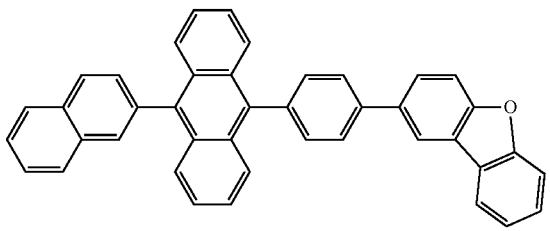
EM81
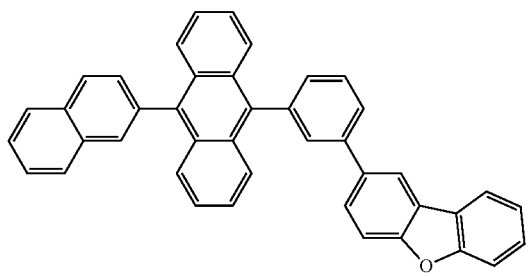
EM82
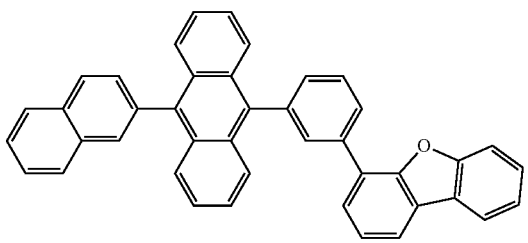
EM83
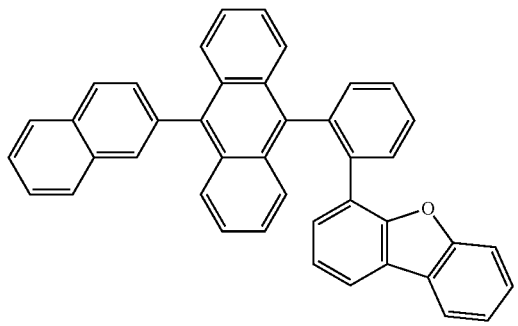
EM84
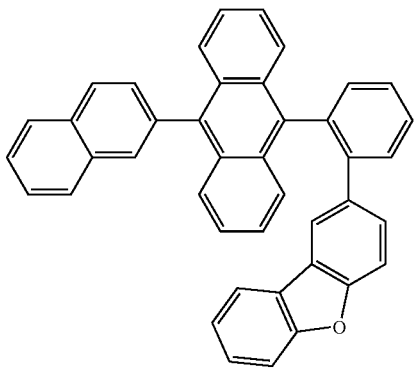
EM85
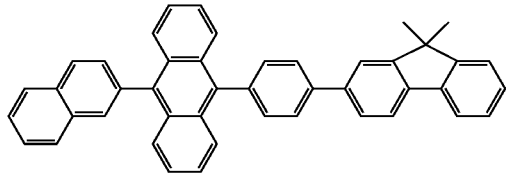
EM86
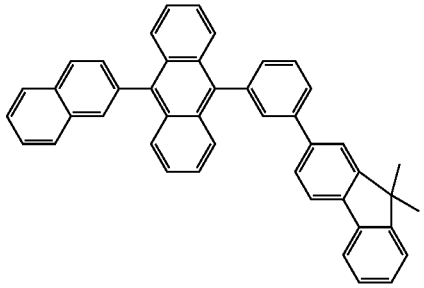

EM87
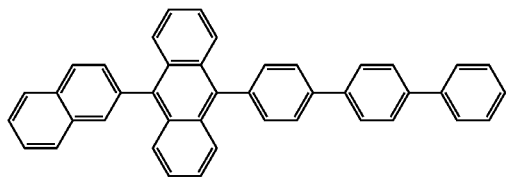
EM88
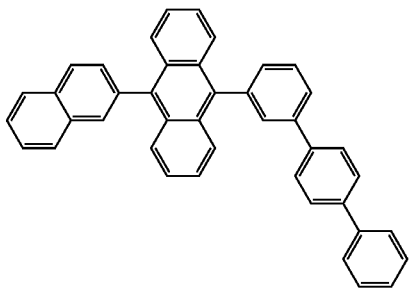
EM89
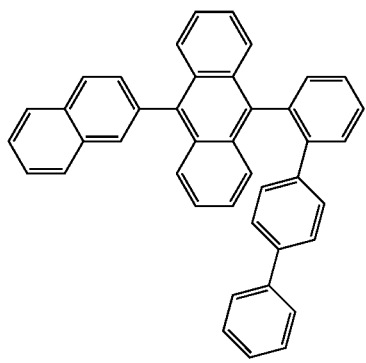
EM90
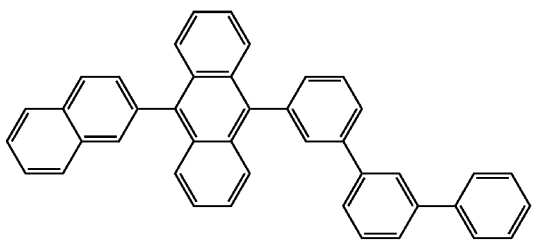
EM91
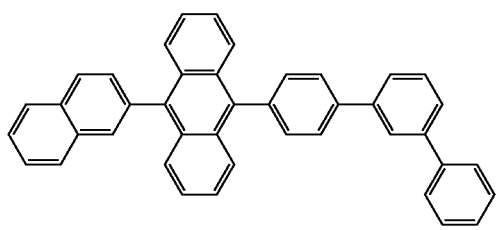
EM92
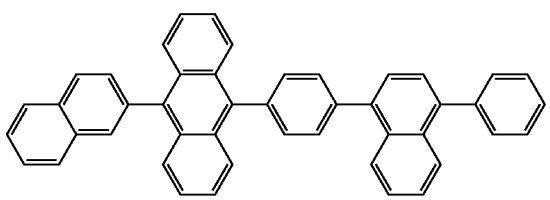
EM93
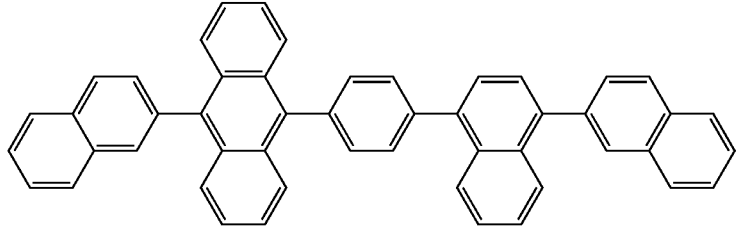
EM94
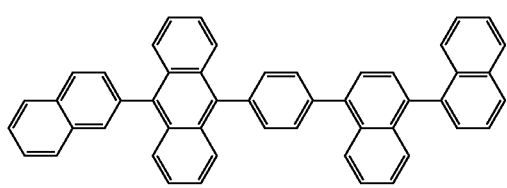
EM95
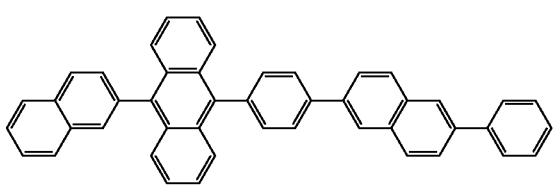
EM96
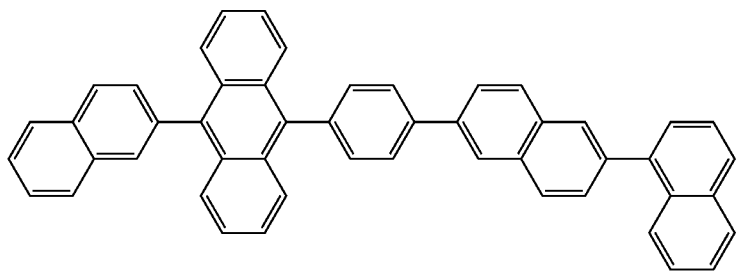

EM97
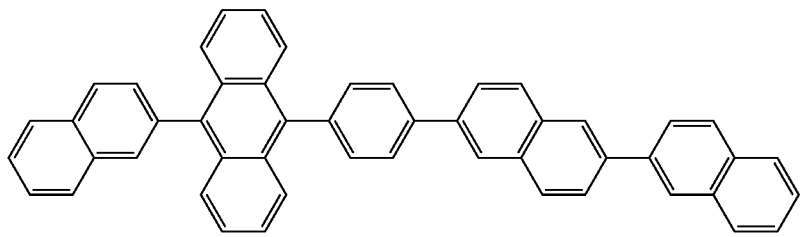
EM98
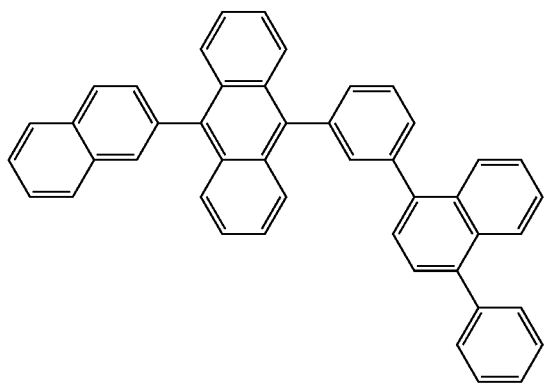
EM99
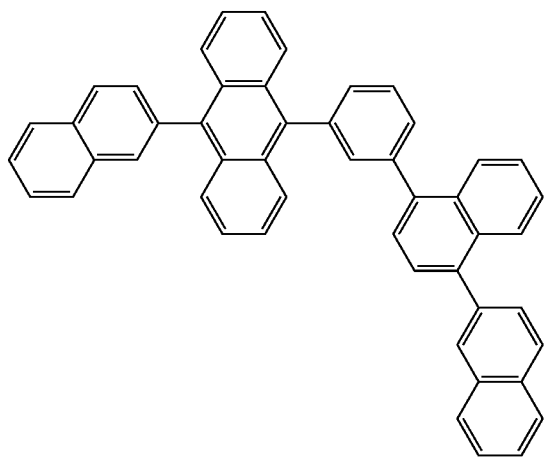
EM100
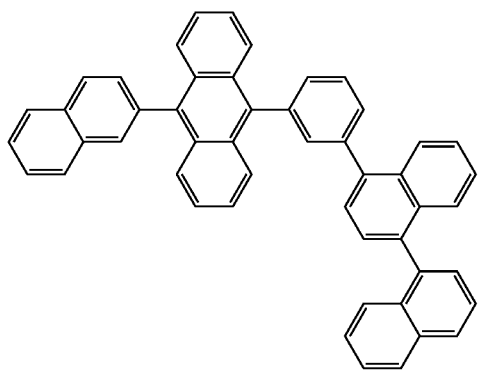
EM101
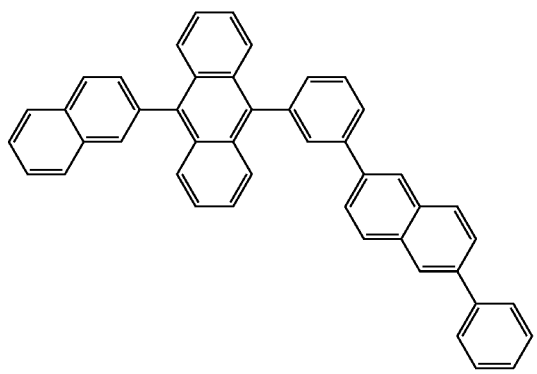
EM102
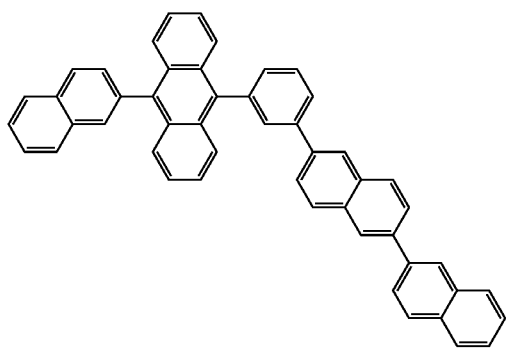
EM103
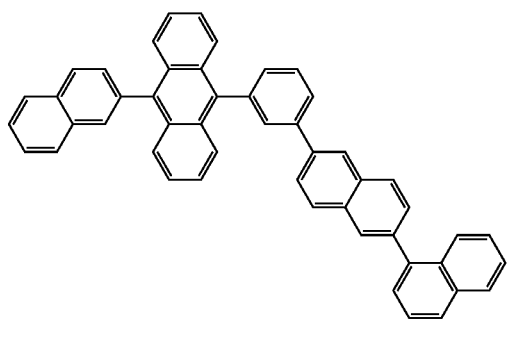

-continued
EM104
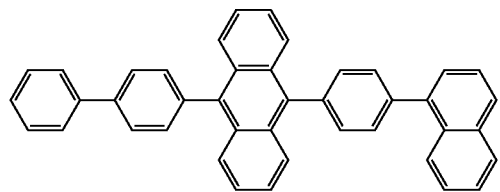
EM105
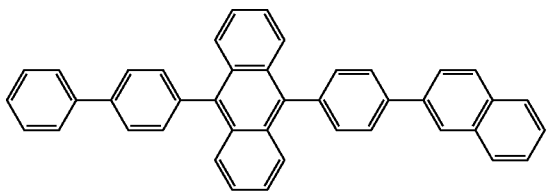
EM106
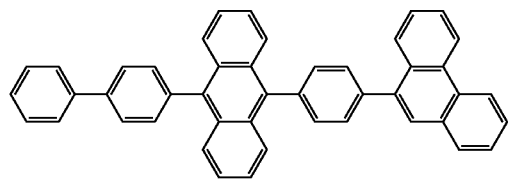
EM107
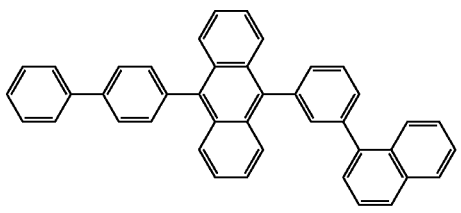
EM108
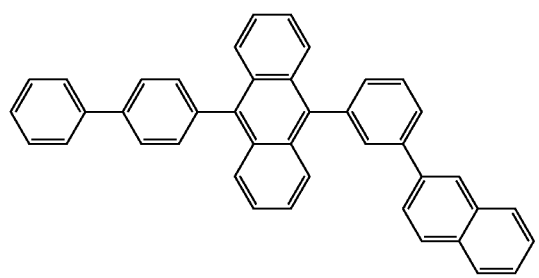
EM109
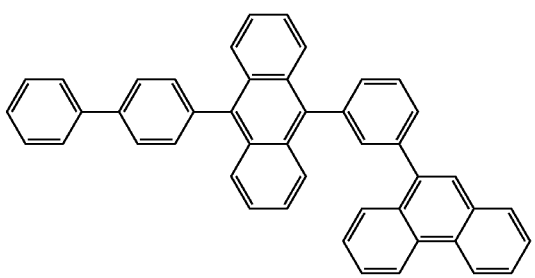
EM110
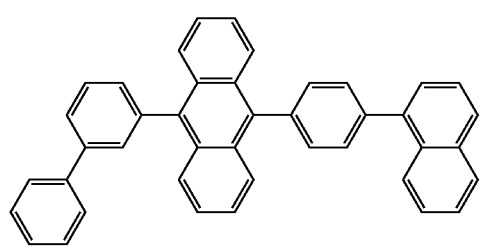
EM111
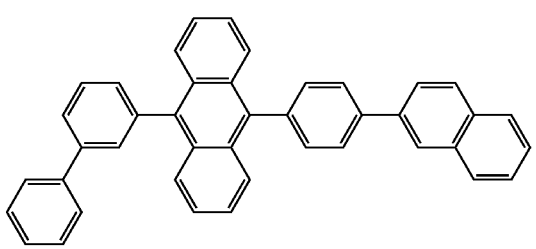
EM112
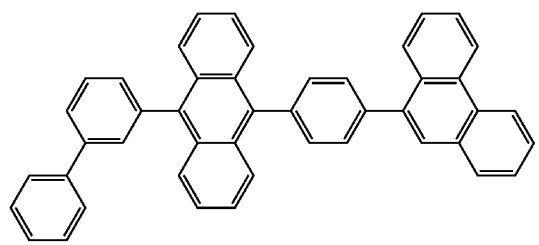
EM113
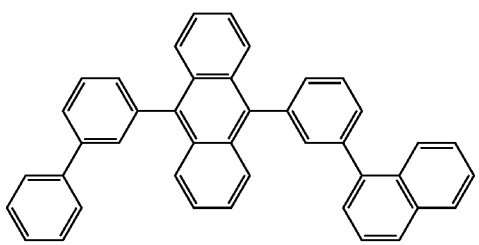
EM114
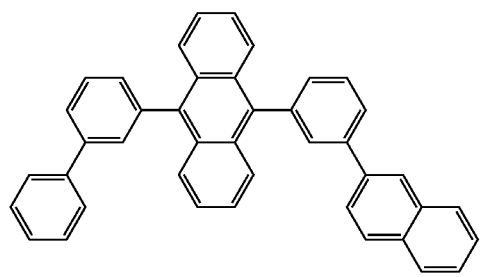
EM115
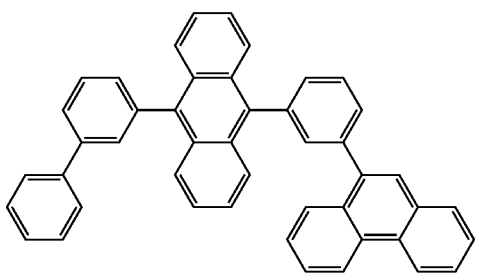

-continued
EM116
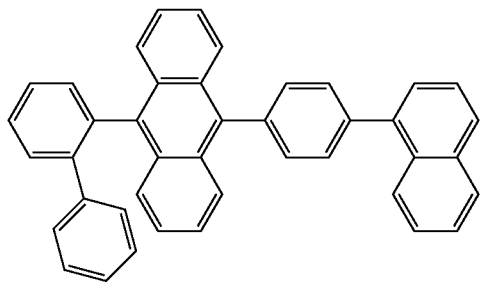
EM117
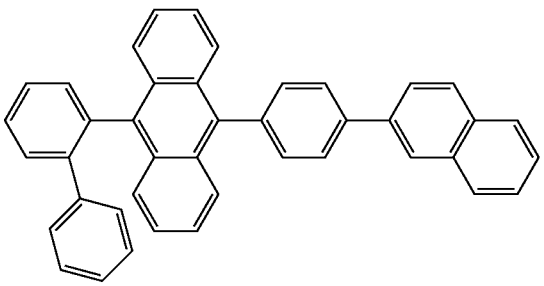
EM118
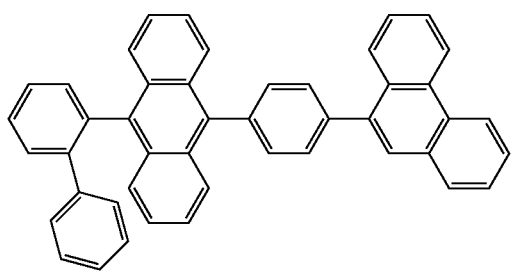
EM119
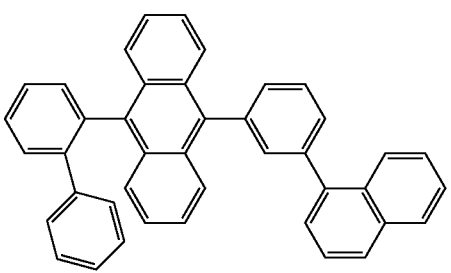
EM120
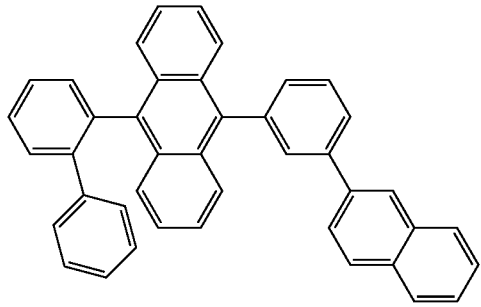
EM121
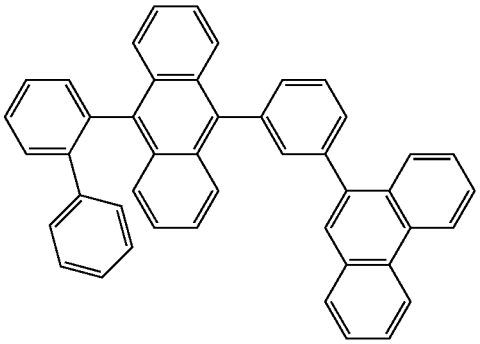
EM122
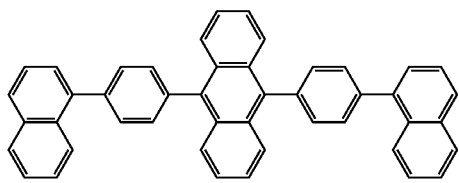
EM123
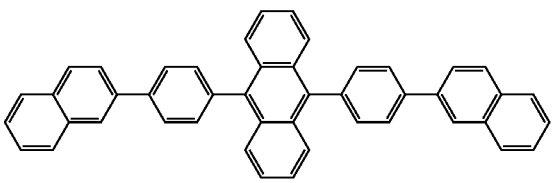
EM124
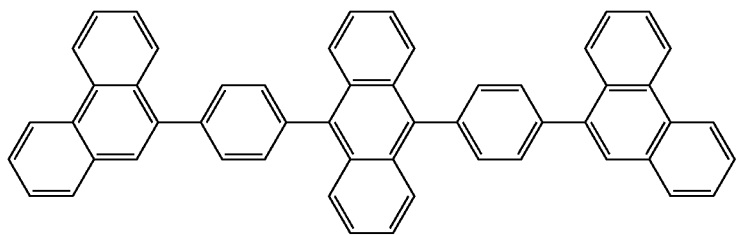
EM125
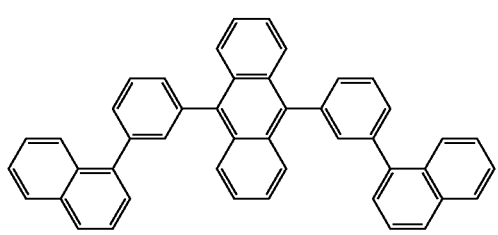
EM126
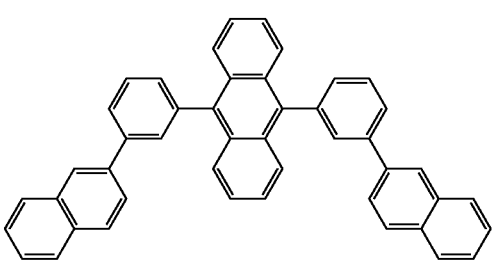

-continued
EM127
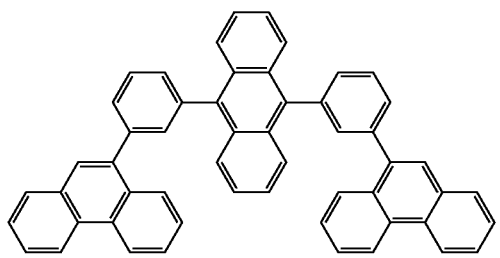
EM128
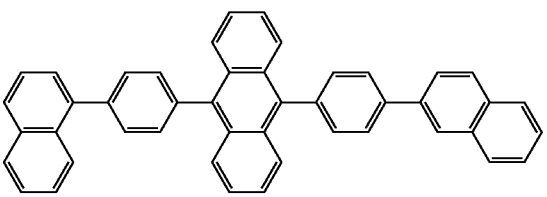
EM129
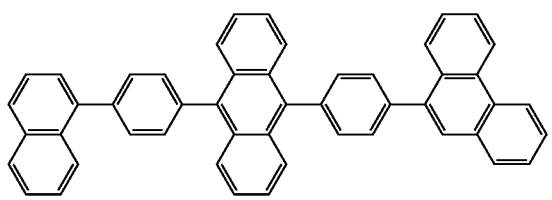
EM130
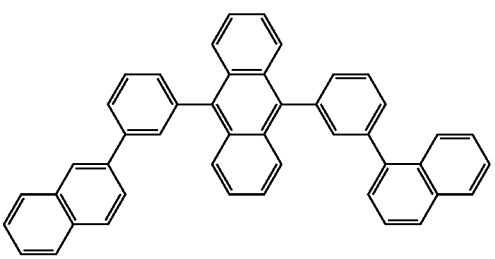
EM131
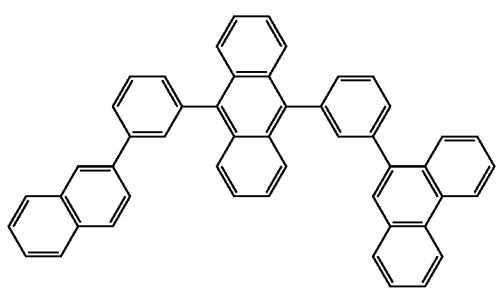
EM132
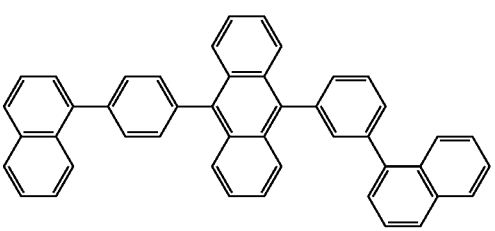
EM133
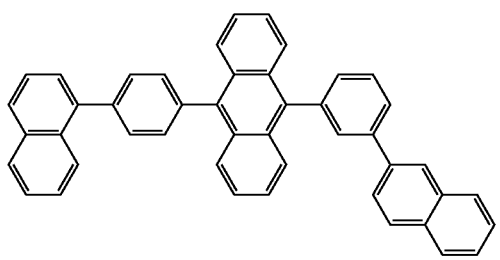
EM134
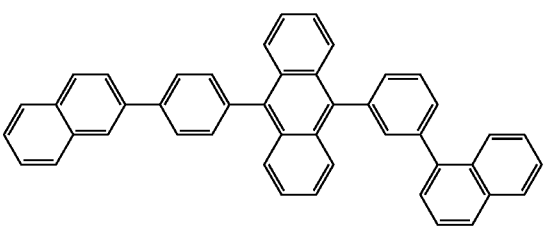
EM135
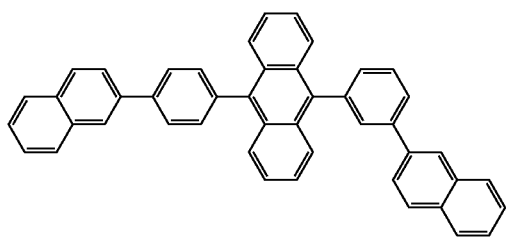
EM136
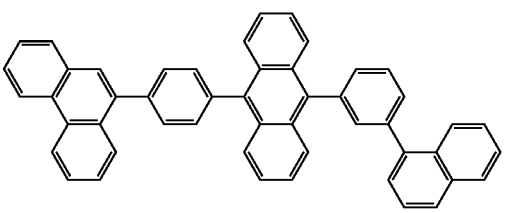

-continued
EM137
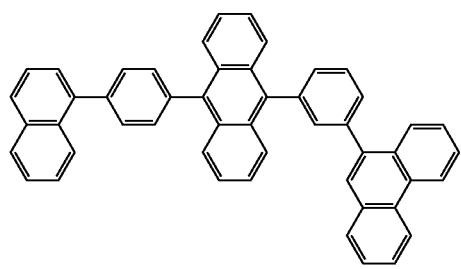
EM138
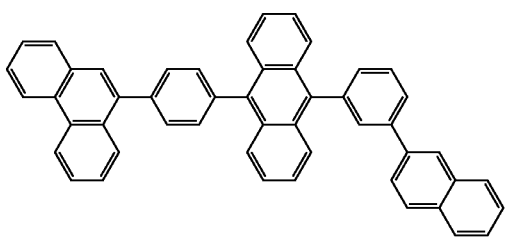
EM139
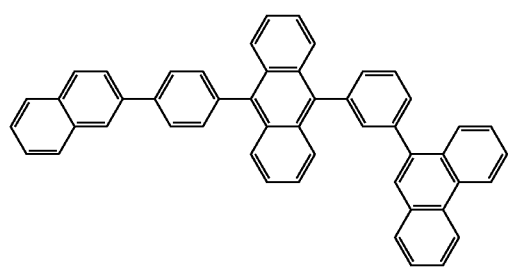
EM140
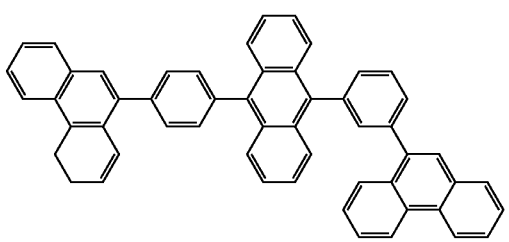
EM141
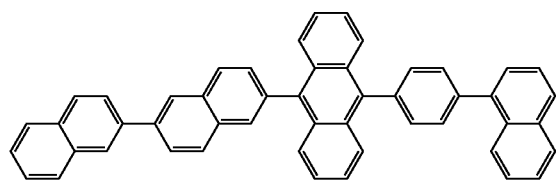
EM142
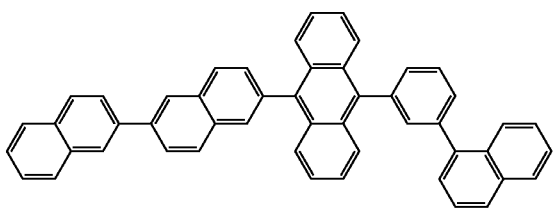
EM143
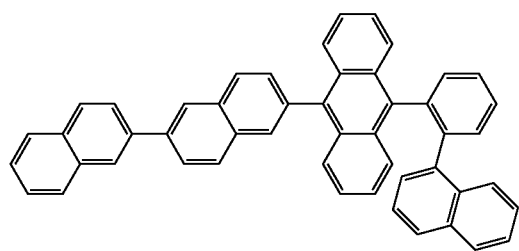
EM144
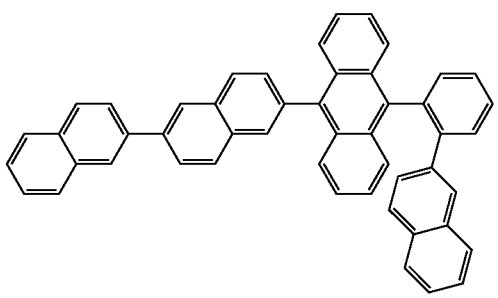
EM145
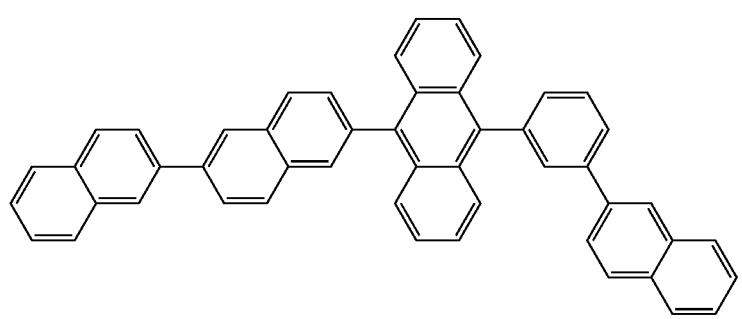

-continued
EM146
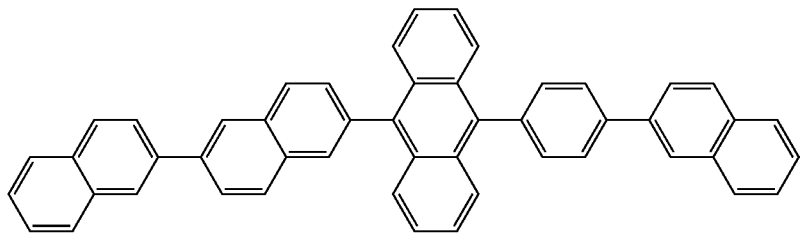
EM147
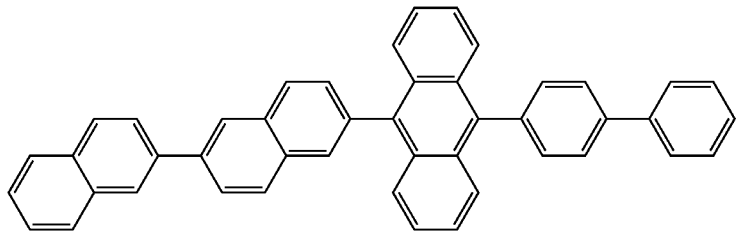
EM148
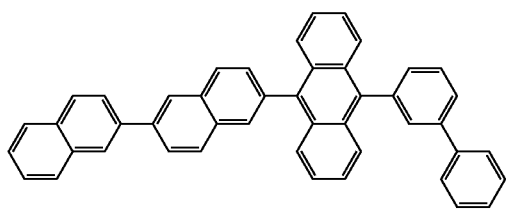
EM149
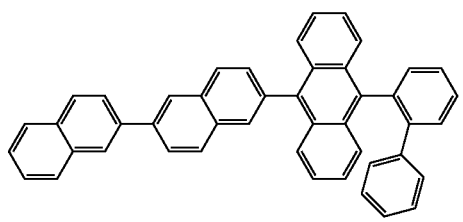
EM150
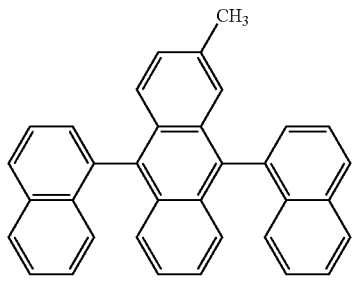
EM151
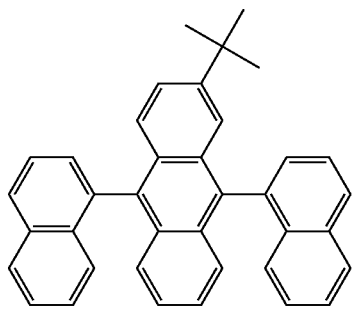
EM152
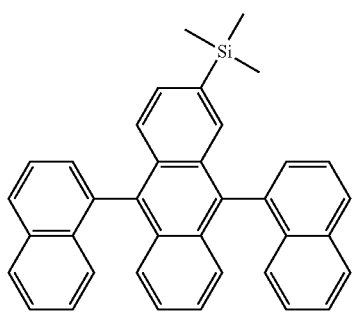
EM153
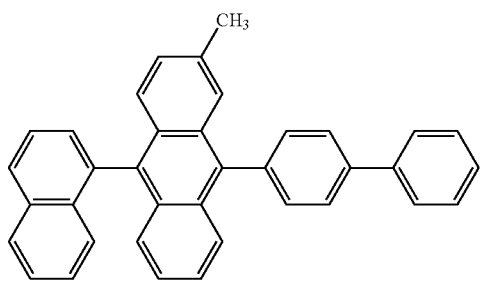

-continued
EM154
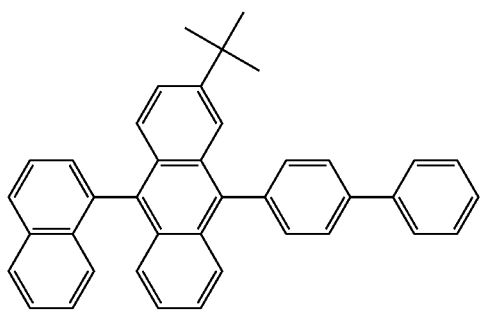
EM155
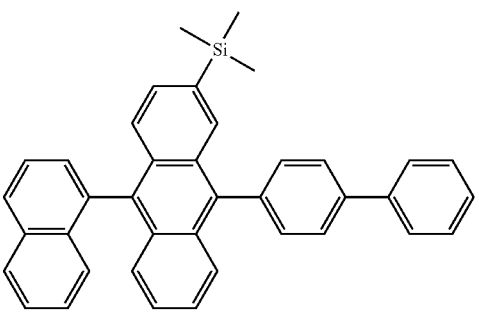
EM156
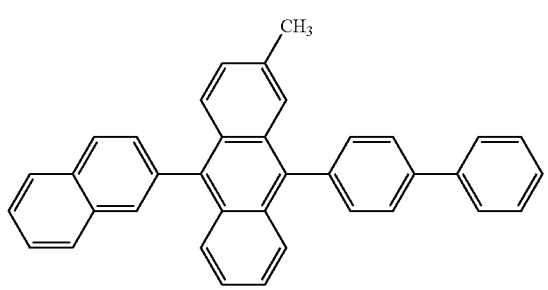
EM157
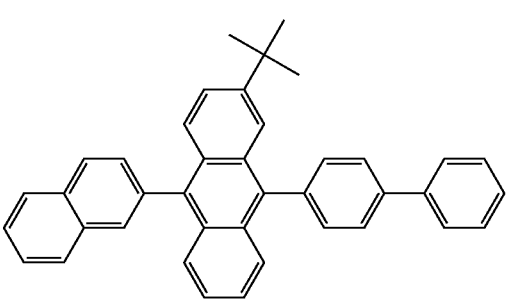
EM158
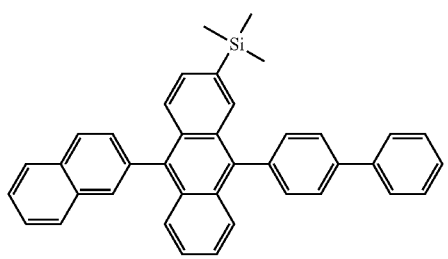
EM159
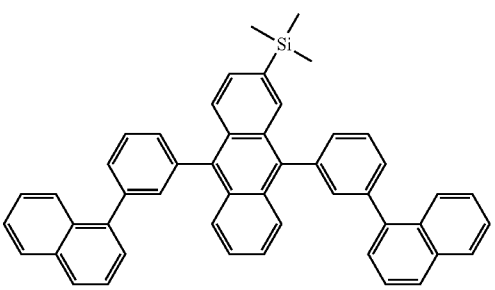
EM160
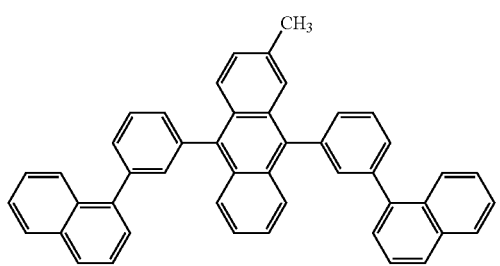
EM161
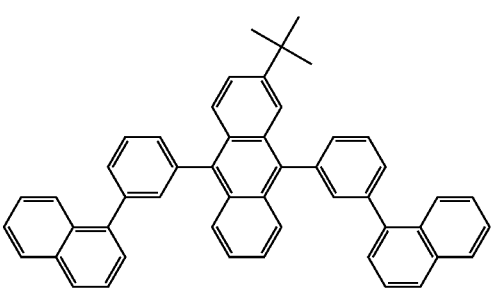
EM162
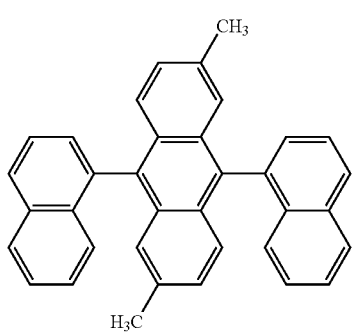
EM163
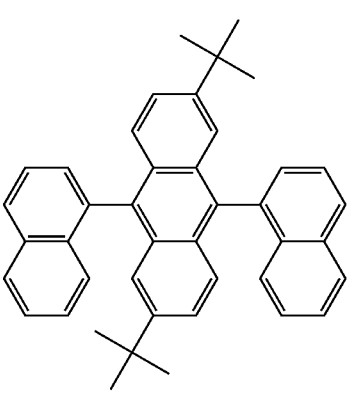

-continued
EM164
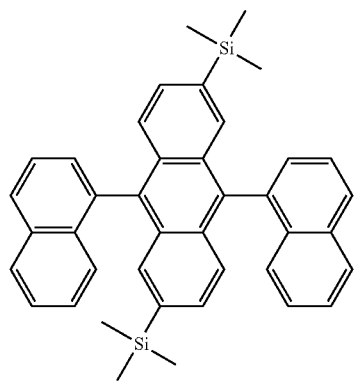
EM165
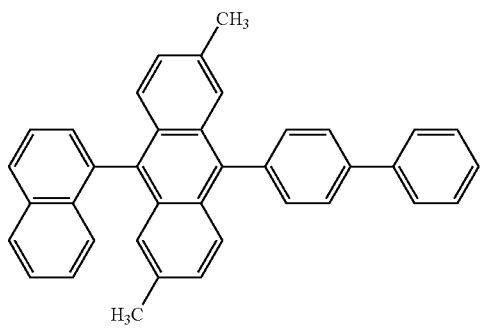
EM166
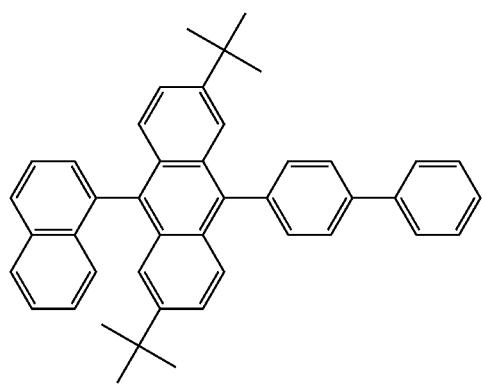
EM167
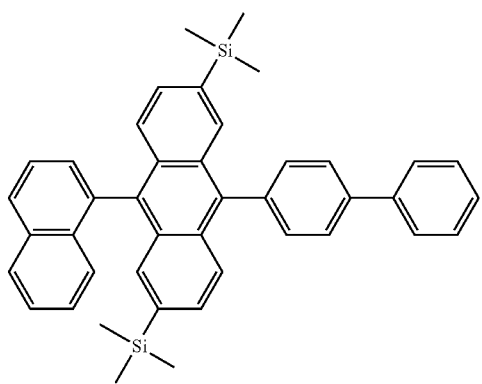
EM168
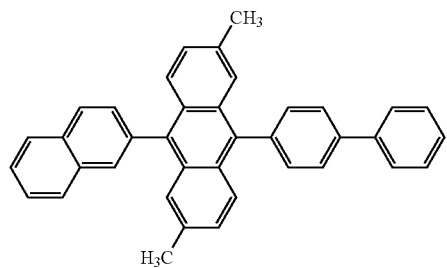
EM169
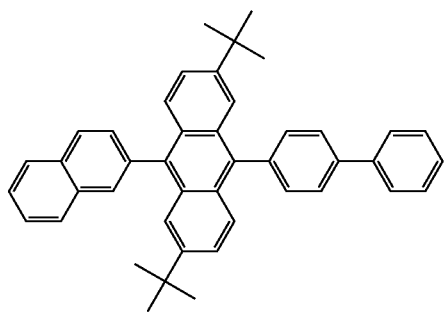
EM170
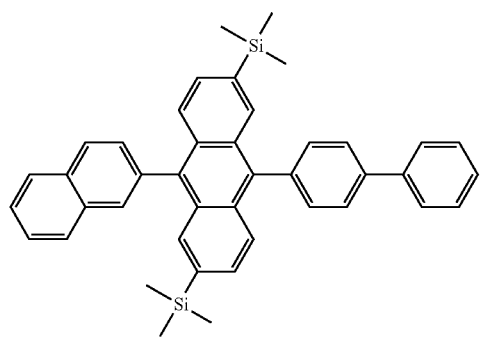
EM171
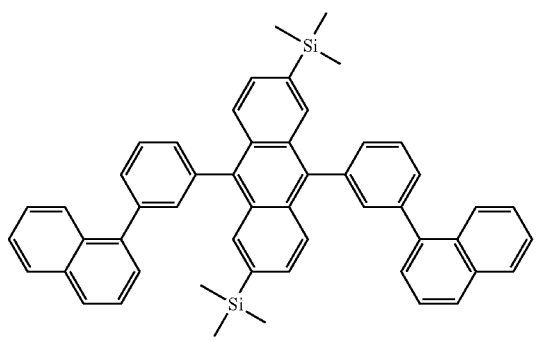

-continued
EM172
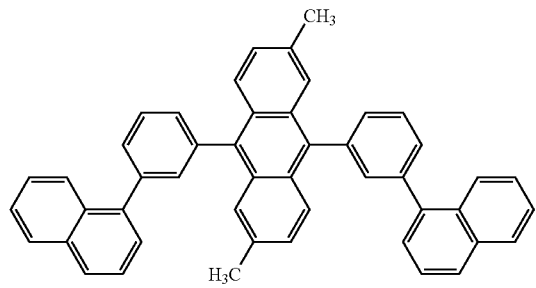
EM173
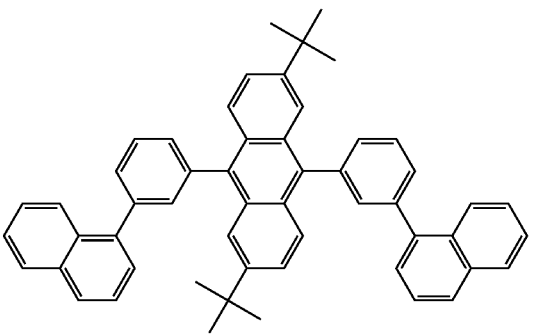
EM174
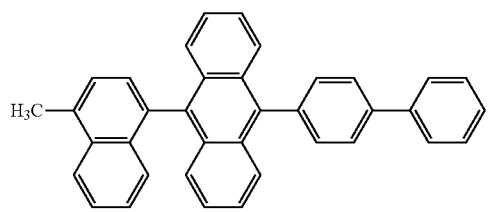
EM175
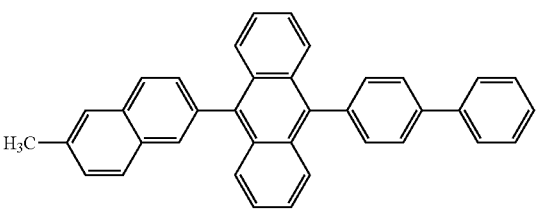
EM176
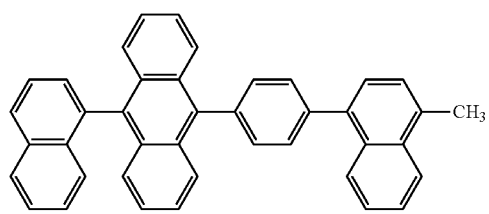
EM177
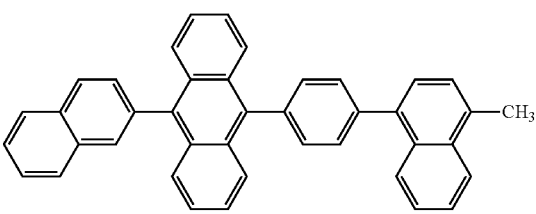
EM178
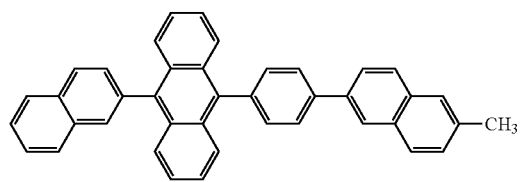
EM179
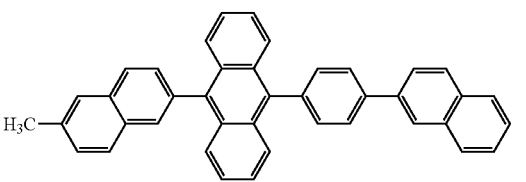
EM180
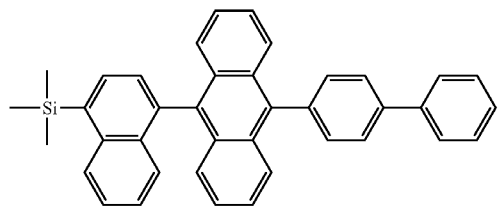
EM181
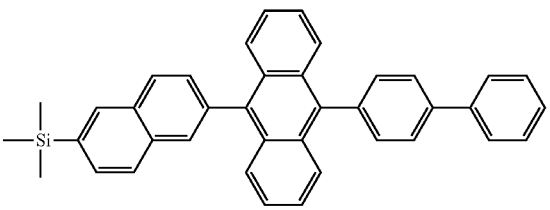
EM182
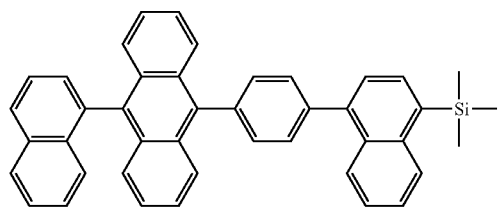
EM183
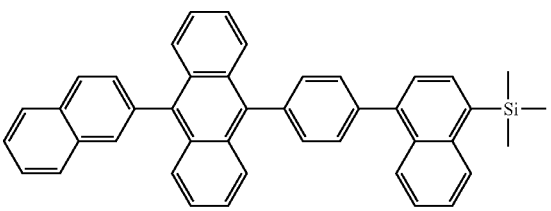

-continued
EM184
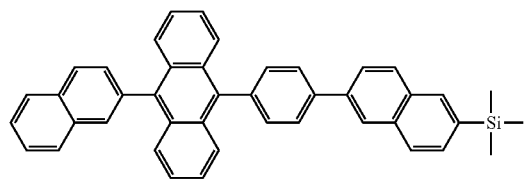
EM185
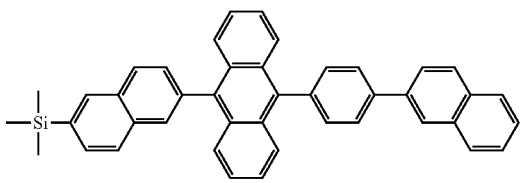
EM186
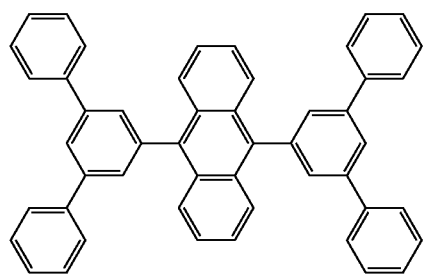
EM187
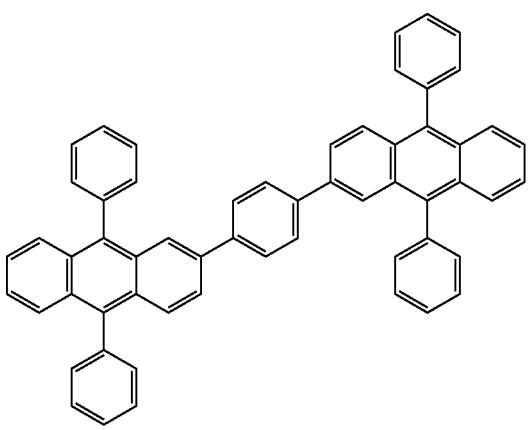
EM188
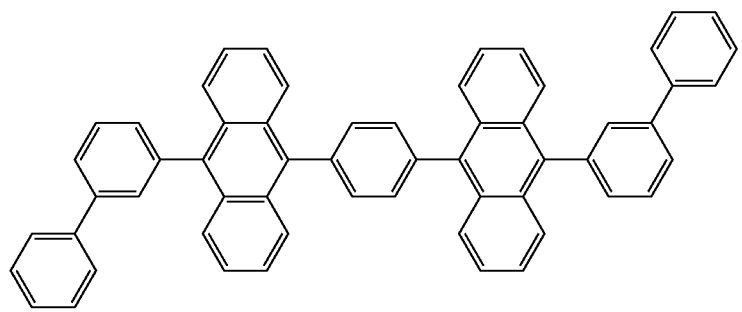
EM189
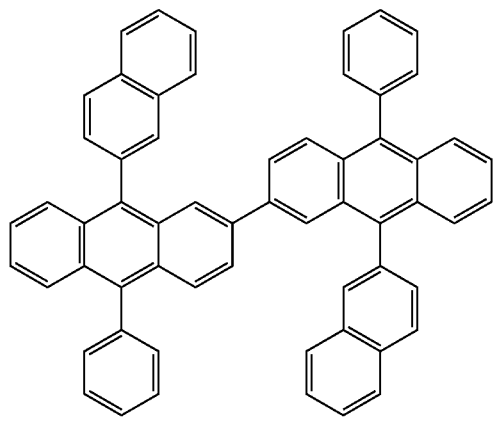
EM190
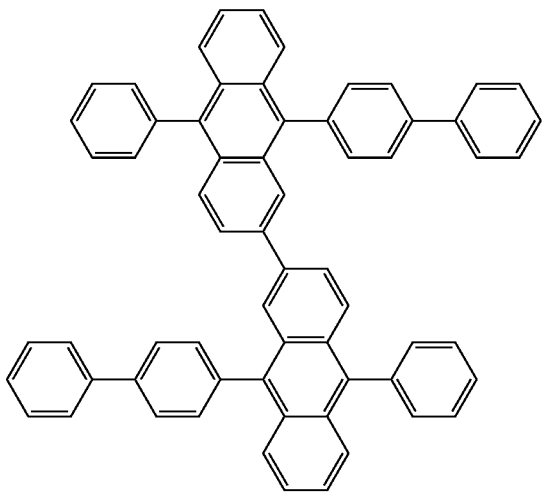

EM191
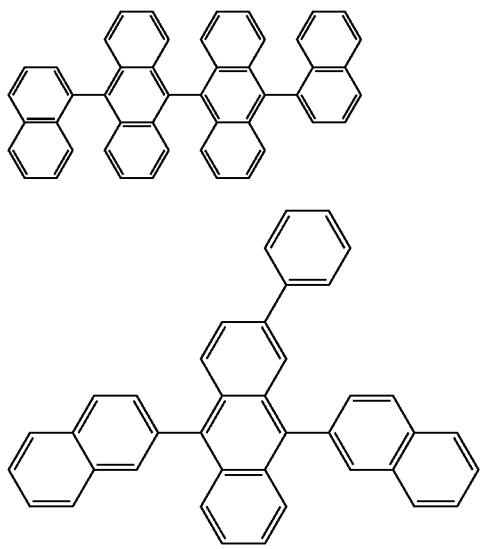
EM192
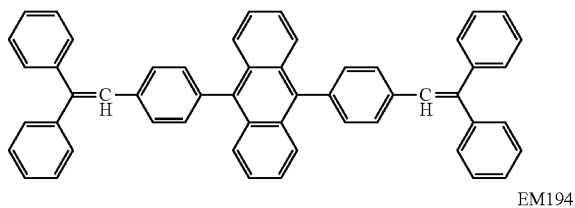
EM193
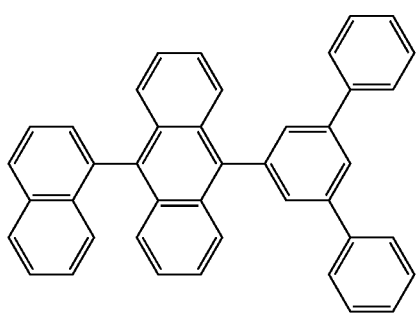
EM194
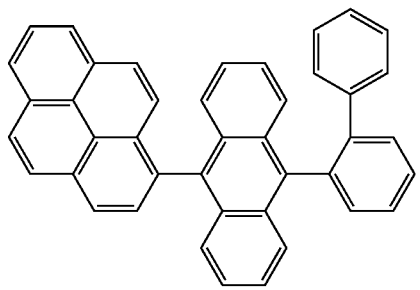
EM195
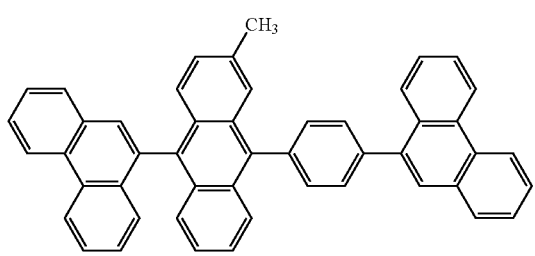
EM196
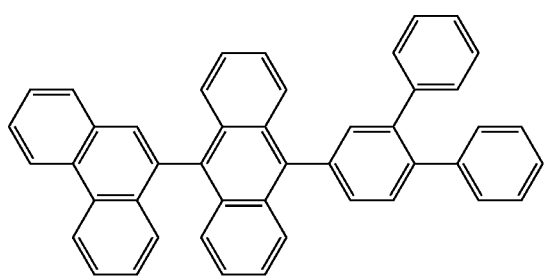
EM197
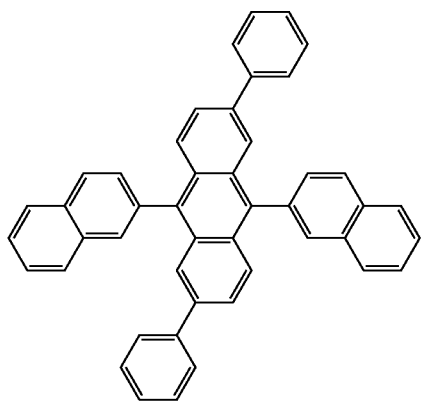
EM198
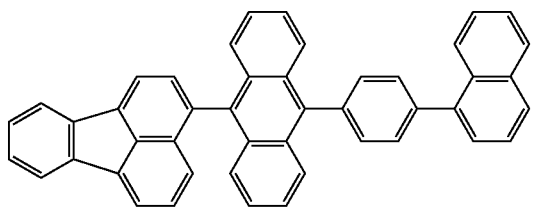
EM199

-continued
EM200
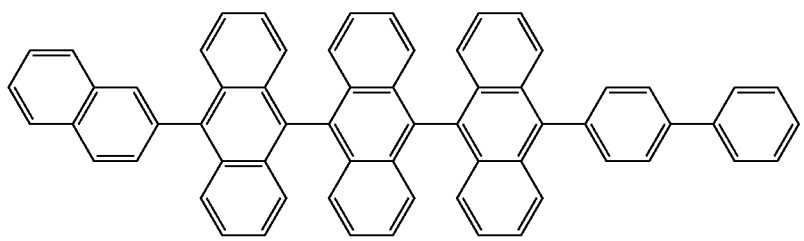
EM201
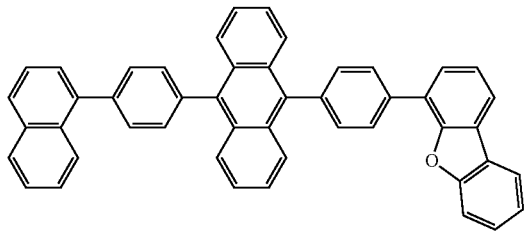
EM202
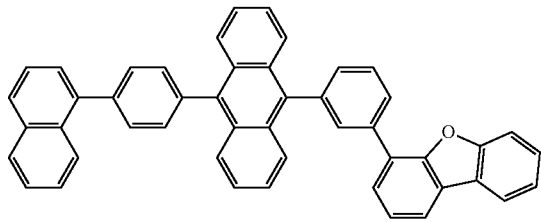
EM203
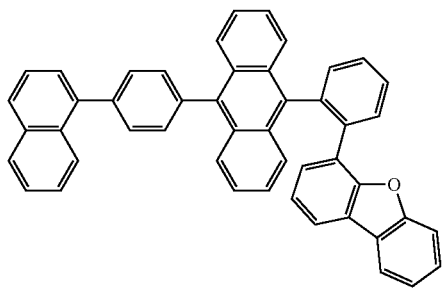
EM204
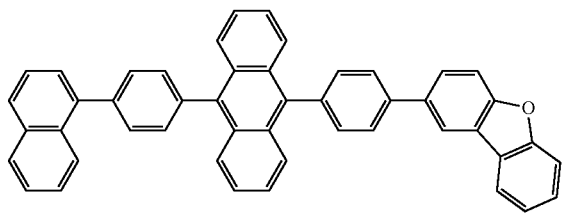
EM205
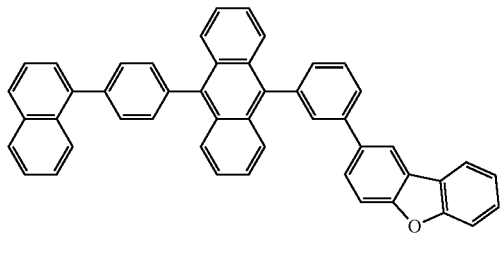
EM206
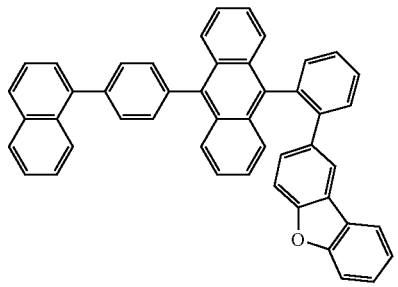
EM207
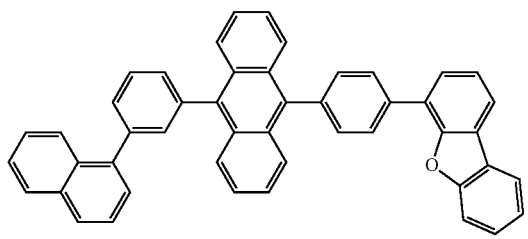
EM208
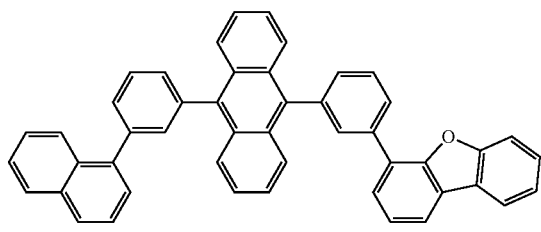

-continued
EM209
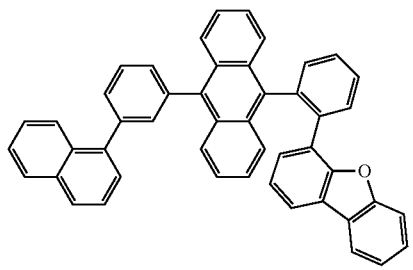
EM210
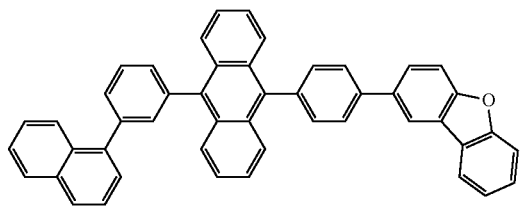
EM211
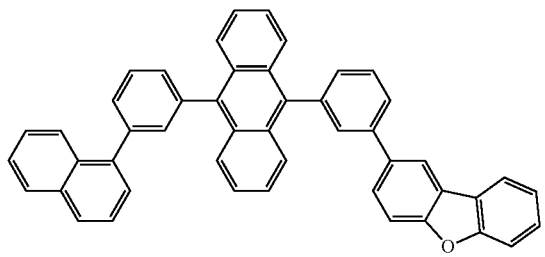
EM212
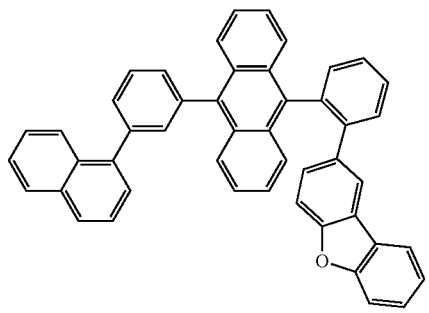
EM213
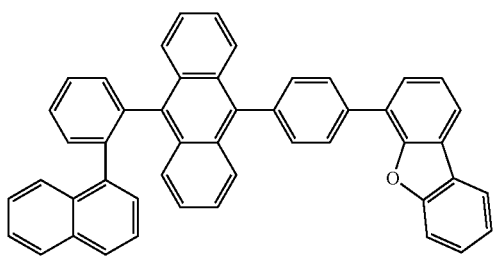
EM214
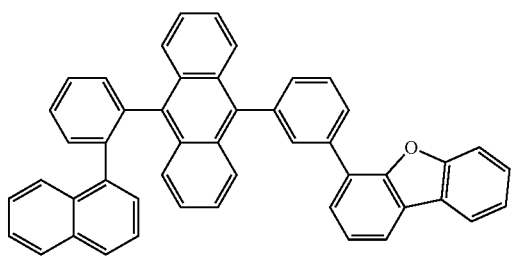
EM215
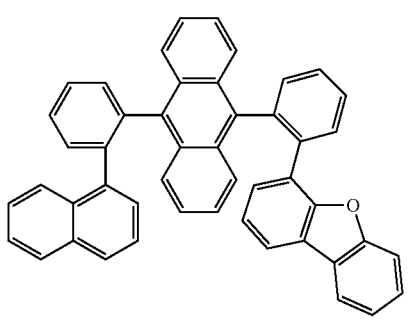
EM216
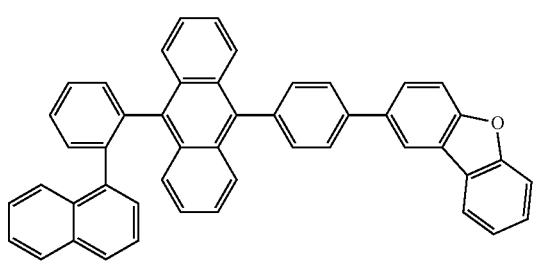
EM217
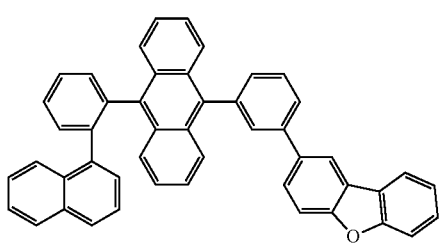
EM218
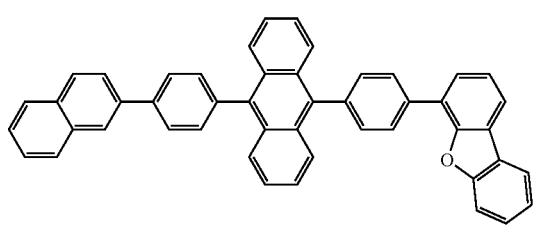

-continued
EM219
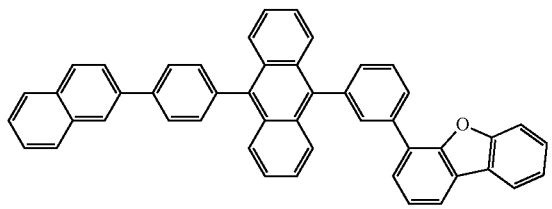
EM220
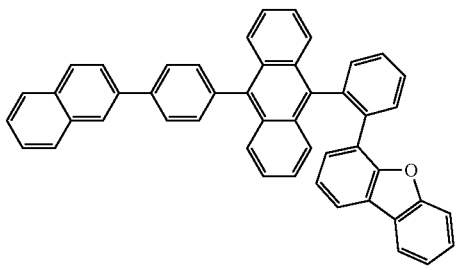
EM221
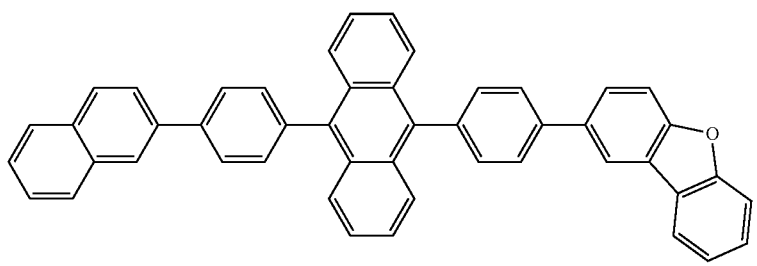
EM222
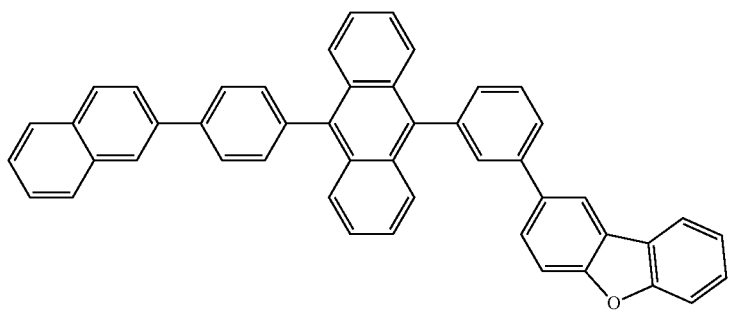
EM223
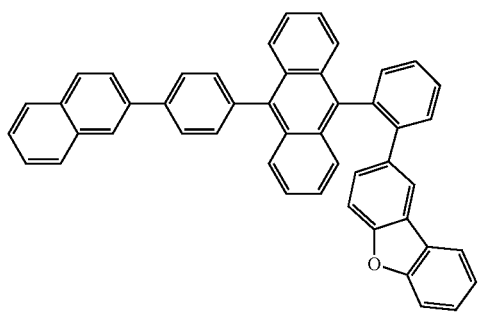
EM224
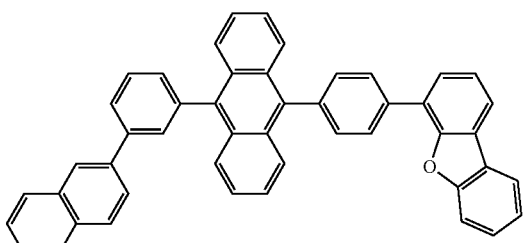
EM225
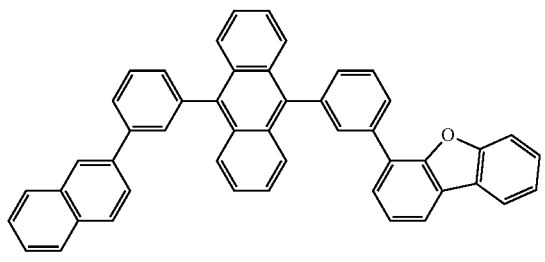
EM226
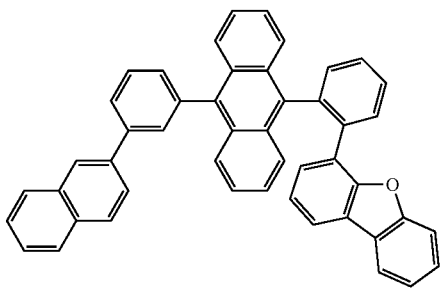

-continued
EM227
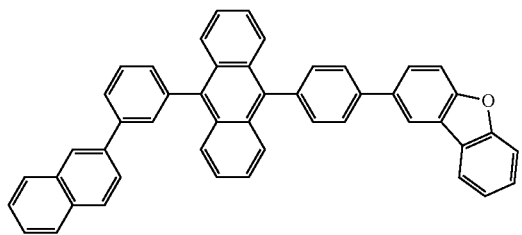
EM228
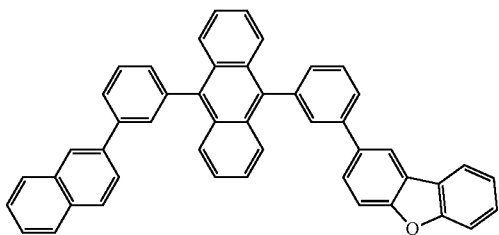
EM229
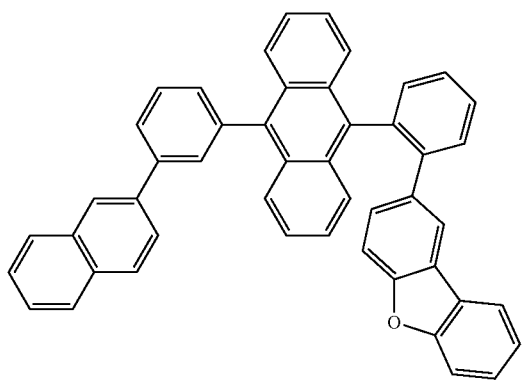
EM230
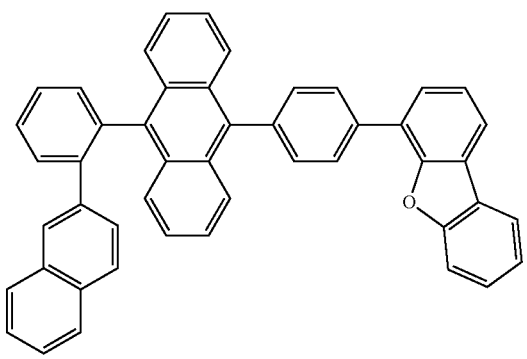
EM231
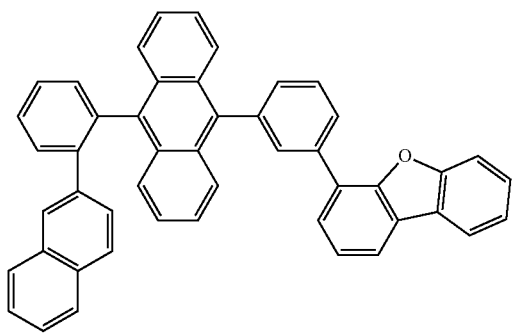
EM232
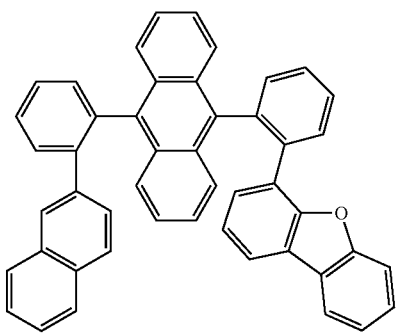
EM233
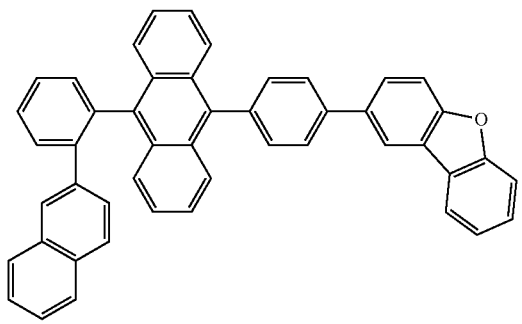
EM234
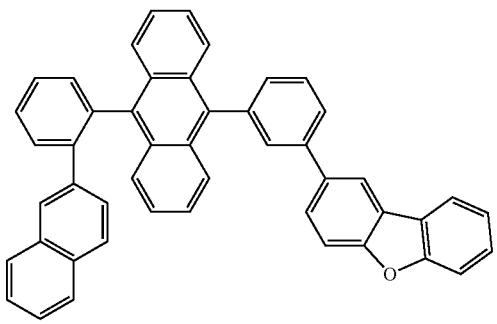

-continued
EM235
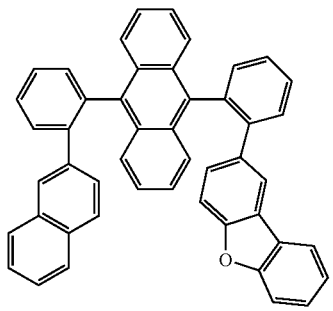
EM236
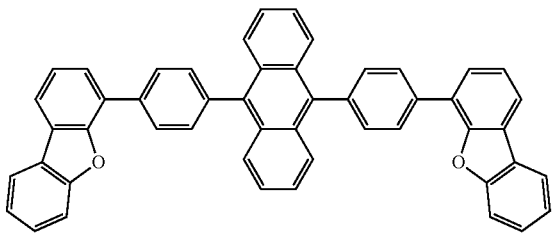
EM237
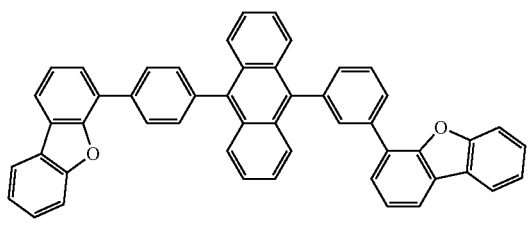
EM238
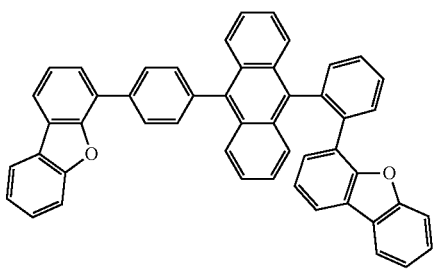
EM239
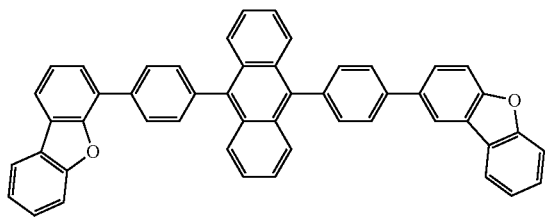
EM240
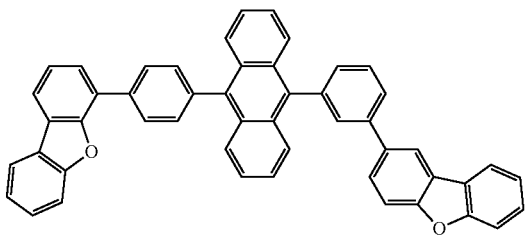
EM241
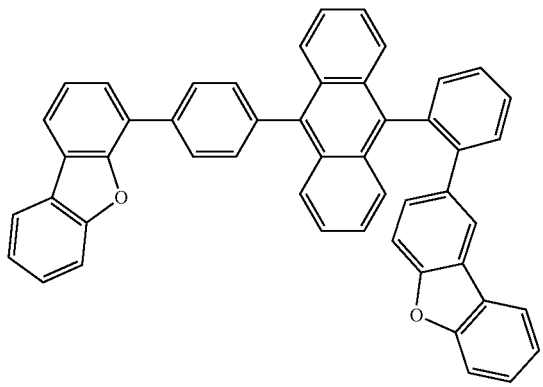
EM242
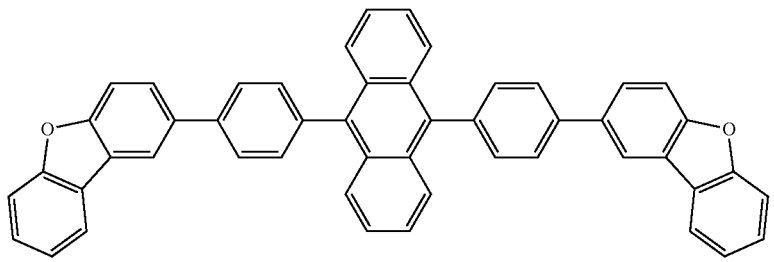

EM243
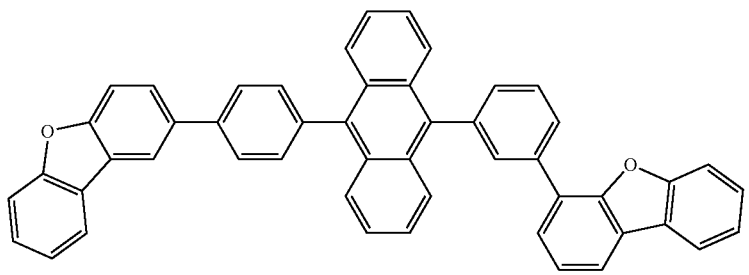
EM244
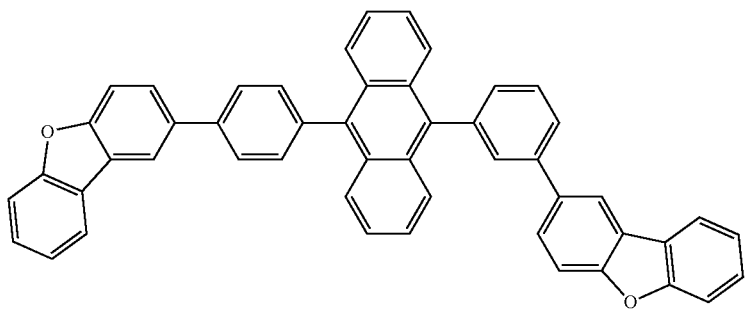
EM245 EM246
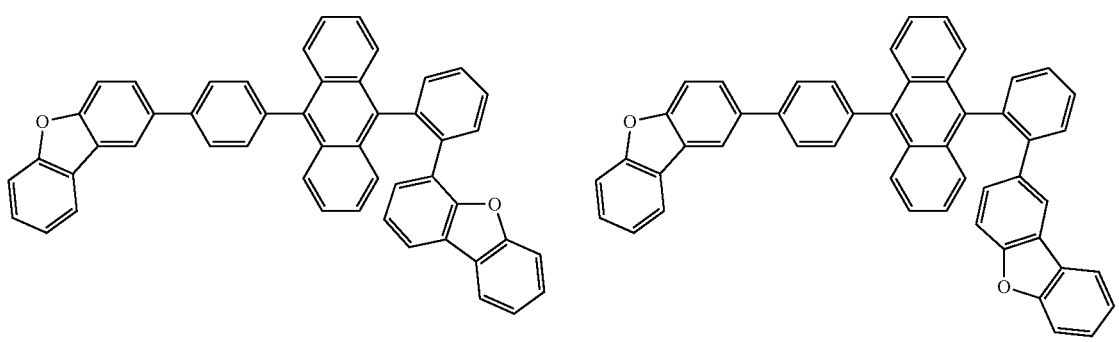
EM247 EM248
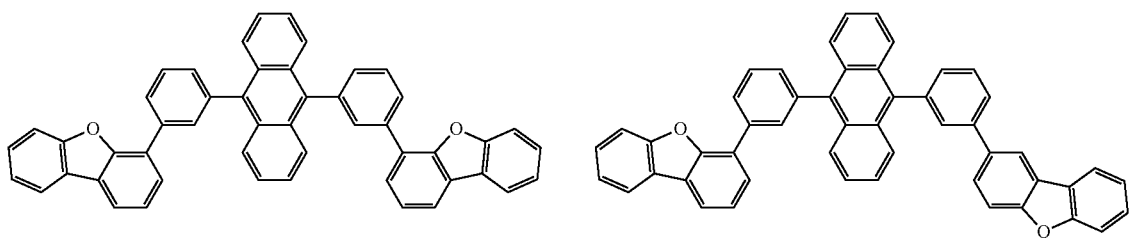
EM249 EM250
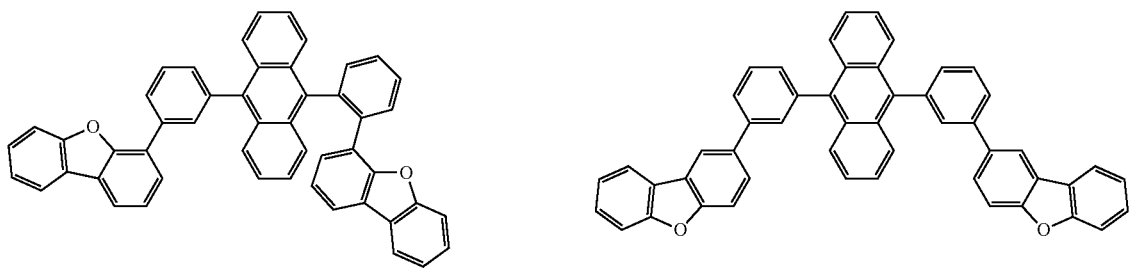

-continued
EM251
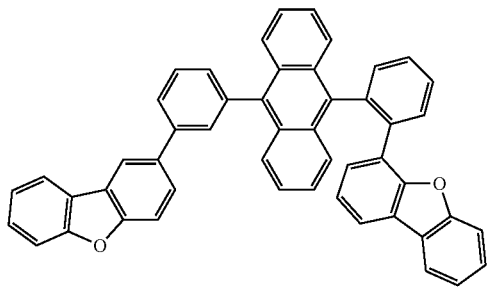
EM252
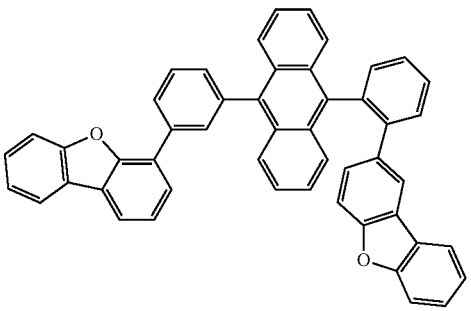
EM253
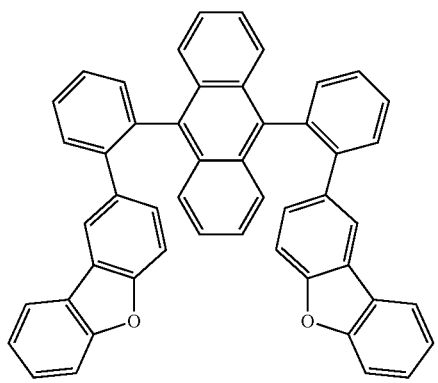
EM254
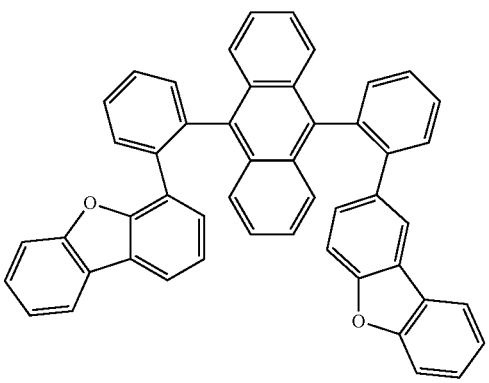
EM255
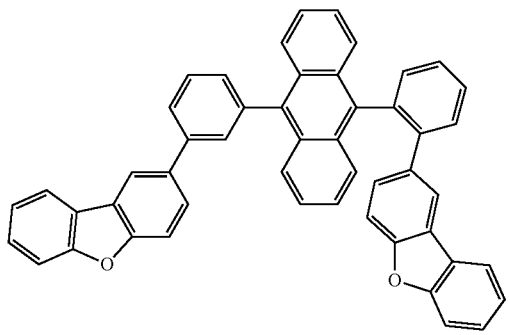
EM256
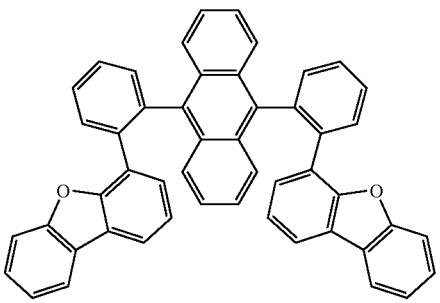
EM257
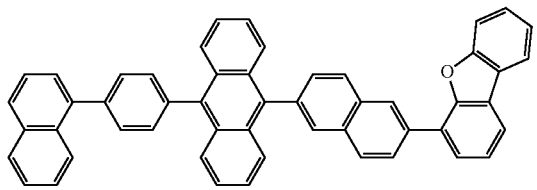
EM258
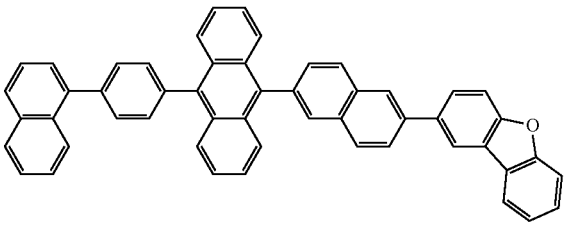
EM259
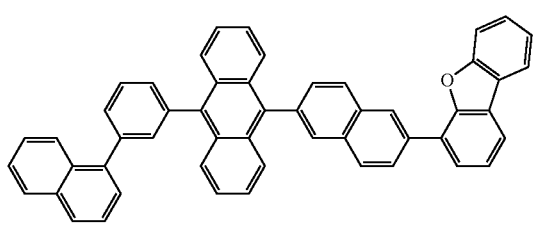
EM260
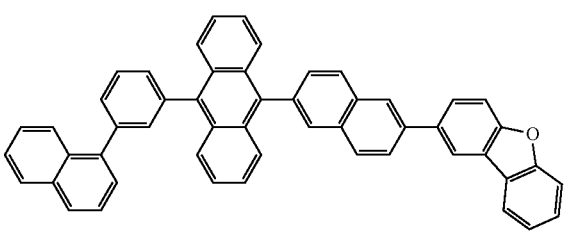

-continued
EM261
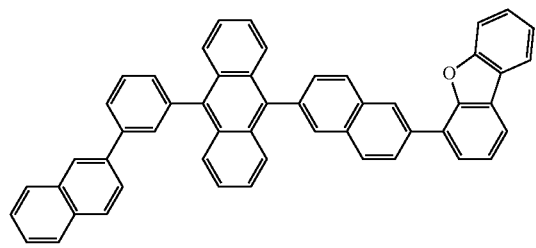
EM262
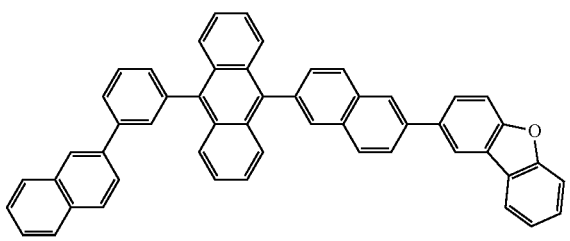
EM263
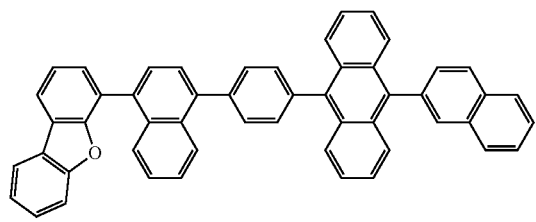
EM264
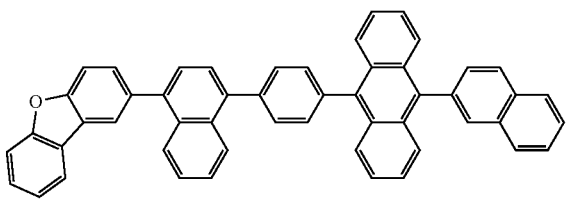
EM265
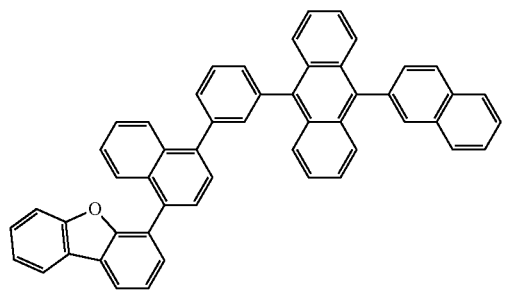
EM266
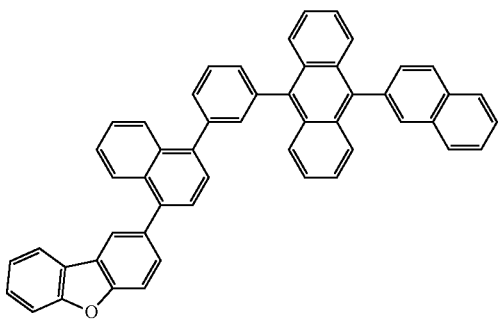
EM267
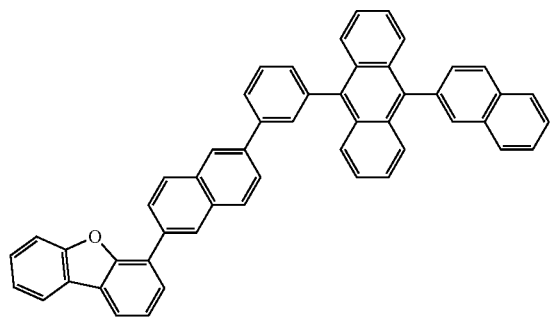
EM268
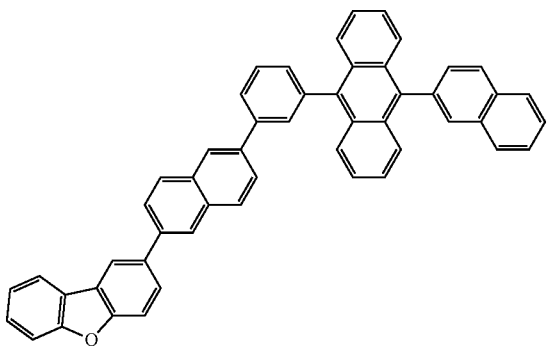
EM269
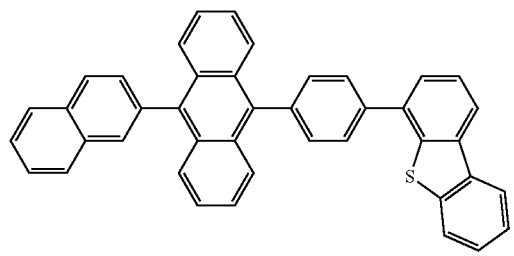
EM270
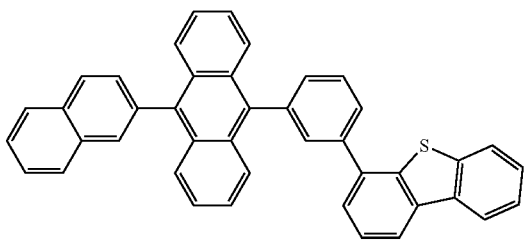

-continued
EM271
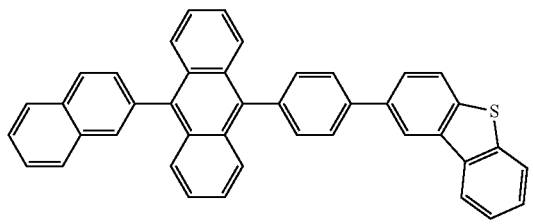
EM272
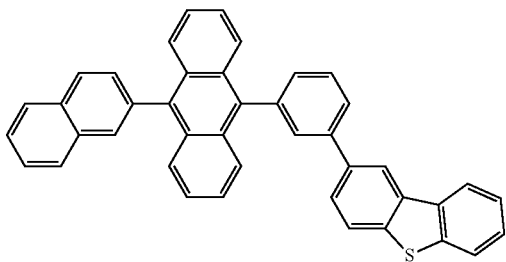
EM273
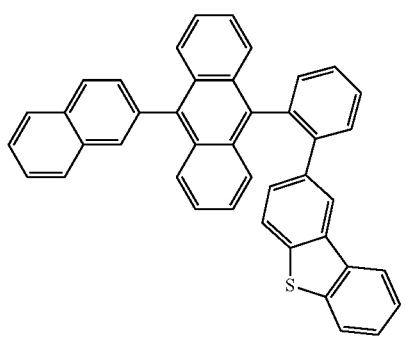
EM274
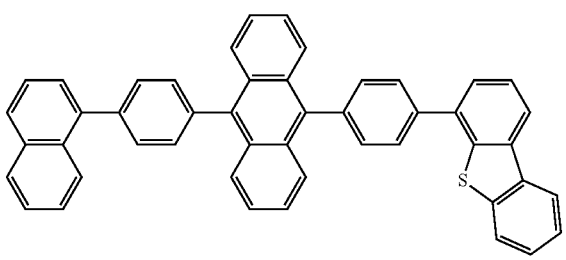
EM275
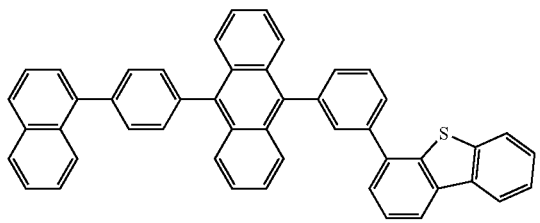
EM276
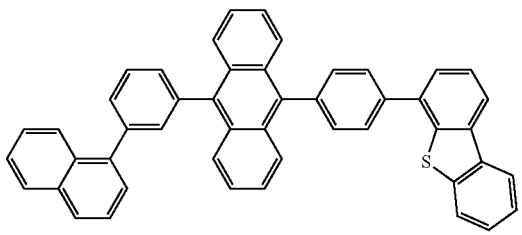
EM277
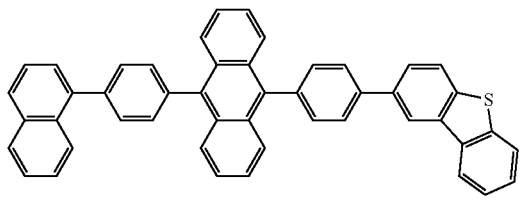
EM278
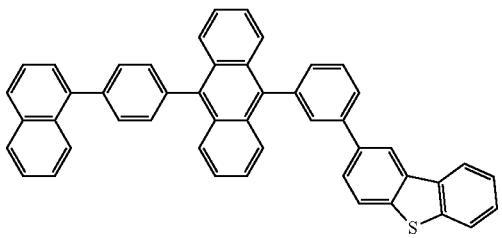
EM279
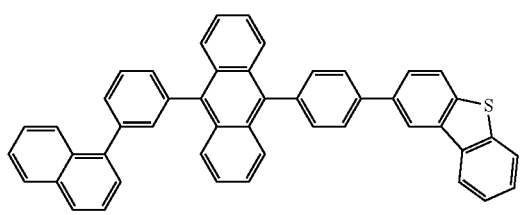
EM280
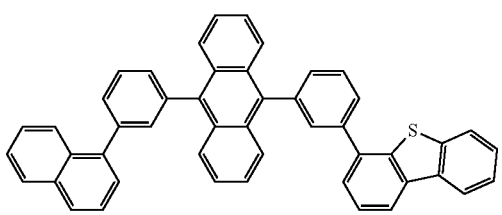

-continued
EM281
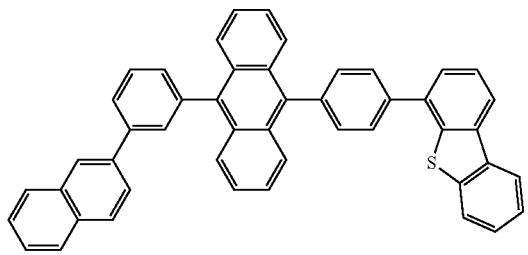
EM282
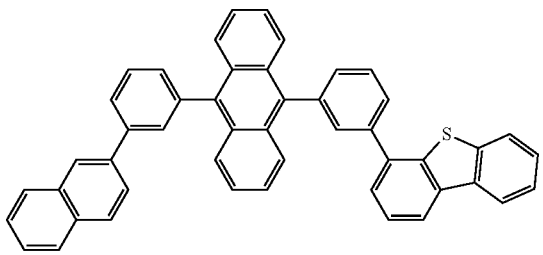
EM283
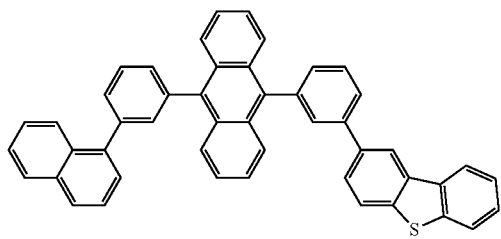
EM284
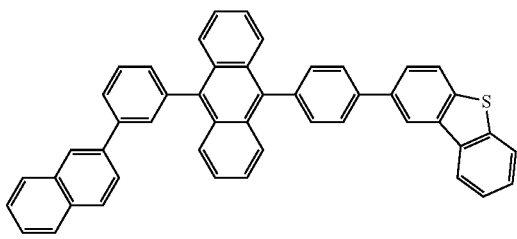
EM285
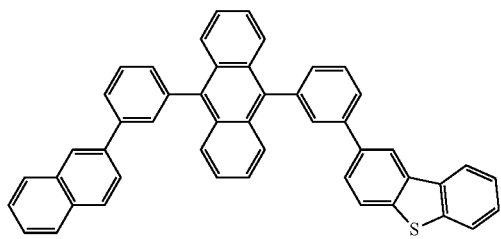
EM286
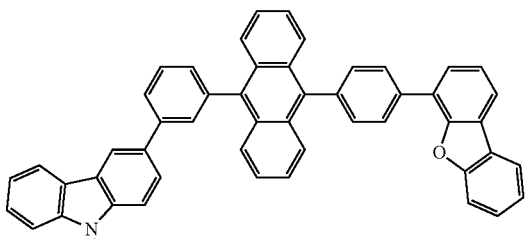
EM287
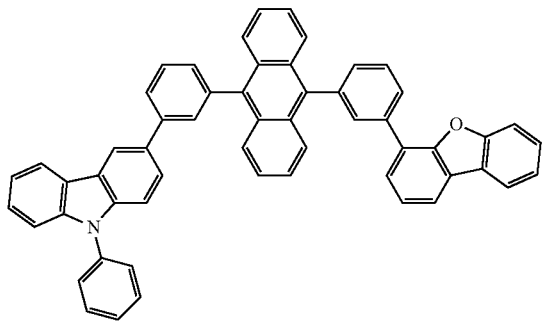
EM288
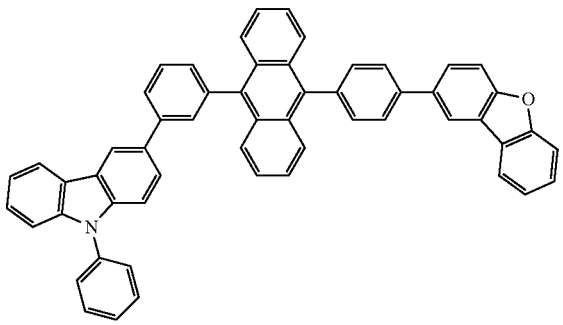
EM289
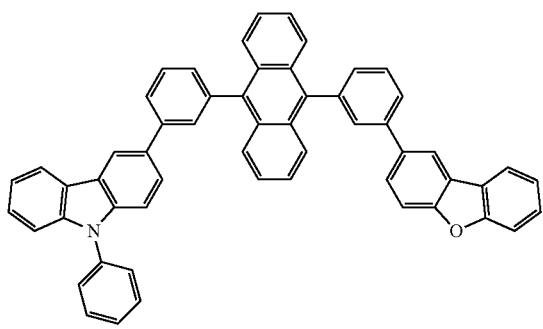
EM290
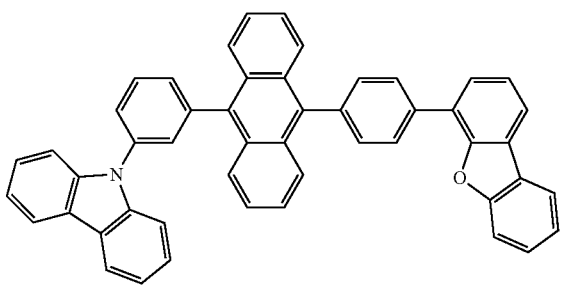

-continued
EM291
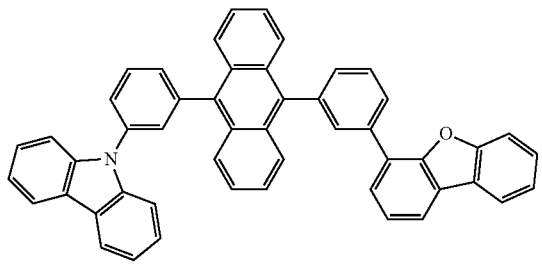
EM292
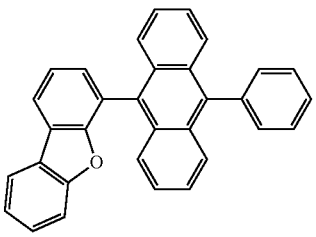
EM293
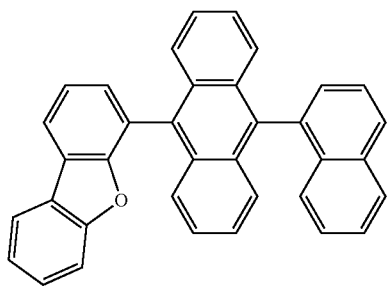
EM294
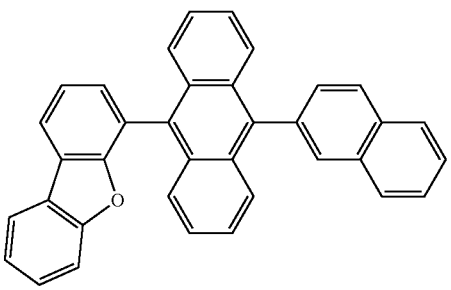
EM295
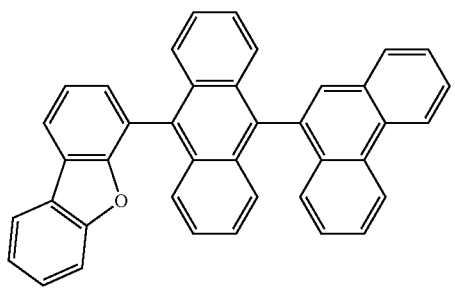
EM269
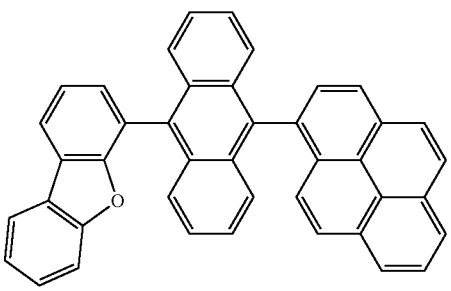
EM297
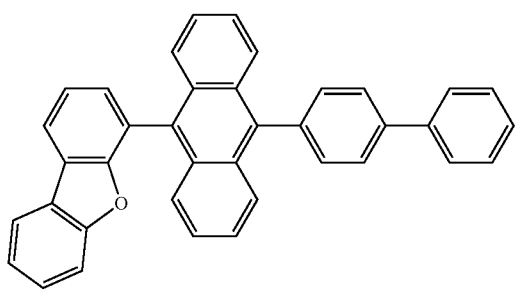
EM298
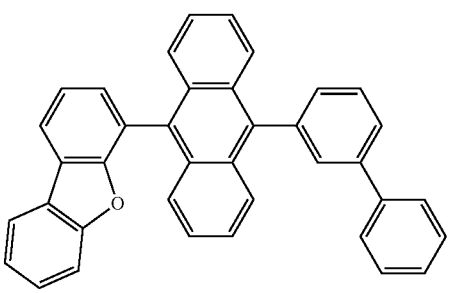
EM299
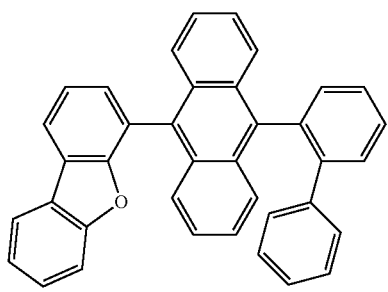
EM300
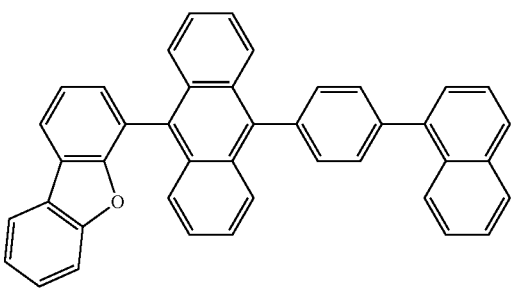

-continued
EM301
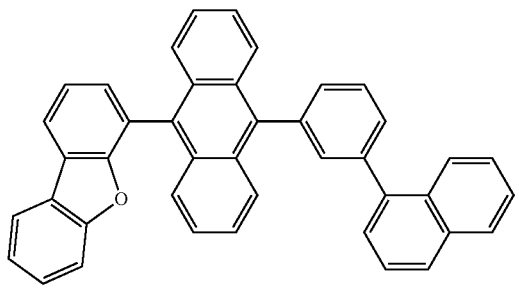
EM302
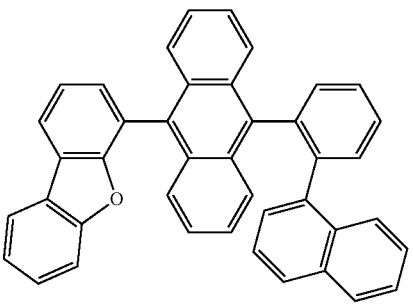
EM303
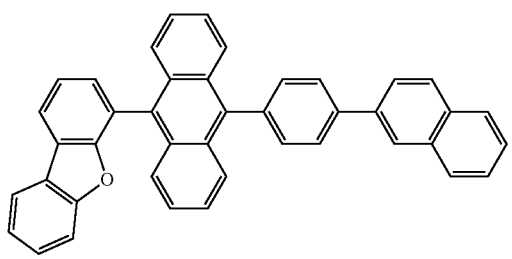
EM304
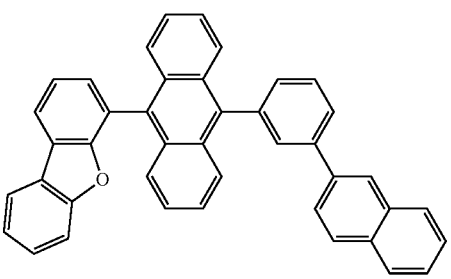
EM305
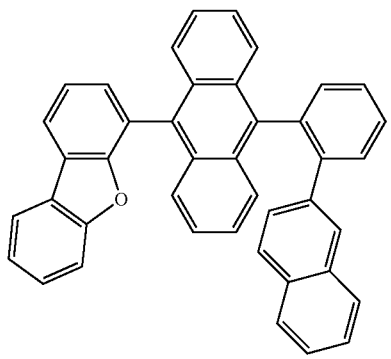
EM306
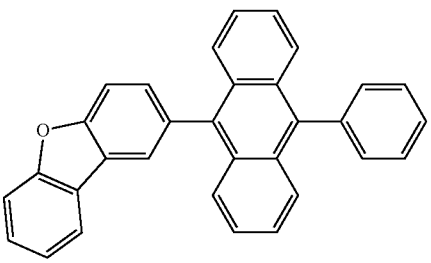
EM307
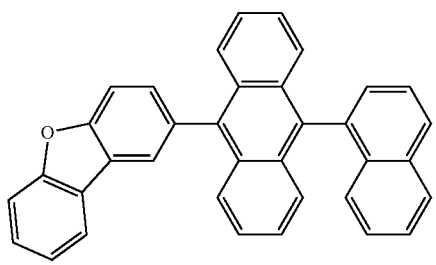
EM308
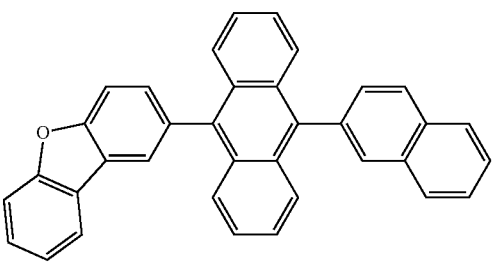
EM309
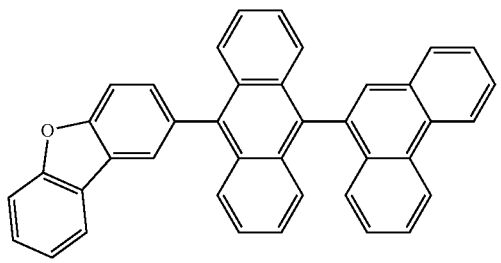
EM310
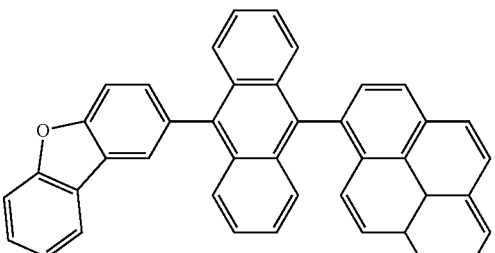

-continued
EM311
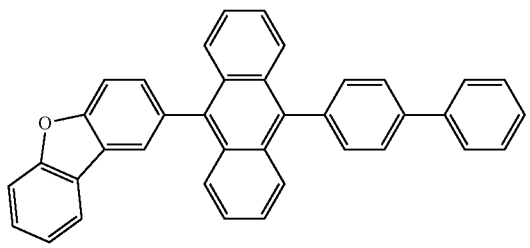
EM312
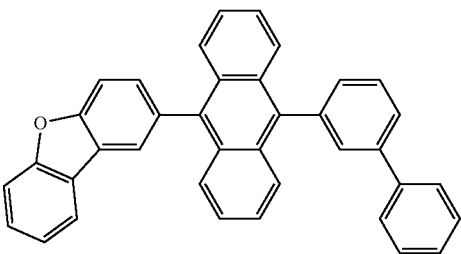
EM313
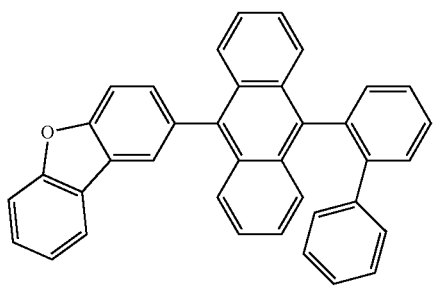
EM314
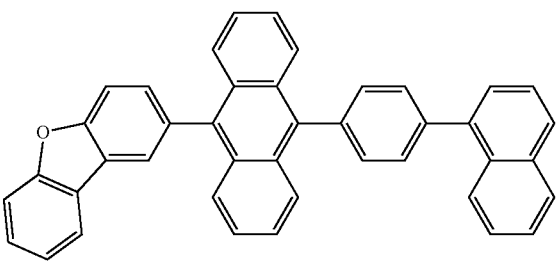
EM315
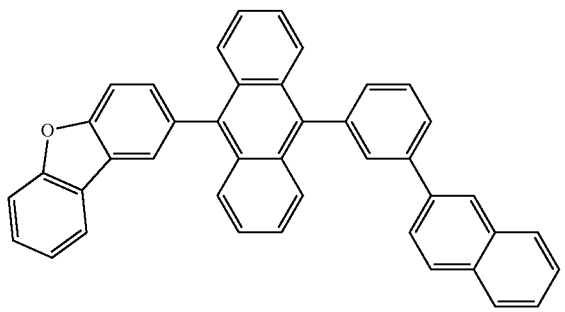
EM316
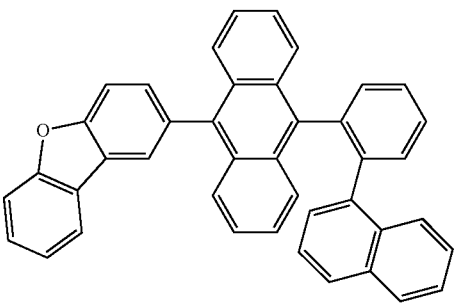
EM317
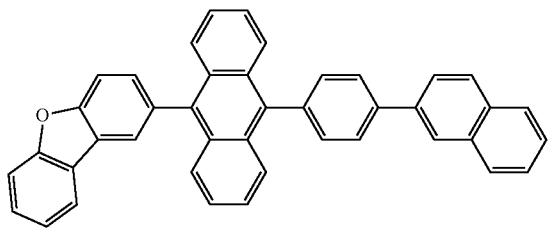
EM318
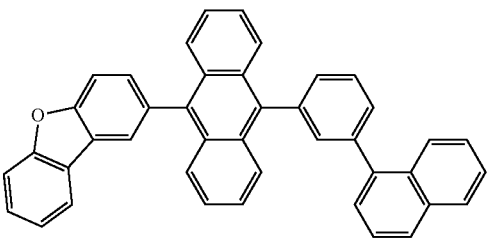
EM319
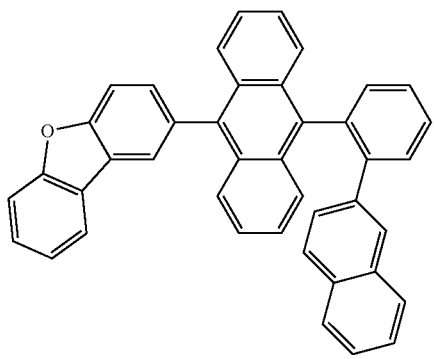
EM320
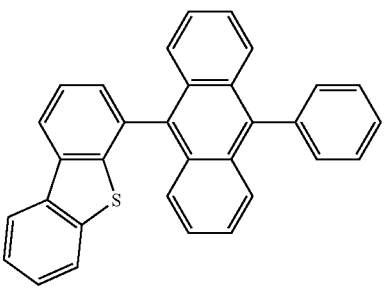

-continued
EM321
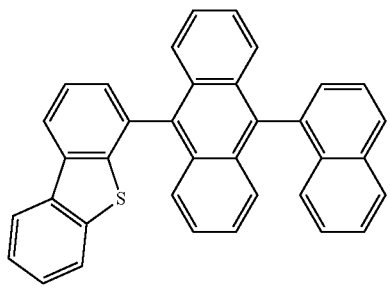
EM322
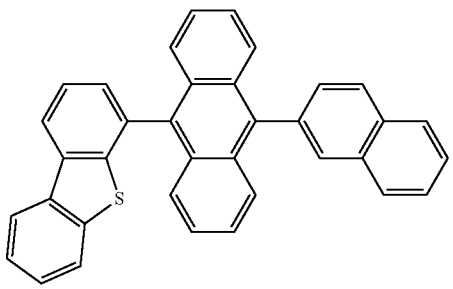
EM323
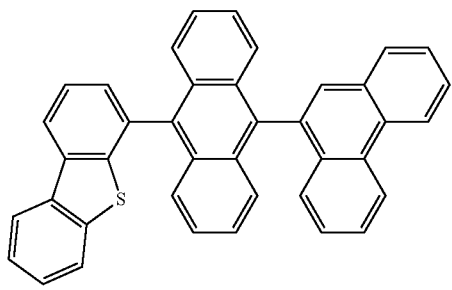
EM324
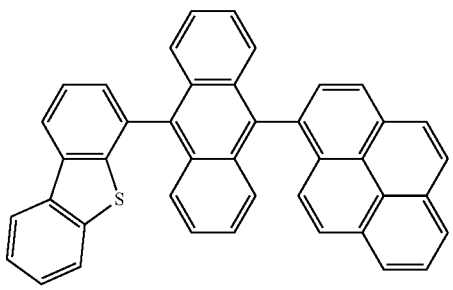
EM325
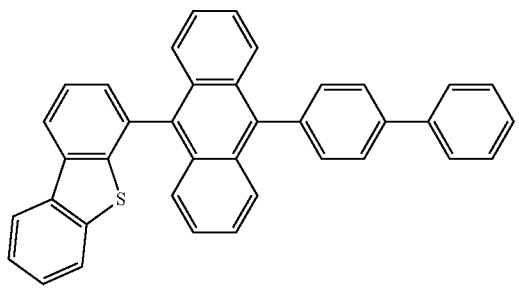
EM326
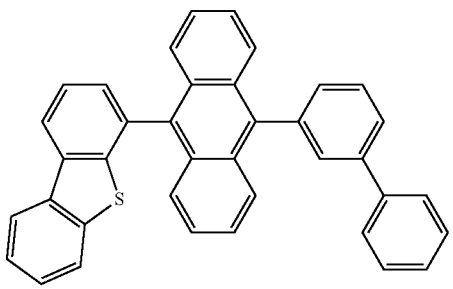
EM327
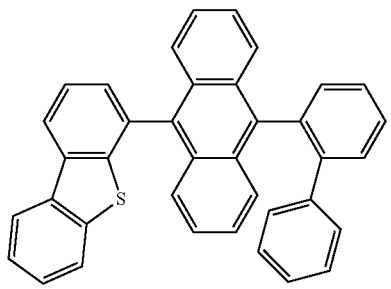
EM328
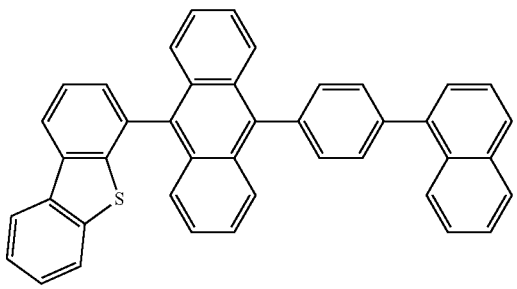
EM329
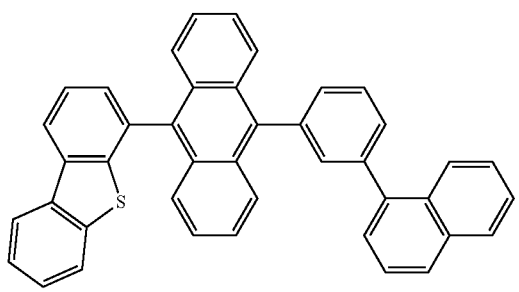
EM330
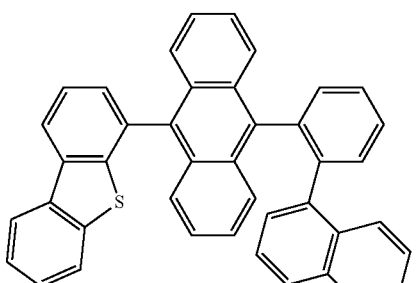

-continued
EM331
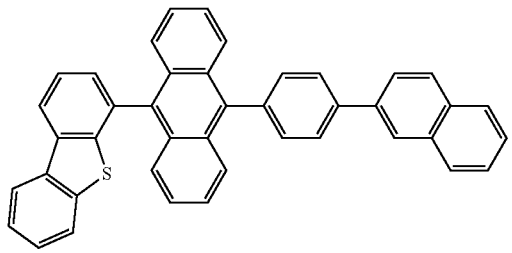
EM332
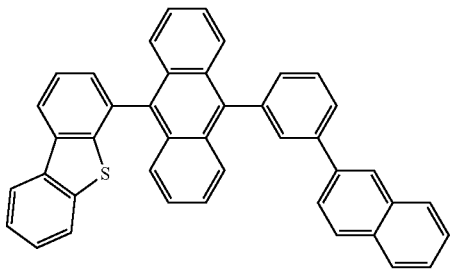
EM333
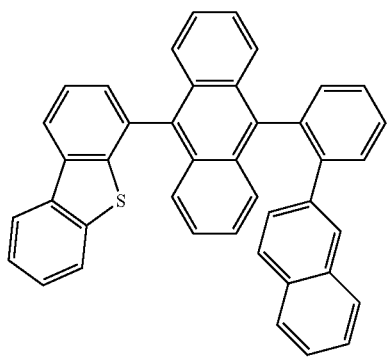
EM334
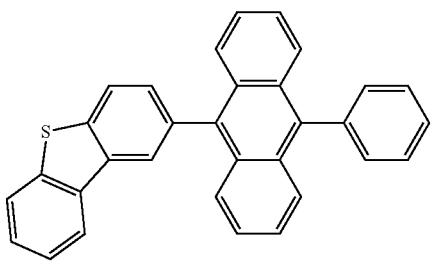
EM335
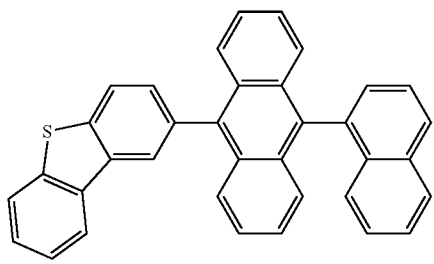
EM336
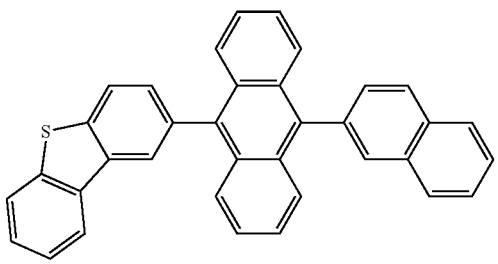
EM337
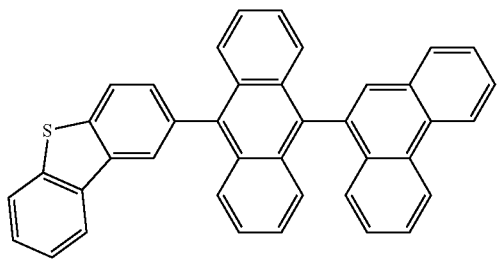
EM338
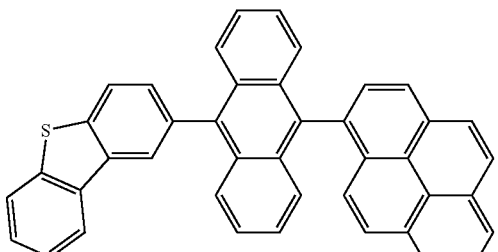
EM339
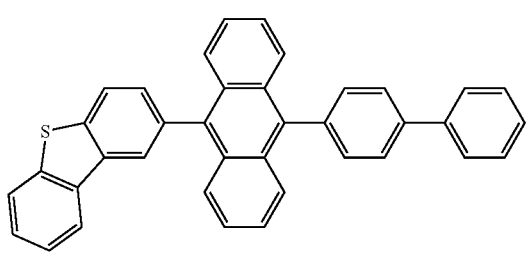
EM340
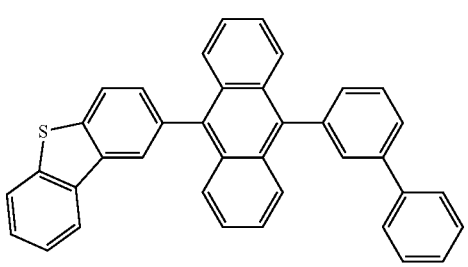

-continued
EM341
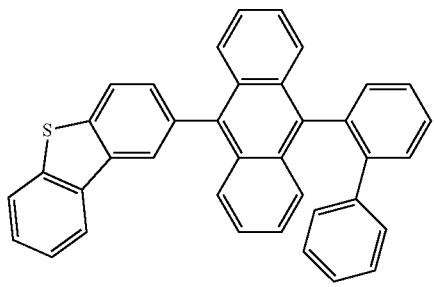
EM342
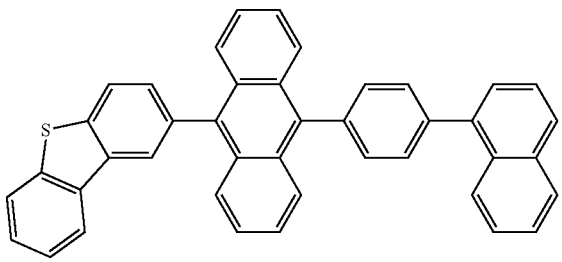
EM343
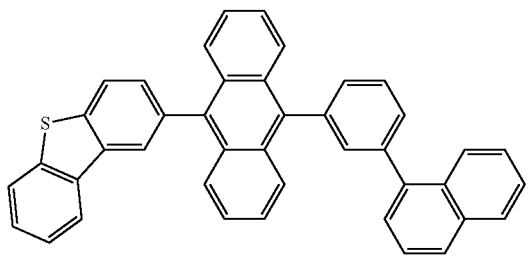
EM344
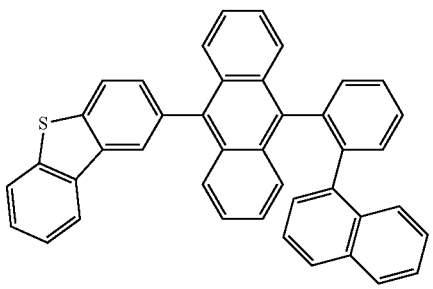
EM345
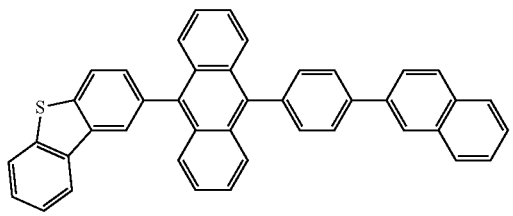
EM346
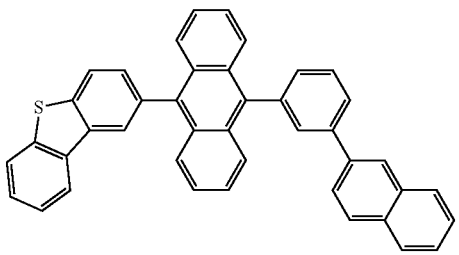
EM347
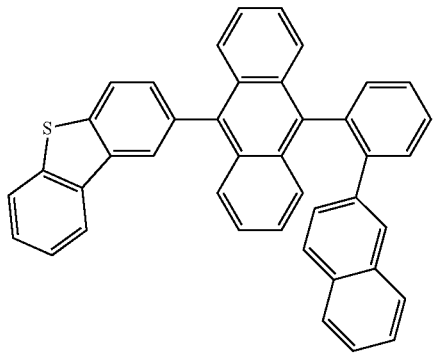
EM348
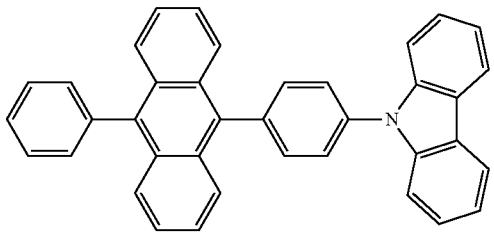
EM349
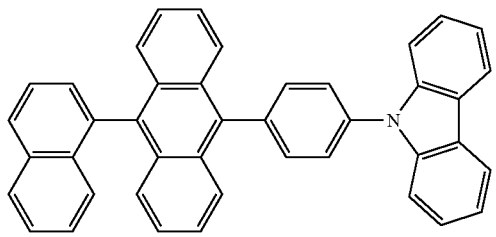
EM350
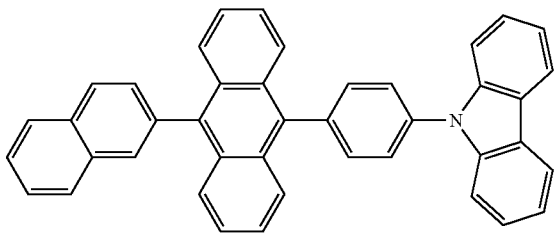

-continued
EM351
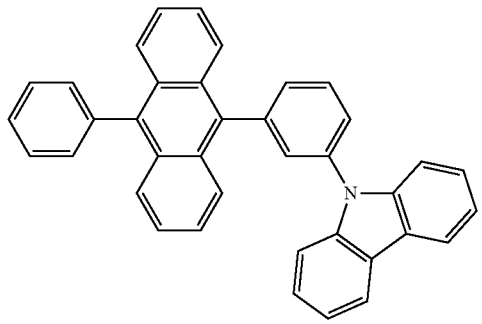
EM352
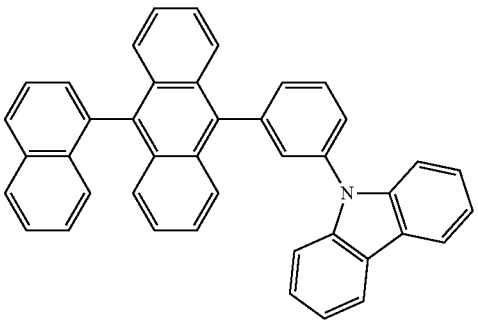
EM353
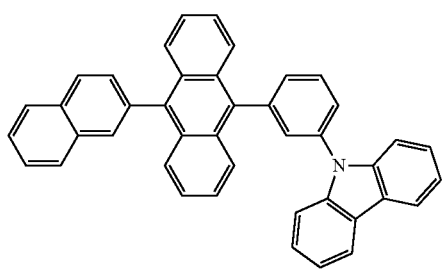
EM354
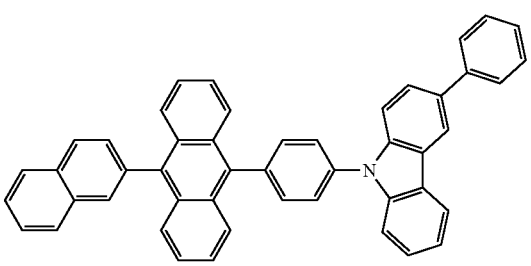
EM355
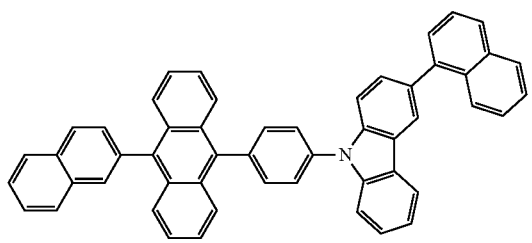
EM356
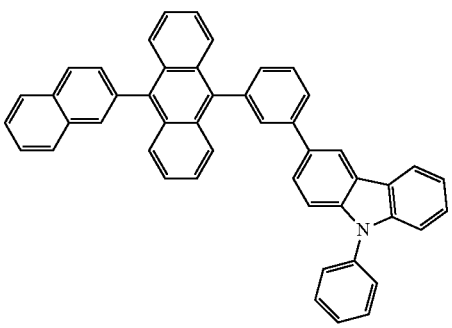
EM357
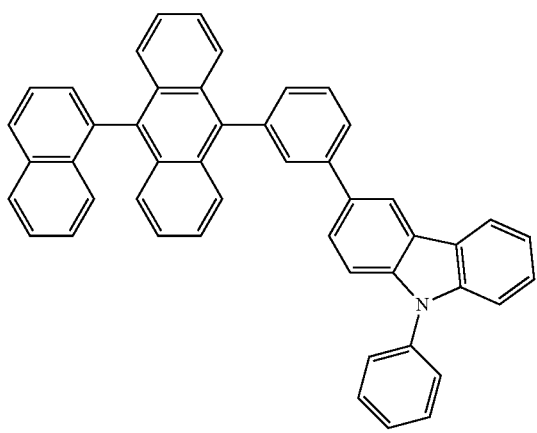
EM358
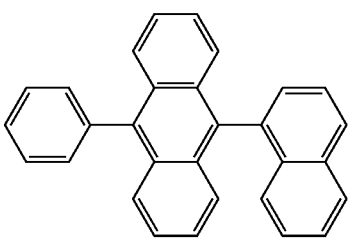
EM359
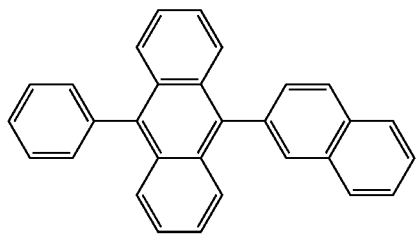
EM360
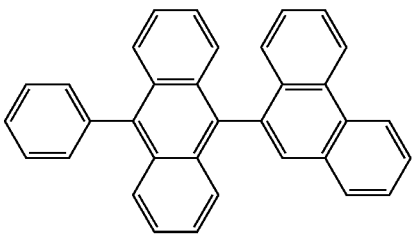

-continued
EM361
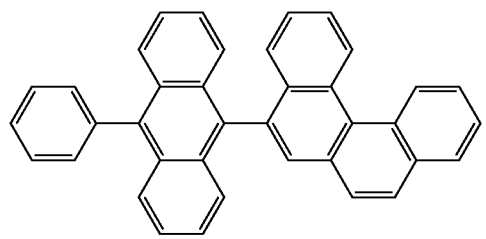
EM362
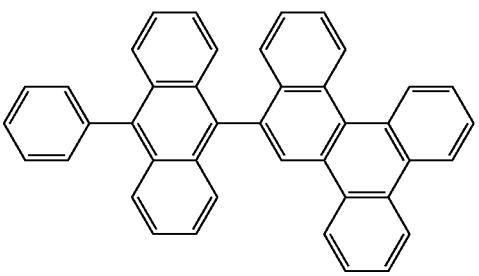
EM363
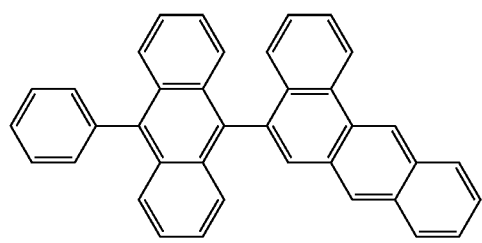
EM364
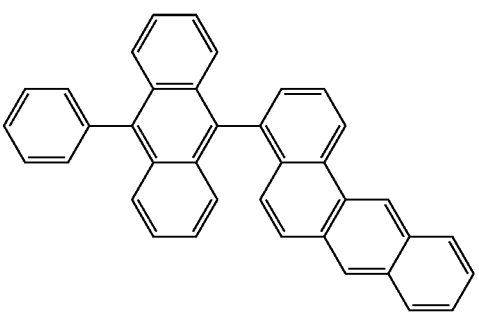
EM365
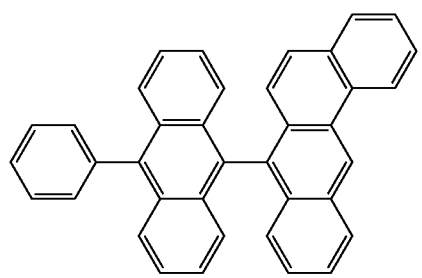
EM366
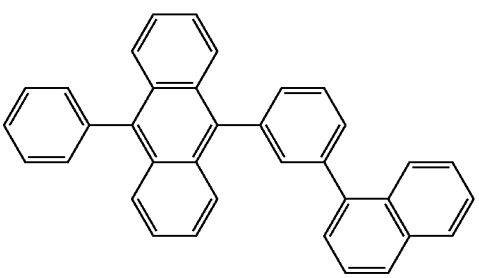
EM367
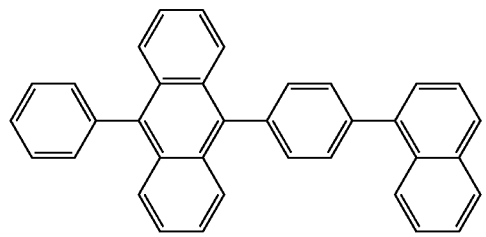
EM368
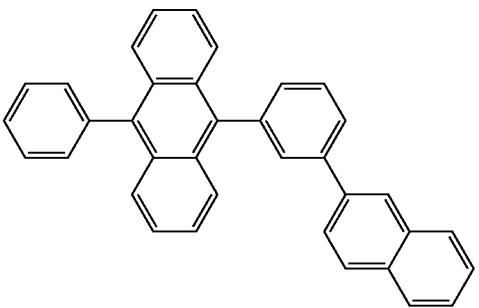
EM369
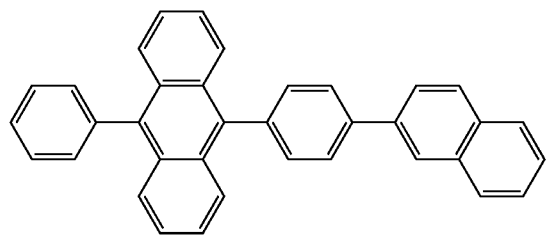
EM370
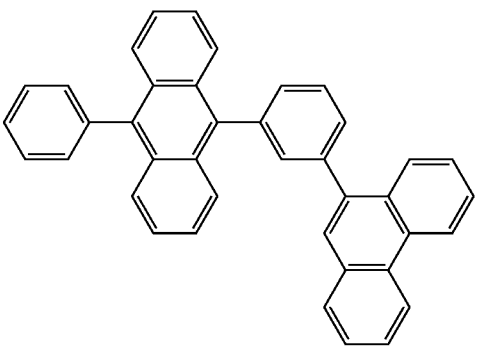

-continued
EM371
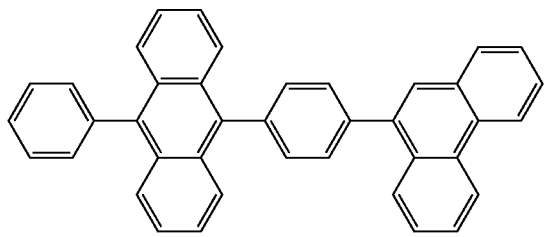
EM372
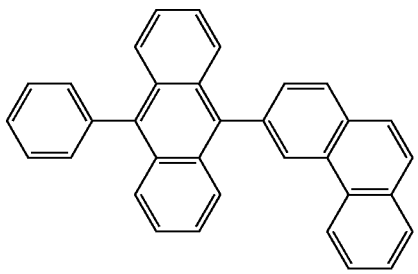
EM373
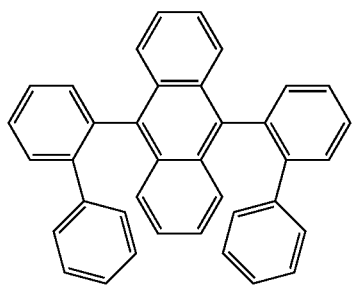
EM374
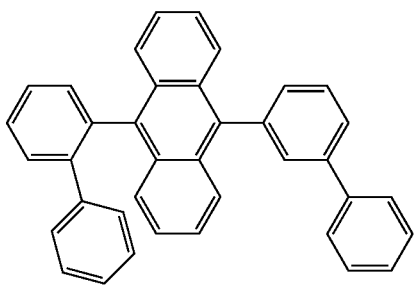
EM375
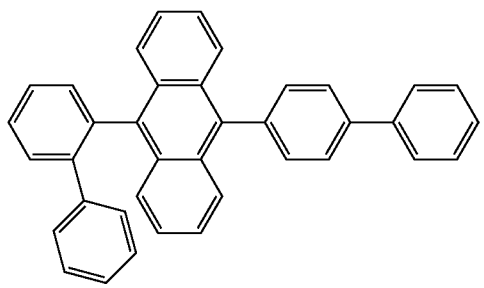
EM376
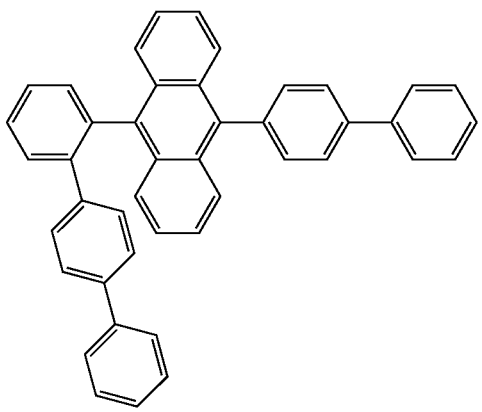
EM377
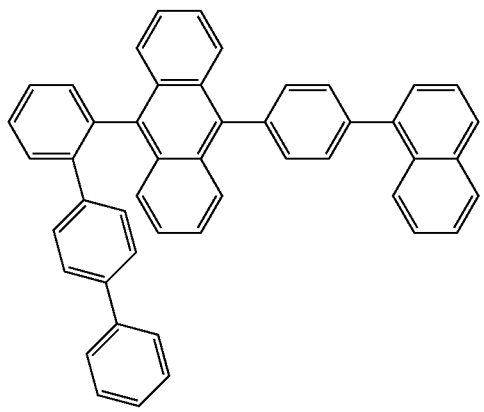
EM378
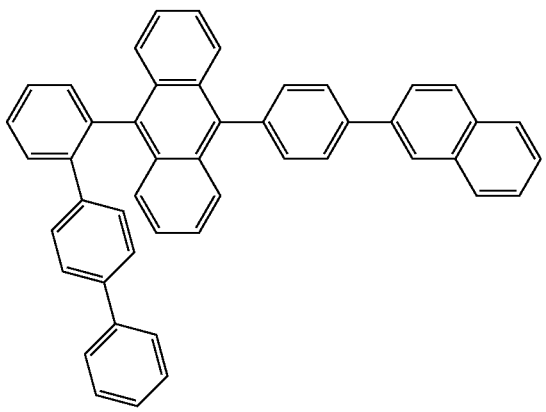

-continued
EM379
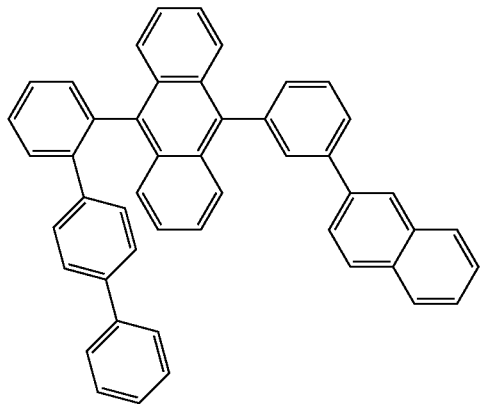
EM380
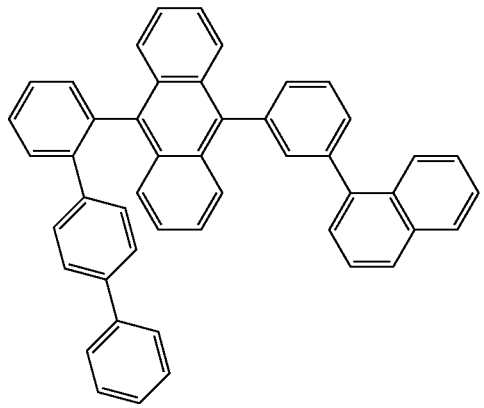
EM381
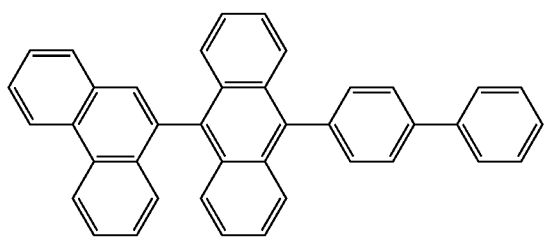
EM382
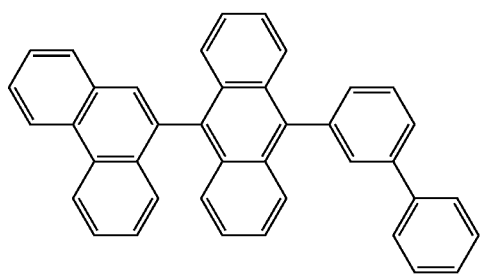
EM383
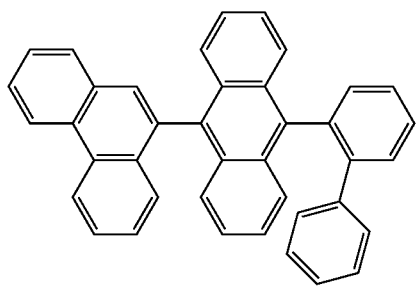
EM384
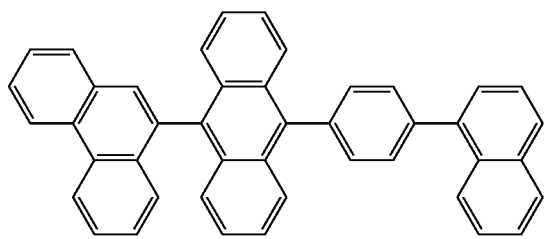
EM385
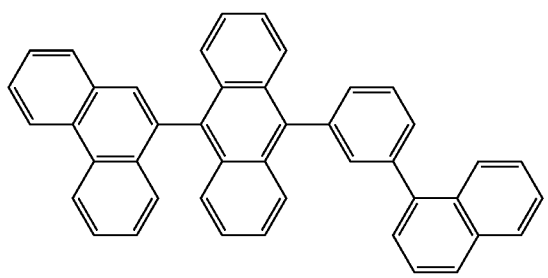
EM386
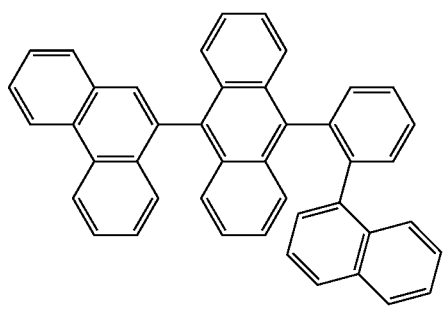
EM387
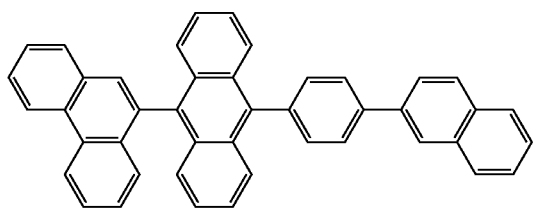
EM388
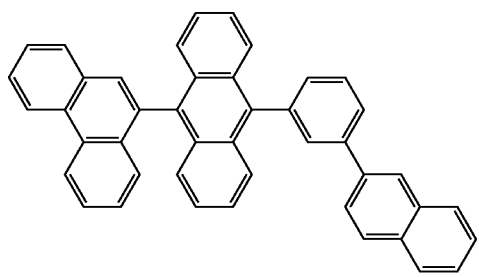

-continued
EM389
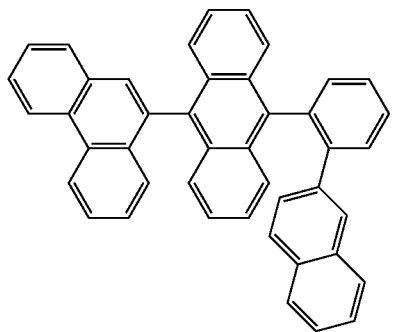
EM390
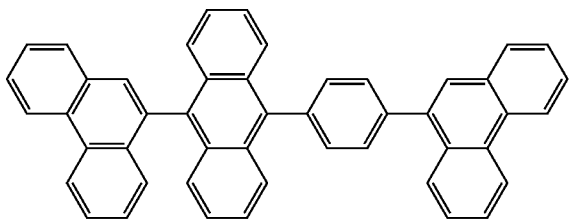
EM391
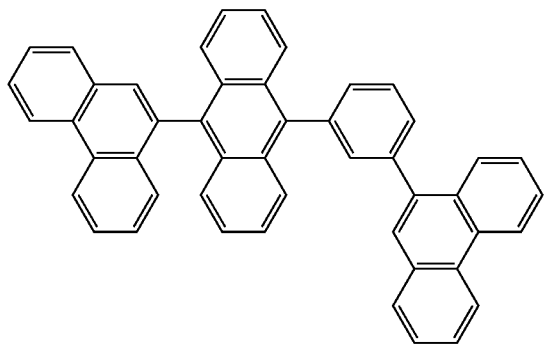
EM392
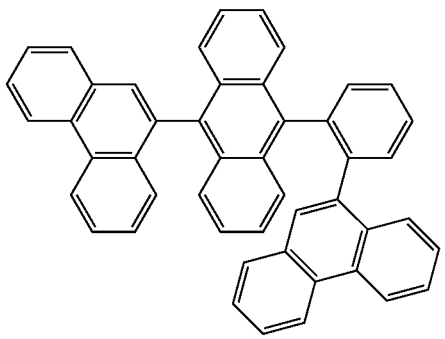
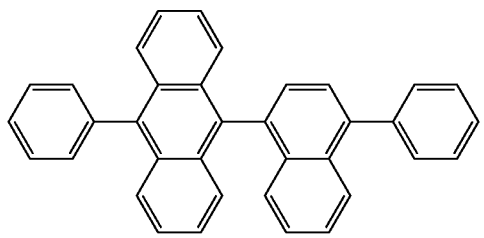
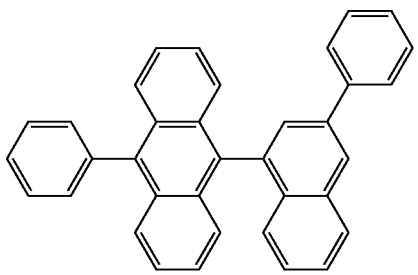
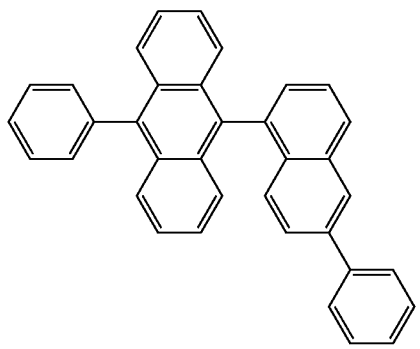
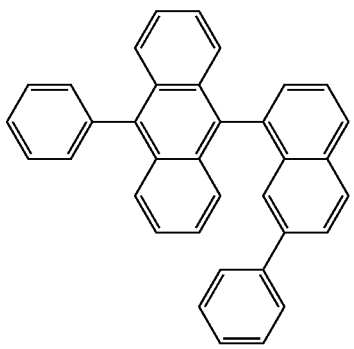
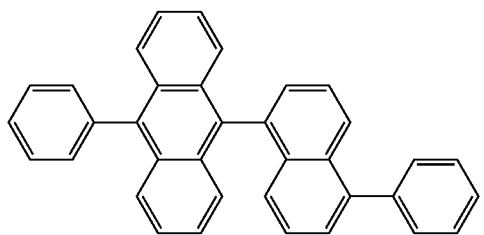
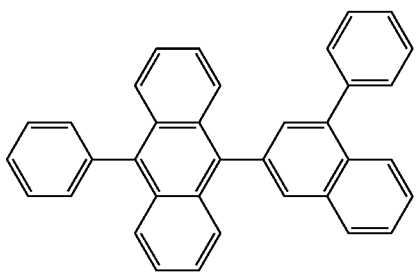

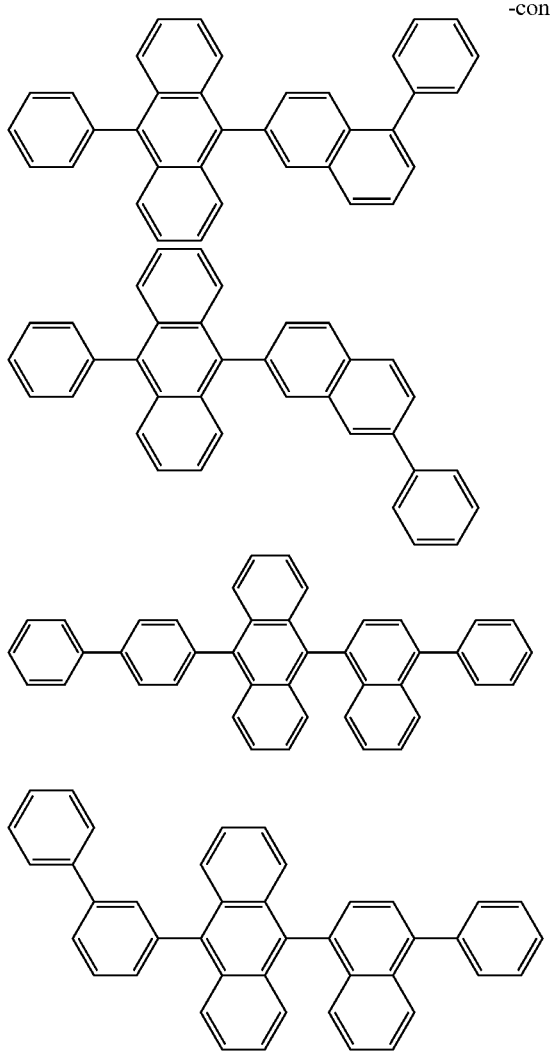
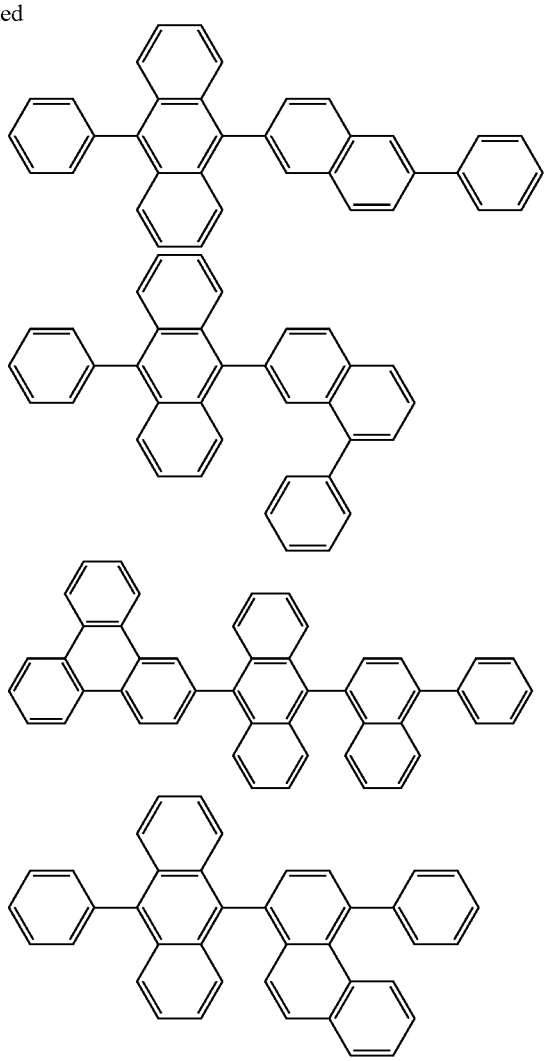

Electron-Donating Dopant

The organic EL device of the invention preferably comprises an electron-donating dopant in the interfacial region between the cathode and the light emitting unit. With such a construction, the organic EL device has an improved luminance and an elongated lifetime. The electron-donating dopant is a metal having a work function of 3.8 eV or less or a compound containing such a metal. Examples thereof include at least one selected from an alkali metal, an alkali metal complex, an alkali metal compound, an alkaline earth metal, an alkaline earth metal complex, an alkaline earth metal compound, a rare earth metal, a rare earth metal complex, and a rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and a mixture thereof, such as $Ba_xSr_{1-x}O$ (0<x<1) and $Ba_xCA^1_{-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, and rare earth metal ions, respectively. Examples of the ligand include quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and a derivative thereof.

The electron-donating dopant is added to the interfacial region preferably into a form of layer or island. The electron-donating dopant is added preferably by co-depositing the electron-donating dopant with the organic compound (light emitting material, electron injecting material, etc.) for forming the interfacial region by a resistance heating deposition method, thereby dispersing the electron-donating dopant into the organic material. The disperse concentration expressed by the molar ratio of the organic material and the electron-donating dopant is 100:1 to 1:100.

When the electron-donating dopant is formed into a form of layer, a light emitting material or an electron injecting material is made into a layer to form an interfacial organic layer, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island to form an interfacial organic layer, and then, the electron-donating dopant alone is deposited by a resistance heating deposition method into a form of island having a thickness preferably 0.05 to 1 nm.

The molar ratio of the main component and the electron-donating dopant in the organic EL device is preferably 5:1 to 1:5.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently.

An aromatic heterocyclic compound having one or more heteroatoms in its molecule is preferably used as the electron transporting material for the electron transporting layer, with a nitrogen-containing ring derivative being particularly preferred. The nitrogen-containing ring derivative is preferably an aromatic ring compound having a nitrogen-containing 6- or 5-membered ring or a fused aromatic ring compound having a nitrogen-containing 6- or 5-membered ring.

The nitrogen-containing ring derivative is preferably, for example, a chelate metal complex having a nitrogen-containing ring represented by formula (A):

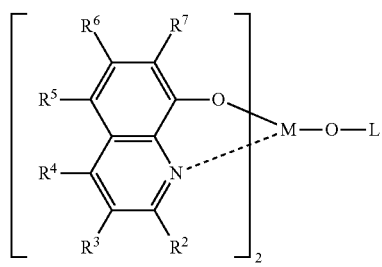
(A)

wherein $R^2$ to $R^7$ each independently represent a hydrogen atom, a halogen atom, a hydroxyl group, an amino group, a hydrocarbon group having 1 to 40, preferably 1 to 20, more preferably 1 to 10, and still more preferably 1 to 6 carbon atoms, an alkoxy group having 1 to 40, preferably 1 to 20, more preferably 1 to 10, and still more preferably 1 to 6 carbon atoms, an aryloxy group having 6 to 40, preferably 6 to 20, more preferably 6 to 12 ring carbon atoms, an alkoxycarbonyl group having 2 to 40, preferably 2 to 20, more preferably 2 to 10, and still more preferably 2 to 5 carbon atoms, or an aromatic heterocyclic group having 9 to 40, preferably 9 to 30, more preferably 9 to 20 ring atoms, each optionally having a substituent.

M is aluminum (Al), gallium (Ga), or indium (In), with In being preferred.

L is a group represented by formula (A') or (A"):

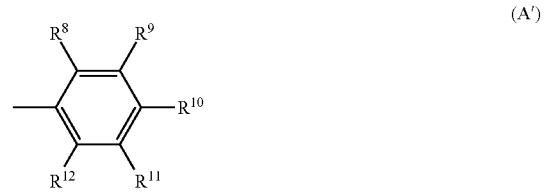
(A')

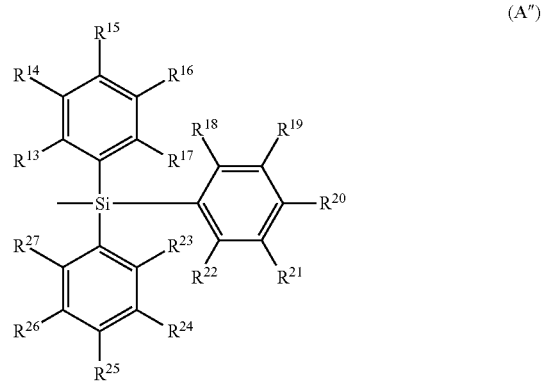
(A")

wherein $R^8$ to $R^{12}$ in formula (A') each independently represent a hydrogen atom or a substituted or unsubstituted hydrocarbon group having 1 to 40, preferably 1 to 20, more preferably 1 to 10, and still more preferably 1 to 6 carbon atoms, and adjacent groups may form a ring structure; and $R^{13}$ to $R^{27}$ in formula (A") each independently represent a hydrogen atom or a substituted or unsubstituted hydrocarbon group having 1 to 40, preferably 1 to 20, more preferably 1 to 10, and still more preferably 1 to 6 carbon atoms, and adjacent two groups may form a ring structure.

Examples of the hydrocarbon group having 1 to 40 carbon atoms represented by $R^8$ to $R^{12}$ of formula (A') and $R^{13}$ to $R^{27}$ of formula (A") are the same as mentioned above with respect to $R^2$ to $R^7$ of formula (A).

Examples of the divalent group to be formed when adjacent groups selected from $R^8$ to $R^{12}$ and $R^{13}$ to $R^{27}$ form a ring structure include a tetramethylene group, a pentamethylene group, a hexamethylene group, a diphenylmethane-2,2'-diyl group, a diphenylethane-3,3'-diyl group, and a diphenylpropane-4,4'diyl group.

The electron transporting compound for the electron transporting layer is preferably a metal complex including 8-hydroxyquinoline or its derivative, an oxadiazole derivative, and a nitrogen-containing heterocyclic derivative.

Electron transporting compounds which have a good thin film-forming property are preferably used. Examples of the electron transporting compound are shown below.

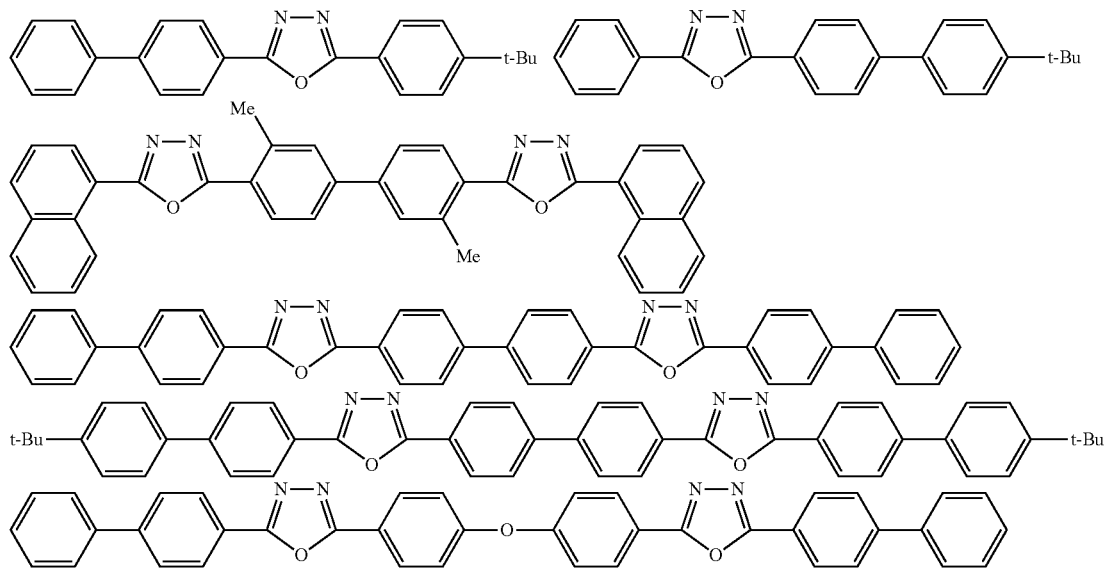

Examples of the nitrogen-containing heterocyclic derivative for use as the electron transporting compound include a nitrogen-containing heterocyclic derivative having a structure represented by formula (D) but not a metal complex:

(D)

The electron transporting layer of the organic EL of the invention particularly preferably comprises at least one of the nitrogen-containing heterocyclic derivatives represented by formulae (60) to (62):

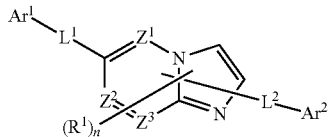
(60)

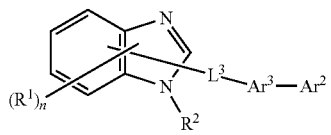
(61)

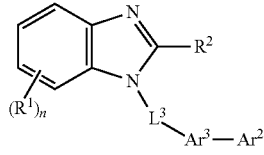
(62)

wherein $Z^1$, $Z^2$, and $Z^3$ each independently represent a nitrogen atom or a carbon atom;

$R^1$ and $R^2$ each independently represent a substituted or unsubstituted aryl group having 6 to 50, preferably 6 to 30, more preferably 6 to 20, and still more preferably 6 to 12 ring carbon atoms, a substituted or unsubstituted heterocyclic group having 5 to 50, preferably 5 to 30, more preferably 5 to 20, and still more preferably 5 to 12 ring atoms, a substituted or unsubstituted alkyl group having 1 to 20, preferably 1 to 10, and more preferably 1 to 6 carbon atoms, a substituted or unsubstituted haloalkyl group having 1 to 20, preferably 1 to 10, and more preferably 1 to 6 carbon atoms, or a substituted or unsubstituted alkoxyl group having 1 to 20, preferably 1 to 10, and more preferably 1 to 6 carbon atoms;

n is an integer of 0 to 5, when n is an integer of 2 or more, groups $R^1$ may be the same or different from each other, and adjacent two groups $R^1$ may bond to each other to form a substituted or unsubstituted hydrocarbon ring;

$Ar^1$ represents a substituted or unsubstituted aryl group having 6 to 50, preferably 6 to 30, more preferably 6 to 20, and still more preferably 6 to 12 ring carbon atoms or a substituted or unsubstituted heterocyclic group having 5 to 50, preferably 5 to 30, more preferably 5 to 20, and still more preferably 5 to 12 ring atoms;

$Ar^2$ represents a hydrogen atom, a substituted or unsubstituted alkyl group having 1 to 20, preferably 1 to 10, and more preferably 1 to 6 carbon atoms, a substituted or unsubstituted haloalkyl group having 1 to 20, preferably 1 to 10, and more preferably 1 to 6 carbon atoms, a substituted or unsubstituted alkoxyl group having 1 to 20, preferably 1 to 10, and more preferably 1 to 6 carbon atoms, a substituted or unsubstituted aryl group having 6 to 50, preferably 6 to 30, more preferably 6 to 20, and still more preferably 6 to 12 ring carbon atoms, or a substituted or unsubstituted heterocyclic group having 5 to 50, preferably 5 to 30, more preferably 5 to 20, and still more preferably 5 to 12 ring atoms;

provided that one of $Ar^1$ and $Ar^2$ is a substituted or unsubstituted fused aromatic hydrocarbon group having 10 to 50, preferably 10 to 30, more preferably 10 to 20, and still more preferably 10 to 14 ring carbon atoms or a substituted or unsubstituted fused aromatic heterocyclic group having 9 to 50, preferably 9 to 30, more preferably 9 to 20, and still more preferably 9 to 14 ring atoms;

$Ar^3$ represents a substituted or unsubstituted arylene group having 6 to 50, preferably 6 to 30, more preferably 6 to 20, and still more preferably 6 to 12 ring carbon atoms or a substituted or unsubstituted heteroarylene group having 5 to 50, preferably 5 to 30, more preferably 5 to 20, and still more preferably 5 to 12 ring atoms; and $L^1$, $L^2$, and $L^3$ each independently represent a single bond, a substituted or unsubstituted arylene group having 6 to 50, preferably 6 to 30, more preferably 6 to 20, and still more preferably 6 to 12 ring carbon atoms or a substituted or unsubstituted divalent fused aromatic heterocyclic group having 9 to 50, preferably 9 to 30, more preferably 9 to 20, and still more preferably 9 to 14 ring atoms.

Examples of the nitrogen-containing heterocyclic derivatives represented by formulae (60) to (62) are shown below.

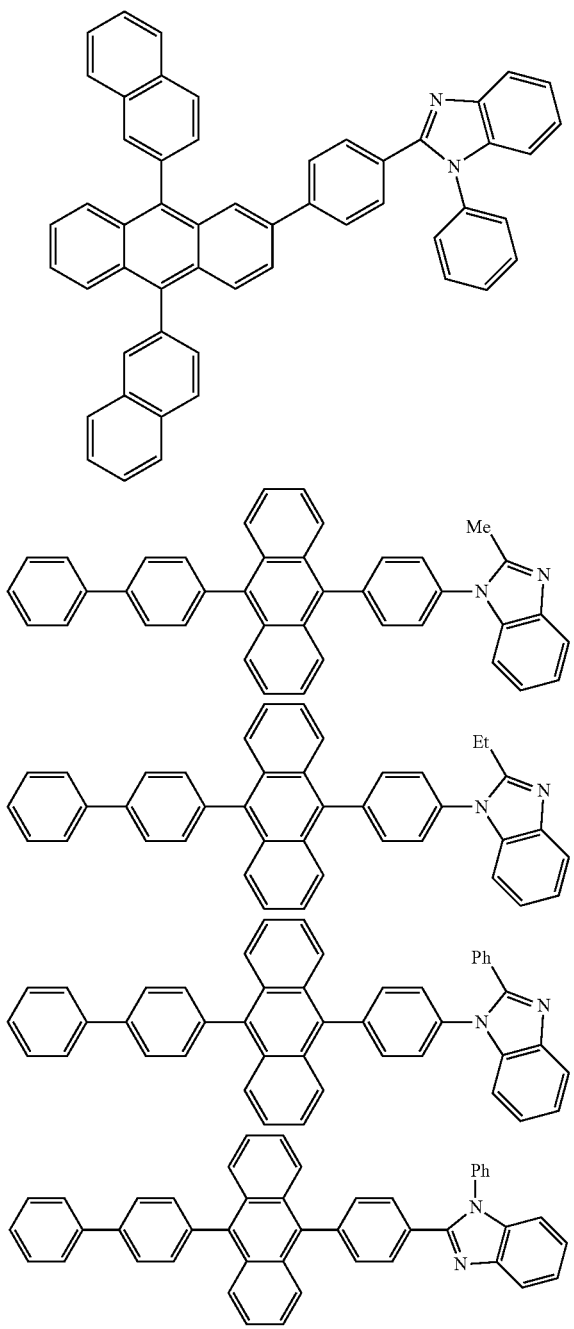

The thickness of the electron transporting layer is preferably 1 to 100 nm, although not particularly limited thereto.

The electron injecting layer which may be formed adjacent to the electron transporting layer preferably includes an inorganic compound, such as an insulating material and a semiconductor in addition to the nitrogen-containing ring derivative. The insulating material or semiconductor incorporated into the electron injecting layer effectively prevents the leak of electric current to enhance the electron injecting properties.

The insulating material is preferably at least one metal compound selected from the group consisting of an alkali metal chalcogenide, an alkaline earth metal chalcogenide, an alkali metal halide, and an alkaline earth metal halide. The alkali metal chalcogenide, etc. incorporated into the electron injecting layer further enhances the electron injecting properties. Preferred examples of the alkali metal chalcogenides include $Li_2O$, $K_2O$, $Na_2S$, $Na_2Se$, and $Na_2O$, and preferred examples of the alkaline earth metal chalcogenides include CaO, BaO, SrO, BeO, BaS, and CaSe. Preferred examples of the alkali metal halides include LiF, NaF, KF, LiCl, KCl, and NaCl. Examples of the alkaline earth metal halides include fluorides such as $CaF_2$, $BaF_2$, $SrF_2$, $MgF_2$, and $BeF_2$ and halides other than fluorides.

Examples of the semiconductor may include an oxide, a nitride or an oxynitride each containing at least one element selected from the group consisting of Ba, Ca, Sr, Yb, Al, Ga, In, Li, Na, Cd, Mg, Si, Ta, Sb and Zn. The semiconductor may be used singly or in combination of two or more. The inorganic compound forming the electron injecting layer preferably forms a microcrystalline or amorphous insulating thin film. When the electron injecting layer is formed from such an insulating thin film, the thin film is made more uniform to decrease the pixel defects such as dark spots. Examples of such an inorganic compound include an alkali metal chalcogenide, an alkaline earth metal chalcogenide, an alkali metal halide, and an alkaline earth metal halide, each being described above.

The thickness of the layer including the insulating material or the semiconductor is preferably about 0.1 to 15 nm. The electron injecting layer may include the electron-donating dopant material described above.

Hole Transporting Layer

The hole transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit.

An aromatic amine compound, for example, an aromatic amine derivative represented by formula (III), is preferably used as the material for forming the hole transporting layer:

wherein $Ar^1$ to $Ar^4$ each represent a substituted or unsubstituted aromatic hydrocarbon group having 6 to 50, preferably 6 to 30, more preferably 6 to 20, and still more preferably 6 to 12 ring carbon atoms; a substituted or unsubstituted fused aromatic hydrocarbon group having 6 to 50, preferably 6 to 30, more preferably 6 to 20, and still more preferably 6 to 12 ring carbon atoms; a substituted or unsubstituted aromatic heterocyclic group having 5 to 50, preferably 5 to 30, more preferably 5 to 20, and still more preferably 5 to 12 ring atoms; a fused aromatic heterocyclic group having 5 to 50, preferably 5 to 30, more preferably 5 to 20, and still more preferably 5 to 12 ring atoms; or a group wherein the aromatic hydrocarbon group or fused aromatic hydrocarbon group is bonded to the aromatic heterocyclic group or fused aromatic heterocyclic group;

$Ar^1$ and $Ar^2$, or $Ar^3$ and $Ar^4$ may form a ring; and

L represents a substituted or unsubstituted aromatic hydrocarbon group having 6 to 50, preferably 6 to 30, more preferably 6 to 20, and still more preferably 6 to 12 ring carbon atoms; a substituted or unsubstituted fused aromatic hydrocarbon group having 6 to 50, preferably 6 to 30, more preferably 6 to 20, and still more preferably 6 to 12 ring carbon atoms; a substituted or unsubstituted aromatic heterocyclic group having 5 to 50, preferably 5 to 30, more preferably 5 to 20, and still more preferably 5 to 12 ring atoms; or a fused aromatic heterocyclic group having 5 to 50, preferably 5 to 30, more preferably 5 to 20, and still more preferably 5 to 12 ring atoms.

Examples of the compound represented by formula (III) are shown below.

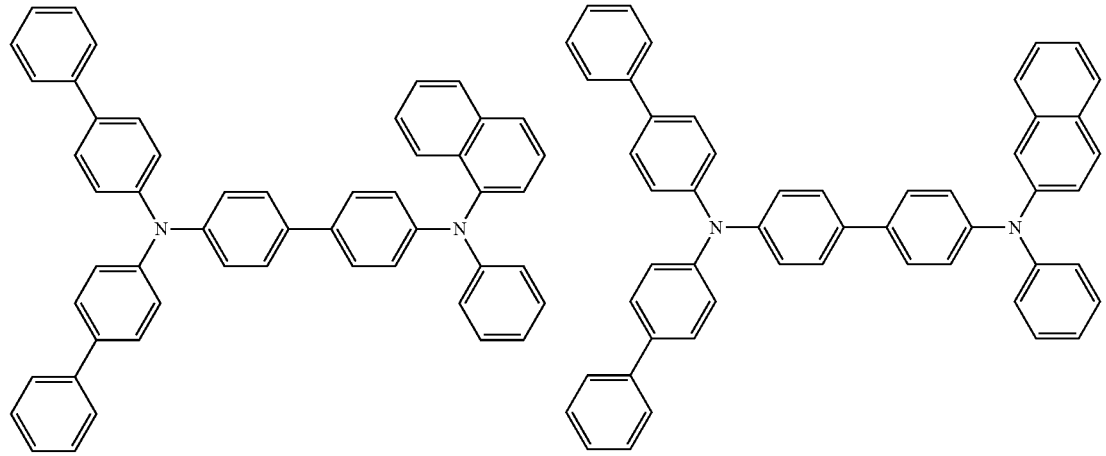

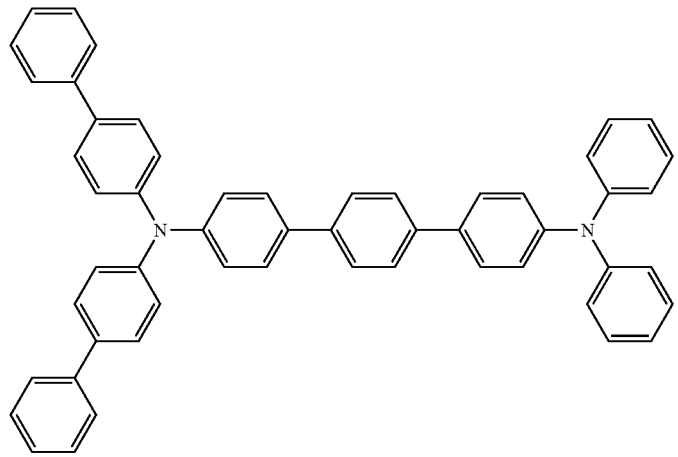
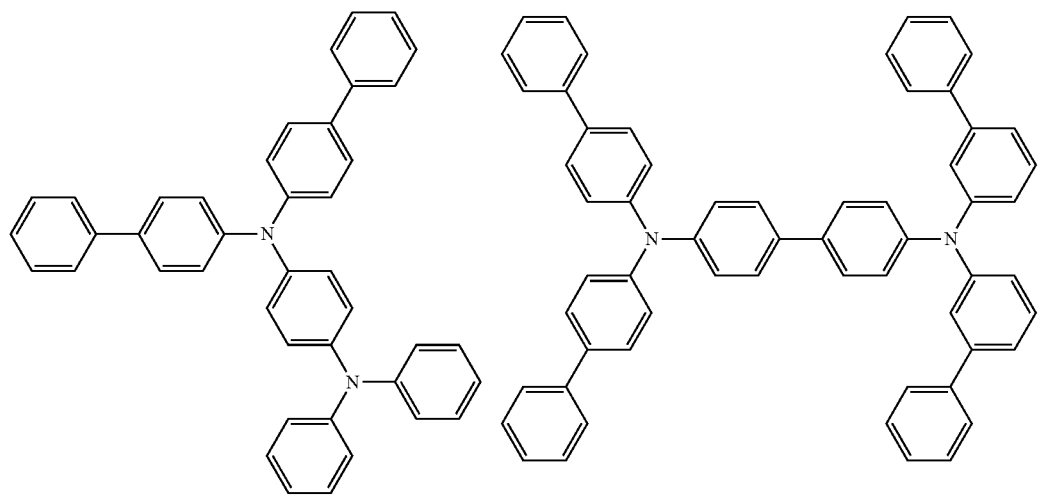
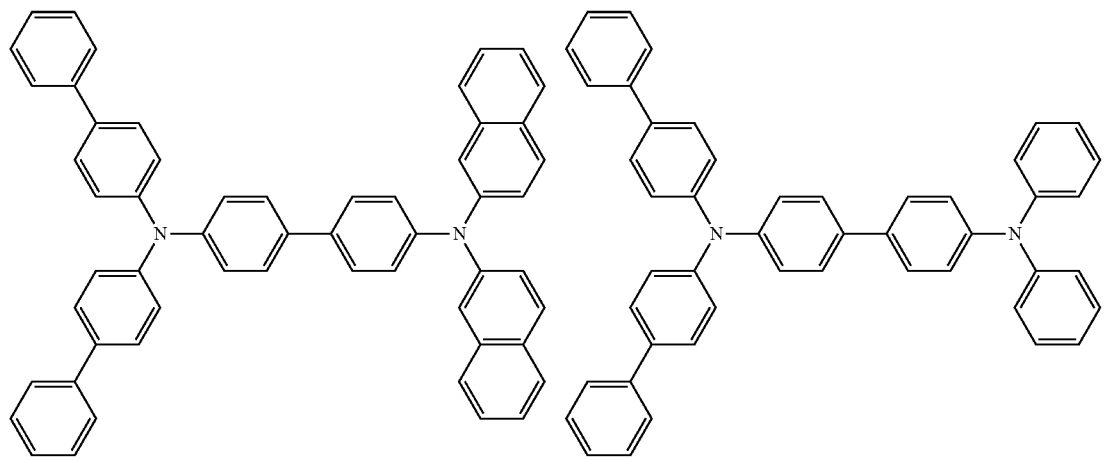

-continued
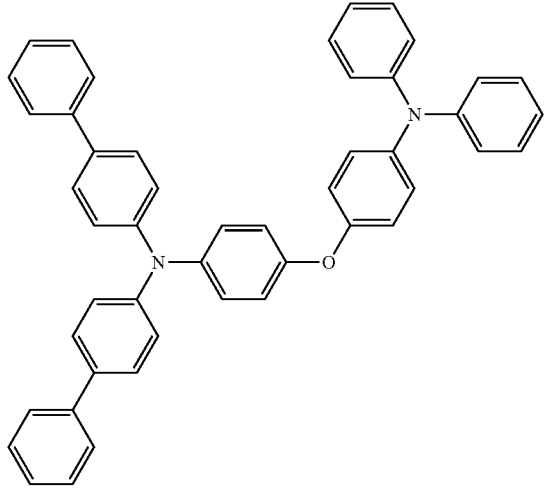
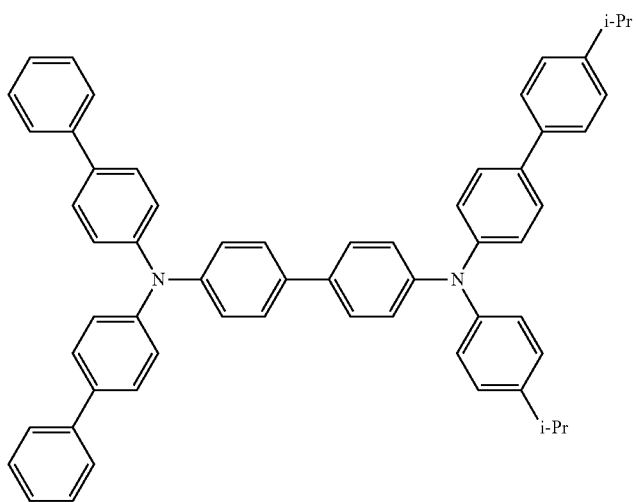
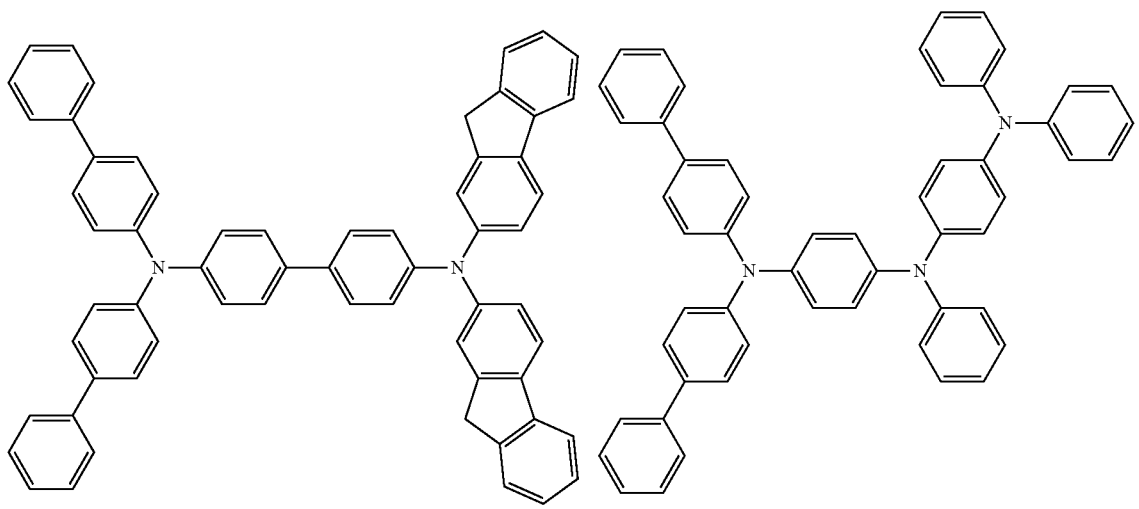

-continued
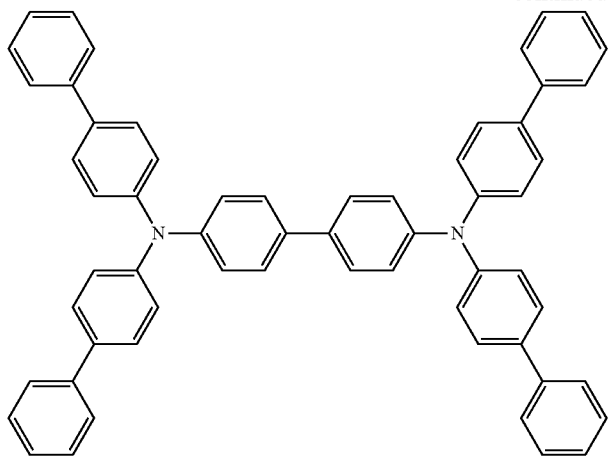
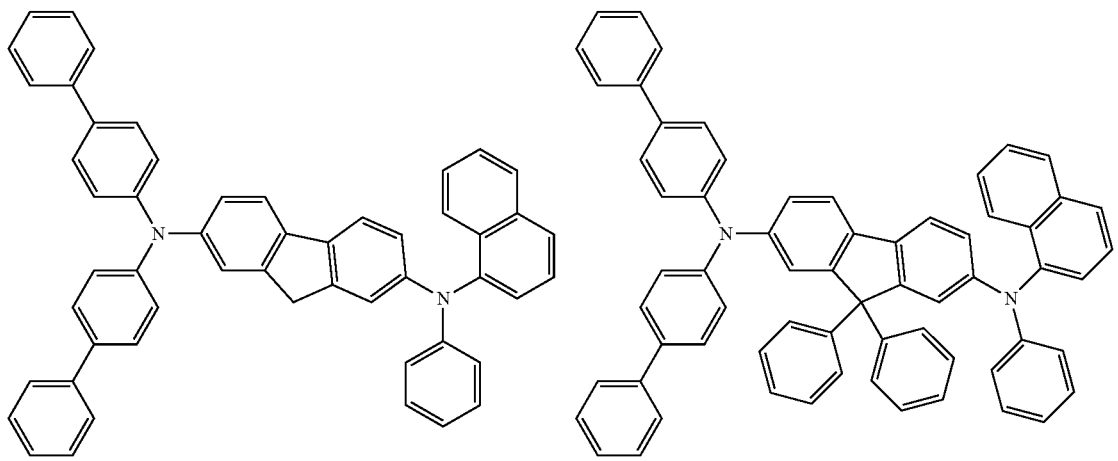
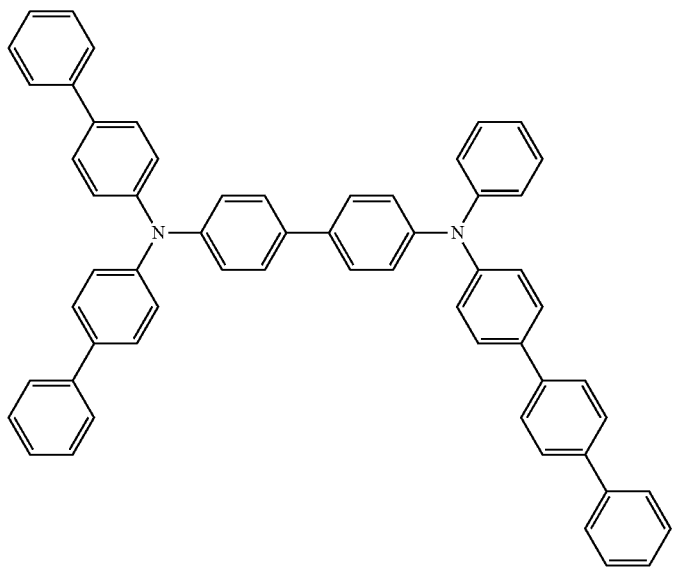

-continued
239
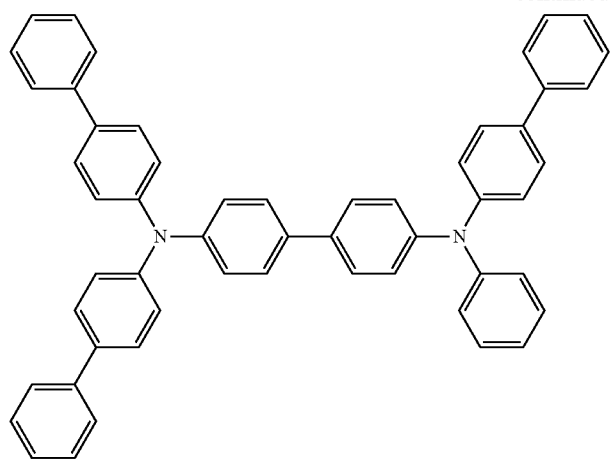
240
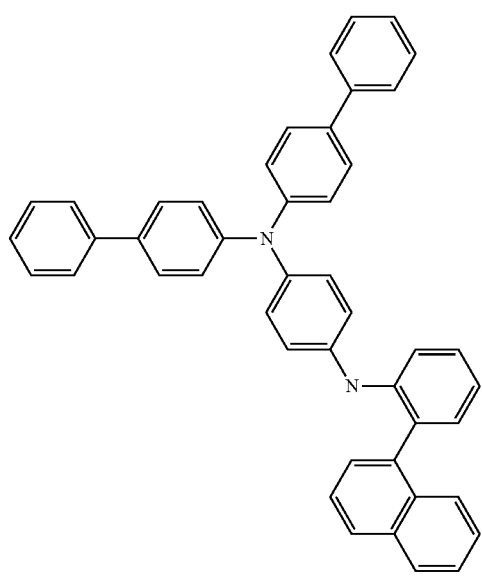
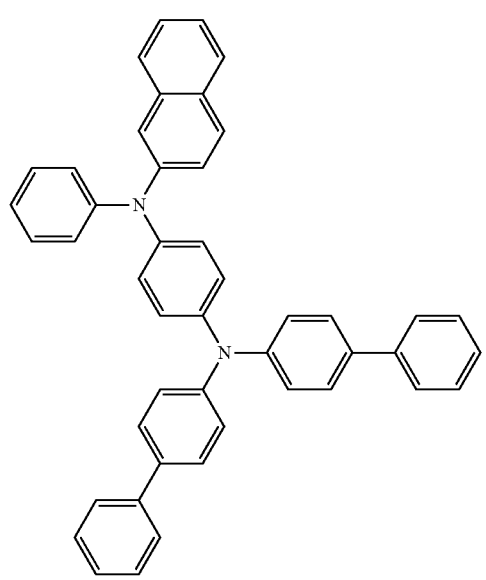
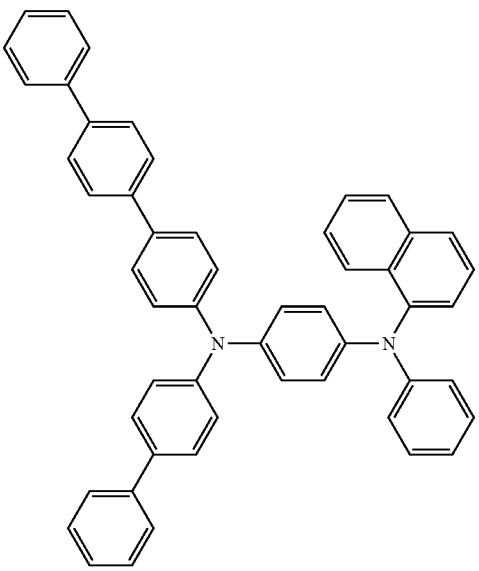
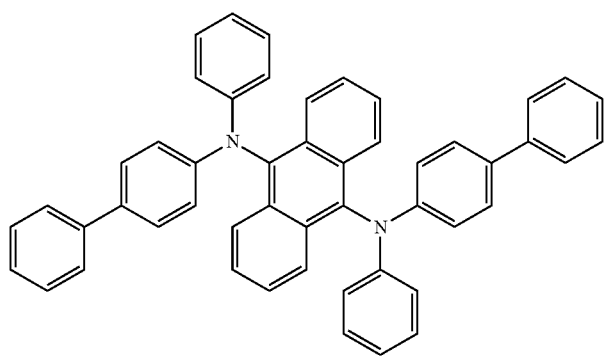

241
242
-continued
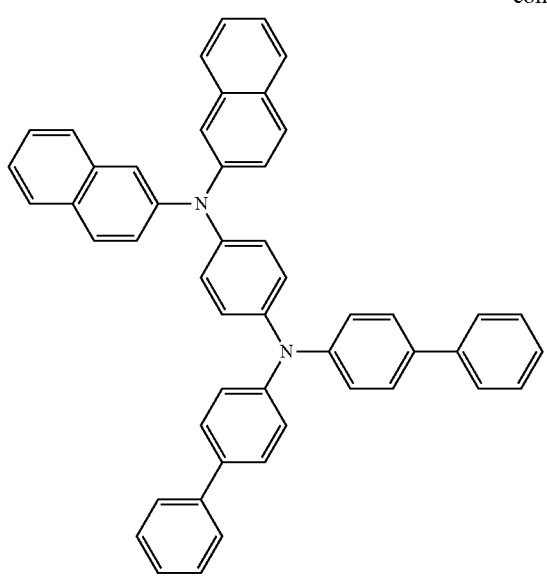
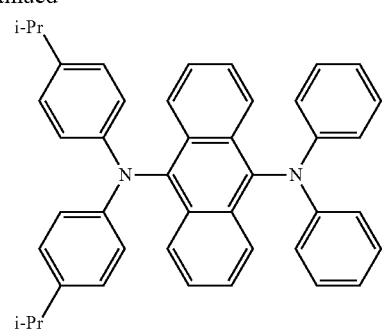
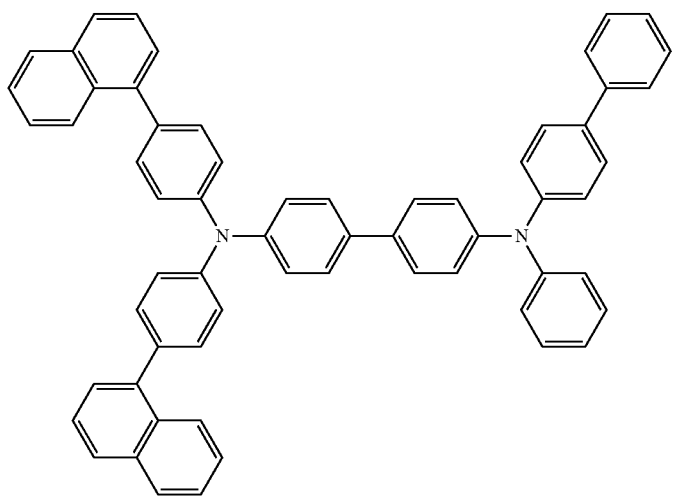
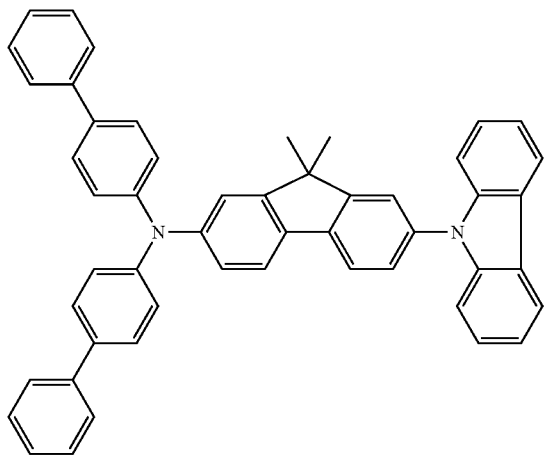

-continued
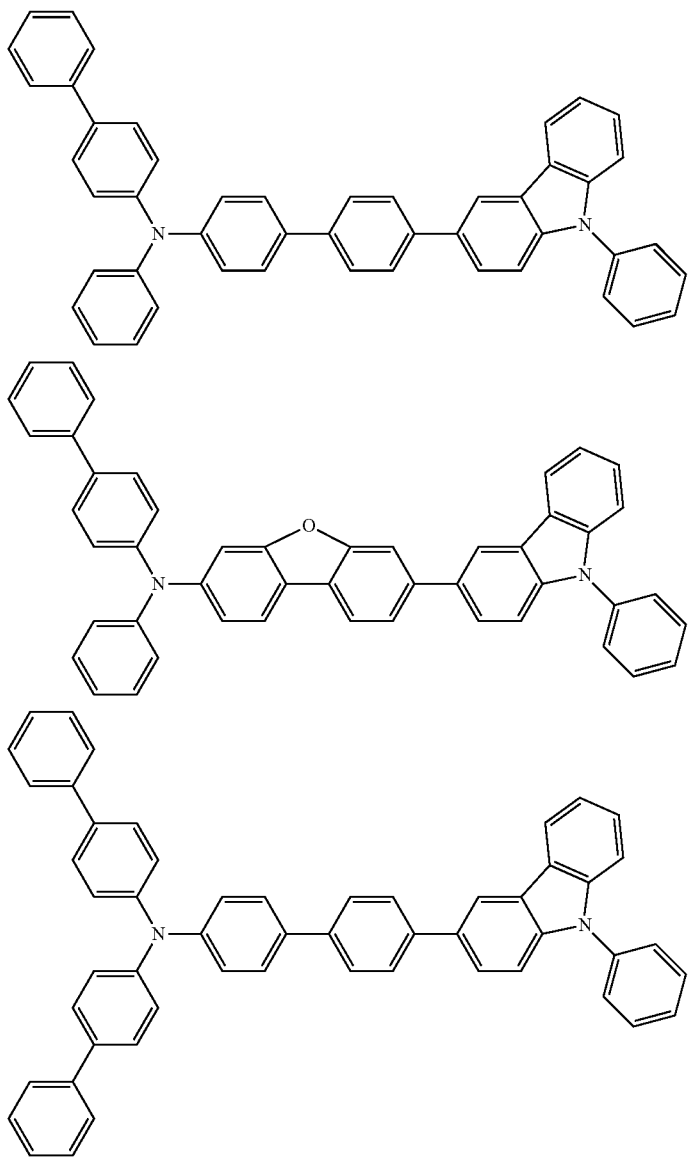
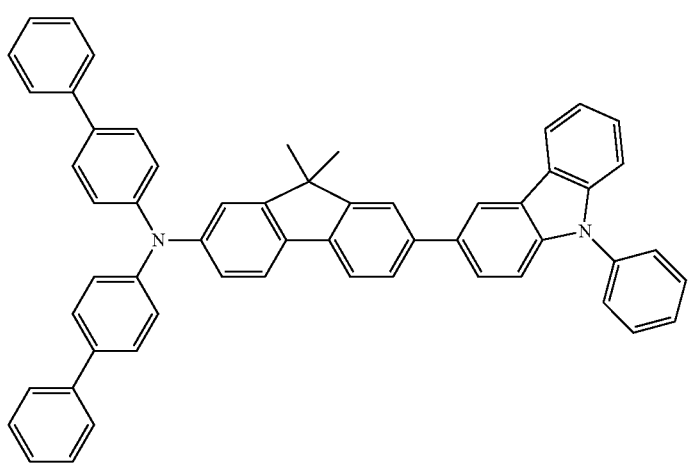

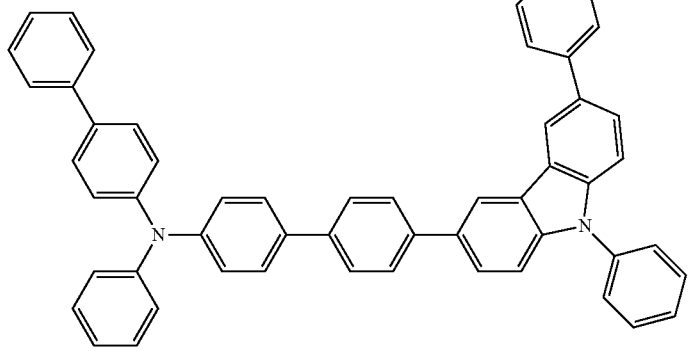
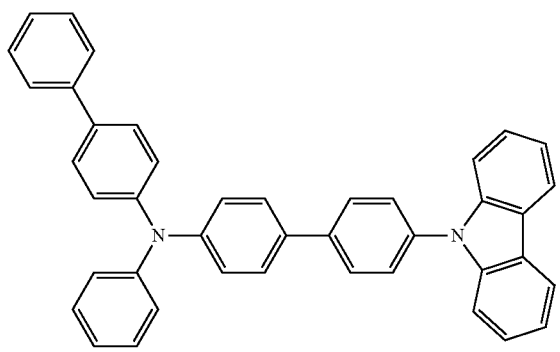
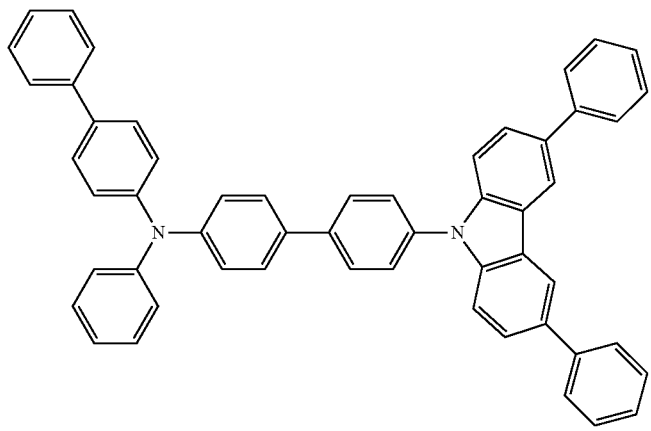
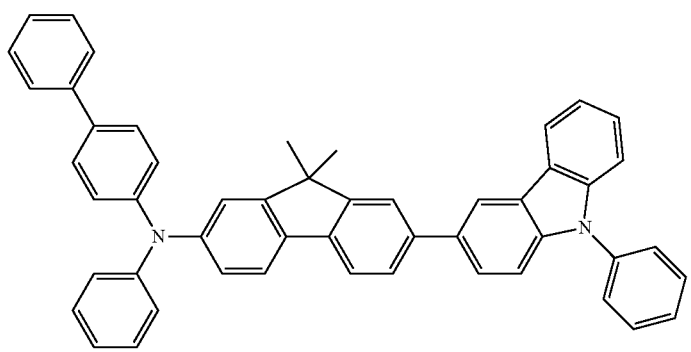

-continued
247
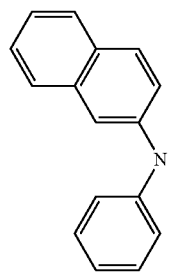
248
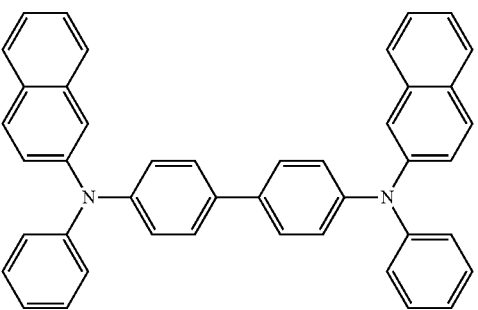
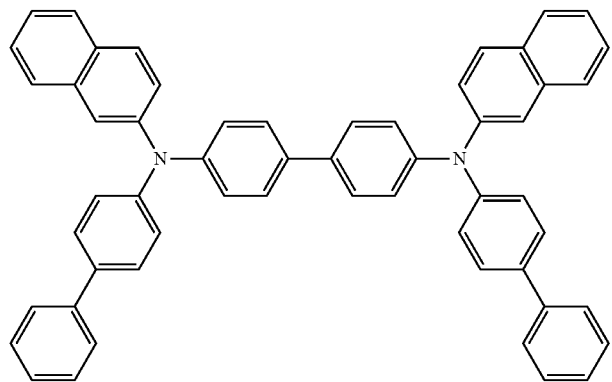
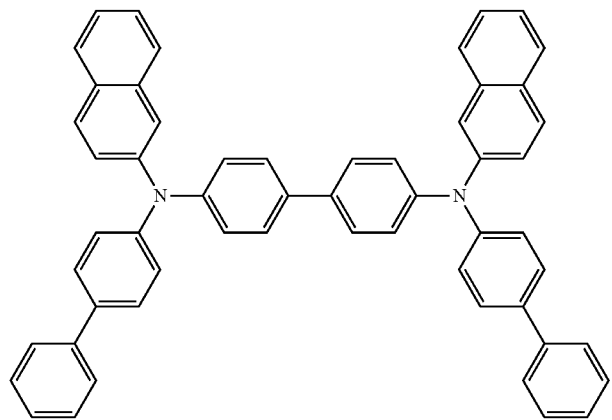
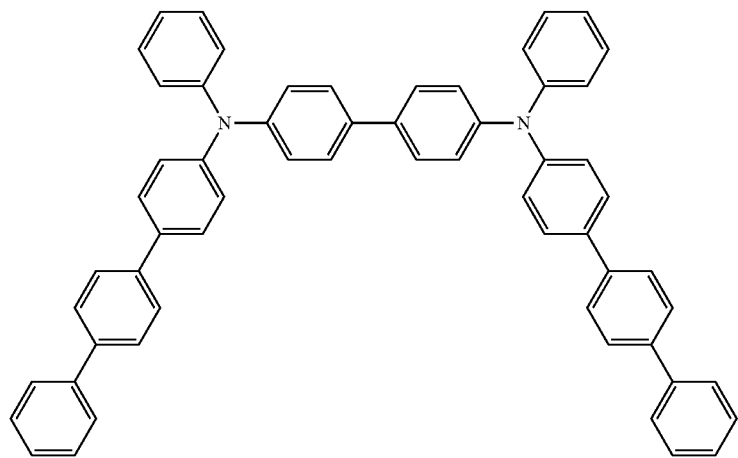

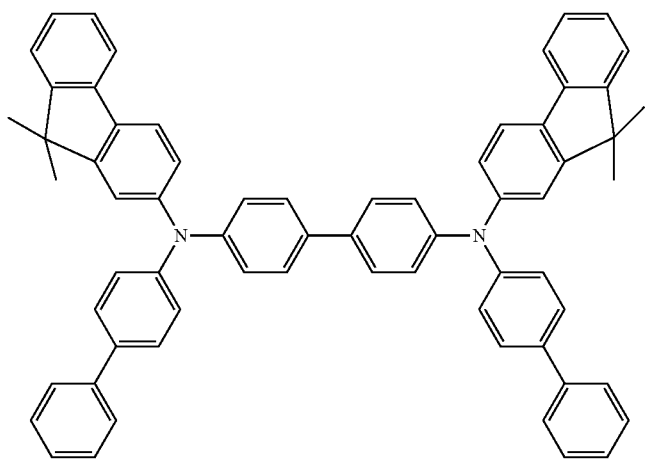
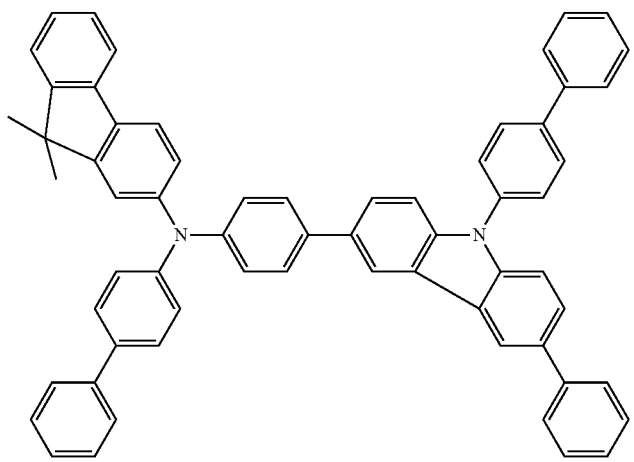
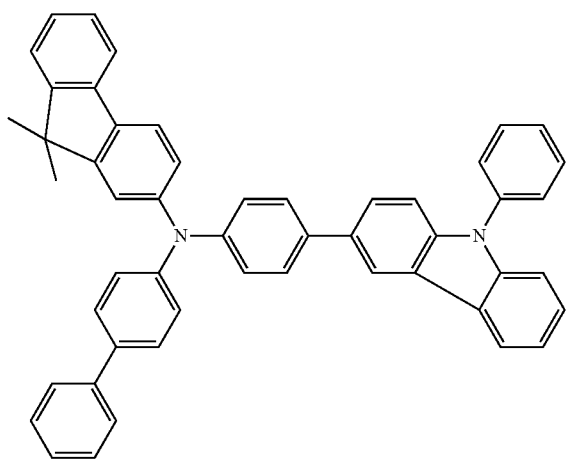

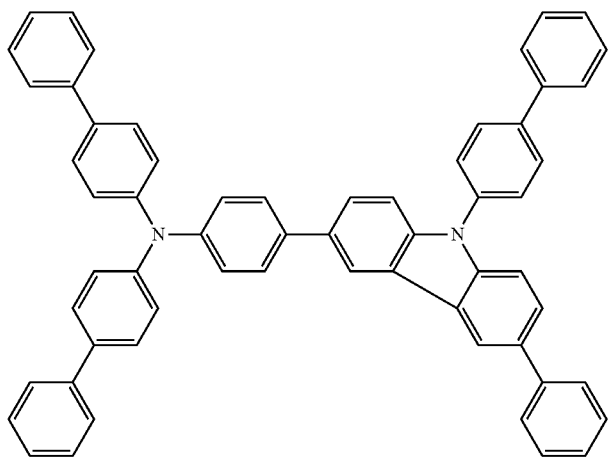
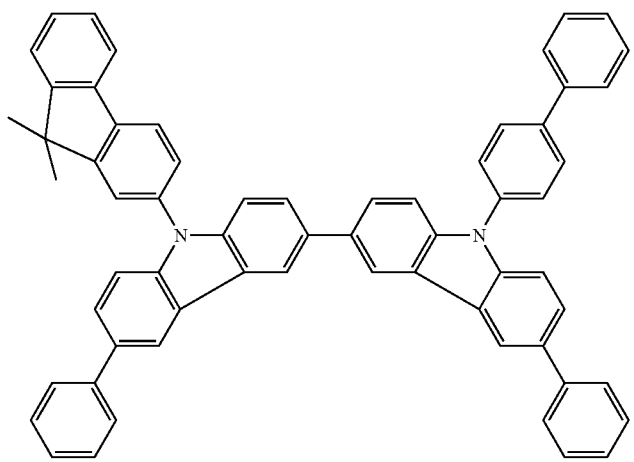
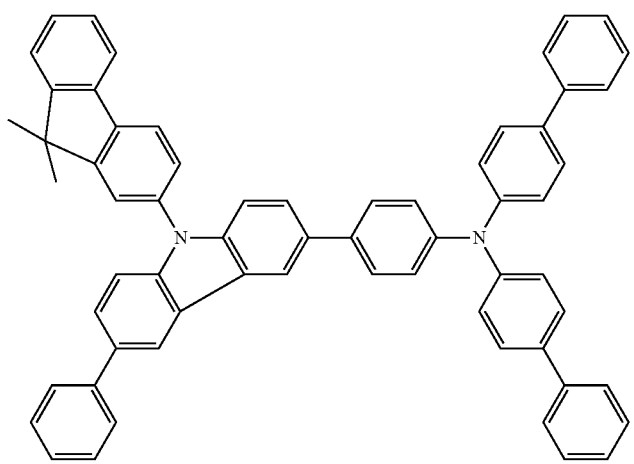

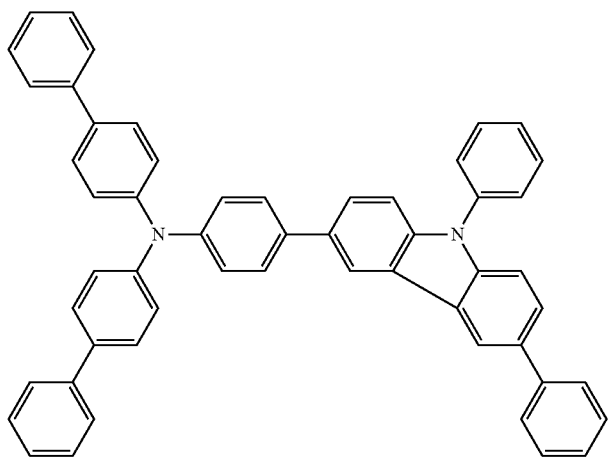
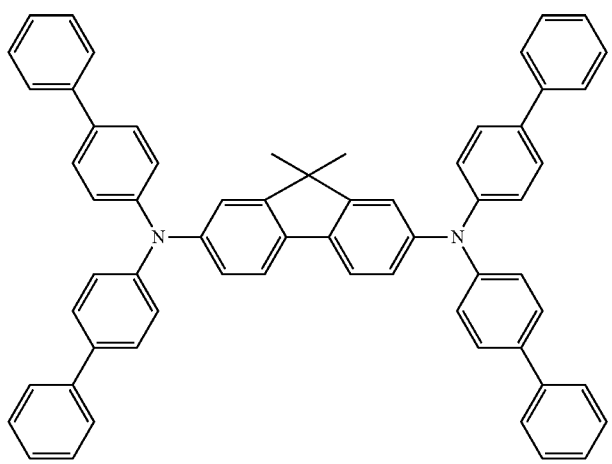
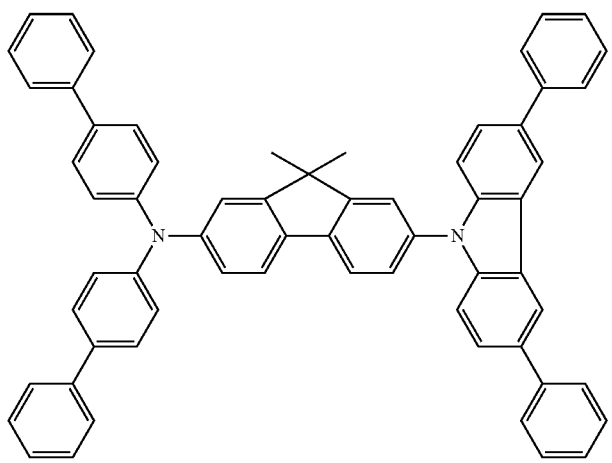

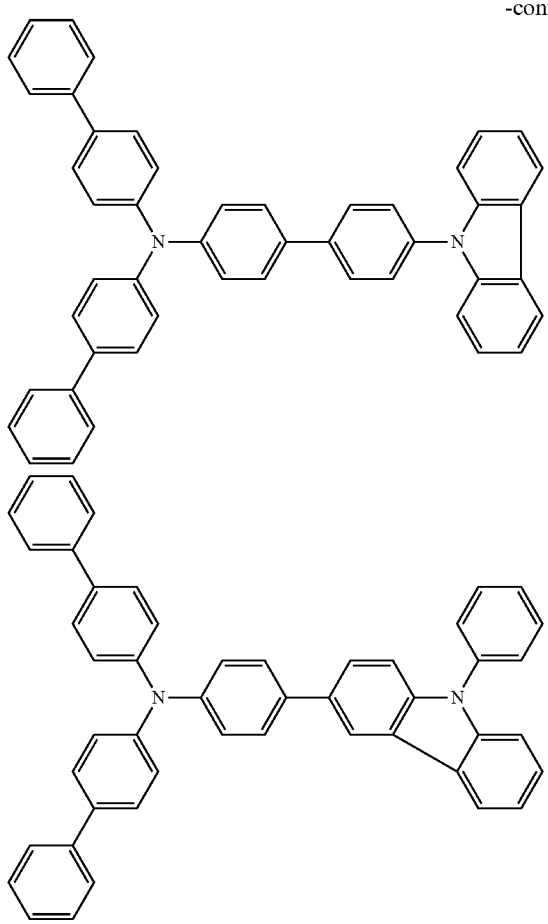
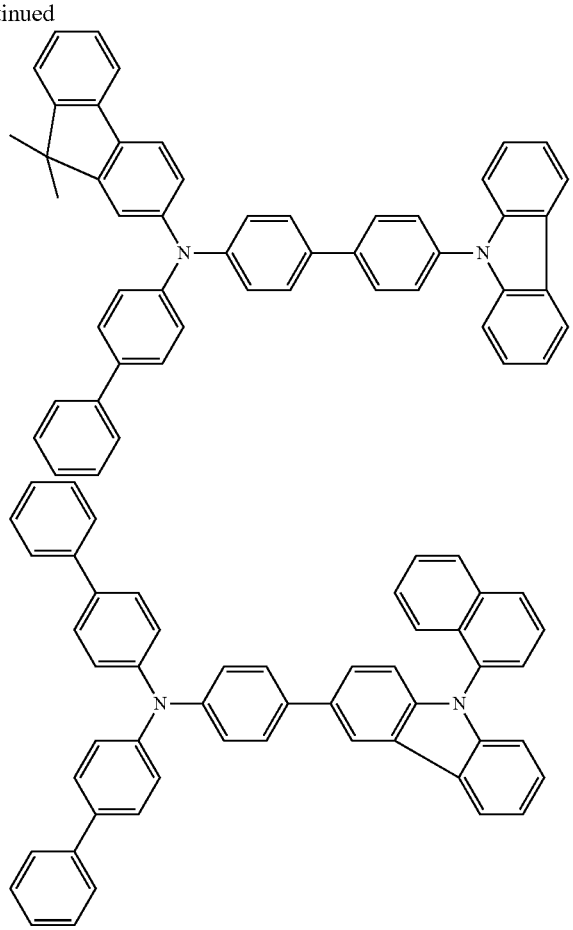
The aromatic amine represented by formula (IV) is also preferably used as the material for forming the hole transporting layer.
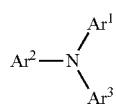
(IV)
wherein $Ar^1$ to $Ar^3$ are as defined above with respect to $Ar^1$ to $Ar^4$ of formula (III). Examples of the compounds represented by formula (IV) are shown below, although not limited thereto.
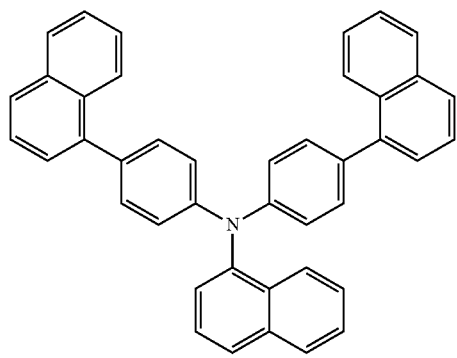
-continued
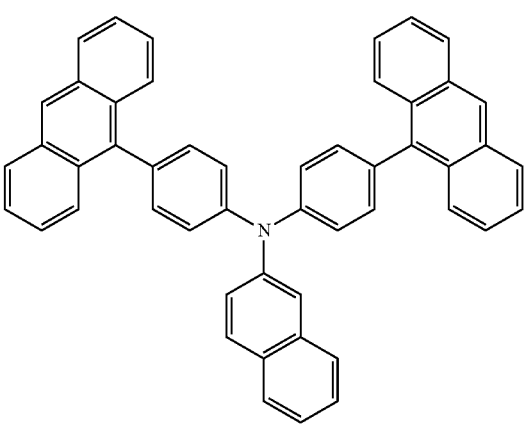

257
-continued
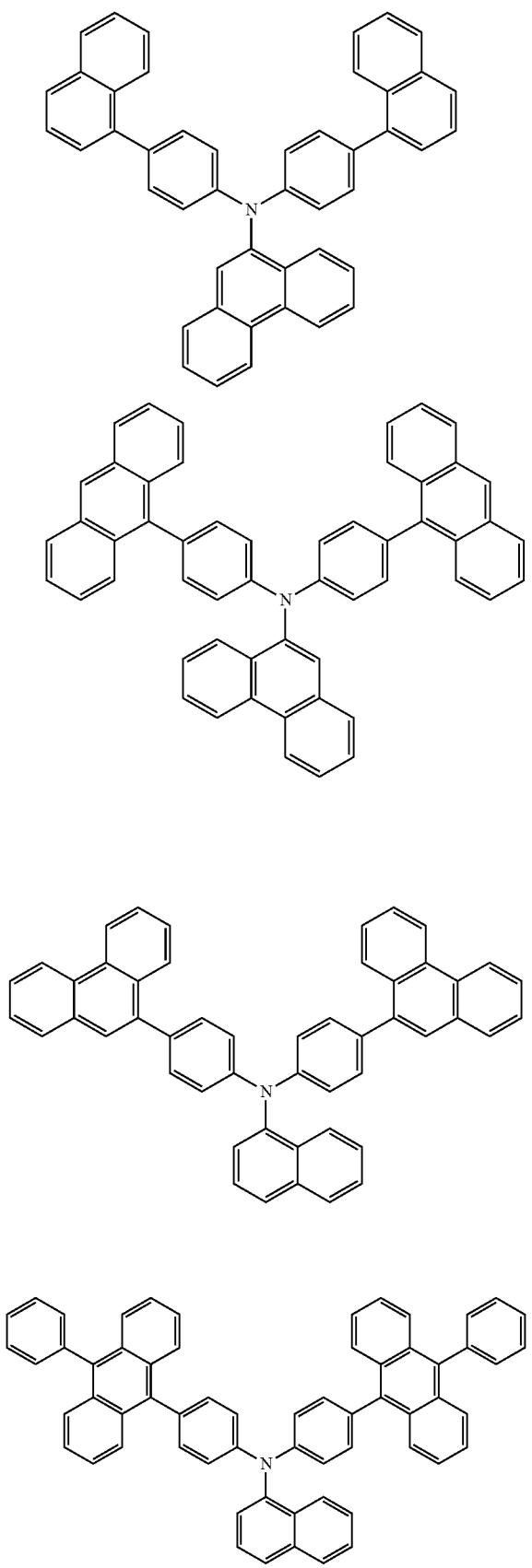
258
-continued
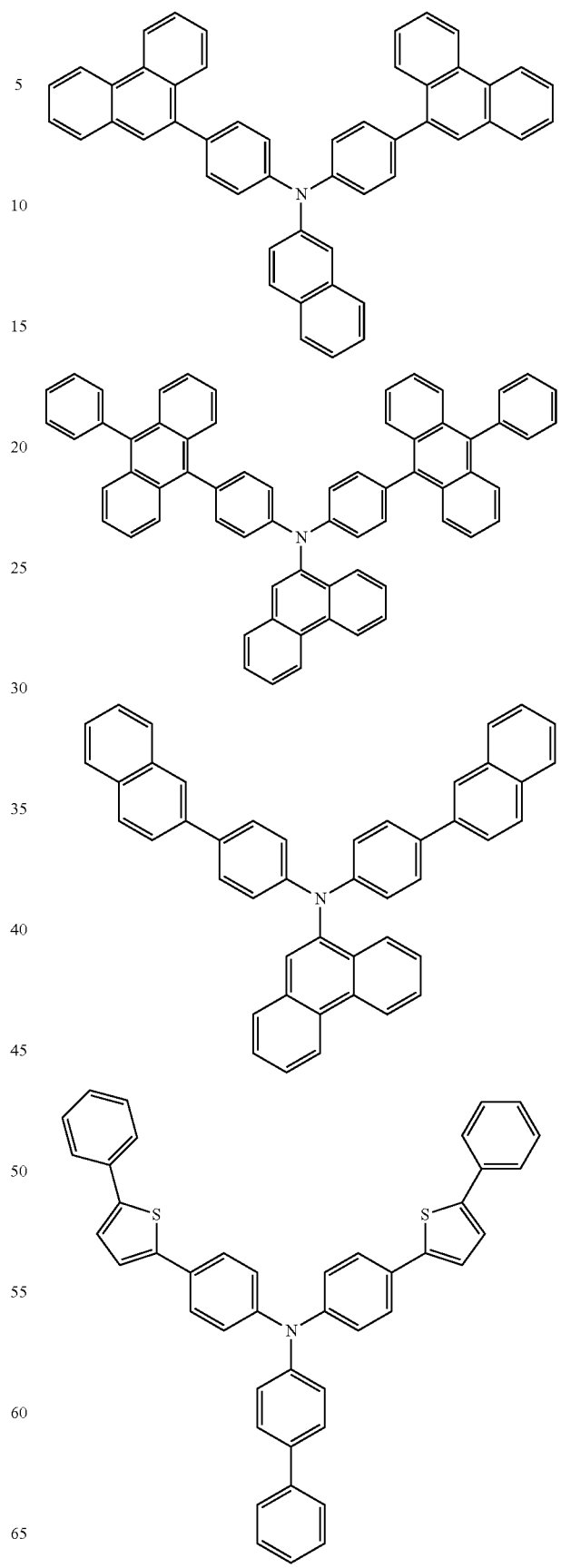

259
-continued
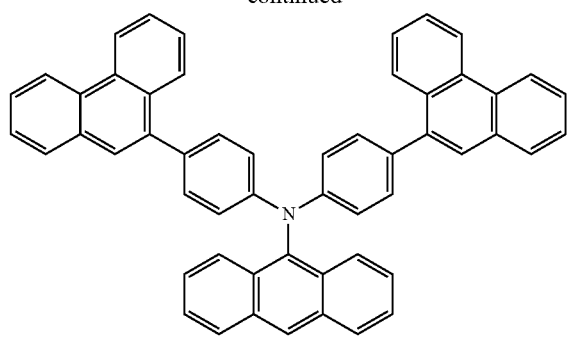
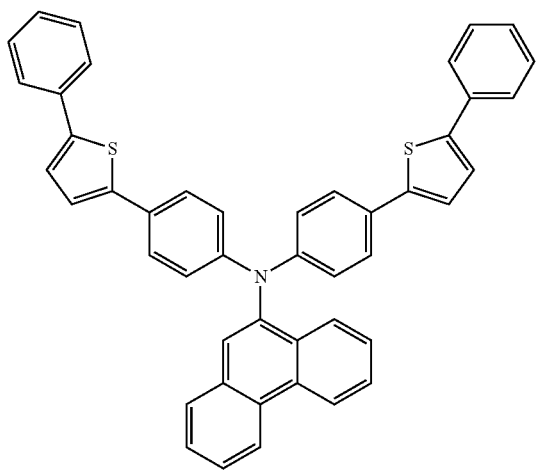
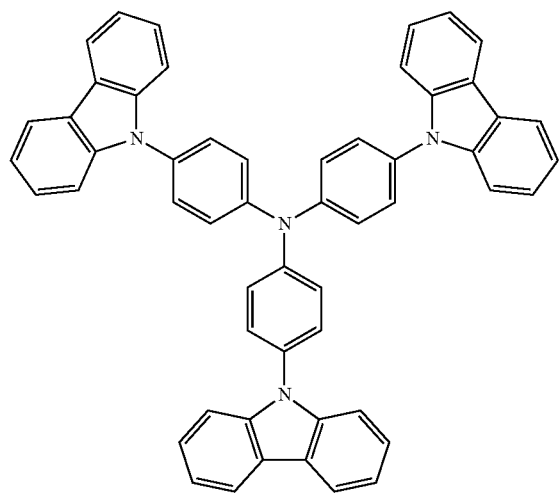
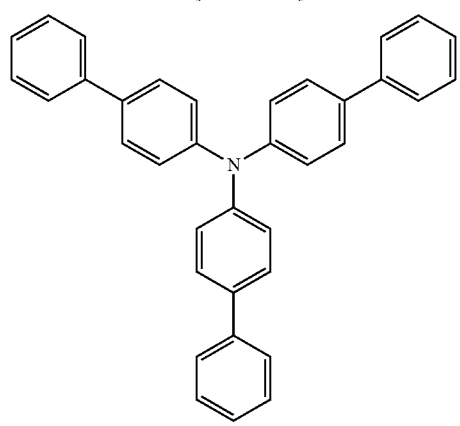
260
-continued
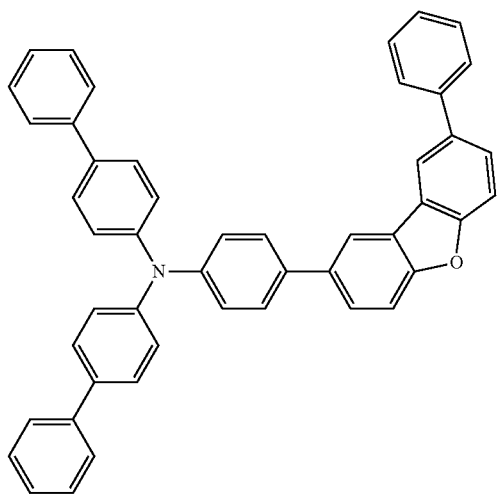
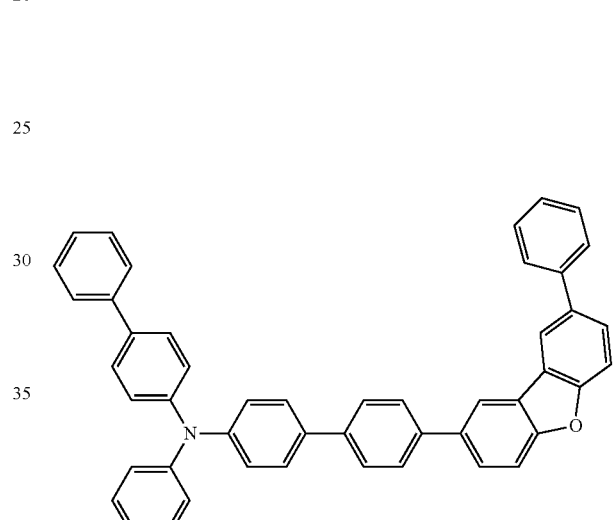
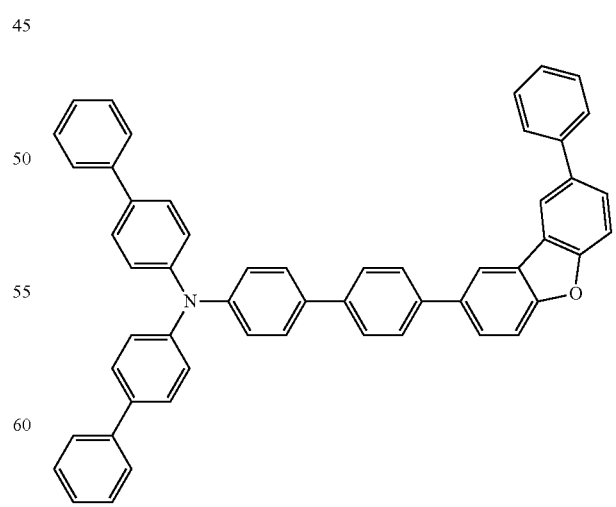

261
-continued
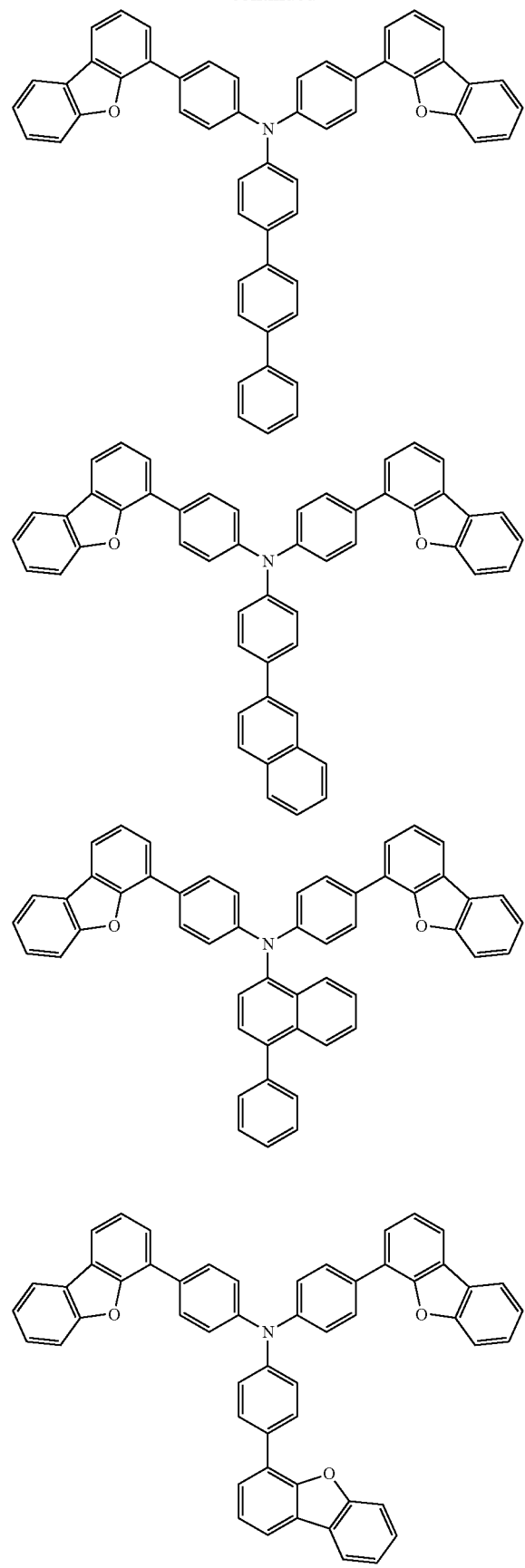
262
-continued
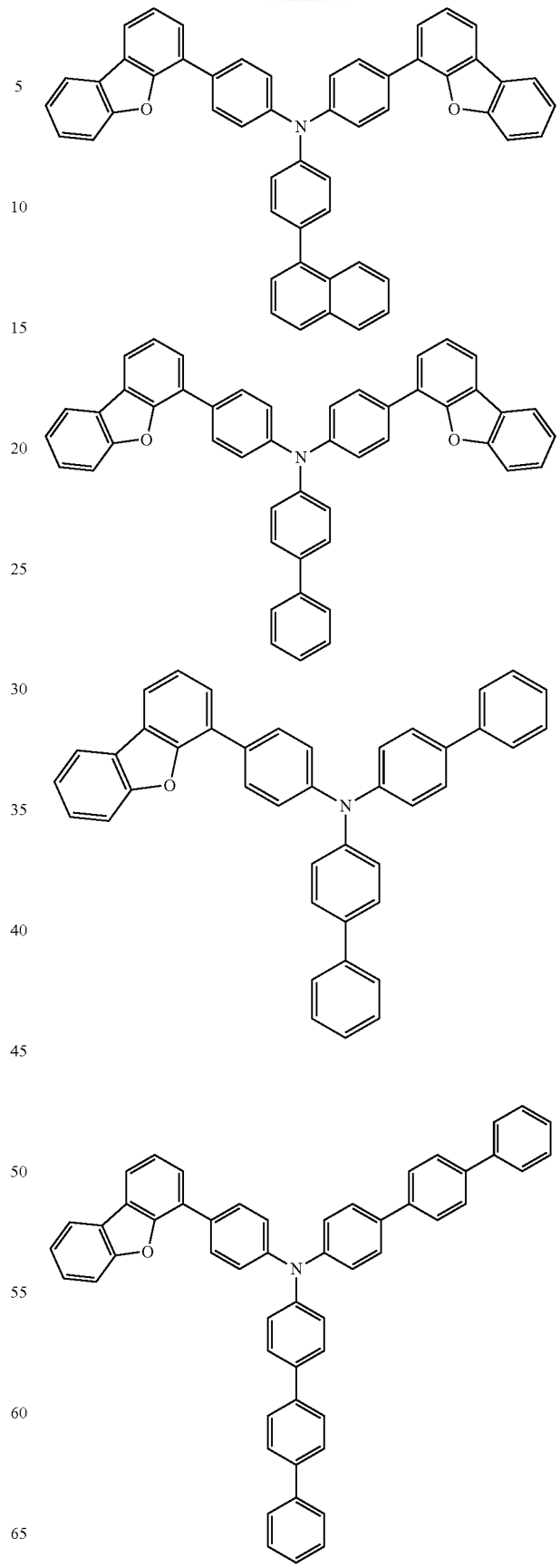

-continued

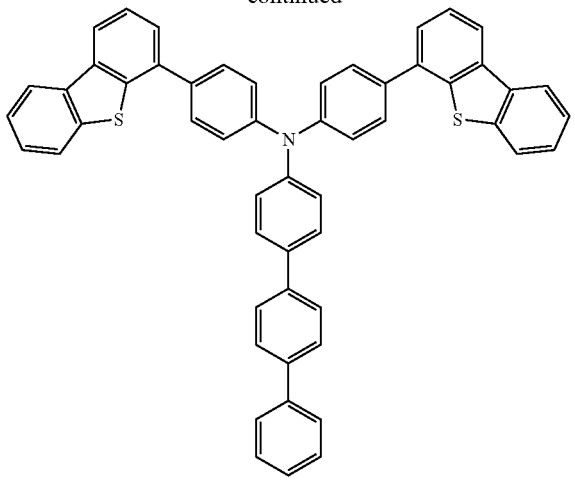

The hole transporting layer of the organic EL device of the invention may be made into a two-layered structure of a first hole transporting layer (anode side) and a second hole transporting layer (cathode side).

The thickness of the hole transporting layer is preferably 10 to 200 nm, although not particularly limited thereto.

The organic EL device of the invention may have a layer comprising an acceptor material which is attached to the anode side of the hole transporting layer or the first hole transporting layer. With such a layer, it is expected that the driving voltage is lowered and the production cost is reduced.

The acceptor material is preferably a compound represented by the following formula:

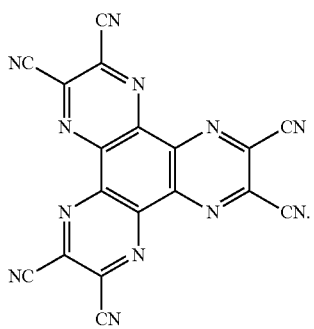 [SMILES: N#Cc1nc2c3nc(C#N)c(C#N)nc3c3nc(C#N)c(C#N)nc3c2nc1C#N]

The thickness of the layer comprising the acceptor material is preferably 5 to 20 nm, although not particularly limited thereto.

N/P Doping

The carrier injecting properties of the hole transporting layer and the electron transporting layer can be controlled by, as described in JP 3695714B, the doping (n) with a donor material or the doping (p) with an acceptor material.

A typical example of the n-doping is an electron transporting material doped with a metal, such as Li and Cs, and a typical example of the p-doping is a hole transporting material doped with an acceptor material such as, $F_4$TCNQ.

Space Layer

For example, in an organic EL device wherein a fluorescent emitting layer and a phosphorescent emitting layer are laminated, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

The organic EL device of the invention preferably comprises a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer.

The triplet blocking layer prevents the diffusion of triplet excitons generated in the light emitting layer to adjacent layers and has a function of confining the triplet excitons in the light emitting layer, thereby preventing the deactivation of energy on molecules other than the emitting dopant of triplet excitons, for example, on molecules in the electron transporting layer.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

Each layer of the organic EL device may be formed by a dry film-forming method, such as vacuum deposition, sputtering, plasma, and ion plating, or a wet film-forming method, such as spin coating, dipping, and flow coating. The thickness of each layer is not particularly limited, but preferably within an appropriate range, generally 5 nm to 10 µm and more preferably 10 nm to 0.2 µm.

In the wet film-forming method, the thin film layer is formed by using a solution or dispersion of the material for each layer in a suitable solvent, for example, any of solvents, such as ethanol, chloroform, tetrahydrofuran, or dioxane.

For example, a solution of the anthracene derivative as a material for organic EL devices in a solvent is suitable as a solution for use in the wet film-forming method.

Each organic thin film layer may comprise a resin or an additive suitable for improving the film-forming properties and preventing a pin hole in the layer.

The organic EL device of the present invention can be applied to various electronic equipment, for example, a flat emitting source, such as a flat panel display of a wall-mounting television; a light source for a copying machine, a printer, a backlight of a liquid crystal display or a measuring instrument; a display panel; and a signal lamp. In addition to the organic EL device, the compound of the invention is usable in the fields of an electrophotographic photoconductor, a photoelectric converter, a solar cell, and an image sensor.

EXAMPLES

The present invention will be described in more detail with reference to the examples. However, it should be noted that the scope of the invention is not limited thereto.

Synthesis Example 1: Synthesis of Compound 1

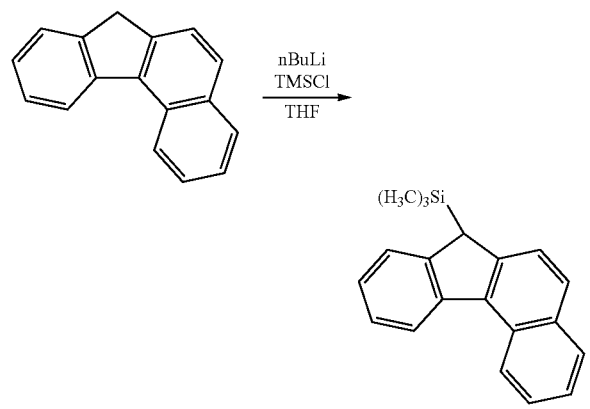

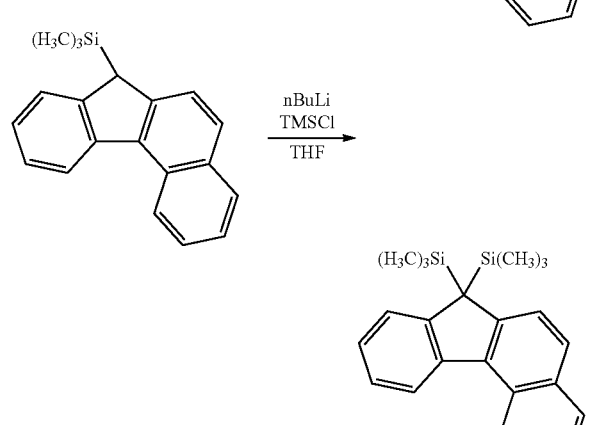

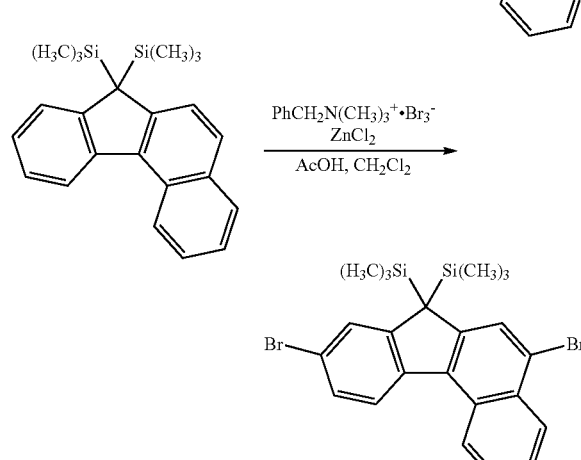

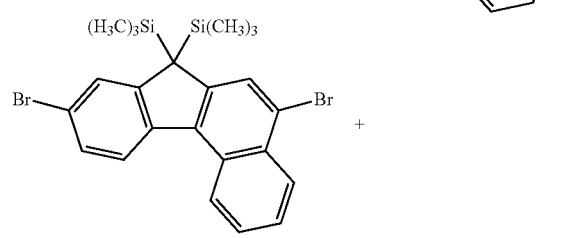

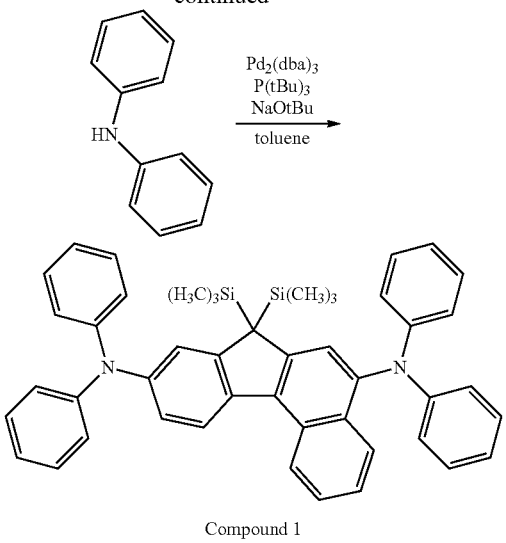

Compound 1

(1-1) Synthesis of 7-trimethylsilylbenzo[c]fluorene

A mixture of 22.8 g of benzo[c]fluorene synthesized in the same manner as the method described in Organic Letters, Vol. 11, No. 20, 2009, 4588 to 4591 and 500 mL of dehydrated tetrahydrofuran was cooled to −65° C. After adding 70 mL of a 1.65 M hexane solution of n-butyllithium, the mixture was stirred for one hour. After adding 18 mL of trimethylsilyl chloride dropwise, the temperature was raised gradually and the mixture was stirred at room temperature for 4 h.

After adding water, the mixture was extracted with toluene and allowed to separate into layers. The organic layer was washed with an aqueous solution of sodium carbonate and a saturated saline, dried over sodium sulfate, and concentrated. The obtained crude product was purified by silica gel column chromatography and the obtained solid was dried under reduced pressure to obtain 27.3 g of a white solid.

(1-2) Synthesis of 7,7-bis(trimethylsilyl)benzo[c]fluorene

The procedures of the synthesis of 7-trimethylsilylbenzo[c]fluorene were repeated except for using 7-trimethylsilyl-benzo[c]fluorene in place of benzo[c]fluorene.

The result of FD-MS (field desorption mass spectrometry) of the obtained compound ($C_{23}H_{28}Si_2$) is shown below:

FDMS: m/z=360 (M+).

(1-3) Synthesis of 5,9-dibromo-7,7-bis(trimethylsilyl)benzo[c]fluorene

After adding 11.7 g of benzyltrimethylammonium tribromide to a mixed solution of 4.9 g of 7,7-bis(trimethylsilyl) benzo[c]fluorene in 42 mL of acetic acid and 42 mL of dichloromethane, 15 g of zinc chloride was added so as to completely dissolve benzyltrimethylammonium tribromide. The resultant solution was allowed to react at room temperature for 8 h.

After adding a 5% aqueous solution of sodium hydrogen sulfite, the reaction mixture was extracted with dichloromethane. After washing with an aqueous solution of potassium carbonate and a saturated saline, the dichloromethane layer was dried over anhydrous sodium sulfate and then the solvent was evaporated off under reduced pressure. The obtained residue was purified by silica gel column chromatography and recrystallization to obtain 4.2 g (yield: 60%) of a white solid of 5,9-dibromo-7,7-bis(trimethyl silyl)benzo[c]fluorene.

The result of FD-MS (field desorption mass spectrometry) of the obtained compound ($C_{23}H_{26}Br_2Si_2$) is shown below:
FDMS: m/z=515 (M+).

(1-4) Synthesis of Compound 1

In an argon atmosphere, a mixture of 4.0 g of 5,9-dibromo-7,7-bis(trimethylsilyl)benzo[c]fluorene obtained in synthesis (1-1), 3.3 g of diphenylamine, 0.21 g of tris(dibenzylideneacetone) dipalladium(0), 1.5 g of sodium t-butoxide, 155 mg of tri-tert-butylphosphine, and 40 mL of toluene was stirred at 85° C. for 8 h.

After cooling to room temperature, the reaction solution was filtered through celite and then the solvent was evaporated off. The obtained residue was purified by silica gel column chromatography and recrystallization to obtain 4.2 g (yield: 55%) of a yellow solid of the compound 1.

The result of FD-MS (field desorption mass spectrometry) of the obtained compound ($C_{47}H_{46}N_2Si_2$) is shown below:
FDMS: m/z=694 (M+).

Example 1

Production of Organic EL Device

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min. The thickness of the ITO transparent electrode was 130 nm.

The cleaned glass substrate having an ITO transparent electrode line was mounted to a substrate holder of a vacuum vapor deposition apparatus. The following compound HI-1 was vapor-deposited so as to cover the transparent electrode to form a HI-1 film with a thickness of 5 nm, thereby forming a hole injecting layer.

On the hole injecting layer, the following compound HT-1 (first hole transporting material) was vapor-deposited to form a HT-1 film with a thickness of 80 nm, thereby forming a first hole transporting layer.

On the first hole transporting layer, the following compound HT-2 was vapor-deposited to form a HT-2 film with a thickness of 15 nm, thereby forming a second hole transporting layer.

On the second hole transporting layer, the compound BH-1 (host material) and the compound 1 (dopant material) were vapor co-deposited to form a co-deposited film with a thickness of 25 nm. The concentration of the compound 1 was 5.0% by mass. The co-deposited film works as a light emitting layer.

On the light emitting layer, the following compound ET-1 was vapor-deposited to form a ET-1 film with a thickness of 20 nm, thereby forming a first electron transporting layer.

On the first electron transporting layer, the following compound ET-2 was vapor-deposited to form a ET-2 film with a thickness of 5 nm, thereby forming a second electron transporting layer.

On the second electron transporting layer, LiF was vapor-deposited to form a LiF film with a thickness of 1 nm at a film-forming speed of 0.01 nm/sec, thereby forming an electron injecting electrode (cathode).

On the LiF film, metallic Al was vapor-deposited to from a film of metallic Al with a thickness of 80 nm, thereby forming a metallic Al cathode.

Evaluation of Organic EL Device

By applying a voltage to the organic EL device thus produced so as to adjust the current density to 10 mA/cm², the driving voltage, the external quantum efficiency EQE, and the emission peak wavelength λp were determined. The external quantum efficiency and the emission peak wavelength thus determined are shown in Table 1.

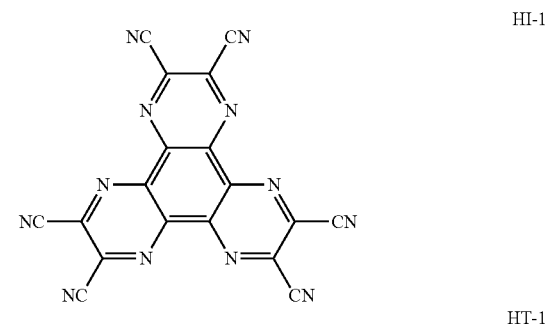

HI-1

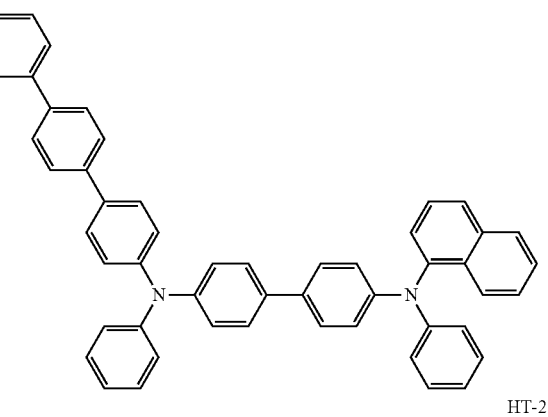

HT-1

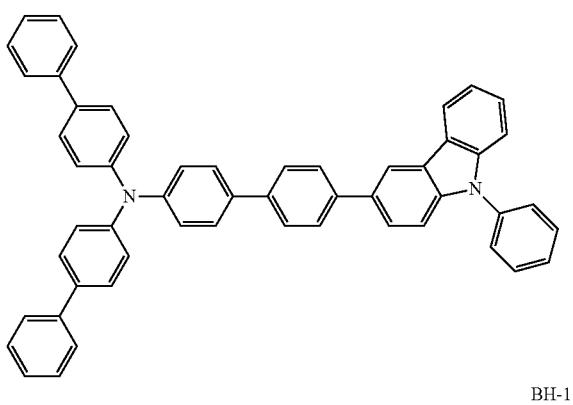

HT-2

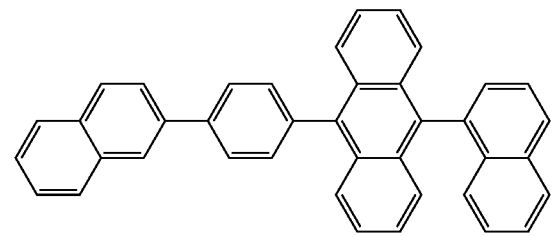

BH-1

ET-1

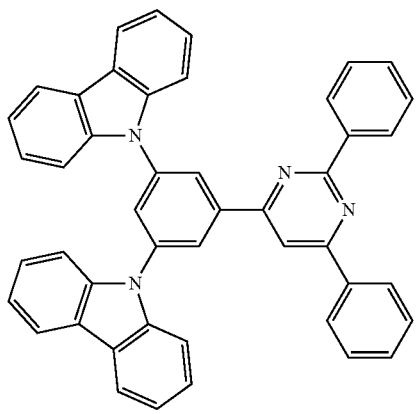

ET-2

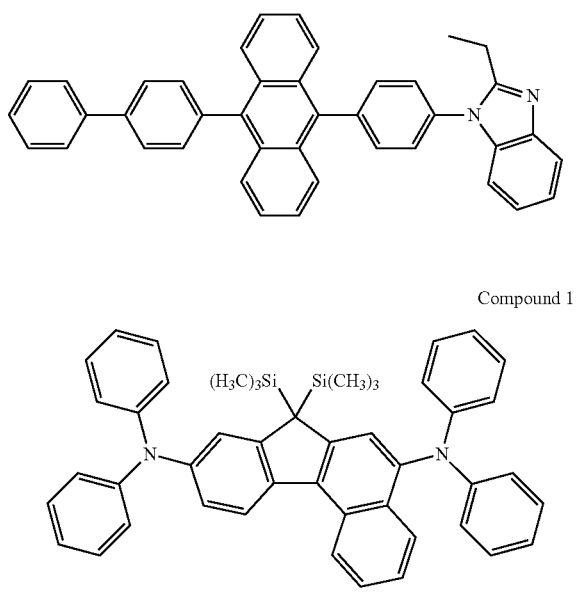

Compound 1

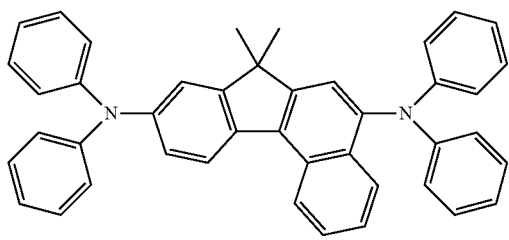

Comparative Example 1

A device was produced and evaluated in the same manner as in Example 1 except for using the following comparative compound in place of the compound 1.

Comparative compound

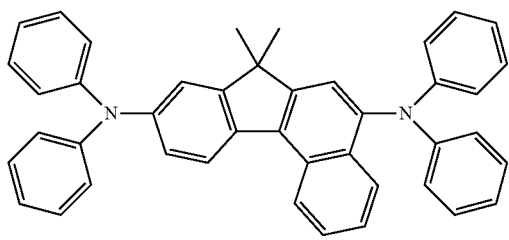

TABLE 1

| | Dopant material | Emission peak wavelength (nm) | External quantum efficiency (%) |
|---|---|---|---|
| Example 1 | Compound 1 | 458 | 9.9 |
| Comparative example 1 | Comparative compound | 460 | 8.5 |

The amine compound of the invention is useful as a material for realizing an organic EL device capable of driving with high efficiency.

REFERENCE SIGNS LIST

1: Organic electroluminescence device
2: Substrate
3: Anode
4: Cathode
5: Light emitting layer
6: Hole transporting layer
7: Electron transporting layer
10: Emission unit

What is claim is:

1. An amine compound represented by formula (1):

$$B\text{-}(A)_n \qquad (1)$$

in formula (1):
n represents an integer of 1 to 4, B represents a structure represented by formula (2), and A represents an amine moiety represented by formula (4);
when n is 2 or more, the amine moieties A may be the same or different;

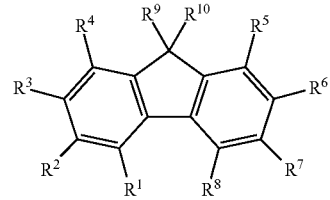

(2)

in formula (2):
at least one pair selected from $R^1$ and $R^2$, $R^2$ and $R^3$, $R^3$ and $R^4$, $R^5$ and $R^6$, $R^6$ and $R^7$, and $R^7$ and $R^8$ represents a bond to a divalent group represented by formula (3);
$R^9$ represents a substituted or unsubstituted alkyl group having 1 to 20 carbon atoms, a substituted or unsubstituted cycloalkyl group having 3 to 20 carbon atoms, a substituted or unsubstituted aryl group having 6 to 30 ring carbon atoms, a substituted or unsubstituted heteroaryl group having 5 to 30 ring atoms, or a group represented by formula (I);
$R^{10}$ is represented by formula (II):

(I)

(II)

in formulae (I) and (II):

X$^1$ to X$^6$ each independently represent a hydrogen atom, a substituted or unsubstituted alkyl group having 1 to 20 carbon atoms, a substituted or unsubstituted cycloalkyl group having 3 to 20 carbon atoms, a substituted or unsubstituted alkenyl group having 2 to 20 carbon atoms, a substituted or unsubstituted alkoxy group having 1 to 20 carbon atoms, a substituted or unsubstituted aryl group having 6 to 30 ring carbon atoms, or a substituted or unsubstituted aralkyl group having 7 to 20 carbon atoms, and X$^1$ to X$^6$ may be bonded to each other to form a ring;

(3)

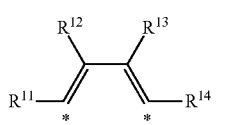

in formula (3) each * represents a bonding site to which the at least one pair representing the bond to the divalent group represented by formula (3) as defined in formula (2) is bonded;

in formulae (2) and (3), n variable or variables selected from R$^1$ to R$^8$ and R$^{11}$ to R$^{14}$ represents or represent a bond or bonds to A;

R$^1$ to R$^8$ and R$^{11}$ to R$^{14}$ other than those defined above each independently represent a hydrogen atom, a fluorine atom, a cyano atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a mono-, di- or tri-substituted silyl group wherein the substituent is selected from an alkyl group having 1 to 20 carbon atoms and an aryl group having 6 to 30 ring carbon atoms, a substituted or unsubstituted aryl group having 6 to 30 ring carbon atoms, or a substituted or unsubstituted heteroaryl group having 5 to 30 ring atoms;

(4)

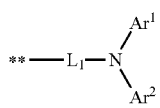

in formula (4), Ar$^1$ and Ar$^2$ each independently represent a substituted or unsubstituted aryl group having 6 to 30 ring carbon atoms or a substituted or unsubstituted heteroaryl group having 5 to 30 ring carbon atoms;

L$_1$ represents a single bond, an arylene group having 6 to 30 ring carbon atoms, a heteroarylene group having 5 to 30 ring atoms, or a divalent linking group wherein two to four selected from the arylene group and the heteroarylene group are linked together; and

** represents a bonding site to B.

2. The amine compound according to claim 1, wherein B in formula (1) is represented by any of formulae (11) to (13):

(11)

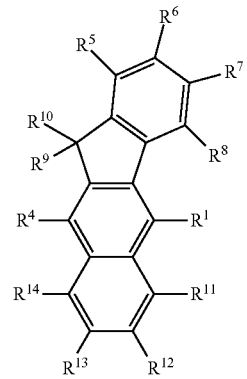

(12)

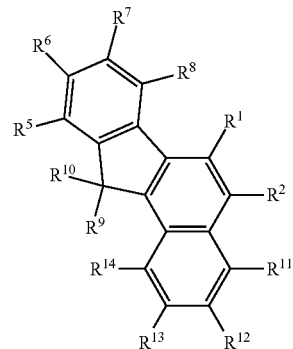

(13)

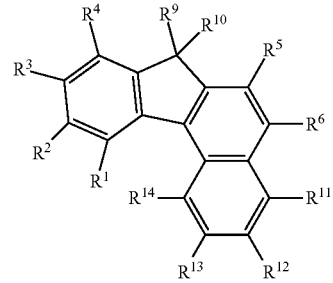

in formulae (11) to (13), R$^1$ to R$^{14}$ are as defined in formulae (2) and (3).

3. The amine compound according to claim 1, wherein two pairs selected from R$^1$ and R$^2$, R$^2$ and R$^3$, R$^3$ and R$^4$, R$^5$ and R$^6$, R$^6$ and R$^7$, and R$^7$ and R$^8$ in formula (2) represent bonds to the divalent group represented by formula (3).

4. The amine compound according to claim 1, wherein B in formula (1) is represented by any of formulae (14) to (20):

(14)

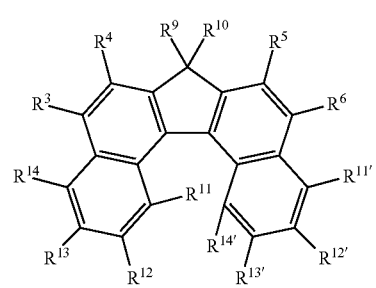

-continued

(15)
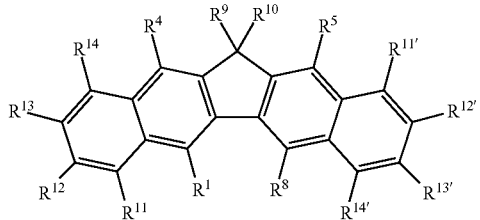

(16)
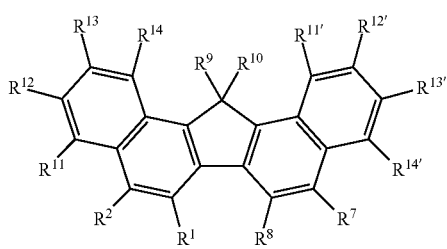

(17)
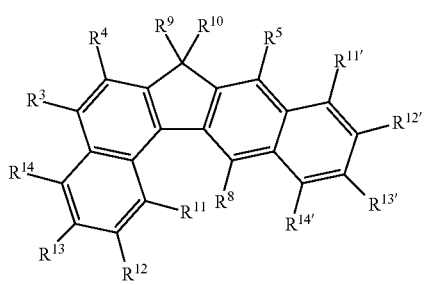

(18)
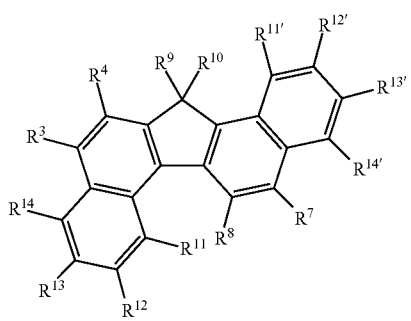

(19)
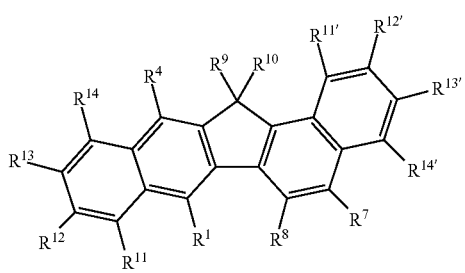

-continued

(20)
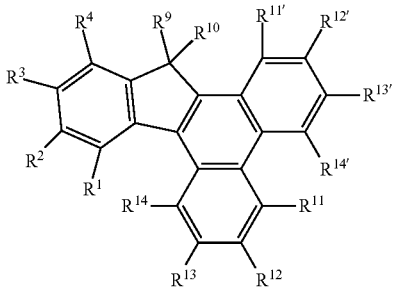

in formulae (14) to (20), $R^1$ to $R^{14}$ are as defined in formulae (2) and (3) and $R^{11'}$ to $R^{14'}$ are the same as $R^{11}$ to $R^{14}$.

5. The amine compound according to claim 4, wherein B in formula (1) is represented by any of formulae (14) to (16).

6. The amine compound according to claim 1, wherein $L_1$ in formula (4) is a single bond.

7. The amine compound according to claim 1, wherein n in formula (1) is 1 or 2.

8. The amine compound according to claim 1, wherein the amine compound is represented by formula (13-1):

(13-1)
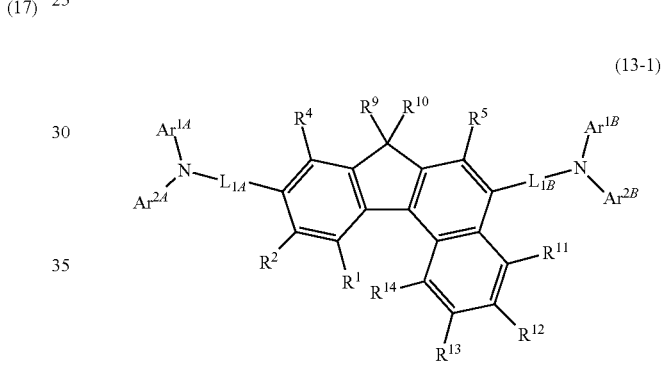

in formula (13-1), $L_{1A}$ and $L_{1B}$ are each independently the same as $L_1$, $Ar^{1A}$ and $Ar^{1B}$ are each independently the same as $Ar^1$, and $Ar^{2A}$ and $Ar^{2B}$ are each independently the same as $Ar^2$.

9. The amine compound according to claim 1, wherein $R^9$ of B is represented by formula (I) and $R^{10}$ is represented by formula (II).

10. The amine compound according to claim 1, wherein $R^9$ of B is a substituted or unsubstituted alkyl group having 1 to 20 carbon atoms or a substituted or unsubstituted aryl group having 6 to 30 ring carbon atoms and $R^{10}$ is represented by formula (II).

11. The amine compound according to claim 1, wherein $X^1$ to $X^6$ each independently represent a substituted or unsubstituted alkyl group having 1 to 20 carbon atoms, a substituted or unsubstituted cycloalkyl group having 3 to 20 carbon atoms, or a substituted or unsubstituted aryl group having 6 to 30 ring carbon atoms.

12. The amine compound according to claim 1, wherein $Ar^1$ and $Ar^2$ in formula (4) each independently represent a substituted or unsubstituted phenyl group, a substituted or unsubstituted naphthyl group, or a substituted or unsubstituted biphenylyl group.

13. The amine compound according to claim 8, wherein $Ar^{1A}$, $Ar^{1B}$, $Ar^{2A}$, and $Ar^{2B}$ in formula (13-1) each independently represent a substituted or unsubstituted phenyl group, naphthyl group, or biphenylyl group.

14. The amine compound according to claim 8, wherein $L_{1A}$ and $L_{1B}$ in formula (13-1) each represents a single bond.

15. A material for organic electroluminescence devices comprising the amine compound according to claim 1.

16. An organic electroluminescence device comprising an organic thin film layer between a cathode and an anode, wherein the organic thin film layer comprises one or more layers which comprise a light emitting layer and at least one layer of the organic thin film layer comprises at least one compound selected from the amine compound according to claim 1.

17. The organic electroluminescence device according to claim 16, wherein the light emitting layer comprises the amine compound.

18. The organic electroluminescence device according to claim 16, wherein the at least one layer comprises said amine and an anthracene derivative represented by formula (5):

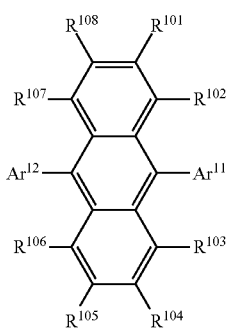

(5)

in formula (5):
- $Ar^{11}$ and $Ar^{12}$ each independently represent a substituted or unsubstituted monocyclic group having 5 to 50 ring atoms or a substituted or unsubstituted fused ring group having 8 to 50 ring atoms; and
- $R^{101}$ to $R^{108}$ each independently represent a group selected from a hydrogen atom; a substituted or unsubstituted monocyclic group having 5 to 50 ring atoms; a substituted or unsubstituted fused ring group having 8 to 50 ring atoms; a group comprising a combination of the monocyclic group and the fused ring group; a substituted or unsubstituted alkyl group having 1 to 50 carbon atoms; a substituted or unsubstituted cycloalkyl group having 3 to 50 ring carbon atoms; a substituted or unsubstituted alkoxy group having 1 to 50 carbon atoms; a substituted or unsubstituted aralkyl group having 7 to 50 carbon atoms; a substituted or unsubstituted aryloxy group having 6 to 50 ring carbon atoms; a substituted or unsubstituted silyl group; a halogen atom; and a cyano group.

19. The organic electroluminescence device according to claim 18, wherein $Ar^{11}$ and $Ar^{12}$ each independently represent a substituted or unsubstituted fused ring group having 8 to 50 ring atoms.

20. The organic electroluminescence device according to claim 18, wherein one of $Ar^{11}$ and $Ar^{12}$ represents a substituted or unsubstituted monocyclic group having 5 to 50 ring atoms and the other represents a substituted or unsubstituted fused ring group having 8 to 50 ring atoms.

21. The organic electroluminescence device according to claim 18, wherein $Ar^{12}$ represents a naphthyl group, a phenanthryl group, a benzanthryl group, a 9, 9-dimethylfluorenyl group, or a dibenzofuranyl group and $Ar^{11}$ represents an unsubstituted phenyl group or a substituted phenyl group having a substituent selected from a monocyclic group and a fused ring group.

22. The organic electroluminescence device according to claim 18, wherein $Ar^{12}$ represents a substituted or unsubstituted fused ring group having 8 to 50 ring atoms and $Ar^{11}$ represents an unsubstituted phenyl group.

23. The organic electroluminescence device according to claim 18, wherein $Ar^{11}$ and $Ar^{12}$ each independently represent a substituted or unsubstituted monocyclic group having 5 to 50 ring atoms.

24. The organic electroluminescence device according to claim 18, wherein $Ar^{11}$ and $Ar^{12}$ each independently represent a substituted or unsubstituted phenyl group.

25. The organic electroluminescence device according to claim 18, wherein $Ar^{11}$ represents an unsubstituted phenyl group and $Ar^{12}$ represents a substituted phenyl group having a substituent selected from a monocyclic group and a fused ring group.

26. The organic electroluminescence device according to claim 18, wherein $Ar^{11}$ and $Ar^{12}$ each independently represent a substituted phenyl group having a substituent selected from a monocyclic group and a fused ring group.

27. An electronic equipment comprising the organic electroluminescence device according to claim 16.

* * * * *